US010207006B2

(12) United States Patent
McGiven et al.

(10) Patent No.: US 10,207,006 B2
(45) Date of Patent: Feb. 19, 2019

(54) OLIGOSACCHARIDE CONJUGATES AND METHODS OF USE

(71) Applicants: THE SECRETARY OF STATE FOR ENVIRONMENT, FOOD AND RURAL AFFAIRS, Addlestone (GB); THE GOVERNORS OF THE UNIVERSITY OF ALBERTA, Edmonton (CA)

(72) Inventors: John McGiven, Addlestone (GB); David Bundle, Edmonton (CA); Laurence Howells, Addlestone (GB); Julie Guiard, Verdigny (FR); Vijaya Ganesh Narayanaswamy, Toronto (CA)

(73) Assignees: THE SECRETARY OF STATE FOR ENVIRONMENT FOOD AND RURAL AFFAIRS, Surrey (GB); THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 0 days.

(21) Appl. No.: 15/662,699

(22) Filed: Jul. 28, 2017

(65) Prior Publication Data

US 2018/0021439 A1 Jan. 25, 2018

Related U.S. Application Data

(62) Division of application No. 14/784,662, filed as application No. PCT/GB2014/051202 on Apr. 16, 2014, now Pat. No. 9,744,245.

(60) Provisional application No. 61/812,396, filed on Apr. 16, 2013, provisional application No. 61/812,402, filed on Apr. 16, 2013.

(30) Foreign Application Priority Data

Apr. 16, 2013 (GB) .................................. 1306882.0

(51) Int. Cl.

| | |
|---|---|
| *A61K 47/50* | (2017.01) |
| *A61K 47/64* | (2017.01) |
| *A61K 47/54* | (2017.01) |
| *G01N 33/53* | (2006.01) |
| *G01N 33/569* | (2006.01) |

(52) U.S. Cl.
CPC ............ *A61K 47/549* (2017.08); *A61K 47/50* (2017.08); *A61K 47/646* (2017.08); *A61K 47/6415* (2017.08); *G01N 33/53* (2013.01); *G01N 33/5308* (2013.01); *G01N 33/56911* (2013.01); *G01N 2333/23* (2013.01); *G01N 2400/00* (2013.01); *G01N 2400/10* (2013.01)

(58) Field of Classification Search
CPC ........... G01N 2333/23; G01N 2333/24; G01N 2400/50; G01N 33/5438; G01N 33/56911
See application file for complete search history.

(56) References Cited

U.S. PATENT DOCUMENTS

| | | | |
|---|---|---|---|
| 4,831,126 A | 5/1989 | Bundle et al. | |
| 9,744,245 B2 * | 8/2017 | McGiven | G01N 33/5308 |

FOREIGN PATENT DOCUMENTS

| | | |
|---|---|---|
| WO | 2014/170681 A2 | 10/2014 |

OTHER PUBLICATIONS

Behan et al., Reduction of *Brucella* Species and Francisella tularensis Cross-Reacting Agglutinins by Dithiothreitol, Journal of Clinical Microbiology, (Oct. 1982); vol. 16(4); pp. 756-757.
Carlsson et al., Enzyme-Linked Immunosorbent Assay for Immunological Diagnosis of Human Tularemia, Journal of Clinical Microbiology, (Nov. 1979); vol. 10(5); pp. 615-621.
Francis et al., Agglutination, Cross-Agglutination, and Agglutinin Absorption in Tularaemia, Public Health Report, (Jun. 25, 1926); vol. 41(26); pp. 1273-1295.
Meikle et al., Fine Structure of A and M Antigens from *Brucella* Biovars, Infection and Immunity, (Sep. 1989); vol. 57(9); pp. 2820-2828.

Prior et al., Characterization of the O antigen gene cluster and structural analysis of the O antigen of *Francisella tularensis* subsp. *tularensis*, Journal of Medical Microbiology, (2003), vol. 52, pp. 845-851.

Vinogradov et al., Structure of the O-antigen of Francisella tularensis strain 15, Carbohydrate Research, (1991); vol. 214; pp. 289-297.

Abdoel et al., "Rapid Latex Agglutination Test for the Serodiagnosis of Human Brucellosis," Diagnostic Microbiology and Infectious Disease, (Feb. 2007), vol. 57, No. 2, pp. 123-128.

(Continued)

*Primary Examiner* — Padmavathi Baskar

(74) *Attorney, Agent, or Firm* — Buchanan Ingersoll & Rooney PC

(57) ABSTRACT

There is provided a method of detecting in a sample the presence of an anti-M and/or anti-A and/or anti-C/Y antibody, the method comprising contacting the sample with a diagnostic conjugate provided according to the invention, comprising an oligosaccharide which comprises at least two units of 4,6-dideoxy-4-acylamido-α-pyranose and comprising at least one -(1-3)- link between adjacent 4,6-dideoxy-4-acylamido-α-pyranose units, in which the carbon at position 5 in the pyranose is linked to an R group, where R is independently selected from —$CH_2$OH, —H or an alkyl group having at least one C atom, the oligosaccharide being covalently linked to a non-saccharide molecule or to a surface.

6 Claims, 32 Drawing Sheets

(56) References Cited

OTHER PUBLICATIONS

Abdoel et al., "Simple and Rapid field tests for Brucellosis in Livestock," Veterinary Microbiology, (Aug. 25, 2008), vol. 130, No. 3-4, pp. 312-319.
Alonso-Urmeneta et al., Evaluation of Lipopolysaccharides and Polysaccharides of Different Epitopic Structures in the Indirect Enzyme-Linked Immunosorbent Assay for Diagnosis of Brucellosis in Small Ruminants and Cattle, Clinical and Diagnostic Laboratory Immunology, (Nov. 1998), vol. 5, No. 6, pp. 749-754.
Alton et al., "Techniques for the Brucellosis Laboratory," Paris: INRA, (1994), pp. 42-60.
Angewandte, Chem. Int. Ed. Engl. 18, (1979) No. 8. p. 614.
Boschiroli et al., "Brucellosis: a Worldwide Zoonosis," Current Opinion in Microbiology, (Feb. 2001), vol. 4, No. 1, pp. 58-64.
Bundle et al., "Definition of *Brucella* A and M Epitopes by Monoclonal Typing Reagents and Synthetic Oligosaccharides," Infection and Immunity, (Sep. 1989), vol. 57, No. 9, pp. 2829-2836.
Bundle et al., "Structural Elucidation of the *Brucella melitensis* M Antigen by High-Resolution NMR at 500 MHz," Biochemistry, (1987), vol. 26, No. 26, pp. 8717-8726.
Cardoso et al., "*Brucella* spp Noncanonical LPS: Structure, Biosynthesis, and Interaction with host Immune System," Microbial Cell Factories, (2006), vol. 5, No. 13, pp. 1-11.
Caroff et al., "Structure of the O-Chain of the Phenol-Phase Soluble Cellular Lipopolysaccharide of Yersinia Enterocolitica Serotype O:9," European Journal of Biochemistry, (Feb. 1984), vol. 139, No. 1, pp. 195-200.
Cheng et al., "Paper-Based ELISA," Angewandte Chemie International Edition, (Jun. 28, 2010), vol. 49, No. 28, pp. 4771-4774.
Corbel, "Recent Advances in the Study of *Brucella* Antigens and their Serological Cross-Reactions," Veterinary Bulletin, (Dec. 1985), vol. 55, No. 12, pp. 927-942.
Ding et al., "A New Era in Pyrogen Testing," Trends in Biotechnology, (Aug. 2001), vol. 19, No. 8, pp. 277-281.
Douglas et al., "Use of Monoclonal Antibodies to Identify the Distribution of A and M Epitopes on Smooth *Brucella* Species," Journal of Clinical Microbiology, (Jul. 1988), vol. 26, No. 7, pp. 1353-1356.
Du et al., "Efficient and Practical Syntheses of Three Pentasaccharides core Structures Corresponding to N-Glycans," Tetrahedron, (Feb. 25, 2001), vol. 57, No. 9, pp. 1757-1763.
El Fangour et al., "Total Synthesis of the Eight Diastereomers of the Syn-Anti-Syn Phytoprostanes F1 Types I and II," The Journal of Organic Chemistry, (Apr. 2, 2004), vol. 69, No. 7, pp. 2498-2503.
Franco et al., "Human Brucellosis," The Lancet Infectious Diseases, (Dec. 2007), vol. 7, No. 12, pp. 775-786.
Gerbier et al., "False Positive Serological Reactions in Bovine Brucellosis: Evidence of the role of Yersinia Enterocolitica Serotype 0:9 in a Field Trial," Veterinary Research, BioMed Central, (Jul.-Aug. 1997), vol. 28, No. 4, pp. 375-383.
González et al., "Brucellosis Vaccines: Assessment of *Brucella melitensis* Lipopolysaccharide Rough Mutants Defective in Core and O-Polysaccharide Synthesis and Export," PLoS One, (Jul. 2008), vol. 3, No. 7, e2760, pp. 1-15.
Greiser-Wilke et al., "Monoclonal Antibodies and Characterization of Epitopes of Smooth *Brucella* Lipopolysaccharides," Annales de l'Institut Pasteur/Microbiologie, (Sep.-Oct. 1987), vol. 138, No. 5, pp. 549-560.
Hanashima et al., "Synthesis of a Sialic Acid α(2-3) Galactose Building Block and Its Use in a Linear Synthesis of Sialyl Lewis X," Organic Letters, (Apr. 2007), vol. 9, No. 9, pp. 1777-1779.
Hanley et al., "The Meaning and Use of the Area Under a Receiver Operating Characteristic (ROC) Curve," Diagnostic Radiology, (Apr. 1982), vol. 143, No. 1, pp. 29-36.
Hanley et al., "A Method of Comparing the Areas under Receiver Operating Characteristic Curves Derived from the Same Cases," Diagnostic Radiology, (Sep. 1983), vol. 148, No. 3, pp. 839-843.
Hou et al., "Enhanced Stereoselectivity of α-Mannosylation Under Thermodynamic Control using Trichloroacetimidates," Carbohydrate Research, (May 27, 2010), vol. 345, No. 8, pp. 999-1007.
Jungersen et al., "Differentiation Between Serological Responses to *Brucella suis* and Yersinia Enterocolitica Serotype O:9 after Natural or Experimental Infection in Pigs," Epidemiology and Infection, (Apr. 2006), vol. 134, No. 2, pp. 347-357.
Kamath et al., "Use of Diethyl Squarate for the Coupling of Oligosaccharide Amines to Carrier Proteins and Characterization of the Resulting Neoglycoproteins by MALDI-TOF Mass Spectrometry," Glycoconjugate Journal, (Apr. 1996), vol. 13, No. 2, pp. 315-319.
Kittelberger et al., "Serological cross-reactivity between *Brucella abortus* and Yersinia enterocolitica 0:9: IV. Evaluation of the M- and C-epitope antibody response for the specific detection of *B. abortus* infections," Veterinary Microbiology, (Feb. 1998), vol. 60, No. 1, pp. 45-57.
Kubler-Kielb et al., "Reinvestigation of the structure of *Brucella* O-antigens," Carbohydr Research, (Aug. 30, 2013), vol. 378, pp. 144-147.
Lemieux et al., "The Properties of a "Synthetic" Antigen Related to the Human Blood-Group Lewis a," Journal of the American Chemical Society, (Jul. 9, 1975), vol. 97, No. 14, pp. 4076-4083.
Martinez et al., "Three-Dimensional Microfluidic Devices Fabricated in Layered Paper and Tape," Proceedings of the National Academy of Sciences of the United States of America, (Dec. 16, 2008), vol. 105, No. 50, pp. 19606-19611.
Mawas et al., "Immunogenicity in a Mouse Model of a Conjugate Vaccine Made with a Synthetic Single Repeating Unit of Type 14 Pneumococcal Polysaccharide Coupled to CRM197," Infection and Immunity, (Sep. 2002), vol. 70, No. 9, pp. 5107-5114.
McGiven et al., "A new Homogeneous Assay for High Throughput Serological Diagnosis of Brucellosis in Ruminants," Journal of Immunological Methods, (Aug. 20, 2008), vol. 337, No. 1, pp. 7-15.
Nasir et al., "Fluorescence Polarization: An Analytical Tool for Immunoassay and Drug Discovery," Combinatorial Chemistry & High Throughput Screening, (Aug. 1999), vol. 2, No. 4, pp. 177-190.
OIE Terrestrial Manual 2009, Chapter 2.4.3.—Bovine Brucellosis, pp. 2-35.
Nielsen et al., "Serological Diagnosis of Brucellosis," Contributions, Sec. Biol. Med. Sci., (2010), vol. 31, No. 1, pp. 65-89.
Ogawa et al., "Synthesis of eight Glycosides of Hexasaccharide Fragments Representing the Terminus of the O-Polysaccharide of Vibrio Cholerae O:1, Serotype Inaba and Ogawa, Bearing Aglycons Suitable for Linking to Proteins," Carbohydrate Research, (Oct. 31, 1996), vol. 293, No. 2, pp. 173-194.
Porcine Brucellosis, NB: Version adopted by the World Assembly of Delegates of the OIE in May 2009, Chapter 2.8.5, OIE Terrestrial Manual 2009, pp. 1-7.
Peters et al., "Synthetic Antigenic Determinants of the *Brucella* A Polysaccharide: A Disaccharide Thioglycoside for Block Synthesis of Pentasaccharide and Lower Homologues of α1,2-linked 4,6-dideoxy-4-formamido-α-D-mannose," Canadian Journal of Chemistry, (1989), vol. 67, No. 3, pp. 491-496.
Porte et al., "Role of the *Brucella suis* Lipopolysaccharide O Antigen in Phagosomal Genesis and in Inhibition of Phagosome-Lysosome Fusion in Murine Macrophages," Infection and Immunity, (Mar. 2003), vol. 71, No. 3, pp. 1481-1490.
Rhodes et al., "A Blocking ELISA for the Detection of Specific Antibodies to Bovine Respiratory Syncytial Virus," J Vet Diagn Invest, (Oct. 1989), vol. 1 No. 4, pp. 324-328.
Ruhaak et al., "Oligosaccharide Analysis by Graphitized Carbon Liquid Chromatography—mass Spectrometry," Anal Bioanal Chem., (May 2009), vol. 394, No. 1, pp. 163-174.
Saksena et al., "Immunogens from a Synthetic Hexasaccharide Fragment of the O-SP of Vibrio Cholerae O:1, Serotype Ogawa," Tetrahedron Asymmetry, (Jan. 10, 2005), vol. 16, No. 1, pp. 187-197.
Sussich et al., "The Kinetics of Periodate Oxidation of Carbohydrates: a Calorimetric Approach," Carbohydrate Research, (Oct. 20, 2000), vol. 329, No. 1, pp. 87-95.
Svenson et al., "Artificial *Salmonella* Vaccines: *Salmonella typhimurium* O-Antigen-Specific Oligosaccharide-Protein Conjugates Elicit Pro-

(56) References Cited

OTHER PUBLICATIONS tective Antibodies in Rabbits and Mice," Infection and Immunity, (May 1981), vol. 32, No. 2, pp. 490-496.
Verez-Bencomo et al., "A Synthetic Conjugate Polysaccharide Vaccine Against Haemophilus Influenzae Type B," Science, (Jul. 23, 2004), vol. 305, No. 5683, pp. 522-525.
Wang et al., "The Variation of Antigens in Gram-Negative Bacteria," Subcellular Biochemistry, (2010), vol. 53, pp. 123-152.
Wang et al., "Simple Glycosylation of Allyl Glycosides," The Journal of Organic Chemistry, (2007), vol. 72, No. 15, pp. 5870-5873.
Wattam et al., "Comparative Genomics of Early-Diverging *Brucella* Strains Reveals a Novel Lipopolysaccharide Biosynthesis Pathway," MBio, (Sep./Oct. 2012), vol. 3, No. 5, e00246-12, pp. 1-11.
Westphal et al., "Über die Extraktion von Bakterien mit Pheno/Wasser," Zeitschrift für Naturforschung B, (Mar. 1952), vol. 7, No. 3, pp. 148-155.
Zaccheus et al., "The Epitopic and Structural Characterization of *Brucella suis* Biovar 2 O-Polysaccharide Demonstrates the Existence of a New M-Negative C-Negative Smooth *Brucella* Serovar," PLoS One, (Jan. 2013), vol. 8, No. 1, e53941, pp. 1-7.
K. Nielsen, et al., "A homogeneous fluorescence polarization assay for detection of antibody to *Brucella abortus*" Journal of Immunological Methods, 195 (1996) 161-168.
Poester et al., The Open Veterinary Science Journal, 2010, vol. 4, No. 1, pp. 46-68.
Meikle et al., Infection and Immunity 1989, p. 2820-2828.

* cited by examiner

OLIGOSACCHARIDE CONJUGATES AND METHODS OF USE

FIELD OF THE INVENTION

The invention relates to a novel diagnostic conjugate comprising an oligosaccharide, which can be used within assays for the reliable diagnosis of brucellosis. Furthermore, these assays can provide a DIVA (Differentiating Infected from Vaccinated Animals) test for vaccination with a novel vaccination conjugate also disclosed herein.

BACKGROUND

Brucellosis is a serious transboundary global zoonosis that is spread by livestock and wildlife and is primarily due to infection with *Brucella abortus, B. melitensis* or *B. suis*. Although the disease is serious in humans, human to human transmission is rare and nearly all cases of disease are due to contact with infected animals or animal products (Franco et al. (2007) The Lancet Infectious Diseases 7, 775-786). Brucellosis (with the exception of canine brucellosis) is caused by infection with smooth strains of *Brucella*, those that present O-polysaccharide (OPS) as part of the smooth lipopolysaccharide (sLPS) on their outer membrane (Cardoso et al. (2006) Microbial Cell Factories 5, 13).

The sLPS is a macromolecule comprising lipid A with a diaminoglucose backbone attached to a set of core sugars which, in the case of smooth *Brucella* strains, is attached to the OPS which extends into the extracellular environment. This OPS is a recognised and established virulence factor (Porte et al. (2003) Infection and Immunity 71, 1481-1490) and induces a strong antibody response in the host against which classical and contemporary serodiagnostic assays are directed (Nielsen & Yu (2010) Prilozi 31, 65-89). Unfortunately, infection with other Gram negative bacteria having OPS of similar structure, but which may be phylogenetically unrelated, may give rise to antibodies which cross react in the classical and contemporary serodiagnostic assays (Corbel (1985) Vet. Bull. 55, 927-942). Such false positive serological reactions (FPSRs) become particularly problematic in regions of low to zero prevalence of brucellosis, whereby the positive predictive value of the serological assays becomes extremely small.

Attempts to improve the specificity of brucellosis serodiagnosis have revolved mainly around efforts to identify and apply recombinant protein antigens. Whilst many studies have been published extolling the virtues of one antigen or another for the resolution of false positives, none have made it into assays that have progressed beyond the research laboratory into routine and effective use.

Antibodies raised owing to infection with *Yersinia enterocolitica* O:9 cross react significantly with the OPS from *Brucella* smooth strains, owing to the considerable similarity in the structure (McGiven et al. (2008) Journal of Immunological Methods 337, 7-15) and are believed to cause many of the false positive serological reactions in diagnostic testing (Gerbier et al. (1997) Vet Res 28, 375-383). Likewise, antibodies raised against the OPS from smooth *Brucella* strains show considerable reaction against *Y. enterocolitica* O:9 OPS (Jungersen et al. (2006) Epidemiol Infect 134, 347-357).

The *Brucella* OPS is an unbranched variable length homopolymer formed by, on average, 50-100 units of the rare sugar 4,6-dideoxy-4-formamido-D-mannopyranose (N-formyl perosamine) (Meikle et al. (1989) Infect Immun. 57, 2820-2828). The 4,6-dideoxy-4-formamido-D-mannopyranose unit itself is only found in nature within the OPS structure of *Brucella* organisms and of *Y. enterocolitica* O:9. In almost all *Brucella* organisms, neighbouring 4,6-dideoxy-4-formamido-D-mannopyranose units are variably α-1,2 or α-1,3 linked. The structural data demonstrates that it is only the α-1,3 linkage which differentiates *Brucella* and *Y. enterocolitica* O:9 OPS, as the latter is an exclusively α-1,2 linked 4,6-dideoxy-4-formamido-D-mannopyranose homopolymer (Caroff et al. (1984) Eur. J. Biochem. 139, 195-200). Between *Brucella* strains, the proportion of α-1,3 linkages varies between 2-20% (Meikle et al. (1989) Infect. Immun. 57, 2820-2828).

Even in *Brucella* strains with as much as 20% α-1,3 linkages, the OPS will contain many contiguous α-1,2 linkages (Bundle et al. (1987) Biochemistry 26, 8717-8726). It is not known, however, if the sequence of linkages is ordered and regular. There are three main biosynthesis pathways for OPS, the Wzx/Wzy, ABC (Wzm/Wzt) and Synthase systems (Wang et al. (2010) In "Endotoxins: structure, function & recognition"; Springer Netherlands, pp. 123-152). *Brucella* utilises the ABC system (Gonzalez et al. (2008) PLoS ONE 3, e2760), as is more commonly found in organisms that have homopolymeric OPS (including *Y. enterocolitica* O:9). In this pathway the saccharides are added to the growing OPS chain individually rather than being constructed into repeating units and then added, as is the case in the Wzx/Wzy pathway where OPS is frequently made up of repeating blocks of three to five different monosaccharides. As such, it is quite possible that there is no regularity to the location of the α-1,3 links and they are distributed stochastically with regions of extended contiguous α-1,2 linkages even in strains with a relatively high proportion of α-1,3 linkages. The control and fidelity of the enzymes that synthesise the OPS have yet to be established.

The proportion of the two linkage types affects the shape of the OPS and the different shapes are recognisable by monoclonal (Douglas et al. (1988) J Clin Microbiol 26, 1353-1356) and polyclonal antibodies such as those used for serotyping *Brucella* into A (low number of α-1,3 linkages, typically 2%) and M (relatively high proportion of α-1,3 linkages, typically 20%) dominant strains or serotypes (Alton et al. (1994) Techniques for the Brucellosis Laboratory, pages 53-54; INRA Editions, ISBN-10: 2738000428).

The *B. suis* biovar 2 strain (Zaccheus et al. (2013) PLoS One 8, e53941) and *B. inopinata* 1302 (Wattam et al. (2012) mBio 3: 00246-12) do not appear to contain any α-1,3 linkages. *B. inopinata* BO2 is a highly unusual and distantly related member of the *Brucella* genus as well as being extremely rare. Although it is a smooth strain, it is lacking most of the genes required for the synthesis of 4,6-dideoxy-4-formamido-D-mannopyranose OPS (Wattam et al (2012) mBio, 3:5). Its OPS structure is of a different form which has not yet been identified.

The relative proportions and distribution of α-1,2 and α-1,3 linkages within the *Brucella* and *Y. enterocolitica* O:9 homopolymeric OPS create distinct, but not necessarily completely described, antibody binding epitopes. In *Brucella*, there are three different antigenic epitopes which can be found in the OPS for which there has been firm structural evidence (Bundle et al. (1989) Infect. Immun. 57, 2829-2836) as summarised in Table 1:

TABLE 1

OPS epitopes

| Name of epitope | Number of perosamines | Characteristics | Present in which OPS |
|---|---|---|---|
| C/Y | 3 to 4 | N-formyl perosamines are exclusively joined by α1,2 linkages | All smooth *Brucella* strains and also *Y. enterocolitica* O:9 |
| A | 5 or more | N-formyl perosamines are joined by α1,2 linkages | Predominantly within all A-dominant *Brucella* strains and also *Y. enterocolitica* O:9 |
| M | 2-6 | At least one α1,3 link present with at least one adjacent α1,2 linkages; location of α1,3 link within epitope undefined | Predominantly within M-dominant OPS *Brucella* strains but also, to a lesser extent, A-dominant strains. Not found in *Y. enterocolitica* O:9 |

Exclusively α-1,2 linked tri- and tetrasaccharide sequences are found in high abundance within the OPS from *B. abortus, melitensis* and *suis* as well as in the OPS from *Y. enterocolitica* O:9. Such sequences are termed 'C/Y epitopes' as they are common within all smooth strains of economically significant *Brucella* and also to *Y. enterocolitica* O:9. Monoclonal antibodies that bind such sequences are termed anti-C/Y.

Longer sequences of more than four saccharides that are exclusively α-1,2 linked are more likely to be found in *Brucella* strains with lower proportions of α-1,3 links. This also includes *Y. enterocolitica* O:9 which contains only α-1,2 links. Such sequences are termed 'A epitopes' and, of course, contain C/Y epitopes within them (C/Y epitopes being α-1,2 linked perosamine chains up to 4 saccharides in length, as outlined above). Monoclonal antibodies that bind such epitopes are termed anti-A antibodies. Strains of *Brucella* with OPS containing low proportions of α-1,3 links and, therefore, more abundant and longer sequences of uninterrupted α-1,2 links, are termed "A dominant" strains (including most strains of *B. abortus*), even though the OPS may contain a proportion of α-1,3 links at least once every 50 residues (Bundle et al. (1989) Infect. Immun. 57, 2829-2836). The OPS from A-dominant strains of course contains C/Y epitopes, as well as A epitopes.

An anti-C/Y antibody will be expected to bind to both a C/Y epitope and to an A-epitope, since the shorter C/Y epitope structure forms part of the longer A-epitope structure.

Sequences of saccharides that contain a single α-1,3 linkage with limited contiguous α-1,2 linkages are termed 'M epitopes'. Monoclonal antibodies that bind to such sequences are termed anti-M antibodies. Strains of *Brucella* with a high proportion of α-1,3 links are termed M dominant strains. Such strains comprise C/Y epitopes, but fewer A epitopes, if any, since the series of α-1,2 linkages is "broken up" by the presence of more frequent α-1,3 linkages.

The structure of the M epitope has not been defined and, in detailed terms, may vary according to the antibody. However, any M epitope must be sufficient in size to enable the binding of monoclonal antibodies raised against antigens containing the α-1,3 linkage and be sufficiently limited in α-1,2 linkages so as not to bind effectively to antibodies raised against antigens (or parts of antigens) that are exclusively α-1,2 linked. Thus, the presence of the α-1,3 linkage is critical, as is a limitation on the number of α-1,2 linkages. The structure of these antigens has been partially described previously (Bundle et al. (1989) Infect Immun 57, 2829-2836) although the allocation of *Brucella* strains into A and M types (and also mixed A and M) predates this considerably. This allocation is a fundamental part of the classical biotyping of *Brucella* strains (Nielsen et al. (2009) "Bovine brucellosis" In: Manual of Diagnostic Tests & Vaccines for Terrestrial Animals 2009; Office International Des Epizooties, Paris, pg 10-19). Recent work suggests that the M dominant OPS contains a repeating structural determinant that contains one α-1,3 link for every three α-1,2 links. (Kubler-Kielb & Vinogradov (2013) Carbohydr. Res. 378, 144-147).

The typing of strains into A, M or mixed A and M (where there is a proportion of α-1,3 linkages of between 2-20% (Meikle et al. (1989) Infect Immun 57, 2820-2828)) is performed using sera from hyperimmunised rabbits. The rabbits are inoculated with repeated doses of killed *Brucella* cells of either A or M dominant type until a high antibody titre has been obtained. The polyclonal sera is then absorbed with the heterologous cell type (e.g., sera from rabbits hyperimmunised with A dominant strains are absorbed with M dominant cells) to remove antibodies that cross react. After careful selection and empirical testing, the process leaves a population of polyclonal (now termed monospecific) antibodies that are more specific to the immunising type and can be used in agglutination assays to determine the A, M or mixed A and M status of an untyped strain (Alton et al. (1994) Techniques for the Brucellosis Laboratory, pages 53-54; INRA Editions, ISBN-10: 2738000428).

Presumptive diagnosis of Brucellosis depends on detection of antibodies to *Brucella* A, C/Y and M antigens and is confirmed by microbiological culture (Nielsen et al. (2009) "Bovine brucellosis" In: Manual of Diagnostic Tests & Vaccines for Terrestrial Animals 2009; Office International Des Epizooties, Paris, pg 3-7). The A, C/Y and M antigenic determinants are expressed simultaneously on the O-antigen polysaccharide domain of *Brucella* smooth lipopolysaccharides (s-LPS) and this sLPS is used to detect antibodies present in sera of animals or humans suspected of being infected. Unfortunately, *Brucella* is a virulent pathogen that must be grown under level 3 bio-containment. This makes the production of diagnostic O-antigens a demanding, specialised and costly task, with significant health risks. Furthermore, since A, C/Y and M epitopes each may be expressed on a single *Brucella* sLPS and since this antigen is resistant to common partial degradation methods, it has proved difficult to isolate pure A or M antigenic determinants.

In summary, the *Brucella* OPS is highly immunogenic and many antibodies are raised against it in infected animals. This OPS contains a number of overlapping antibody epitopes, some of which are unique to *Brucella* and some that are not. The existence of non-unique epitopes within the *Brucella* OPS compromises its use as a serodiagnostic antigen and is a major factor in the occurrence of false positive serological results. It has previously been reported, by some workers (Alonso-Urmeneta et al. (1998) Clinical and Diagnostic Laboratory Immunology 5, 749-754), that antibodies to common OPS epitopes dominate the humoral response in cases of animal brucellosis and that the epitopic structure of the LPS, be it A, M or mixed A and M dominance, is not relevant in serodiagnosis.

However, given the problems of cross-reactivity of antibodies raised against different strains of *Brucella*, as well as other organisms, there is a need to identify antigens and methods capable of discriminating between antibodies raised against a *Brucella* bacterium and those raised against other organisms.

SUMMARY OF INVENTION

According to a first aspect of the invention, there is provided a method of detecting in a sample the presence of anti-M and/or anti-C/Y and/or anti-A antibodies, for example anti-O-polysaccharide antibodies such as anti-*Brucella* and/or anti-*Y. enterocolitica* O:9 antibodies, the method comprising contacting the sample with a diagnostic conjugate as defined below according to the second aspect (or third or fourth aspects) of the invention. The method may comprise detecting binding of the conjugate to at least one antibody present in the sample. In an embodiment, the diagnostic conjugate for use in the first aspect of the invention may be a "universal antigen" for anti-M and anti-C/Y and anti-A antibodies, as described below. The diagnostic conjugate comprises an oligosaccharide which comprises at least two 4,6-dideoxy-4-acylamido-α-pyranose units and comprises at least one -(1-3)- link between adjacent 4,6-dideoxy-4-acylamido-α-pyranose units, the oligosaccharide being covalently linked to a non-saccharide carrier molecule or to a solid entity.

In an embodiment, there is provided a method of detecting in a sample the presence of anti-M antibodies, for example anti-OPS antibodies such as anti-*Brucella* antibodies, the method comprising contacting the sample with a diagnostic conjugate as defined below according to the second aspect (or third or fourth aspects) of the invention and detecting binding of the conjugate to at least one anti-M antibody present in the sample. The diagnostic conjugate for use in this embodiment of the invention is a "specific M-antigen", as described below, capable of distinguishing between an anti-A (and/or anti-C/Y) antibody and an anti-M antibody. That is, the specific M-antigen diagnostic conjugate binds preferentially (i.e., with greater specificity) to anti-M antibodies as compared to anti-A (and/or anti-C/Y) antibodies. This embodiment of the method, therefore, may provide a method for detecting the presence in a sample of anti-*Brucella* antibodies whilst avoiding detection of antibodies against a non-*Brucella* organism. The inventors have observed an unexpected specificity within the polyclonal antibody response, in the vast majority of *Brucella* infected animals, to the α-1,3 linkage, the presence of which structurally differentiates most strains of *Brucella* from *Y. enterocolitica* O:9 OPS. Given the very low number of α-1,3 links in the OPS of the majority of *Brucella*, it is completely surprising that the method of the invention is effective in detecting the presence of antibodies raised against almost all strains of *Brucella*.

Detection of binding of the diagnostic conjugate to an antibody, as mentioned herein, may be by any known technique, for example, an ELISA, fluorescence polarisation assay (FPA), TR-FRET assay, lateral flow assay or bead-based agglutination assay, as described in more detail below. The invention is not limited to any of these assays and the skilled person may readily contemplate alternative assays which might be used.

An anti-M antibody is one which is capable of binding to an M-epitope from a *Brucella* OPS or to an M-dominant antigen. An anti-A antibody is one which is capable of binding to an antigen comprising an A-epitope, or to an A-dominant antigen, as found in the *Brucella* OPS or the *Y. enterocolitica* O:9 OPS. An anti-C/Y antibody is one which is capable of binding to an antigen comprising a C/Y epitope, as found in the *Brucella* OPS or the *Y. enterocolitica* O:9 OPS. This epitope may, in some occurrences, be found within an A- or an M-dominant antigen. An anti-M antibody may preferentially bind to an antigen comprising an M-epitope compared to binding of the antibody to an antigen comprising an A or C/Y epitope (i.e., it will bind with greater specificity to an antigen comprising an M-epitope). Examples of such epitopes, antibodies and antigens are known in the art, as described above. Examples of anti-M antibodies include BM40 (Greiser et al. (1987) Am. Inst. Pasteur Microbiol. 138, 549-560), BM28 or BM10 (Bundle et al. (1989) Infect. Immun. 57, 2829-2836). Examples of anti-A antibodies include YsT9.1 and YsT9.2 (Bundle et al. (1989) Infect. Immun. 57, 2829-2836).

According to a second aspect of the invention, there is provided a diagnostic conjugate comprising an oligosaccharide which comprises at least two 4,6-dideoxy-4-acylamido-α-pyranose units and comprising at least one -(1-3)- link between adjacent 4,6-dideoxy-4-acylamido-α-pyranose units, the oligosaccharide being covalently linked to a non-saccharide carrier molecule or to a solid entity, such as a surface or a bead (encompassing, for example, any non-liquid structure such as a gel or latex bead or surface).

The diagnostic conjugate described herein may prove useful in the detection of antibodies to the A, C/Y and M epitopes described herein and, in some embodiments, for distinguishing between antibodies to the A or C/Y and M epitopes. Therefore, the diagnostic conjugate may be termed a "diagnostic antigen".

The oligosaccharide may comprise 2, 3, 4, 5, 6, 7, 8, 9, 10, 11, 12, 13, 14 or 15 4,6-dideoxy-4-acylamido-α-pyranose units.

A "specific M-antigen", as mentioned throughout this specification, may be provided where the diagnostic conjugate of the invention comprises an oligosaccharide comprising 2, 3, 4 or 5 4,6-dideoxy-4-acylamido-α-pyranose units. A "universal antigen" for anti-M and anti-A antibodies, as mentioned throughout this specification, may be provided where the diagnostic conjugate of the invention comprises an oligosaccharide comprising 6 or more 4,6-dideoxy-4-acylamido-α-pyranose units. These specific embodiments of the diagnostic conjugate are described further elsewhere herein.

The term "-(1-3)- link" as used throughout this specification indicates an α-1,3 link (also known as an α-1→3 link) between adjacent 4,6-dideoxy-4-acylamido-α-pyranose units in the oligosaccharide. Likewise, the term "-(1-2)- link" as used throughout this specification indicates an α-1,2 link (also known as an α-1→2 link) between adjacent 4,6-dideoxy-4-acylamido-α-pyranose units.

The at least one -(1-3)- link may be centrally positioned, as defined below. Where four or more 4,6-dideoxy-4-acylamido-α-pyranose units are present, the at least one -(1-3)- link may be internally positioned and optionally also centrally positioned, as defined below.

The term "internally positioned -(1-3)- link" indicates that the -(1-3)- link is not the final link at either end of the molecule, that is, it is positioned between 4,6-dideoxy-4-acylamido-α-pyranose units neither of which forms a terminal unit of the oligosaccharide.

The term "centrally positioned -(1-3)- link" in the context of an oligosaccharide having an even number of 4,6-dideoxy-4-acylamido-α-pyranose units indicates that the -(1-3)- link is in the central position of the molecule with an equal number of 4,6-dideoxy-4-acylamido-α-pyranose units to either side. In the context of an oligosaccharide having an odd number of 4,6-dideoxy-4-acylamido-α-pyranose units, the term "centrally positioned -(1-3)- link" indicates that the -(1-3)- link is positioned immediately to one side of the 4,6-dideoxy-4-acylamido-α-pyranose unit which is in the middle of the molecule, i.e., the unit which has an equal number of other units to either side of it. For example, in a trisaccharide the central unit is the second unit and the centrally positioned -(1-3)- link is the first link (between units one and two) or the second link (between units two and three); in a pentasaccharide the central unit is the third unit and the centrally positioned -(1-3)- link is the second link (between units two and three) or the third link (between units three and four).

In an embodiment, the oligosaccharide forming part of the diagnostic conjugate has no more than one -(1-3)- link, i.e., there is a single -(1-3)- link present in the oligosaccharide, with all other links between 4,6-dideoxy-4-acylamido-α-pyranose units being a link which is not an α-1,3 link, for example, which is an α-1,2 link.

Throughout this specification, the term "pyranose" indicates a sugar (for example, a pentose or hexose) comprising a pyran ring. In any aspect or embodiment of the present invention, the C5 (carbon at position 5 in the pyranose) in each 4,6-dideoxy-4-acylamido-α-pyranose unit is linked to an R group, where R is independently selected from —CH$_2$OH, —H or an alkyl group having at least one C. The "independent selection" of the R group indicates that it may be different in each 4,6-dideoxy-4-acylamido-α-pyranose contained in the oligosaccharide. In some embodiments, the alkyl group may be a hydrocarbon having 1-5 C atoms, for example, 1, 2, 3, 4 or 5 C atoms.

In any aspect or embodiment of the invention, the alkyl group may be a saturated hydrocarbon which is branched or unbranched. The alkyl group may be a methyl, ethyl, propyl, butyl or pentyl group, for example. In an embodiment, R is methyl.

In any aspect or embodiment of the invention, the acylamido in each 4,6-dideoxy-4-acylamido-α-pyranose unit may be independently selected from formamido, acetamido, propionamido or butyramido, i.e., each acylamido present in the overall molecule may be any of formamido, acetamido, propionamido or butyramido, so that a mixture of groups may be present in the oligosaccharide. In any embodiment, 4,6-dideoxy-4-acylamido-α-pyranose may be 4,6-dideoxy-4-formamido-α-D-mannopyranose.

In any embodiment of the oligosaccharide described herein, in any aspect of the invention, the reducing end of the oligosaccharide may be closed by an —OCH$_3$ group, formed by substitution by —CH$_3$ of the —H on the —OH moiety which is linked to C1 (carbon at position 1) on the pyranose ring. The reducing end may alternatively be "closed" with a -1-O—(CH$_2$)$_n$—COO—CH$_3$ group where n=3-9, which may enable linkage to protein and/or non-protein molecules and/or to a solid entity. In a further alternative, a non-perosamine sugar may be attached at any suitable position to the oligosaccharide defined herein, optionally for the purpose of linkage to other molecules. Other linking systems are described below.

The oligosaccharide covalently linked to form part of the diagnostic conjugate may be a disaccharide having Formula I;
4,6-dideoxy-4-acylamido-α-pyranosyl-(1-3)-4,6-dideoxy-4-acylamido-α-pyranose (Formula I).

In an embodiment, the disaccharide consists of Formula II:
4,6-dideoxy-4-formamido-α-D-mannopyranosyl-(1-3)-4,6-dideoxy-4-formamido-α-D-mannopyranose (Formula II).

The oligosaccharide may be a trisaccharide having Formula III or IV:
4,6-dideoxy-4-acylamido-α-pyranosyl-(1-3)-4,6-dideoxy-4-acylamido-α-pyranosyl-(1-2)-4,6-dideoxy-4-acylamido-α-pyranose (Formula III);
4,6-dideoxy-4-acylamido-α-pyranosyl-2)-4,6-dideoxy-4-acylamido-α-pyranosyl-(1-3)-4,6-dideoxy-4-acylamido-α-pyranose (Formula IV).

The oligosaccharide may be a tetrasaccharide having Formula V, VI or VII:
4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranose (Formula V);
4,6-dideoxy-4-acylamido-α-pyranosyl-(1-2)-4,6-dideoxy-4-acylamido-α-pyranosyl-2)-4,6-dideoxy-4-acylamido-α-pyranosyl-(1-3)-4,6-dideoxy-4-acylamido-α-pyranosyl (Formula VI); 4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranose (Formula VII).

In an embodiment of Formula VII, the tetrasaccharide consists of Formula VIII:
4,6-dideoxy-4-formamido-α-D-mannopyranosyl-(1-2)-4,6-dideoxy-4-formamido-α-D-mannopyranosyl-(1-3)-4,6-dideoxy-4-formamido-α-D-mannopyranosyl-(1-2)-4,6-dideoxy-4-formamido-α-D-mannopyranose (Formula VIII)

In an embodiment, the oligosaccharide is a pentasaccharide of Formula IX, X, XI or XII:
4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-2)-4,6-dideoxy-4-acylamido-α-pyranose (Formula IX);
4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-3)-4,6-dideoxy-4-acylamido-α-pyranose (Formula X);
4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranose (Formula XI);
4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranose (Formula XII).

By way of example, in both Formulae XI and XII above, a link which is not an internally positioned link is shown in bold. It can be seen, therefore, that the -(1-3)-link in each of these molecules is internally positioned. In addition, in both Formulae, the central 4,6-dideoxy-4-acylamido-α-pyranose unit is underlined, showing that that the -(1-3)- link in these molecules is also centrally positioned, according to the above definition.

Any of the oligosaccharides of Formulae I-XII may be covalently linked to a non-saccharide molecule or to a solid entity, to form a diagnostic conjugate which may be a specific M-antigen. The inventors found that anti-*Brucella* OPS antibodies raised by infection with non-*Brucella* organisms did not bind effectively to a diagnostic conjugate comprising the disaccharide, trisaccharide, tetrasaccharide and pentasaccharide described above. In light of this, the inventors' finding that polyclonal antibodies raised against A dominant as well as M dominant strains of *Brucella* can bind to a diagnostic conjugate comprising the disaccharide, trisaccharide, tetrasaccharide and pentasaccharide described above was very surprising. This is surprising because A dominant *Brucella* strains have few M epitopes in the OPS. This interaction is of sufficiently high specificity that antibodies that cross react with the native OPS, but have not been raised against *Brucella*, fail to bind these oligosaccharides effectively, if at all. Binding specificity is apparently greatest when no or few contiguous -(1-2)- links are present in the oligosaccharide.

The oligosaccharide may be a hexasaccharide having Formula XIII or XIV:

4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranose (Formula XIII);

4,6-dideoxy-4-acylamido-α-pyranosyl-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-2)-4,6-dideoxy-4-acylamido-α-pyranose (Formula XIV).

The -(1-3)- link is internally positioned in these molecules, as defined above.

In an embodiment of the invention, the oligosaccharide may be a nonasaccharide having Formula XV:

4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranosyl-(1-2)-4,6-dideoxy-4-acylamido-α-pyranose-(1-2)-4,6-dideoxy-4-acylamido-α-pyranosyl-(1-2)-4,6-dideoxy-4-acylamido-α-pyranose (Formula XV).

Any of the oligosaccharides having Formulae XIII-XV are covalently linked to a non-saccharide molecule or to a solid entity, to form a diagnostic conjugate which may be a universal antigen, especially when the conjugate comprises the oligosaccharide of Formula XIV or XV.

The term "covalently linked" as used herein indicates that the oligosaccharide is joined to the non-saccharide molecule or solid entity via a link or bridge which comprises at least one covalent bond. Therefore, the term "conjugate" or "diagnostic conjugate" as used herein refers to a structure comprising an oligosaccharide that has been covalently linked or coupled to a "carrier" entity which is a non-oligosaccharide molecule such as (i) a protein or other molecule, for example one with a known biological activity such as the ability to fluoresce, or (ii) an inert amphiphilic polymer, or (iii) a solid material entity such as a surface or a bead. In all three cases, the coupling allows for various assay formats that detect the presence of antibody in a sample, for example, ELISA, FPA, TR-FRET, lateral flow assay or bead-based agglutination assay, as outlined elsewhere herein. The oligosaccharide may be conjugated through the glycosidic oxygen atom or a sulfur atom. The covalent coupling may be directly to the protein, molecule, polymer or solid entity, or may be achieved via covalent coupling to a linker as described below.

In the case of the conjugates described herein, the oligosaccharide is covalently attached through a linker to a carrier entity such as a protein carrier, polymer or solid entity such as a surface, using chemical techniques providing for linkage of the oligosaccharide to the said carrier. The linker may form a direct bridge between the oligosaccharide and the carrier, or may be attached directly to the oligosaccharide and then be attached to the carrier via a coupling reagent, as outlined further below. In one embodiment, reaction chemistries are used that result in covalent linkages between the linker and the carrier, as well as between the linker and the oligosaccharide. Such chemistries can involve direct attachment of the oligosaccharide-linker entity to the carrier, or attachment of the oligosaccharide-linker entity to a coupling reagent which itself attaches to the carrier. For example, this may comprise the use of complementary functional groups on hetero- or homo-bifunctional cross-coupling reagents, described further below. Preferably, the complementary functional groups are selected relative to the functional groups available on the oligosaccharide and/or carrier for bonding, or which can be introduced onto the oligosaccharide and/or carrier for bonding.

Either of two approaches can be adopted for attachment of a linker to the oligosaccharide. The first, as taught in (Lemieux et al. (1975) J. Am. Chem. Soc. 97, 4076-4083), assembles oligosaccharide on a linker. When the oligosaccharide-linker has been assembled, groups superfluous to further use, that were used to protect the oligosaccharide during assembly, are removed from the completed oligosaccharide-linker construct and the linker is activated for covalent attachment to protein (for example, to form an acyl azide group as shown in row 2 of Table 2). The second approach attaches the linker to the completed oligosaccharide after synthesis (Ogawa et al. (1996) Carbohydr. Res. 293, 173-94) and then removes protecting groups prior to conjugation with protein. In the first approach, the functionality used to establish the linkage to protein, either latent or exposed, must survive all chemical transformation used to build and subsequently deprotect the oligosaccharide. In the second approach, the linker only has to survive the deprotection step(s). In the work described herein, the inventors employed the first method and preserved the ester functionality throughout oligosaccharide synthesis and removal of protecting groups.

The term "linker" or "linking group" refers to the bridge structure produced between the oligosaccharide and the carrier, after covalent bonding of a linking agent, homobifunctional cross coupling reagent, or heterobifunctional cross coupling reagent to the oligosaccharide and to the carrier, as described below.

Suitable complementary functional groups for use in forming covalent linkages are well known in the art. By way of example, reaction between a carboxylic acid of either the linker or the protein carrier and a primary or secondary amine of the protein carrier or the linker in the presence of suitable, well-known activating agents results in formation of an amide bond; reaction between an amine group of either the linker or the protein carrier and a sulfonyl halide of the protein carrier or the linker results in formation of a sulfonamide bond covalently; and reaction between an alcohol or phenol group of either the linker or the protein carrier and an alkyl or aryl halide of the carrier or the linker results in formation of an ether bond covalently linking the carrier to the linker. Similarly, these complimentary reactions can occur between the linker and the oligosaccharide to form a linkage between the oligosaccharide and the linker.

The following Table 2 illustrates numerous complementary reactive groups and the resulting bonds formed by reactions between them.

TABLE 2

Complementary Reactive Groups and Resulting Linkages

| First reactive group | Second reactive group | Resulting linkage |
| --- | --- | --- |
| squarate | amine | Amide type |
| acyl azide | amine | Amide |
| carboxyl | amine | Amide |
| ketone | aminooxy | oxime |
| thiol | bromo or iodoacetyl | thioether |
| carbonate | amine | Carbamate |
| epoxide | sulfhydryl | β-hydroxythioether |
| maleimide | sulfhydryl | Thioether |
| hydroxyl | alkyl/aryl halide | Ether |
| amine | epoxide | β-hydroxyamine |
| amine | ketone | Imine |
| amine | ketone | secondary amine |
| sulfonyl halide | amine | Sulfonamide |
| epoxide | alcohol | β-hydroxyether |
| hydroxyl | isocyanate | urethane |

The term "linking agent" refers to a reagent that is used to couple two other molecules or species together. Thus, linking agents include heterobifunctional cross coupling reagents and homobifunctional cross coupling reagents. In one embodiment, the linking agent comprises a functional group selected from the "first reactive group" in Table 2. In another embodiment, the linking agent comprises a functional group selected from the "second reactive group" in Table 2. For example, a linking agent can comprise a functional group selected from the "first reactive group" in Table 2 while a mannopyranose derivative can comprise a functional group selected from the "second reactive group" in Table 2, or vice versa.

The term "heterobifunctional cross coupling reagents" refers to a reagent that is used to couple two other molecules or species together by having at least two different functional groups built into one reagent. Such cross coupling reagents are well known in the art and include, for example, X-Q-X', where each of X and X' are preferably independently cross coupling groups selected, for example, from —OH, —CO$_2$H, epoxide, —SH, —N=C—S, and the like. Preferably, Q is a group covalently coupling X and X' having from about 1 to about 20 atoms or alternatively, can be from about 1 to about 15 carbon atoms. Examples of suitable heterobifunctional cross coupling reagents include N-ε-maleimidocaproic acid, m-maleimidobenzoyl-N-hydroxysuccinimide ester, 3-(2-pyridyldithio)propionylhydrazide, N-succinimidyl iodoacetate, NHS-PEG-maliemide and N-succinimidyl 3-(2-pyridyldithio) propionate. The heterobifunctional cross coupling reagents may also be a lipid or lipid mimic, where the carbohydrate hapten may be covalently linked to the lipid or the lipid is co-administered as an immunological adjuvant.

The term "homobifunctional cross coupling reagents" refers to a reagent that is used to couple two other molecules or species together by having at least two of the same functional groups built into one reagent. Such cross coupling reagents are well known in the art and include, for example, X-Q-X, where X and Q are as defined above. Examples of suitable homobifunctional cross coupling reagents include squarate derivatives, as well as entities derived from succinic anhydride, maleic anhydride, polyoxyalkylenes, adipic acid (CO$_2$H—C$_6$—CO$_2$H), and azelaic acid (CO$_2$H—C$_9$—CO$_2$H). 1,2-diaminoethane, a dicarboxylic acid chloride and diethyl squarate are particular examples of such homobifunctional cross coupling reagents. Homobifunctional cross coupling reagents may also be derived from lipids and lipid mimics.

A preferred embodiment employs the heterobifunctional 5-methoxycarbonylpentanol as linker. The oligosaccharide is synthesised by attaching one or more sugar units via an alpha linkage to the hydroxyl group of the linker. The linker is chosen such that its second functional group remains unchanged throughout the chain extension of the oligosaccharide. Close variants of this linker type are alkanes bearing a terminal alcohol and a terminal ester group composed of 4 to 10 carbon atoms, or di or triethylene glycols bearing a terminal alcohol and a terminal ester group.

After removal of protecting group from the sugar residues and introduction of crucial formamido functionalities, the linker ester is converted to an amide which is conjugated to protein or polymer with primary amino group using a homobifunctional coupling reagent, di-alkyl squarate.

Other methods are known to practitioners of the art. For example (as taught by Lemieux) the linker ester may be converted to an acyl hydrazide and, by reaction with nitrous acid or dinitrogen tetroxide, a highly reactive acyl azide species is produced. Without isolation, this rapidly conjugates with protein or polymer primary amino groups. Less useful are methods whereby the linker ester under goes reaction to yield an aldehyde which may be conjugated by reductive amination. Methods of this type are less effective, because the chemistry to convert the ester group to appropriate functionalities may be incompatible with functional groups present in the oligosaccharide.

By way of non-limiting example, as in the work exemplified herein, the oligosaccharide may be linked to Bovine Serum Albumin (BSA) (or co-povidone) by being synthesised with a 5-methoxycarbonylpentanol linker molecule, the other end of which is reacted with a dialkyl squarate coupling reagent to provide a squarate half ester, which forms amide bonds to amino groups present in the BSA protein (or co-povidone).

In the conjugate according to the invention, the oligosaccharide is covalently attached as described above to a carrier, for example, a non-oligosaccharide entity such as a protein, for example, Bovine Serum Albumin (BSA), to a non-protein carrier molecule comprising hydrophobic elements, or to a fluorophore to enable detection in, for example, a TR-FRET or FPA system. The oligosaccharide may be covalently attached to a carrier which is a solid entity such as a surface and/or a membrane and/or a bead, by way of non-limiting example. A "solid" bead encompasses non-liquid structures such as gel beads or latex beads. Therefore, the diagnostic conjugate may be in the form of a surface having at least one oligosaccharide as described herein attached thereto via a linking system which includes a covalent attachment to the oligosaccharide. Attachment may be, for example, via passive absorption mediated by a protein carrier, or a non-protein carrier molecule comprising hydrophobic elements, covalently attached to the oligosaccharide. The passive absorption being due to, for example, hydrophobic and ionic interactions with a surface such as polystyrene, polyvinyl chloride, latex, glass, nitrocellulose, polyvinylidene difluoride. The protein carrier may be, for example, BSA. The attachment may alternatively be via hydrazone conjugation, which includes providing aldehyde groups on the oligosaccharide by periodate oxidation. Where hydrazone conjugation is used, the surface may be a Carbo-BIND™ ELISA plate. Other functional groups available on the solid entity surface may also be utilised, such as maleimide (binds to sulfhydryls), amine (numerous binding options available through use of a linker, as outlined in Table 2), aldehydes (bind to amines), or carboxyl (bind to amines).

The diagnostic conjugate described herein may be a synthetic conjugate, for example, the oligosaccharide and conjugate being synthesised by methods such as those outlined below.

In the method according to the invention, the sample may be a biological sample obtained from an animal, for example, an animal which is or has been, or is suspected of being or having been, infected with a *Brucella* bacterium. The animal may be a ruminant, camelid or suid animal such as a bovine or swine animal, for example, a cow, pig, sheep or goat, or may be a human being. The biological sample may be a blood, plasma, serum, tissue, saliva or milk sample. In particular, a biological sample is not a laboratory sample comprising only antibodies and/or oligosaccharides (plus laboratory reagents), but is a complex sample also comprising many other components including other antibodies, unrelated to the method to be conducted. The presence of anti-M antibodies in a sample from an animal indicates that the animal is, or has previously been, infected with a smooth strain *Brucella* bacterium so as to elicit an immune response and raising of antibodies. The *Brucella* may be any smooth strain (those that present OPS on their surface) which is not *B. suis* biovar 2 or *B. inopinata* BO2.

The method may take the form of an ELISA assay, for example an indirect ELISA or a competitive ELISA, the design of which is within the routine ability of the skilled person. For example, in an indirect ELISA, the oligosaccharide described herein is immobilised on an ELISA plate to form a diagnostic conjugate according to the invention, for example via hydrazone binding to a Carbo-BIND™ plate as described herein, or to a non-functionalised ELISA plate via the use of a conjugated carrier molecule such as BSA, capable of passive absorption to the plate. The biological sample to be tested is then added to the plate and incubated for a period of time, after which the plate is washed. A detection conjugate (such as HRP-conjugated Protein-G) is added and the plate incubated, washed and subsequently developed by a method appropriate to the detection conjugate being used (in the case of HRP, ABTS may be suitable, as described below). This allows determination of the level of binding, if any, of antibodies present in the biological sample to the oligosaccharide present on the plate. Specific examples are described in detail below.

In a competitive ELISA, the oligosaccharide may be immobilised on an ELISA plate to form a diagnostic conjugate according to the invention, for example, via hydrazone binding to a Carbo-BIND™ plate as described herein, or to a non-functionalised ELISA plate via the use of a conjugated carrier molecule such as BSA, capable of passive absorption to the plate. The biological sample to be tested is then added to the plate in conjunction with an anti-M monoclonal antibody (such as the BM40 antibody) and incubated for a period of time, after which the plate is washed. Binding of the anti-M monoclonal antibody is then detected by the addition to the plate of a suitable enzyme conjugate that specifically binds to the anti-M monoclonal antibody and a further incubation, after which time the plate is washed. (If the anti-M antibody has already been enzyme labelled, for example with HRP, the additional conjugate and incubation step would not be required.) The plate is subsequently developed by a method appropriate to the conjugate being used (in the case of HRP, ABTS may be suitable, as described below). This allows determination of the level of binding of the anti-M monoclonal antibody. Any anti-M antibodies in the sample will compete with the monoclonal anti-M antibody for binding to the immobilised antigen, resulting in a reduction of assay signal. This is used as a measure of the presence of anti-M antibodies in the biological sample.

Other ELISA variants, such as a blocking ELISA (Rhodes et al. (1989) J. Vet. Diagn. Invest. 1, 324-328), are well known to the skilled person and may be utilised without application of inventive skill.

The method according to the invention may comprise use of TR-FRET methods, such as are described, for example, in WO2009/118570 and WO2011/030168. In this context, the oligosaccharides may be conjugated, directly or indirectly, to a TR-FRET label such as a lanthanide chelate (donor fluorophore) or fluorescein (acceptor fluorophore) as described in those patent publications.

As mentioned above, the oligosaccharides may also be conjugated, directly or indirectly, to fluorophores that will enable the detection of antigen-antibody binding by fluorescence polarisation (Nasir and Jolley (1999) Comb. Chem. High Throughput Screen., 2, 177-190) as described, for example, in U.S. Pat. No. 5,976,820. This forms the basis of a fluorescence polarisation assay (FPA) as referred to elsewhere herein.

By way of non-limiting example, other assay formats which may be utilised in the invention include a lateral flow assay, in which antigen is absorbed to a membrane along which a serum (comprising serum antibodies) may be caused to flow. The serum may be mixed with anti-species antibodies, labelled with colloidal gold or latex beads (Abdoel et al. (2008) Vet. Microbiol. 130, 312-319). A further alternative is a bead based agglutination assay, for example in which an antigen-BSA conjugate is passively coated to a latex bead. The bead is then added to a serum sample and the occurrence or absence of agglutination observed (indicating antibody binding to antigen on the bead) (Abdoel & Smiths (2007) Diagn. Microbiol. Infect. Dis. 57, 123-128).

The method may be a diagnostic method of determining that an animal is or has been infected with a *Brucella* organism, the method comprising contacting a biological sample previously obtained from the animal with a diagnostic conjugate according to the second aspect (and/or third and/or fourth aspects, described below) of the invention. The animal may be a human being or a cow, pig, sheep or goat. The biological sample may be a blood, plasma, serum, tissue, saliva or milk sample.

Also provided is the diagnostic conjugate according to the second aspect of the invention for use in a diagnostic method of determining that an animal is or has been infected with a *Brucella* organism, as outlined above.

The methods described herein utilise the diagnostic conjugate also described herein and provide, for the first time, a method for detection of anti-A and/or anti-C/Y and/or anti-M antibodies, for example anti-OPS antibodies such as anti-*Brucella* antibodies, using a synthetic antigen. As mentioned above, since *Brucella* must be grown under level 3 bio-containment, production of diagnostic O-antigens is a demanding, specialised and costly task. Provision of a synthetic antigen is, therefore, a significant advantage. The data presented herein show that chemical syntheses have successfully provided a universal antigen to detect *Brucella* antibodies that arise during infection by all *Brucella* strains producing a sLPS (as well as other bacteria with an antigen having "A" epitope characteristics). This provides an extremely valuable and convenient antigen for presumptive diagnosis and one that can be deployed in virtually any assay format, including those that do not require sophisticated equipment, unavailable in remote locations (Martinez et al. (2007) Proc. Natl. Acad. Sci. 105, 19606-19611).

Furthermore, the provision in some embodiments of the present invention of a specific M-antigen, capable of preferentially binding to anti-M antibodies, provides for the first time a method enabling detection of antibodies against a *Brucella* bacterium whilst avoiding detection of antibodies against a non-*Brucella* organism (such as a Gram-negative organism in possession of an OPS of highly similar structure to that of *Brucella*, such as *Y. enterolitica* O:9). Therefore, in the method of the invention, the proportion of such false positive results due to detection of infection by such a non-*Brucella* bacterium is significantly reduced compared to a serodiagnostic assay method not according to the invention, e.g., as described in Nielsen et al. ("Bovine brucellosis" In: Manual of Diagnostic Tests & Vaccines for Terrestrial Animals 2009; Office International Des Epizooties, Paris, pg 10-19). In this context, the *Brucella* bacterium may be a *B. abortus, B. melitensis* or *B. suis* (with the exception of strains of *B. suis* biovar 2) bacterium. The presence of antibodies to *B. suis* biovar 2 or *B. inopinata* BO2 may not be detected using this embodiment of the method, as outlined above. The utility of the diagnostic conjugates disclosed herein, which are a specific M-antigen, for detection of almost all smooth strains of *Brucella*, both A-dominant and M-dominant strains, is a completely unexpected result, due to the low occurrence of the M-epitope in A-dominant strains.

In any case, the application of a discrete, isolated, M epitope (i.e., a specific M-antigen as described herein) for use in diagnosis has not previously been proposed. This is because the epitope has not previously been clearly defined, has been reported as having no diagnostic significance and is of variable occurrence in the OPS from different and significant *Brucella* strains. This is due to its dependency on the frequency of the α-1,3 linkage, which in most A dominant strains is as low as 2% (apart from in *B. suis* biovar 2). A diagnostic assay that can only detect sera derived from infection with M dominant strains is of limited application, since infection with A dominant strains is also possible. As mentioned, it is completely unexpected that a specific M-antigen as described herein would be useful for detection of A-dominant, as well as M-dominant, strains of *Brucella.*

The method according to the invention may be a method for determining whether an animal has been exposed to and/or infected with a *Brucella* organism, the method comprising a first step of contacting a first sample obtained from the animal with a diagnostic conjugate which is a universal antigen and detecting binding of the conjugate to at least one antibody present in the sample, the method optionally further comprising a second step of contacting a second sample obtained from the animal with a diagnostic conjugate which is a specific M-antigen and detecting binding of the conjugate with at least one anti-M antibody present in the sample. The first and second samples may be the same sample. The second step may be carried out only if the first step provides a positive indication that anti-A and/or anti-C/Y and/or anti-M antibodies (for example, anti-OPS antibodies such as anti-*Brucella* antibodies) are present in the sample. This is because a negative outcome to this first contacting step may be taken as an indication that the animal has not been or is not infected with or exposed to a *Brucella* organism. The method may encompass an initial step of obtaining the sample(s) from the animal.

Detection of binding of the diagnostic conjugate to an antibody, as mentioned herein, may be by any known technique such as an ELISA, fluorescence polarisation assay (FPA), TR-FRET assay, lateral flow assay or bead-based agglutination assay, as described in more detail above.

The universal antigen may comprise an oligosaccharide selected from Formulae XIII-XV. The specific M-antigen may comprise an oligosaccharide selected from Formulae I-XII. The method as described here may provide, therefore, a method for reducing the occurrence of false positive serological reactions (FPSRs) when conducting a method for determining whether an animal is infected with, or has been exposed to, a *Brucella* organism. "Reducing the occurrence" may be an indication that a lower proportion of FPSRs (as determined using conventional, prior art, serological methods) is determined as positive by the method of the invention, whilst effective determination of true positives is maintained. Alternatively or additionally, "reducing the occurrence" may be an indication that a greater proportion of animals determined by the method of the invention to be infected with a *Brucella* organism are in fact so infected, as compared to the proportion of animals determined to be infected using prior art methods. Confirmation of infection with a *Brucella* organism can be confirmed, for example, by microbiological culture (Nielsen et al. ("Bovine brucellosis" In: Manual of Diagnostic Tests & Vaccines for Terrestrial Animals 2009; Office International Des Epizooties, Paris, pg 3-7).

The method according to the invention may be a method for differentiating animals infected with *Brucella* from animals vaccinated with a vaccine conjugate according to the sixth aspect of the invention, as outlined below. Such a vaccine conjugate comprises an oligosaccharide having at least two 4,6-dideoxy-4-acylamido-α-pyranose units, each unit being joined to an adjacent unit by a -(1-2)- link, the oligosaccharide being covalently linked to a vaccine carrier molecule. The use of the method, comprising use of the diagnostic conjugate according to the invention, enables the development of useful synthetic vaccines against *Brucella*, since the method provides a DIVA (Differentiating Infected from Vaccinated Animals) test to distinguish infected animals from animals vaccinated with a vaccine comprising exclusively -(1-2)- linked 4,6-dideoxy-4-acylamido-α-pyranose units.

According to a third aspect of the invention there is provided a diagnostic conjugate comprising an oligosaccharide comprising at least six 4,6-dideoxy-4-acylamido-α-pyranose units and comprising overlapping tetrasaccharides of Formula VII, such that the third and fourth 4,6-dideoxy-4-acylamido-α-pyranose units in one tetrasaccharide form the first and second 4,6-dideoxy-4-acylamido-α-pyranose units in the next tetrasaccharide, to form an oligosaccharide in which all links between multiple 4,6-dideoxy-4-acylamido-α-pyranose units are alternating -(1,2)- and -(1,3)- links, the oligosaccharide being covalently linked to a non-saccharide molecule or to a solid entity.

The oligosaccharide may be 6-100 4,6-dideoxy-4-acylamido-α-pyranose units in length, for example about 6, 8, 10, 12, 24, 36, 48, 60, 72, 84 or about 96 units in length. Whatever the overall length, the pattern of 4,6-dideoxy-4-acylamido-α-pyranose units and links is as follows, where "S" indicates a single 4,6-dideoxy-4-acylamido-α-pyranose unit, "2" indicates a -(1,2)- link and "3" indicates a -(1,3)- link:

*1 2 3 4*

1 2 3 4

-S-2-S-3-S-2-S-3-S-2-S-3-S-2-S-3-S-2-S-3-S-2-S-3-S-2-S-3-

That is, there are never consecutive links which are of the same type. Overlapping tetrasaccharides are underlined in the sequence above. 4,6-dideoxy-4-acylamido-α-pyranose unit numbers for the first tetrasaccharide in the chain are shown above the sequence in italics, with unit numbers for the second tetrasaccharide in the chain shown above the sequence in bold. This shows how the tetrasaccharides overlap such that the third and fourth units in one tetrasaccharide form the first and second units in the next tetrasaccharide.

Therefore, the oligosaccharide comprises at least one "S-2-S-3-S-2-S-3-S-2-S" subunit wherein each subunit is linearly linked to another subunit by an α-1,3 link.

According to a fourth aspect of the invention there is provided a diagnostic conjugate comprising an oligosaccharide comprising at least seven 4,6-dideoxy-4-acylamido-α-pyranose units and comprising overlapping tetrasaccharides of Formula VII, such that the fourth 4,6-dideoxy-4-acylamido-α-pyranose unit in one tetrasaccharide forms the first 4,6-dideoxy-4-acylamido-α-pyranose unit in the next tetrasaccharide, the oligosaccharide being covalently linked to a non-saccharide molecule or to a solid entity.

The oligosaccharide may be 7-100 4,6-dideoxy-4-acylamido-α-pyranose units in length, for example about 7, 10, 13, 16, 19, 21, 27, 33, 39, 45, 51, 57, 63, 69, 75, 81, 87, 93, 99 or about 105 units in length. Whatever the overall length, the pattern of 4,6-dideoxy-4-acylamido-α-pyranose units and links is as follows, where "S" indicates a single 4,6-dideoxy-4-acylamido-α-pyranose unit, "2" indicates a -(1,2)- link and "3" indicates a -(1,3)- link:

$$\begin{array}{cccc} 1 & 2 & 3 & 4 \\ \mathbf{1} & \mathbf{2} & \mathbf{3} & \mathbf{4} \end{array}$$
-S-2-S-3-S-2-S-2-S-3-S-2-S-2-S-3-S-2-S-2-S-3-S-2-S That is, there are never more than two consecutive α-1,2 links. Overlapping tetrasaccharides are underlined in the sequence above. 4,6-dideoxy-4-acylamido-α-pyranose unit numbers for the first tetrasaccharide in the chain are shown above the sequence in italics, with unit numbers for the second tetrasaccharide in the chain shown above the sequence in bold. This shows how the tetrasaccharides overlap such that the fourth unit in one tetrasaccharide forms the first unit in the next tetrasaccharide.

Therefore, the oligosaccharide comprises at least one "S-2-S-3-S-2-S-2-S-3-S" subunit wherein each subunit is linearly linked to another subunit by an α-1,2 link.

The diagnostic conjugate according to the third or fourth aspects of the invention each provide a specific M-antigen, capable of preferentially binding to an anti-M antibody as compared to the level of binding to an anti-C/Y or anti-A antibody.

A fifth aspect of the invention provides a kit for carrying out a method according to the invention, comprising a diagnostic conjugate according to the second and/or third and/or fourth aspects of the invention. The kit may also comprise means for obtaining and/or containing a biological sample from an animal. This kit may comprise, for example, laboratory reagents useful for conducting an antibody-antigen binding detection assay, such as an ELISA. The kit may comprise packaging materials and/or materials providing instructions for use of the kit.

The diagnostic conjugate contained in the kit may be in the form of a solid entity having attached thereto at least one oligosaccharide which comprises at least two 4,6-dideoxy-4-acylamido-α-pyranose units and comprising at least one -(1-3)- link between adjacent 4,6-dideoxy-4-acylamido-α-pyranose units. The solid entity may have attached thereto an oligosaccharide according to any of Formulae XIII-XV, thus providing a universal antigen, or an oligosaccharide according to any of Formulae I-XII, thus providing a specific M-antigen. The solid entity may be, for example, a surface such as an ELISA plate. The kit may comprise a diagnostic conjugate which is a universal antigen, or may comprise a diagnostic conjugate which is a specific M-antigen, and/or may comprise both a diagnostic conjugate which is a universal antigen and a diagnostic conjugate which is a specific M-antigen. A kit comprising both types of diagnostic conjugate is advantageously useable initially to detect in an animal infection by or exposure to an organism expressing an OPS (for example, a *Brucella* organism) and subsequently to confirm that the animal is infected with, or has been exposed to, a *Brucella* organism, as opposed to an organism such as *Yersinia enterocolitica* O:9.

According to a sixth aspect of the invention, there is provided a vaccine conjugate comprising an oligosaccharide having at least two 4,6-dideoxy-4-acylamido-α-pyranose units and comprising a -(1-2)- link between adjacent units, the oligosaccharide being covalently linked to a vaccine carrier molecule. The oligosaccharide within the vaccine conjugate comprises only -(1-2)- links. The linkage to the carrier molecule is achieved in accordance with the methods outlined above in relation to the diagnostic conjugate of the invention. A vaccine carrier molecule may be, for example, a protein or peptide which may be any known in the art to be useful as a conjugate to an antigenic molecule to form a vaccine. For example, the vaccine carrier molecule may be tetanus toxoid (Verez-Bencomo et al. (2004) Science 305, 522-525), CRIM 197 (Mawas et al. (2002) Infect. Immun. 70, 5107-5114) or other highly immunogenic proteins (Svenson & Lindberg (1981) Infect. Immun. 32, 490-496). The vaccine carrier molecule may also be an immunogenic particle such as a liposome or inactive viral particle wherein the oligosaccharide is incorporated at the surface of the particle.

A seventh aspect of the invention provides a vaccine composition comprising a vaccine conjugate according to the sixth aspect of the invention. The vaccine composition may further comprise excipients and/or diluents appropriate for the means by which the composition is to be administered to a subject in need of vaccination against infection by *Brucella*. Selection of appropriate components is within the routine capability of the skilled person without the application of inventive activity.

For example, the vaccine composition of the invention may conveniently be formulated using a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobials, anti-oxidants, chelating agents and inert gases. The pH and exact concentration of the various components the vaccine composition are adjusted according to routine skills.

In certain situations, it may also be desirable to formulate the vaccine composition to comprise an adjuvant to enhance the immune response. Such adjuvants include all acceptable immunostimulatory compounds such as, for example, a cytokine, toxin, or synthetic composition. Commonly used adjuvants include aluminium hydroxide, aluminium phosphate, calcium phosphate, Freund's adjuvants and Quil-A saponin. In addition to adjuvants, it may be desirable to co-administer biologic response modifiers (BRM) with the vaccine conjugate to down regulate suppressor T cell activity.

Possible vehicles for administration of the vaccine composition include liposomes. Liposomes are microscopic vesicles that consist of one or more lipid bilayers surrounding aqueous compartments. Liposomes are similar in composition to cellular membranes and, as a result, liposomes generally can be administered safely and are biodegradable. Techniques for preparation of liposomes and the formulation (e.g., encapsulation) of various molecules with liposomes are well known.

Depending on the method of preparation, liposomes may be unilamellar or multilamellar and can vary in size with diameters ranging from 0.02 µm to greater than 10 µm. Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. In the present context, the vaccine conjugate in the composition according to the invention can be localized on the surface of the liposome, to facilitate antigen presentation without disruption of the liposome or endocytosis. Irrespective of the mechanism or delivery, however, the result is the intracellular disposition of the associated vaccine conjugate.

Liposomal vectors may be anionic or cationic. Anionic liposomal vectors include pH sensitive liposomes which disrupt or fuse with the endosomal membrane following endocytosis and endosome acidification.

Other suitable liposomes that are used in the compositions and methods of the invention include multilamellar vesicles (MLV), oligolamellar vesicles (OLV), unilamellar vesicles (UV), small unilamellar vesicles (SUV), medium-sized unilamellar vesicles (MIN), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing these liposomes are well known in the art.

Other forms of delivery particle, for example, microspheres and the like, also are contemplated for delivery of the vaccine conjugate.

In one embodiment, the vaccine composition may be included in an animal feed (i.e., a foodstuff suitable for consumption by an animal) comprising a composition and/or a vaccine conjugate according to the invention. This may, in non-limiting examples, be in the form of pellets, crumbs or a mash which may further comprise, again for example only, grain, grass and/or protein components. The composition may also be included in drinking liquids and/or administered via a spray into the atmosphere surrounding the animal which is, consequently, inhaled by the animal.

The method and diagnostic conjugate according to the aspects of the invention described above enable such useful vaccine conjugates and compositions to be prepared for use to vaccinate animals against infection by *Brucella*, based on synthetic, exclusively -(1-2)- linked, 4,6-dideoxy-4-acylamido-α-pyranose oligosaccharides. This is because the method according to the invention provides a DIVA test to distinguish animals vaccinated with such a vaccine from animals infected from *Brucella*.

Therefore, the vaccine conjugate and/or vaccine composition according to the invention may be for use in a method of vaccinating an animal against infection by *Brucella*, the method comprising administering the vaccine conjugate and/or vaccine composition to the animal. An eighth aspect of the invention, therefore, provides a method of vaccinating an animal against infection by *Brucella*, the method comprising administering the vaccine conjugate and/or vaccine composition to the animal. The method may further comprise subsequently confirming the presence, in a biological sample obtained from the animal, of anti-A and/or anti-C/Y antibodies, protective against *Brucella* infection, by means of a method according to the first aspect of the invention. For example, this may be by contacting the sample with a diagnostic conjugate which is a universal antigen as defined herein.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE FIGURES

Embodiments of the invention will now be described, by way of example only, with reference to FIGS. 1-27 in which.

Figure 1:
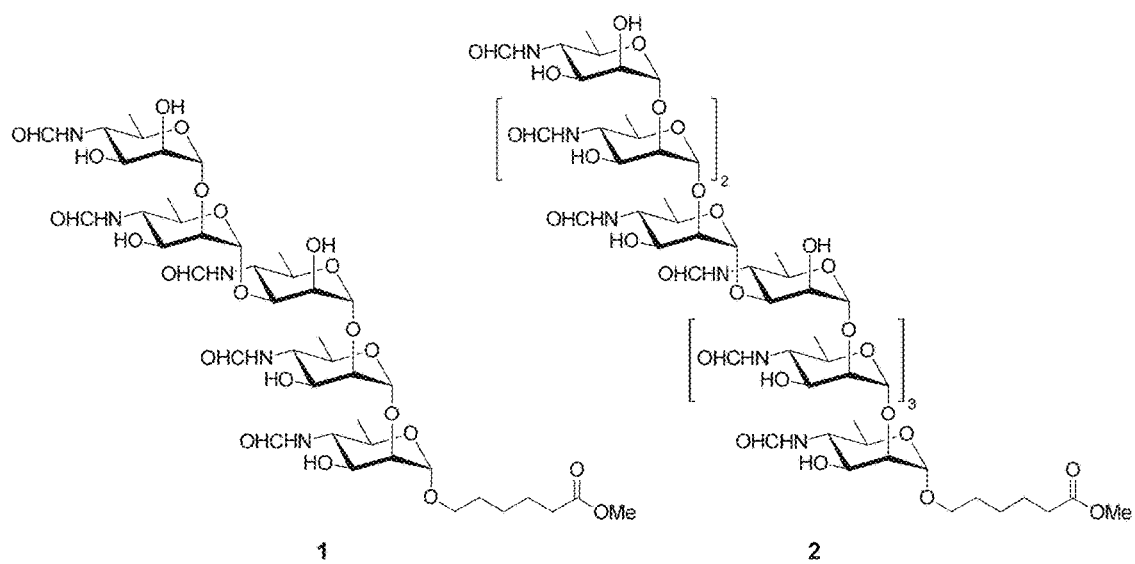
FIG. 1 shows target pentasaccharide (1) which exhibits preferred binding to M-specific antibodies and nonasaccharide (2) designed to bind both A- and M-specific antibodies.

FIG.

Scheme 2.

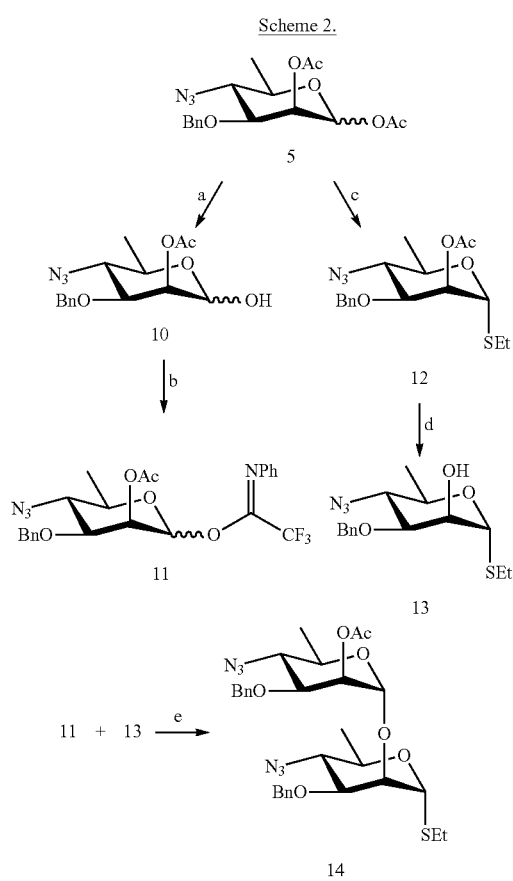

a) 2M Me₂NH/THF, CH₂Cl₂; b) CF₃C(NPh)Cl, Cs₂CO₃, CH₂Cl₂; c) EtSH, BF₃·Et₂O, CH₂Cl₂; d) NaOCH₃, CH₃OH; e) TMSOTf, CH₂Cl₂.

The 1,3-linked trisaccharide building block 15 was created as its allyl glycoside since the selective removal of this anomeric protecting group allows facile access to a hemiacetal and subsequently an imidate leaving group (Du et al. (2001) Tetrahedron 57, 1757-1763). Glycosylation reactions were tried with allyl as a leaving group but all attempts to do so failed (Wang et al. (2007) J. Org. Chem. 72, 5870-2873). Consequently, 15 was selectively deprotected with palladium chloride in acetic acid (Du et al. (2001) Tetrahedron 57, 1757-1763) to give hemiacetal 16 which was in turn converted to the N-phenyl trifluoroacetimidate donor 17 (Scheme 3).

Scheme 3.

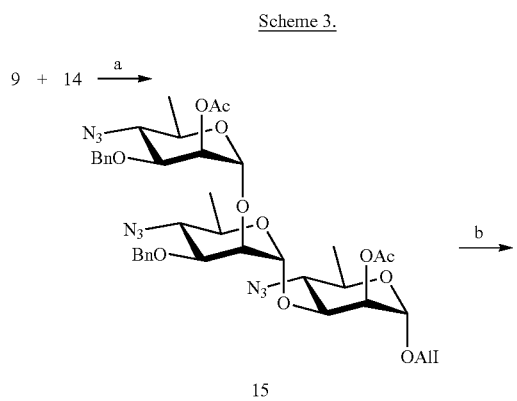

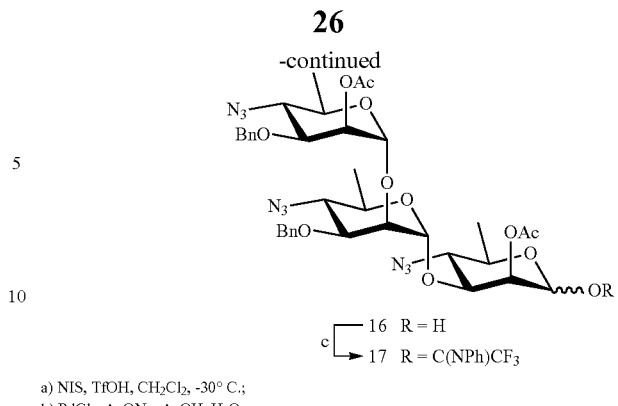

a) NIS, TfOH, CH₂Cl₂, -30° C.;
b) PdCl₂, AcONa, AcOH, H₂O;
c) CF₃C(NPh)Cl, Cs₂CO₃, CH₂Cl₂.

Glycosylation of 5-methoxycarbonylpentanol by thioglycoside 14 gave moderate to poor yields due to the low reactivity of acceptors of this type (Lemieux et al. (1975) J. Am. Chem. Soc. 97, 4076-4083). Hydrolysis of the thioethyl glycoside 14 gave hemiacetal 18 which was converted it to imidate 19. The six carbon linker 20 (El Fangour et al. (2004) J. Org. Chem. 69, 2498-1503) which was glycosylated by 19 to give the protected disaccharide glycoside 21 (Hou & Kováč (2010) Carbohydr. Res. 345, 999-1007). Transesterification of 21 gave the tether glycoside acceptor 22 (Scheme 4).

Scheme 4.

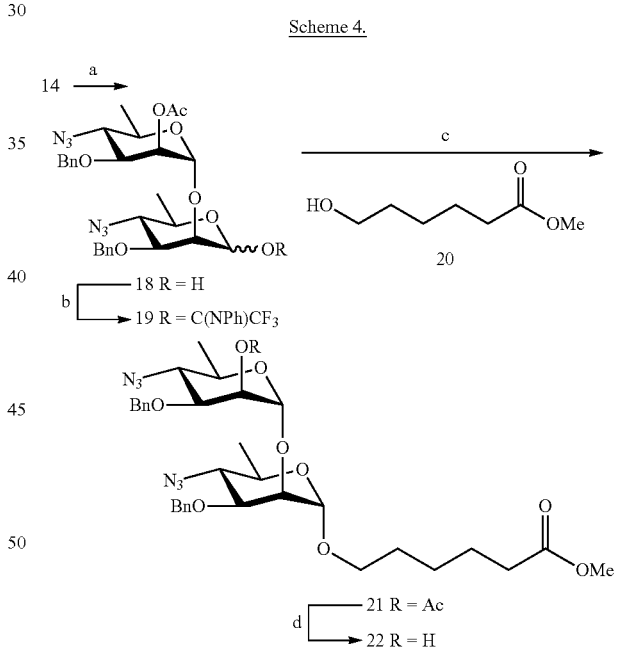

a) NIS, H₂O, acetone; b) CF₃C(NPh)Cl, Cs₂CO₃, CH₂Cl₂; c) TMSOTf, PhMe, 100° C.; d) NaOCH₃, CH₃OH.

Pentasaccharide 23 was obtained from building blocks trisaccharide 17 and disaccharide glycoside 22 in 68% yield using TMSOTf as the activator (Scheme 5). Stepwise deprotection followed the sequence: deacetylation to give 24 in quantitative yield, azido group reduction with hydrogen sulfide to give 25. Compound 25 was directly formylated by a mixed anhydride (acetic anhydride/formic acid 2:1) to give 26 (Bundle et al. (1988) Carbohydr. Res. 174, 239-251). Following introduction of the N-formamido groups, NMR analyses of all subsequent compounds became difficult due to the presence of E/Z rotamers for each formyl group, leading to a potential mixture of 32 isomers. Their identity was confirmed by a limited set of characteristic NMR resonances and high resolution mass measurements. Pentasaccharide 1 was obtained by hydrogenolysis of benzyl ethers.

Scheme 5.

17 + 22 —a→

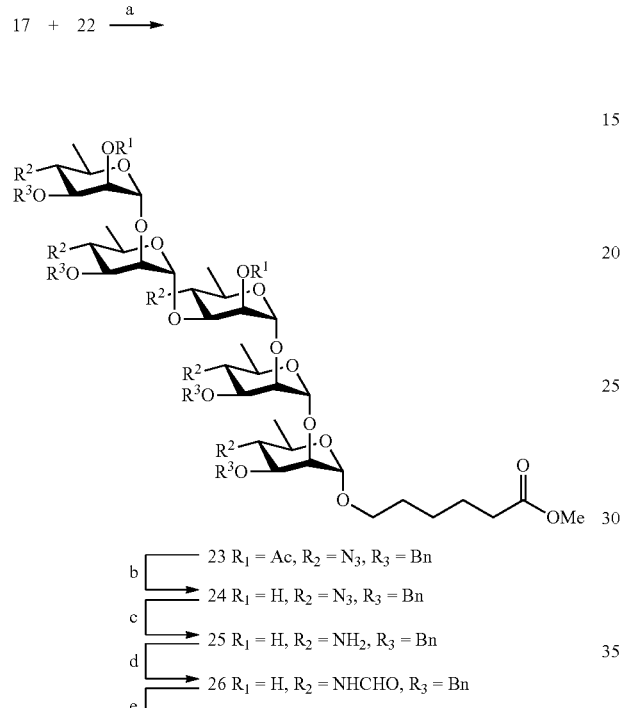

b ┌→ 23 R₁ = Ac, R₂ = N₃, R₃ = Bn
  └→ 24 R₁ = H, R₂ = N₃, R₃ = Bn
c ┌→ 25 R₁ = H, R₂ = NH₂, R₃ = Bn
d ┌→ 26 R₁ = H, R₂ = NHCHO, R₃ = Bn
e └→ 1  R₁ = H, R₂ = NHCHO, R₃ = H a) TMSOTf, CH₂Cl₂; b) NaOCH₃, CH₃OH; c) H₂S, Py•/NEt₃ 1:1; d) Ac₂O/HCOOH 2:1, CH₃OH; e) H₂, Pd/C, AcOH.

The synthesis of nonasaccharide 2 was envisaged as the creation of a pentasaccharide donor terminated by a 1,3 linkage which would then allow for a pentasaccharide donor with a participating group at C-2 to guide the stereoselective α-glycosylation of an exclusively 1,2-linked tetrasaccharide. To achieve the synthesis of the pentasaccharide donor, compound 14 was deprotected to give the corresponding acceptor 27 which was glycosylated by imidate donor 19. Tetrasaccharide 28 was formed in toluene at 100° C. as described for 21 (Hou & Kováč (2010) Carbohydr. Res. 345, 999-1007). Tetrasaccharide thioglycoside 28 was used directly as the donor for glycosylation of the monosaccharide glycoside 9 to give the α1,3-linkage. The allyl group of pentasaccharide 29 was then removed (Du et al. (2001) Tetrahedron 57, 1757-1763) to give 30 and the imidate donor 31 was obtained following reaction with N-phenyl trifluoroacetimidoyl chloride (Scheme 6).

Scheme 6.

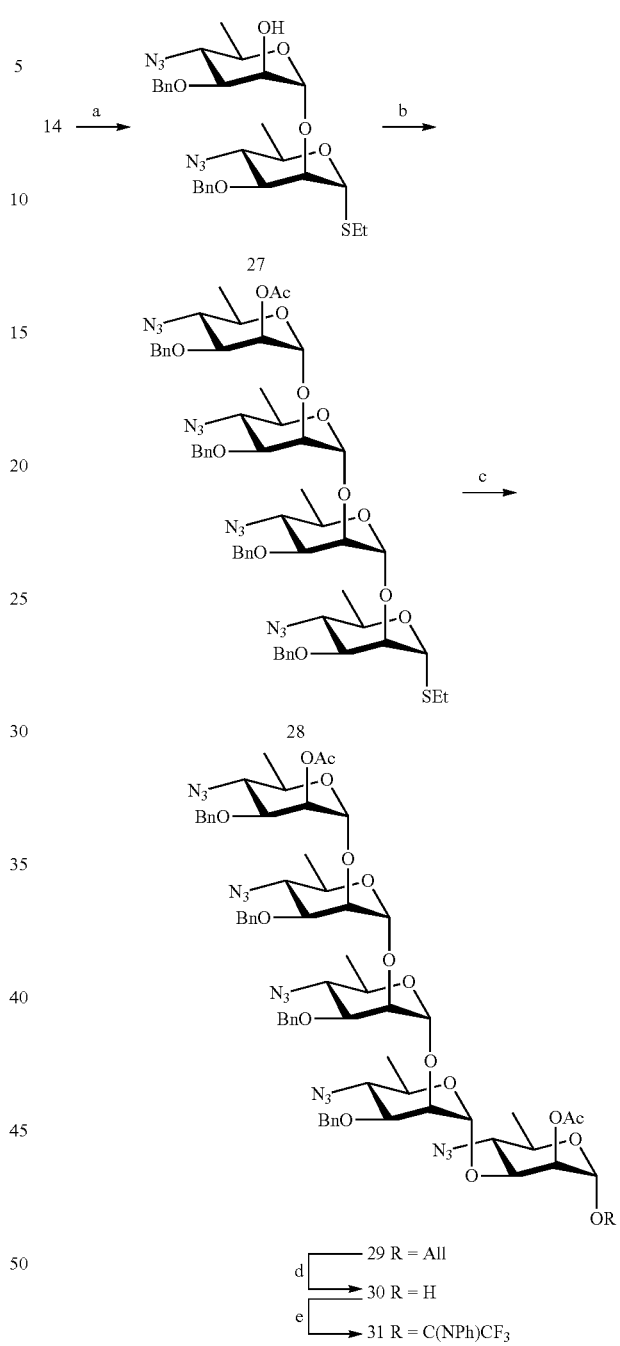

d ┌→ 29 R = All
  └→ 30 R = H
e └→ 31 R = C(NPh)CF₃ a) NaOCH₃, CH₃OH; b) 19, TMSOTf, PhMe, 100° C.; c) 9, NIS, TfOH, CH₂Cl₂; d) PdCl₂, AcONa, AcOH, H₂O; e) CF₃C(NPh)Cl, Cs₂CO₃, CH₂Cl₂.

Tetrasaccharide tether glycoside 32 was obtained by a 2+2 glycosylation of disaccharide acceptor 22 by the disaccharide donor 19 employing the same condition used to prepare 28. Transesterification of 32 gave the tetrasaccharide acceptor 33 which was glycosylated by pentasaccharide donor 31 to give nonasaccharide 34 in 30% yield. The sequence of deprotection steps (deacetylation to 35, reduction of azide to 36, N-formylation to 37 and hydrogenation) to give 2 followed the order used to obtain pentasaccharide 1 (Scheme 7).

Scheme 7.

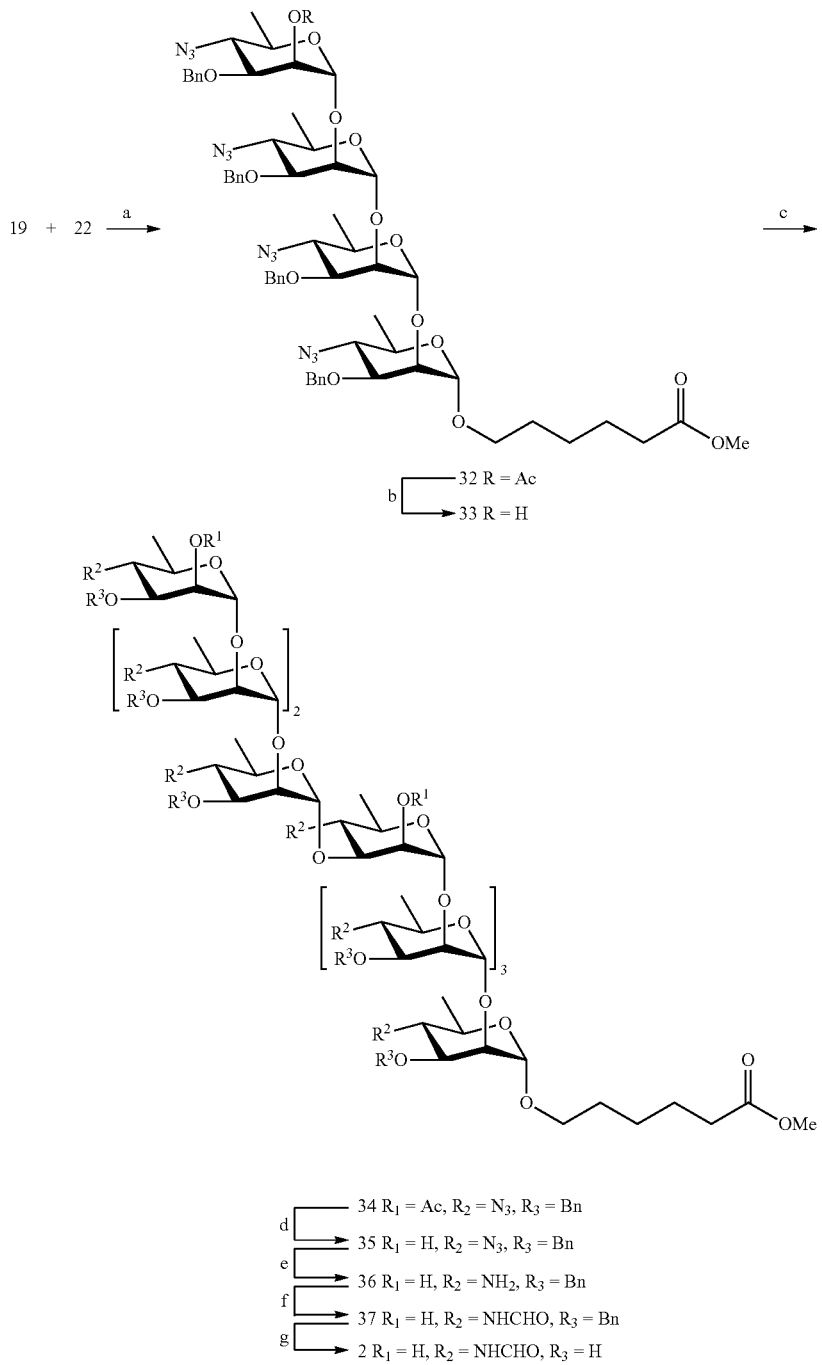

a) TMSOTf, PhMe, 100° C.; b) NaOCH₃, CH₃OH; c) 31, TMSOTf, CH₂Cl₂; d) NaOCH₃, CH₃OH; e) H₂S, py•/NEt₃ 1:1; f) Ac₂O/HCOOH 2:1, CH₃OH g) H₂, Pd/C, AcOH.

The final compounds 1 and 2 were purified by reverse phase HPLC. Full NMR assignments were performed on the azido penta and nonasaccharide derivatives 24 and 35. Selected characteristic NMR resonances and high resolution mass confirmed the identity of derivatives 26 and 37 and the target oligosaccharides 1 and 2.

To enable conjugation to protein, pentasaccharide and nonasaccharide glycosides 1 and 2 were first converted to the respective amides 38 and 39 by reaction with ethylenediamine (Scheme 8). Reaction of 38 and 39 with dibutyl squarate gave the squarate half esters 40 and 41 which were isolated by reverse phase HPLC. The corresponding pentasaccharide and nonasaccharide bovine serum albumin (BSA) glycoconjugates 42 and 43 were prepared by reaction of a twenty to one molar ratio of 40 and 41 with BSA in borate buffer for 3 days. MALDI-TOF mass spectrometry indicated that each conjugate contained approximately 16 copies of the oligosaccharides per molecule of BSA.

Scheme 8. Activation and conjugation of pentasaccharide 1 and nonasaccharide 2 to BSA to obtain glycoconjugates 42 and 43.
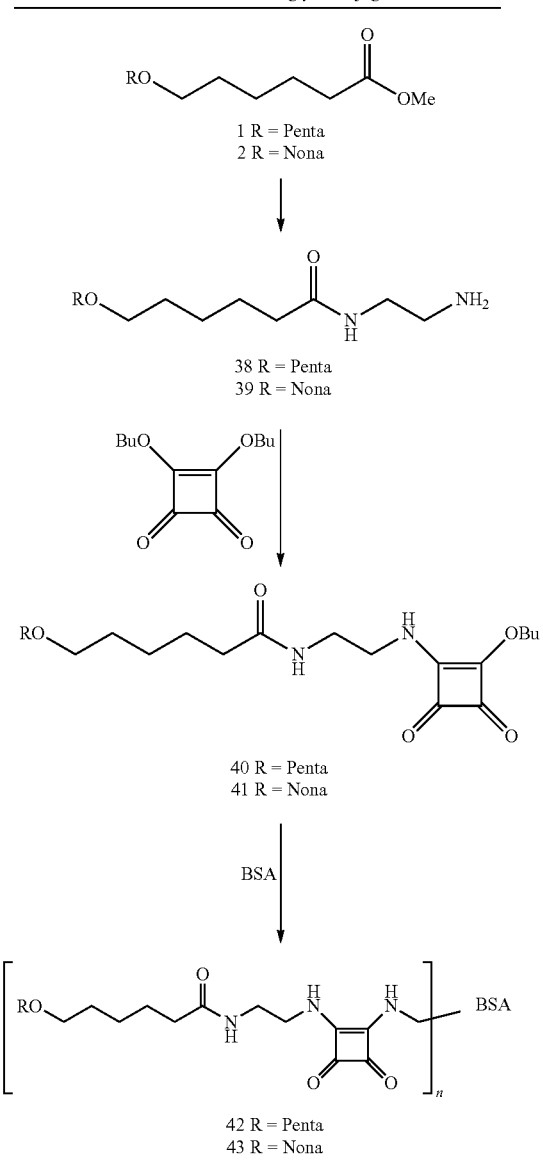
Synthetic Strategy 2
This strategy set out to arrive at shorter oligosaccharides 44-47 that would provide M-specific antigens and achieve the level of discrimination described above.
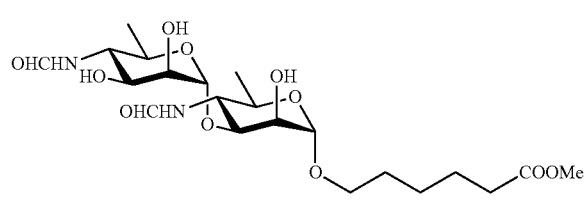
-continued
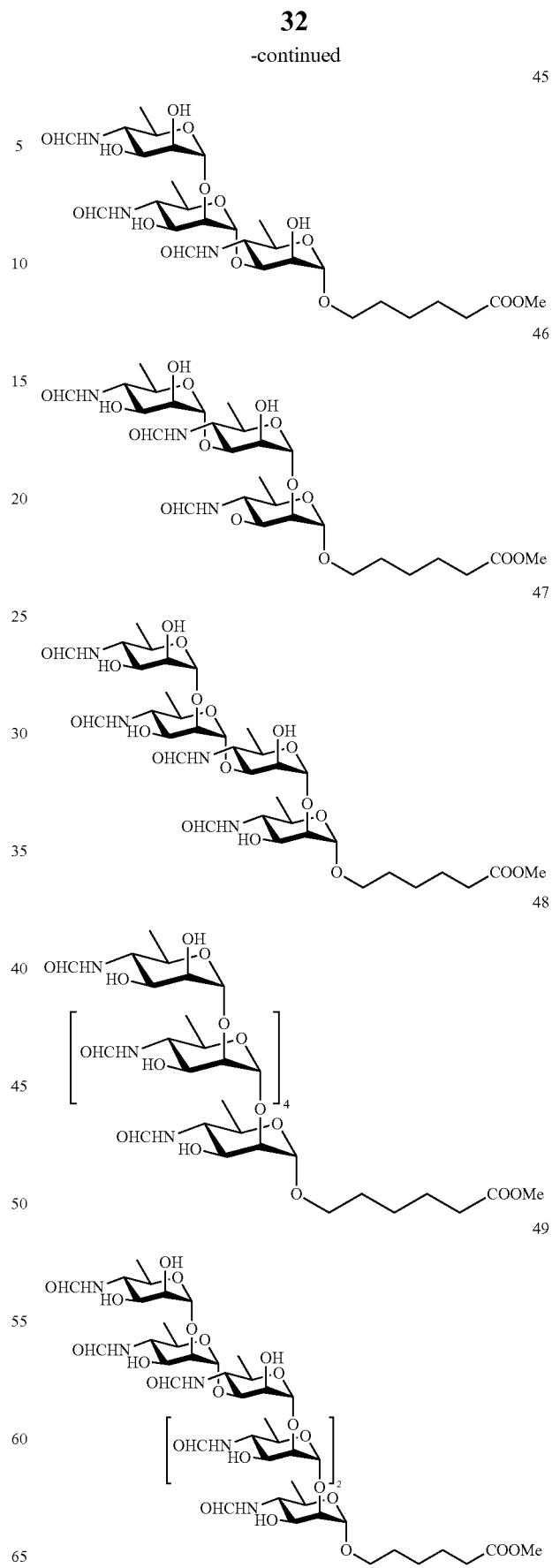

Two additional compounds were synthesized; hexasaccharide 48 to provide a pure A epitope and compound 49 which provides an oligosaccharide of minimal size that encompasses both A and M epitopes. Oligosaccharide 49, along with the nonasaccharide 2, is a universal *Brucella* antigen. It corresponds to the terminal hexasaccharide of the *Brucella* O-antigen disclosed by Kubler-Kielb and Vinogradov (Carbohydr. Res. (2013) 378, 144-147).

Scheme 9.

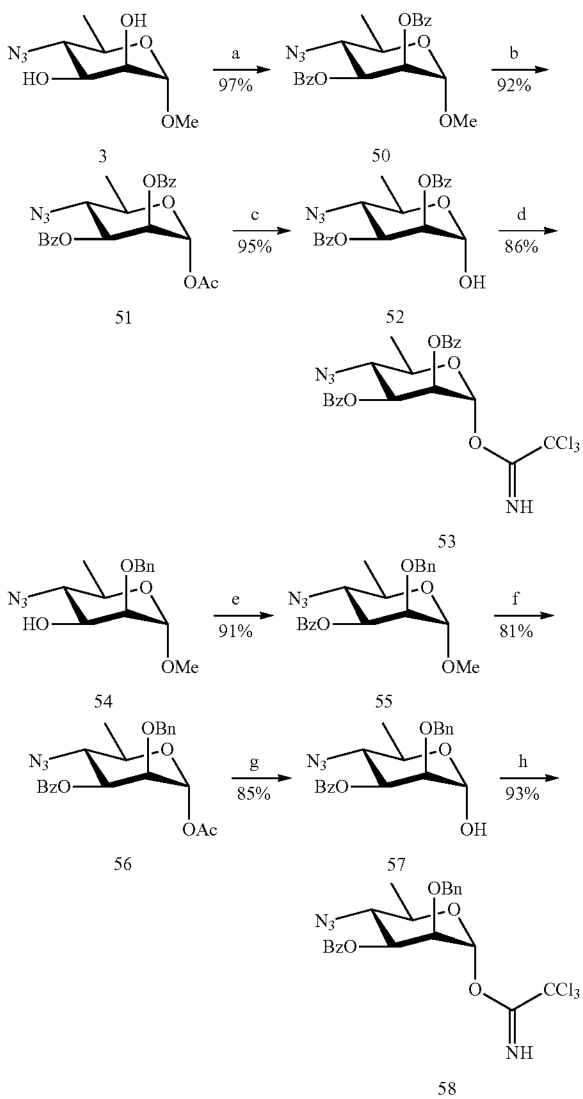

a) BzCl, Py, rt, 10 h; b) $Ac_2O$, AcOH, $H_2SO_4$, rt, 6 h; c) $NH_2NH_2$•AcOH, DMF, 60° C., 0.5 h; d) $CCl_3CN$, DBU, $CH_2Cl_2$, rt, 10 min.; e) BzCl, Py, rt, 3 h; f) $Ac_2O$, AcOH, $H_2SO_4$, rt, 3 h; g) $NH_2NH_2$•AcOH, DMF, 60° C., 0.5 h; h) $CCl_3CN$, DBU, $CH_2Cl_2$, rt, 10 min.

In contrast to the synthesis of 1 and 2 where acetate esters and benzyl ethers were used, the synthesis of oligosaccharides 44-49 made use of benzoate esters and benzyl ether protecting groups to allow for the construction of 1,2 and 1,3 linkages. This distinct difference in protecting group strategy from the earlier synthesis of 1 and 2 allowed the use of trichloroacetimidate donors rather than the more difficult to prepare N-phenyl trifluoroacetimidates 11, 19 and 31. The synthons used to make oligosaccharides 44-49 were compounds 50-66. The monosaccharide imidates 53, 58 and 62 were synthesized as shown (Schemes 9 and 10). Two disaccharide thioglycosides 63 and 64 were prepared by glycosylation of 13 by imidates 53 and 62 (Scheme 10). The two 5-methoxycarbonylpentanol glycosides 65 and 66 were prepared by literature methods (Saksena et al. (2008) Carbohydr. Res. 343, 1693-1706; Saksena et al. (2005) Tetrahedron: Asymmetry 16, 187-197). Imidate 62 was used in the synthesis of 48 and 49.

Scheme 10

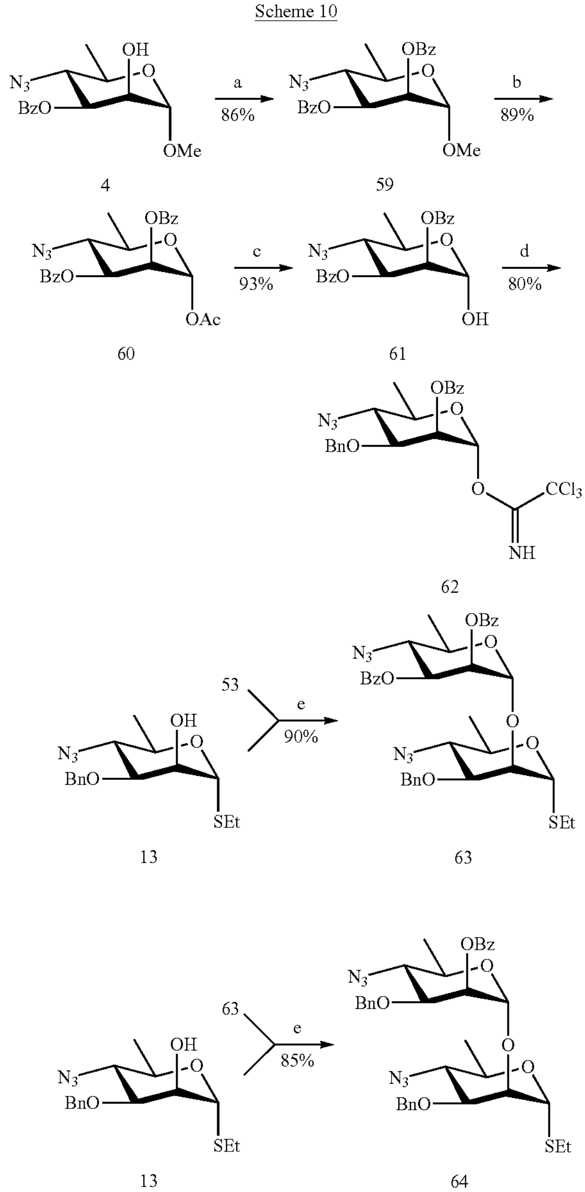

65

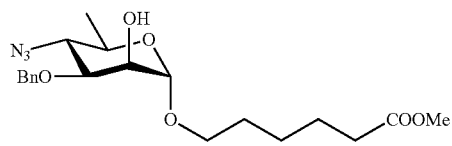

a) BzCl, Py, rt, 3 h; b) Ac$_2$O, AcOH, H$_2$SO$_4$, rt, 3 h; c) NH$_2$NH$_2$·AcOH, DMF, 60° C., 0.5 h; d) CCl$_3$CN, DBU, CH$_2$Cl$_2$, rt, 10 min., e) TMSOTf, 3Å MS, CH$_2$Cl$_2$, rt, 1 h.

The 1,3 linked disaccharide 67 was obtained by reaction of the imidate 53 with the acceptor 65. Trisaccharide 68 was obtained by reaction of the disaccharide thioglycoside 63 with the monosaccharide glycoside 65. Reaction of the monosaccharide imidate 58 with 66 gave the 1,2 linked disaccharide 69. When 69 was de-O-benzoylated the resulting disaccharide 70 could be glycosylated by the monosaccharide imidate 53 to give the trisaccharide 71 with a terminal 1,3 linkage. Disaccharide 70 also provides access to tetrasaccharide 72 when it was reacted with disaccharide thioglycoside 63 (Scheme 11).

Scheme 11.

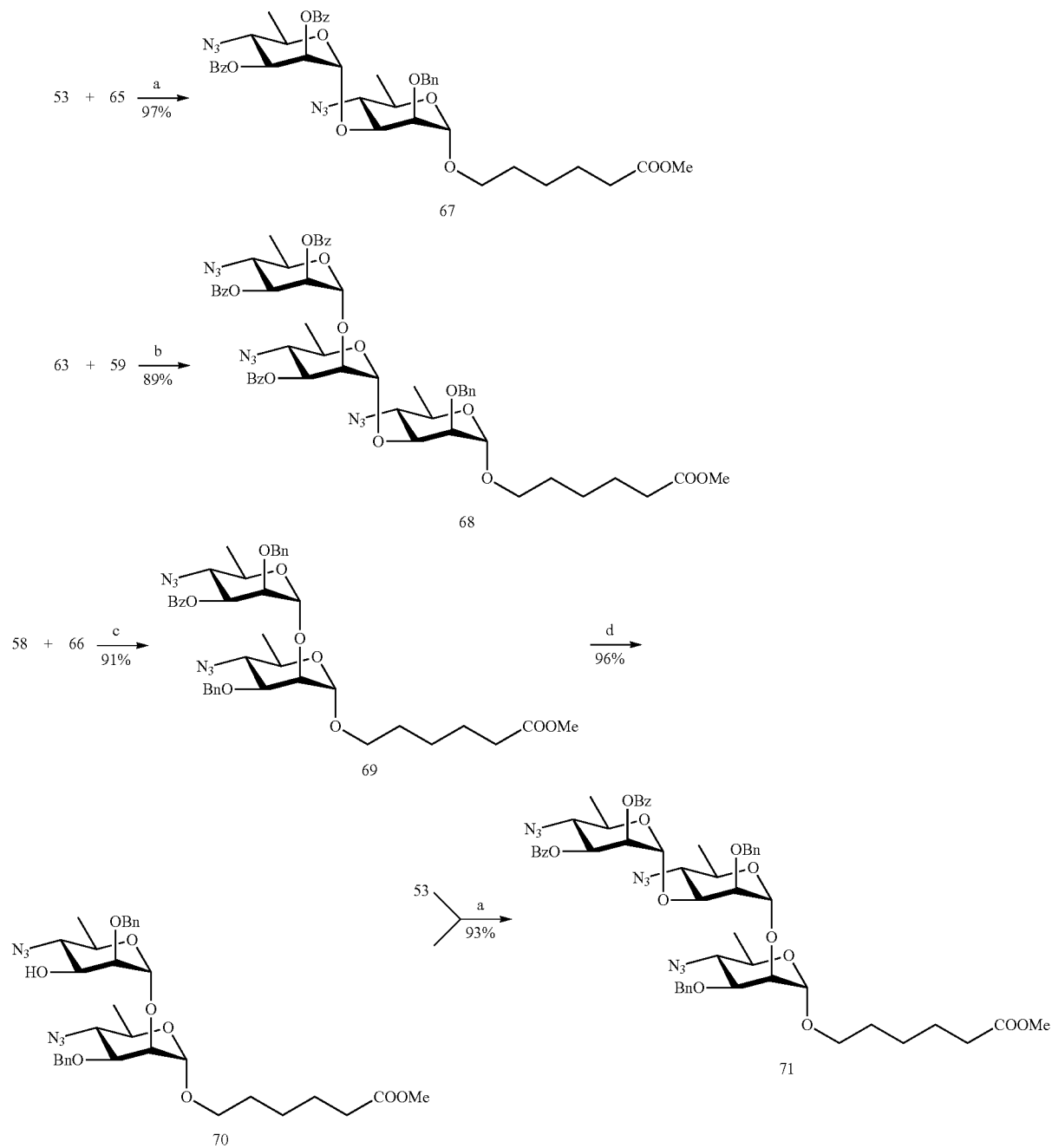

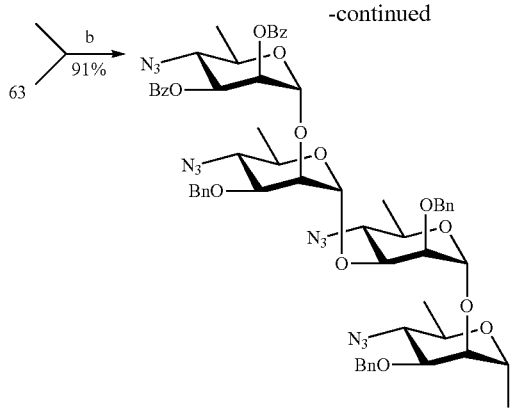

a) TMSOTf, 3Å MS, CH$_2$Cl$_2$, rt, 1 h; b) MeOTf, 3Å MS, CH$_2$Cl$_2$, rt, 48 h; c) TMSOTf, 3Å MS, PhMe, 95° C., 1 h; d) NaOCH$_3$, CH$_3$OH, rt, 4 h.

Hexasaccharides 48 and 49 were elaborated on the monosaccharide glycoside 66 by glycosylation with the disaccharide thioglycoside 64 to give the trisaccharide 73 which after transesterification provides the alcohol acceptor 74, which serves as the common trisaccharide intermediate leading to both hexsaccharides (Scheme 12). The exclusively 1,2-linked hexasaccharide 48 was prepared by glycosylation of 74 by the disaccharide thioglycoside 64 to give pentasaccharide 75. Transesterification of the terminal benzoate group gave the pentasaccharide alcohol 76, which afforded hexasaccharide 77 after glycosylation by the imidate 53. Glycosylation of trisaccharide alcohol 74 by imidate 58 afforded tetrasaccharide 78. After transesterication of 78 the tetrasaccharide alcohol 79 is set up for introduction of a 1,3-linkage. Reaction with the disaccharide thioglycoside 63 gives the protected hexasaccharide 80.

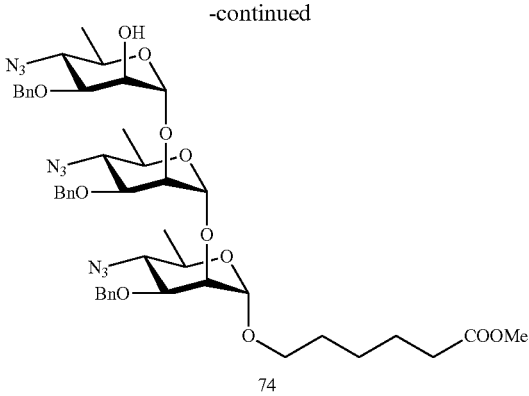

Scheme 12.

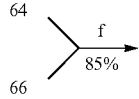

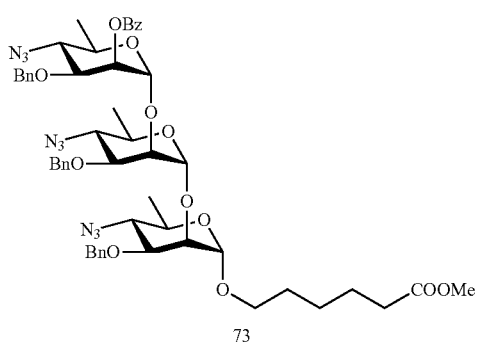

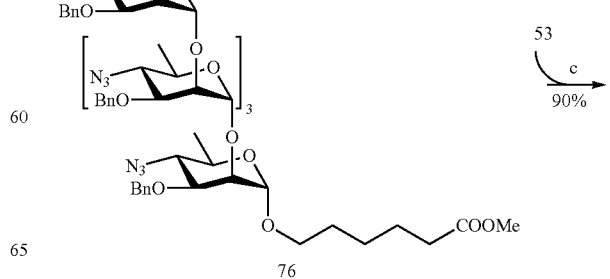

39
-continued
40
Scheme 13.
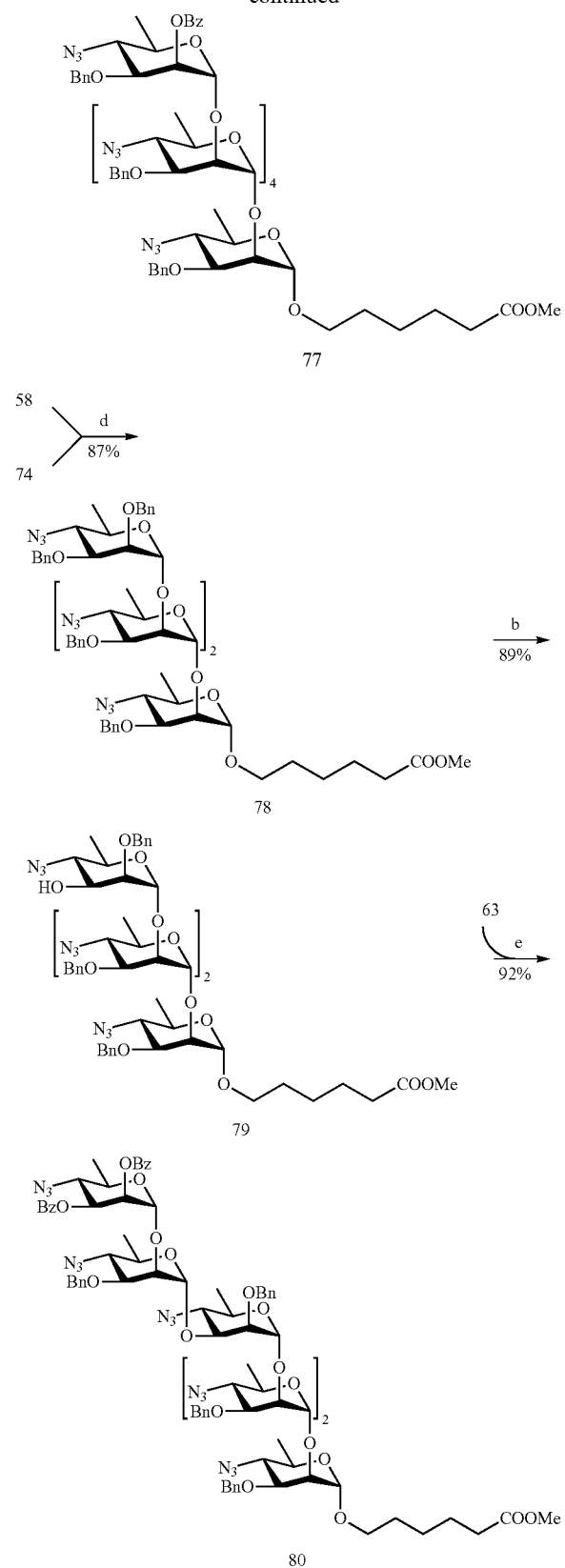
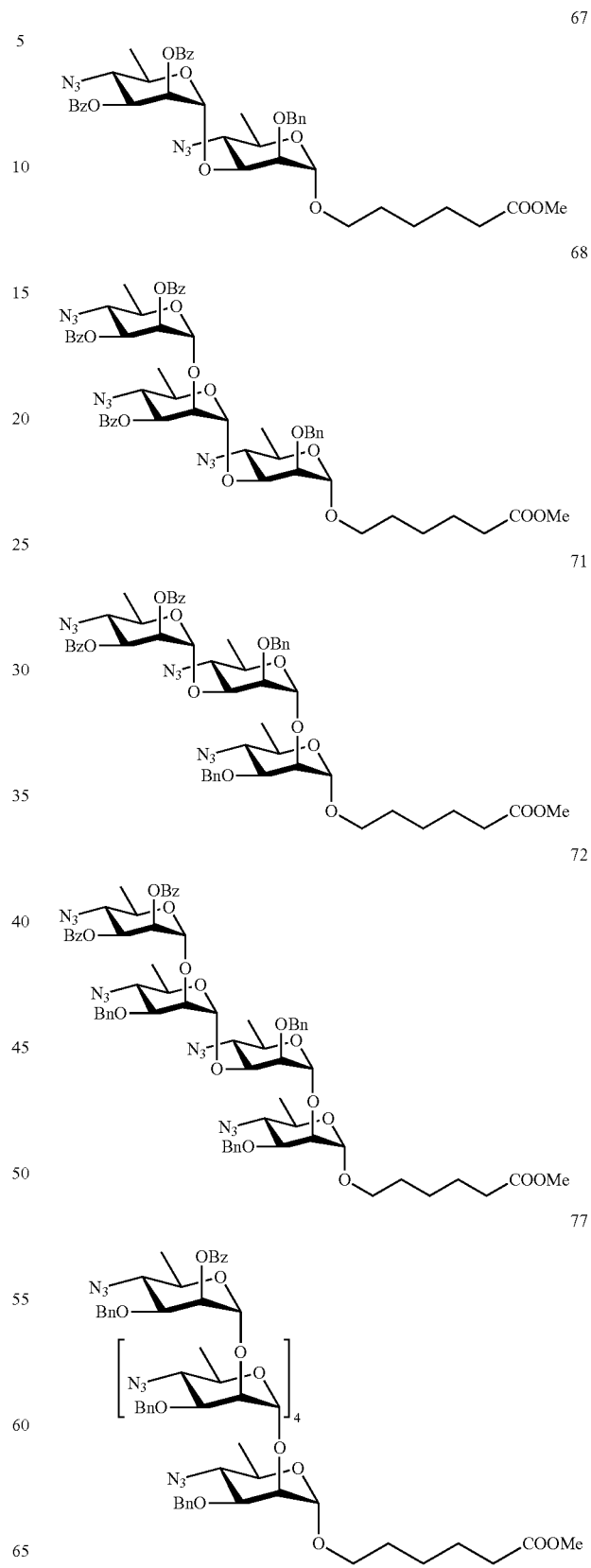
a) MeOTf, 3Å MS, CH₂Cl₂, rt, 48 h; b) NaOCH₃, CH₃OH, rt, 4 h; c) TMSOTf, 3Å MS, CH₂Cl₂, rt, 1 h; d) TMSOTf, 3Å MS, PhMe, 95° C., 1 h.

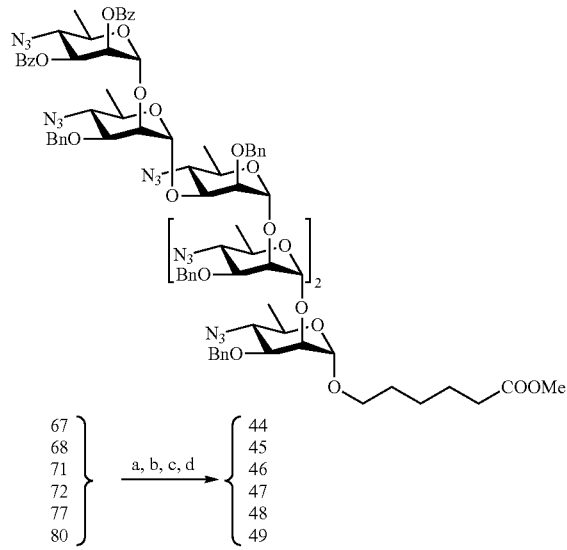

a) NaOCH₃, CH₃OH, rt, 4 h; b) H₂S, Py/H₂O, 40° C., 16 h; c) Formic anhydride, CH₃OH, -20° C., 3 h; d) H₂, Pd(OH)₂, CH₃OH/H₂O, rt, 16 h.

Deprotection of the six oligosaccharides 67, 68, 71, 72, 77 and 80 employed identical reaction conditions (Scheme 13). This involved transesterification to remove benzoate esters, reduction of the azide groups to amines, acylation of amines by formic anhydride to afford formamides and lastly catalytic hydrogenation to afford the target oligosaccharides as 5 methoxycarbonylpentanol glycosides 44-49.

Conversion of the 5 methoxycarbonylpentanol glycosides 44-49 to antigens for diagnostic or vaccine applications followed a similar protocol to that described for the penta and nonasaccharides (Scheme 14).

Scheme 14. Activation and conjugation of oligosaccharides 44-49 to BSA to obtain glycoconjugates 93-98.

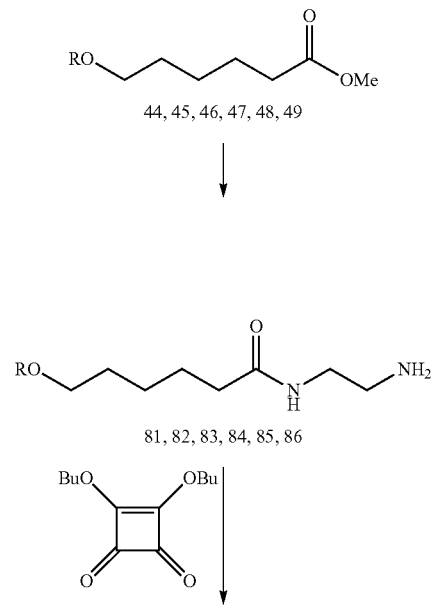

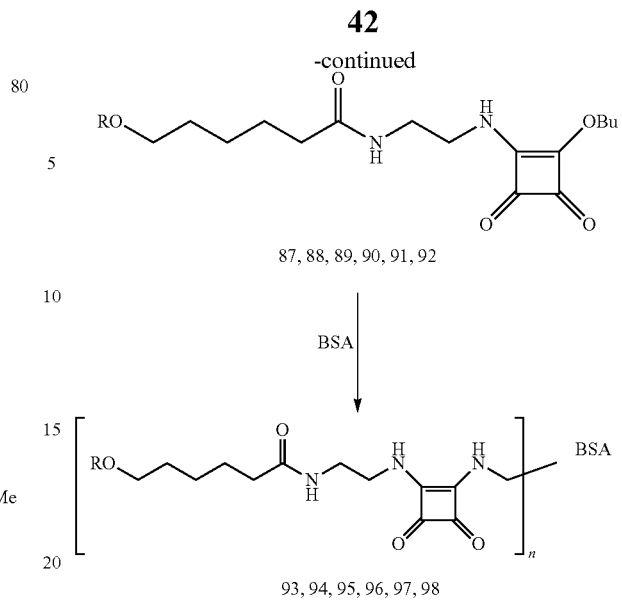

A non-protein polymer aminated co-povidone was also used as an alternative and potential superior antigen for immunoassays. Representative conjugations are described for the disaccharide 44 and the hexasaccharide 48 (Scheme 15).

Scheme 15. Conjugation of oligosaccharides 87 and 91 to co-povidone to obtain glycoconjugates 99 and 100

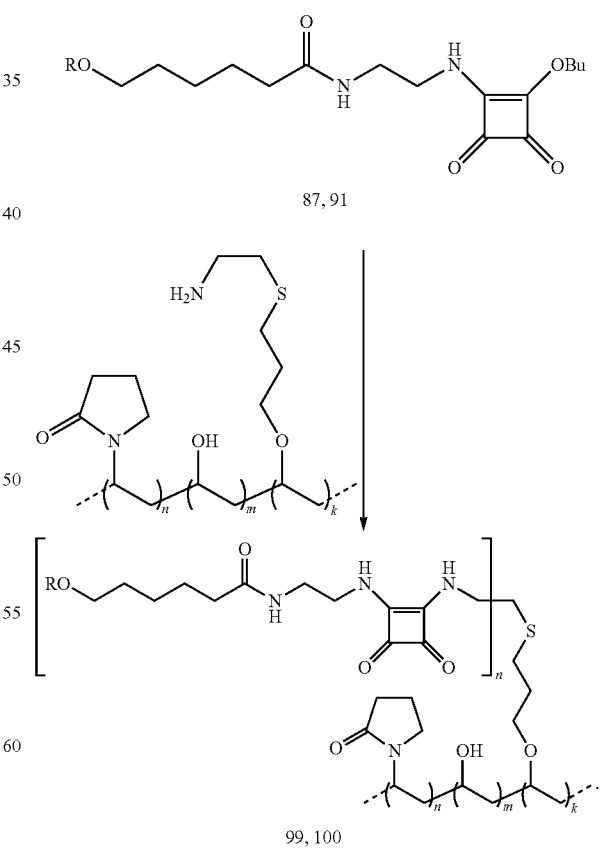

Potential vaccine candidates were synthesized by conjugating the two hexasaccharides 48 and 49 to monomeric tetanus toxoid. The squarate half esters 91 and 92 were each conjugated to tetanus toxoid to provide antigens 101 and 102 (Scheme 16).

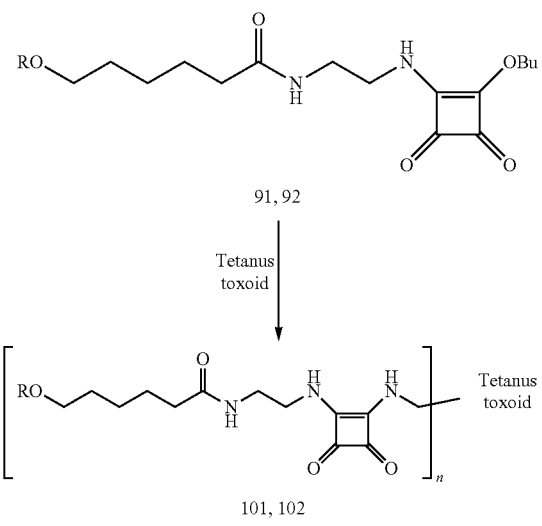

Scheme 16. Conjugation of oligosaccharides 91 and 92 to tetanus toxoid to obtain glycoconjugates 101 and 102.

General Synthesis Methods

Analytical TLC was performed on Silica Gel 60-$F_{254}$ (Merck, Darmstadt) with detection by quenching of fluorescence and/or by charring with 5% sulfuric acid in ethanol. All commercial reagents were used as supplied. Column chromatography was performed on Silica Gel 230-400 mesh, 60 Å (Silicycle, Ontario) with HPLC quality solvents. Molecular sieves were crushed and stored in an oven at 150° C. and flamed dried under vacuum before use. Organic solutions were dried with anhydrous $MgSO_4$ prior to concentration under vacuum at <40° C. (bath). All final compounds were purified by reverse phase chromatography performed on a Waters 600 HPLC system, using a Beckmann semi-preparative C-18 column (10×250 mm, 5µ) with a combination of acetonitrile and water as eluents. Products were detected with a Waters 2487 UV detector.

Optical rotations were measured with a Perkin-Elmer 241 polarimeter for samples in a 10 cm cell at 21±2° C. $[\alpha]_D$ values are given in units of $10^{-1}$ deg $cm^2$ $g^{-1}$, with $[\alpha]_D^{20}$ indicating that the temperature was 20° C. and $[\alpha]_D^{21}$ indicating that the temperature was 21° C.

$^1$H NMR spectra were recorded on 500, 600 or 700 MHz spectrometers. First order proton chemical shifts $\delta_H$ are referenced to either residual $CHCl_3$ ($\delta_H$ 7.27, $CDCl_3$) or $CD_2HOD$ ($\delta_H$ 3.30, $CD_3OD$), or internal acetone ($\delta_H$ 2.225, $D_2O$). $^{13}C$ NMR spectra were recorded at 125 MHz, and chemical shifts are referenced to internal CDCl3 (δ 77.23) or external acetone (δ 31.07). The assignment of resonances for all compounds was made by two-dimensional homonuclear and heteronuclear chemical shift correlation experiments. Mass analysis was performed by positive-mode electrospray ionization on a hybrid sector-TOF mass spectrometer and for protein glycoconjugates by MALDI mass analysis, employing sinapinic acid as matrix.

The numbering used for compounds 4-41 is as follows:

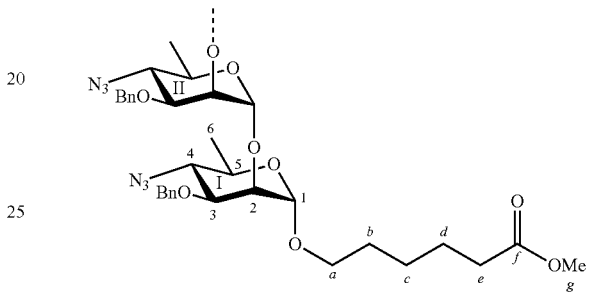

and for compounds 42-92:

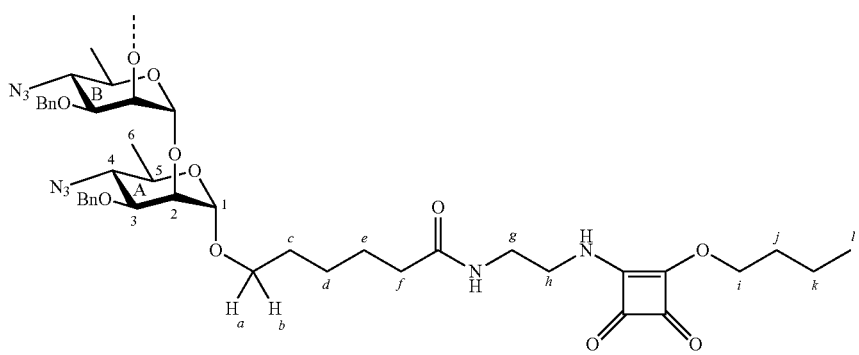

Methyl 4-azido-3-O-benzyl-4,6-dideoxy-α-D-mannopyranoside (4)

A solution of 3 (Bundle et al. (1988) Carbohydr. Res. 174, 239-251) (1.09 g, 5.36 mmol) and $Bu_2SnO$ (1.5 g, 6 mmol) in toluene (50 mL) was stirred at 140° C. for 2 h. Then, after cooling down, benzyl bromide (0.7 mL, 5.9 mmol) and $Bu_4NBr$ (1.9 g, 5.9 mmol) were added and the mixture was stirred overnight at 65° C. After evaporation of the solvent, a purification on a silica gel column (hexane/ethyl acetate 8:1) gave pure 4 (1.38 g, 87%). The NMR parameters are in agreement with the literature (Boschiroli et al. (2001) Curr. Op. Microbiol. 4, 58-64): $^1$H NMR (500 MHz, $CDCl_3$): δ 7.5-7.3 (m, 5H; H—Ar), 4.72 (d, $^3J_{1,2}$=1.7 Hz, 1H; H-1), 3.98 (dt, $^3J_{2,3}$=3.3 Hz, $^3J_{2,OH}$=1.6 Hz, 1H; H-2), 3.72 (dd, $^3J_{3,4}$=9.6 Hz, 1H; H-3), 3.36 (s, 3H; $OCH_3$), 2.39 (d, 1H; OH), 1.44 ppm (d, 3H; H-6); $^{13}C$ NMR (126 MHz, $CDCl_3$): δ 137.2, 128-129, 100.0, 78.3, 72., 67.2, 66.4, 63.9, 55.0, 18.4 ppm; HRMS (ESI): m/z calcd for $C_{14}H_{19}N_3NaO_4$ [M+Na]$^+$: 316.12678; found: 316.12705.

1,2-Di-O-acetyl-4-azido-3-O-benzyl-4,6-dideoxy-α-D-mannopyranoside (5)

A solution of 4 (1.03 g, 5.07 mmol) in acetic anhydride/acetic acid/sulfuric acid (50:20:0.5, 35 mL) was stirred for 1.5 h at room temperature, and then poured into ice-cold 1 M $K_2CO_3$ solution. The product was extracted with dichloromethane and the extract was dried over $MgSO_4$. The solvent was evaporated and co-evaporated with toluene. A chromatography column on silica (hexane/ethyl acetate 10:1) gave 5 as an anomeric mixture (1.4 g, 82%, α/β93:7). The NMR parameters are in agreement with the literature (Boschiroli et al. (2001) Curr. Op. Microbiol. 4, 58-64): $^1$H NMR (500 MHz, CDCl$_3$): δ(α) 7.4-7.3 (m, 5H; H—Ar), 6.02 (d, $^3J_{1,2}$=2 Hz, 1H; H-1), 5.34 (dd, $^3J_{2,3}$=3.3 Hz, 1H; H-2), 2.15, 2.11 (2s, 6H; OAc), 1.34 ppm (d, 3H; H-6); $^{13}$C NMR (126 MHz, CDCl$_3$): δ 169.8, 168.3, 137.0, 128-129, 91.0, 75.8, 71.8, 69.3, 66.3, 63.6, 20.9, 20.8, 18.5 ppm; elemental analysis calcd (%) for $C_{17}H_{21}N_3O_6$: C, 56.2, H, 5.8, N, 11.7; found: C, 56.2, H, 5.7, N, 11.3.

1,2,3-Tri-O-acetyl-4-azido-4,6-dideoxy-α-D-mannopyranoside (6)

Compound 3 (1.03 g, 5.07 mmol) was acetylated with the same protocol used to obtain compound 5. Compound 6 (1.31 g, 82%) was obtained in a α/β95:5 mixture. The separation was done only for analysis: The NMR parameters and physical constants are in agreement with the literature (Bundle et al. (1988) Carbohydr. Res. 174, 239-251): $[α]_D^{20}$ (α)=+122 (c=1.2 in CHCl$_3$); $^1$H NMR (500 MHz, CDCl$_3$): δ(α) 5.98 (d, $^3J_{1,2}$=1.6 Hz, 1H; H-1), 2.15, 2.13, 2.07 (3s, 9H; OAc), 1.36 ppm (d, 3H; H-6); $^{13}$C NMR (126 MHz, CDCl$_3$): δ 169.7, 169.6, 168.3, 90.6, 70.1, 69.3, 67.8, 62.1, 20.9, 20.7, 20.7, 18.4 ppm; HRMS (ESI): m/z calcd for $C_{12}H_{17}N_3NaO_7$ [M+Na]$^+$: 338.09587; found: 338.09559; elemental analysis calcd (%) for $C_{12}H_{17}N_3O_7$: C, 45.7, H, 5.4, N, 13.3; found: C, 45.35, H, 5.45, N, 13.2.

Allyl 2,3-di-O-acetyl-4-azido-4,6-dideoxy-α-D-mannopyranoside (7)

To a solution of 6 (900 mg, 2.85 mmol) in dichloromethane (4 mL), was added BF$_3$.Et$_2$O (0.4 mL, 3.24 mmol). The mixture was stirred for 1 h at room temperature before adding allylic alcohol (0.3 mL, 4.41 mmol) and then stirred again for 2 days. Once the reaction was done, the mixture was cooled to 0° C., a satd. NaHCO$_3$ solution was added and the mixture was stirred for 30 min. The product was extracted with ethyl acetate, the extract was dried (MgSO$_4$), filtrated and concentrated. Purification on column chromatography (hexane/ethyl acetate 10:1) gave the allyl glycoside 7 (625 mg, 70%): $[α]_D^{20}$=+103 (c=1.5 in CHCl$_3$); $^1$H NMR (500 MHz, CDCl$_3$): δ 5.25 (dd, $^3J_{2,3}$=3.6 Hz, $^3J_{3,4}$=10 Hz, 1H; H-3), 5.23 (dd, $^3J_{1,2}$=1.7 Hz, 1H; H-2), 4.76 (d, $^3J_{1,2}$=1.7 Hz, 1H; H-1), 2.15, 2.08 (2s, 6H; OAc), 1.37 ppm (d, 3H; H-6); $^{13}$C NMR (126 MHz, CDCl$_3$): δ 169.9, 169.6, 133.1, 118.1, 96.5, 70.4, 69.2, 68.4, 67.0, 62.7, 20.9, 20.8, 18.3 ppm; elemental analysis calcd (%) for $C_{13}H_{19}N_3O_6$: C, 49.8, H, 6.1, N, 13.4, found: C, 49.9, H, 6.3, N, 13.5.

Allyl 4-azido-4,6-dideoxy-α-D-mannopyranoside (8)

Allyl glycoside 7 (625 mg, 2 mmol) in methanol (20 mL) was treated with a 0.1 M solution of sodium methoxide (0.3 mL). After 1 h, the reaction was complete and neutralized with ion exchange resin H$^+$. Filtration and removal of the solvent under vacuum gave pure diol 8 (447 mg, 98%): $[α]_D^{20}$=+117 (c=1.1 in CHCl$_3$); $^1$H NMR (600 MHz, CDCl$_3$): δ 4.84 (d, $^3J_{1,2}$=1.7 Hz, 1H; H-1), 3.93 (dd, $^3J_{2,3}$=3.4 Hz, 1H; H-2), 1.34 ppm (d, 3H; H-6); $^{13}$C NMR (126 MHz, CDCl$_3$): δ 133.4, 117.7, 98.5, 70.5, 70.2, 68.2, 66.8, 66.0, 18.3 ppm (C-6); HRMS (ESI): m/z calcd for $C_9H_{15}N_3NaO_4$ [M+Na]$^+$: 252.09548; found: 252.09579.

Allyl 2-O-acetyl-4-azido-4,6-dideoxy-α-D-mannopyranoside (9)

To a solution of diol 8 (77 mg, 0.34 mmol) in dichloromethane (3.5 mL) were added triethyl orthoacetate (0.6 mL, 3.3 mmol) and p-toluenesulfonic acid (5 mg, 0.03 mmol). The mixture was stirred for 3 hrs at 50° C. When complete, the reaction was neutralized by triethylamine and concentrated. Acetic acid (80%, 8 mL) was added and the mixture was stirred for 30 min at room temperature, then concentrated. Compound 9 (91 mg, 98%) was purified by chromatography on silica (ethyl acetate/hexanes 1:10): $[α]_D^{20}$=+78 (c=1.0 in CHCl$_3$); $^1$H NMR (500 MHz, CDCl$_3$): δ 5.08 (dd, $^3J_{1,2}$=1.7 Hz, $^3J_{2,3}$=3.6 Hz, 1H; H-2), 4.80 (d, 1H; H-1), 2.15 (s, 3H; OAc), 1.35 ppm (d, 3H; H-6); $^{13}$C NMR (126 MHz, CDCl$_3$): δ 170.8, 133.2, 117.9, 96.5, 71.7, 69.2, 68.3, 66.9, 66.0, 21.0, 18.3 ppm; elemental analysis calcd (%) for $C_{11}H_{17}N_3O_5$: C, 48.7, H, 6.3, N, 15.5; found: C, 48.8, H, 6.2, N, 15.3.

2-O-Acetyl-4-azido-3-O-benzyl-4,6-dideoxy-α-D-mannopyranose (10)

To a solution of 5 (484 mg, 1.33 mmol) in dichloromethane (3 mL), dimethylamine (2 M in THF, 1.8 mL, 3.6 mmol) was added dropwise. The solution was then stirred for 2 days at room temperature. After evaporation of the solvent, pure compound 10 (432 mg) was obtained quantitatively: $^1$H NMR (500 MHz, CDCl$_3$): δ 7.2-7.4 (m, 5H; H—Ar), 5.30 (s, 1H; H-1β), 5.17 (d, 1H; H-1α), 2.19 (s, 3H; OAc β), 2.13 (s, 3H; OAc α), 1.38 (d, 3H; H-6β), 1.33 ppm (d, 3H; H-6α); $^{13}$C NMR (126 MHz, CDCl$_3$): δ 170.8, 170.3, 137.2, 136.8, 128-129, 92.9, 92.5, 78.5, 75.6, 71.7, 71.6, 71.2 (C-5β), 68.5, 67.7, 67.0, 64.0, 63.4, 21.0, 20.9, 18.65, 18.5 ppm (C-6β); elemental analysis calcd (%) for $C_{15}H_{19}N_3O_5$: C, 56.1, H, 6.0, N, 13.1; found: C, 56.0, H, 6.0, N, 13.0.

2-O-Acetyl-4-azido-3-O-benzyl-4,6-dideoxy-α-D-mannopyranosyl N-phenyltrifluoroacetimidate (11)

Compound 10 (1.04 g, 3.2 mmol) was dissolved in dry dichloromethane (30 mL). N-phenyl trifluoroacetimidoyl chloride (1.2 mL, 9.6 mmol) and Cs$_2$CO$_3$ (3.2 g, 9.6 mmol) were added and the mixture was stirred overnight at room temperature. After filtration through celite, compound 11 (1.4 g, 87%) was purify on silica gel column (hexane/ethyl acetate 10:1): $^1$H NMR (500 MHz, CDCl$_3$): δ 7.4-6.8 (m, 10H; H—Ar), 6.2 (br s, 1H; H-1α), 5.85 (br s, 1H; H-2α), 5.8 (br s, 1H; H-1β), 5.46 (br s, 1H; H-2β), 2.2 (s, 3H; OAc β), 2.15 (s, 3H; OAc a), 1.44 (d, $^3J_{5,6}$=6.0 Hz, 3H; H-6α), 1.33 ppm (d, $^3J_{5,6}$=6.1 Hz, 3H; H-6β); HRMS (ESI): m/z calcd for $C_{23}H_{23}F_3N_4NaO_5$ [M+Na]$^+$: 515.15128; found: 515.15147.

Ethyl 2-O-acetyl-4-azido-3-O-benzyl-4,6-dideoxy-α-D-mannopyranosyl (1→2) 4-azido-3-O-benzyl-4,6-dideoxy-1-thio-α-D-mannopyranoside (14)

Donor 11 (3.44 g, 7 mmol) and acceptor 13 (obtained from 5 via 12) (Peters & Bundle (1989) Can. J. Chem. 67, 491-496) (1.75 g, 5.4 mmol) were dissolved in dry dichloromethane (50 mL) and TMSOTf (0.1 mL, 0.55 mol) was added at 0° C. The reaction was complete after 30 min. of stirring at 0° C., then 30 min. at room temperature and was quenched with few drops of NEt$_3$. Disaccharide 14 (3.19 g, 94%) was obtained pure after flash chromatography column (toluene/ethyl acetate 1:0, then 9:1). The NMR parameters and physical constants are in agreement with the literature (Crump et al. (2003) Emerg. Infect. Dis. 9, 539-544): $[\alpha]_D^{20}$=+129 (c=1.2 in CHCl$_3$); $^1$H NMR (500 MHz, CDCl$_3$): δ 7.4-7.2 (m, 10H; H—Ar), 5.39 (dd, $^3J_{1,2}$=1.6 Hz, $^3J_{2,3}$=3.2 Hz, 1H; H-2$^{II}$), 5.16 (d, $^3J_{1,2}$=1.1 Hz, 1H; H-1$^{I}$), 4.81 (d, 1H; H-1$^{II}$), 3.89 (dd, $^3J_{2,3}$=2.9 Hz, 1H; H-2$^{I}$), 2.53 (2qd, $^2J$=13 Hz, $^3J$=7.4 Hz, 2H; S—CH$_2$—CH$_3$), 2.10 (s, 3H; Ac), 1.30 (d, 3H; H-6$^{II}$), 1.29 (d, 3H; H-6$^{I}$), 1.25 ppm (t, 3H; S—CH$_2$—CH$_3$); $^{13}$C NMR (125 MHz, CDCl$_3$): δ 170.0, 137.5, 137.2, 129-128, 99.7, 83.4, 78.2, 76.4, 75.5, 72.3, 71.7, 67.8, 67.7, 67.4, 64.5, 64.0, 25.7, 21.1, 18.6, 18.6, 15.0 ppm; elemental analysis calcd (%) for C$_{30}$H$_{38}$N$_6$O$_7$S: C, 57.5, H, 6.1, N, 13.4, S, 5.1; found: C, 57.5, H, 6.2, N, 13.2, S, 5.2.

Allyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranoside (15)

Donor 14 (188 mg, 0.3 mmol) and acceptor 9 (54 mg, 0.2 mmol) were dissolved in dry dichloromethane (6 mL) with molecular sieves, then NIS (72 mg, 0.32 mmol) and trifluoromethanesulfonic acid (9 μL, 0.1 mmol) were added at −30° C. The reaction was stirred at this temperature for 5 hours and then filtered through celite. The mixture was washed with Na$_2$S$_2$O$_3$ then KHCO$_3$. Trisaccharide 15 (114 mg, 65%) was obtained pure after flash chromatography (hexane/ethyl acetate 10:1): $[\alpha]_D^{20}$=+64 (c=1.3 in CHCl$_3$); $^1$H NMR (600 MHz, CDCl$_3$): δ 7.2-7.4 (m, 10H; H—Ar), 5.05 (dd, $^3J_{1,2=1.8}$ Hz, $^3J_{2,3}$=3.5 Hz, 1H; H-2$^{I}$), 4.97 (d, $^3J_{1,2}$=1.9 Hz, 1H; H-1$^{II}$), 4.9 (d, 1H; H-1$^{III}$), 4.76 (d, 1H; H-1$^{I}$), 4.01 (dd, $^3J_{2,3}$=3.0 Hz, 1H; H-2$^{II}$), 2.10, 2.09 (2s, 6H; OAc), 1.33 (d, $^3J_{5,6}$=6.0 Hz, 3H; H-6$^{I}$), 1.32 (d, $^3J_{5,6}$=6.6 Hz, 3H; H-6$^{III}$), 1.26 ppm (d, 3H; H-6$^{II}$); $^{13}$C NMR (126 MHz, CDCl$_3$): δ 170.0, 169.8, 137.5, 137.1, 133.2, 127-129, 117.9, 101.0, 99.4, 96.2, 77.2, 77.1, 75.4, 73.3, 71.8, 71.6, 70.9, 68.5, 68.2, 67.8, 67.1, 66.9, 64.5, 63.8, 63.7, 21.0, 20.9, 18.5, 18.4 ppm; HRMS (ESI): m/z calcd for C$_{39}$H$_{49}$N$_9$NaO$_{12}$ [M+Na]$^+$: 858.33929; found: 858.33904.

2-O-Acetyl-4-azido-3-O-benzyl-4,6-dideoxy-α-D-mannopyranosyl (1→2) 4-azido-3-O-benzyl-4,6-dideoxy-α-D-mannopyranosyl 2-O-acetyl-4-azido-4,6-dideoxy-α-D-mannopyranose (16)

Allyl glycoside 15 (76 mg, 91 μmol) was dissolved in a solution of AcONa in AcOH/H$_2$O 9:1 (0.2 M, 2 mL) and PdCl$_2$ (32 mg, 180 μmop was added. The mixture was stirred overnight at room temperature and neutralized with NaHCO$_3$. The product was extracted with dichloromethane and washed with water. Chromatography on silica gel (hexane/ethyl acetate 6:1) gave hemiacetal 16 (54 mg, 73%): $^1$H NMR (600 MHz, CDCl$_3$): δ 7.2-7.4 (m, 10H; H—Ar), 5.4 (dd, $^3J_{1,2}$=1.9 Hz, $^3J_{2,3}$=3.2 Hz, 1H; H-2$^{III}$), 5.14 (br s, 1H; H-1$^{I}$), 5.08 (dd, $^3J_{1,2}$=1.9 Hz, $^3J_{2,3}$=3.3 Hz, 1H; H-2$^{I}$), 4.98 (d, $^3J_{1,2}$=2.0 Hz, 1H; H-1$^{II}$), 4.9 (d, 1H; H-1$^{III}$), 2.09 (2s, 6H; OAc), 1.33 (d, 3H; H-6$^{I}$), 1.32 (d, 3H; H-6$^{III}$), 1.26 ppm (d, 3H; H-6$^{II}$); $^{13}$C NMR (126 MHz, CDCl$_3$): δ 170.1, 169.8, 137.5, 137.1, 127-129, 101.0, 99.4, 91.8, 77.2, 76.6, 75.4, 73.4, 71.8, 71.6, 71.2, 68.2, 67.8, 67.2, 66.9, 64.5, 63.8, 63.7, 21.0, 20.9, 18.5, 18.5, 18.4 ppm; HRMS (ESI): m/z calcd for C$_{36}$H$_{45}$N$_9$NaO$_{12}$ [M+Na]$^+$: 818.30799; found: 818.30635.

2-O-Acetyl-4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranosyl N-phenyltrifluoroacetimidate (17)

Compound 17 (147 mg, 79%) was prepared from trisaccharide 16 (153 mg, 192 μmol) as described for 11 and obtained as a mixture α/β 3:2: $^1$H NMR (600 MHz, CDCl$_3$): δ(α) 7.4-6.8 (m, 15H; H—Ar), 6.12 (br s, 1H; H-1$^{I}$), 5.63 (br s, 1H; H-2$^{I}$), 5.39 (dd, $^3J_{1,2}$=1.9 Hz, $^3J_{2,3}$=3.1 Hz, 1H; H-2$^{III}$), 4.97 (br s, 1H; H-1$^{II}$), 4.89 (d, 1H; H-1$^{III}$), 4.0 (br s, 1H; H-2$^{II}$), 2.16, 2.08 (2s, 6H; OAc), 1.46 (d, $^3J_{5,6}$=6.2 Hz, 3H; H-6$^{I}$), 1.29 (d, $^3J_{5,6}$=6.2 Hz, 3H; H-6$^{III}$), 1.26 ppm (d, $^3J_{5,6}$=6.2 Hz, 3H; H-6$^{II}$); HRMS (ESI): m/z calcd for C$_{44}$H$_{49}$F$_3$N$_{10}$NaO$_{12}$ [M+Na]$^+$: 989.33757; found: 989.33761.

2-O-Acetyl-4-azido-3-O-benzyl-4,6-dideoxy-α-D-mannopyranosyl (1→2) 4-azido-3-O-benzyl-4,6-dideoxy-α-D-mannopyranose (18)

To a solution of disaccharide thioglycoside 14 (210 mg, 0.33 mmol) in acetone (6 mL), NIS (90 mg, 0.44 mmol) and water (100 μL) were added at 0° C. and stirred at this temperature for 30 min. and then overnight at room temperature. After completion, NaHCO$_3$ solid was added and acetone evaporated. An extraction dichloromethane/water and then a purification on silica gel gave the hemiacetal 18 (144 mg, 76%): $^1$H NMR (600 MHz, CDCl$_3$): δ(α) 7.4-7.2 (m, 10H; H—Ar), 5.42 (dd, $^3J_{1,2}$=2 Hz, $^3J_{2,3}$=3.2 Hz, 1H; H-2$^{II}$), 5.12 (dd, $^3J_{1,2}$=1.8 Hz, $^3J_{1,OH}$=3.5 Hz, 1H; H-1$^{I}$), 4.87 (d, 1H; H-1$^{II}$), 3.89 (dd, $^3J_{2,3}$=3 Hz, 1H; H-2$^{I}$), 2.10 (s, 3H; Ac), 1.30 ppm (2d, 6H; H-6$^{I}$, H-6$^{II}$); $^{13}$C NMR (126 MHz, CDCl$_3$): δ(α) 169.9, 137.7, 137.2, 129-127, 99.5, 93.6, 77.3, 75.5, 74.1, 72.3, 71.7, 67.7, 67.4, 67.3, 64.3, 64.0, 21.1, 18.8, 18.7 ppm; elemental analysis calcd (%) for C$_{28}$H$_{34}$N$_6$O$_8$: C, 57.7, H, 5.9, N, 14.4; found: C, 57.9, H, 6.0, N, 14.0.

2-O-Acetyl-4-azido-3-O-benzyl-4,6-dideoxy-α-D-mannopyranosyl (1→2) 4-azido-3-O-benzyl-4,6-dideoxy-α-D-mannopyranosyl N-phenyltrifluoroacetimidate (19)

Disaccharide 18 (538 mg, 0.92 mmol) was dissolved in dry dichloromethane (9 mL), N-phenyl trifluoroacetimidoyl chloride (350 μL, 2.8 mmol) and Cs$_2$CO$_3$ (0.9 g, 2.8 mmol) were added and the mixture was stirred overnight at room temperature. After evaporation of the solvent chromatography on silica gel (toluene/ethyl acetate 1:0 to 10:2) gave pure imidate 19 (623 mg, 90%): $^1$H NMR (500 MHz, CDCl$_3$): δ(α) 7.4-6.7 (m, 15H; H—Ar), 6.05 (br s, 1H; H-1$^{I}$), 5.41 (br s, 1H; H-2$^{II}$), 4.86 (br s, 1H; H-1$^{II}$), 3.85 (br s, 1H; H-2$^{I}$), 2.10 (s, 3H; Ac), 1.33 (d, $^3J_{5,6}$=6.2 Hz, 3H; H-6$^{I}$), 1.18 ppm (d, $^3J_{5,6}$=6.2 Hz, 3H; H-6$^{II}$); $^{19}$F NMR (469 MHz, CDCl$_3$): δ(α) −75.7 ppm; $^{13}$C NMR (125 MHz, CDCl$_3$): δ 170.0, 143.3, 137.3, 137.2, 129-128, 124.7, 119.5, 99.5, 95.7, 77.1, 75.5, 72.9, 72.2, 71.8, 70.3, 68.0, 67.2, 63.9, 63.5, 21.1, 18.7, 18.5 ppm; HRMS (ESI): m/z calcd for C$_{36}$H$_{38}$F$_3$KN$_7$O$_8$ [M+K]$^+$: 792.2366; found: 792.2363.

5-Methoxycarbonylpentyl 2-O-acetyl-4-azido-3-O-benzyl-4,6-dideoxy-α-D-mannopyranosyl (1→2) 4-azido-3-O-benzyl-4,6-dideoxy-α-D-mannopyranoside (21)

Donor 19 (110 mg, 0.15 mmol) and 5-methoxycarbonylpentanol 20 (El Fangour et al. (2004) J. Org. Chem. 69, 2498-2503) (30 mg, 0.2 mmol) in solution in toluene (7 mL) with some molecular sieves were heated at 100° C. and TMSOTf (2 µL, 10 µmol) was added. After heating 1 hour at this same temperature, the reaction was quenched with pyridine, and the mixture filtered. Compound 21 (59 mg, 53%) was obtained after purification on silica gel chromatography column (eluent: ethyl acetate/hexane 1/6): $[\alpha]_D^{20}$=+78 (c=1.0 in CHCl$_3$); $^1$H NMR (500 MHz, CDCl$_3$): δ 7.2-7.4 (m, 10H; H—Ar), 5.41 (dd, 1H, $^3J_{1,2}$=1.9 Hz, $^3J_{2,3}$=3.2 Hz, H-2$^{II}$), 4.86 (d, 1H, $^3J_{1,2}$=1.8 Hz, H-1$^{II}$), 4.66 (d, $^3J_{1,2}$=1.8 Hz, 1H; H-1$^I$), 3.84 (dd, $^3J_{1,2}$=2 Hz, $^3J_{2,3}$=2.8 Hz, 1H; H-2$^I$), 2.33 (t, $^3J_{d,e}$=7.5 Hz, 2H; H-e), 2.09 (s, 3H; Ac), 1.65 (quint, $^3J_{c,d}=^3J_{d,e}$=7.6 Hz, 2H; H-d), 1.57 (m, 2H; H-b), 1.36 (m, 2H; H-c), 1.31 (d, $^3J_{5,6}$=6 Hz, 3H; H-6$^{II}$), 1.29 ppm (d, $^3J_{5,6}$=6 Hz, 3H; H-6$^I$); $^{13}$C NMR (125 MHz, CDCl$_3$): δ 174.1, 169.9, 137.7, 137.2, 129-128, 99.5, 98.7, 77.9, 75.5, 74.1, 72.2, 71.7, 67.7, 67.7, 67.4, 67.2, 64.3, 64.0, 51.6, 34.1, 29.2, 25.8, 24.8, 21.1, 18.7, 18.6 ppm; elemental analysis calcd (%) for C$_{35}$H$_{46}$N$_6$O$_{10}$: C, 59.1, H, 6.5, N, 11.8; found: C, 59.0, H, 6.6, N, 11.4.

5-Methoxycarbonylpentyl 4-azido-3-O-benzyl-4,6-dideoxy-α-D-mannopyranosyl (1→2) 4-azido-3-O-benzyl-4,6-dideoxy-α-D-mannopyranoside (22)

Compound 21 (70 mg, 98 µmop in methanol (3 mL) was treated with a 0.1 M solution of sodium methoxide (0.1 mL). After 1 h, the reaction was complete and neutralized with ion exchange resin H$^+$. Filtration and removal of the solvent under vacuum gave quantitatively pure acceptor 22 (65 mg): $[\alpha]_D^{20}$=+90 (c=1.7 in CHCl$_3$); $^1$H NMR (500 MHz, CDCl$_3$): δ 7.3-7.4 (m, 10H; H—Ar), 4.94 (d, $^3J_{1,2}$=1.7 Hz, 1H; H-1$^{II}$), 4.67 (d, $^3J_{1,2}$=2.1 Hz, 1H; H-1$^I$), 3.99 (dd, $^3J_{2,3}$=3.1 Hz, 1H; H-2$^{II}$), 3.84 (dd, $^3J_{2,3}$=3.0 Hz, 1H; H-2$^I$), 3.35 (dt, $^2J$=9.7 Hz, $^3J_{a,b}$=6.4 Hz, 1H; H-a), 2.33 (t, $^3J_{d,e}$=7.5 Hz, 2H; H-e), 1.65 (quint, $^3J_{c,d}$=7.6 Hz, 2H; H-d), 1.57 (m, 2H; H-b), 1.36 (m, 2H; H-c), 1.30 (d, $^3J_{5,6}$=6.2 Hz, 3H; H-6$^{II}$), 1.30 ppm (d, 3H; H-6$^I$); $^{13}$C NMR (125 MHz, CDCl$_3$): δ 174.1, 137.6, 137.3, 129-128, 101.0, 98.9, 78.0, 77.8, 74.1, 72.3, 72.2, 67.7, 67.4, 67.3, 67.2, 64.5, 64.0, 51.6, 34.1, 29.2, 25.8, 24.8, 18.7, 18.6 ppm; elemental analysis calcd (%) for C$_{33}$H$_{44}$N$_6$O$_9$: C, 59.3, H, 6.6, N, 12.6; found: C, 59.2, H, 6.45, N, 12.2.

5-Methoxycarbonylpentyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (23)

Trisaccharide imidate 17 (45 mg, 47 µmol) and disaccharide alcohol 22 (17 mg, 25 µmol) were dissolved in dichloromethane (1 mL) and TMSOTf (1 µL, 5 µmop was added at 0° C. The mixture was stirred 30 min. at 0° C. and 1 hour at room temperature before being quenched with one drop of pyridine. Purification on silica gel column (eluent: ethyl acetate/hexane 1/10) gave pure pentasaccharide 23 (25 mg, 68%): $[\alpha]_D^{20}$=+80 (c=1.0 in CHCl$_3$); $^1$H NMR (500 MHz, CDCl$_3$): δ 7.2-7.4 (m, 20H; H—Ar), 5.41 (dd, $^3J_{1,2}$=1.7 Hz, $^3J_{2,3}$=3.2 Hz, 1H; H-2$^V$), 5.13 (dd, $^3J_{1,2}$=1.9 Hz, $^3J_{2,3}$=3.2 Hz, 1H; H-2$^{III}$), 5.00 (d, $^3J_{1,2}$=1.7 Hz, 1H; H-1$^{II}$), 4.95 (d, $^3J_{1,2}$=1.5 Hz, 1H; H-1$^{IV}$), 4.90 (d, 1H; H-1$^V$), 4.82 (d, 1H; H-1$^{III}$), 4.61 (br s, 1H; H-1$^I$), 3.98 (dd, $^3J_{2,3}$=2.9 Hz, 1H; H-2$^{II}$), 3.84 (dd, $^3J_{2,3}$=2.3 Hz, 1H; H-2$^{IV}$), 3.81 (dd, $^3J_{2,3}$=2.3 Hz, 1H; H-2$^I$), 3.68 (s, 3H; H-g), 3.58 (dt, $^2J$=9.7 Hz, $^3J_{a,b}$=6.6 Hz, 1H; H-a), 3.34 (dt, $^3J_{a,b}$=6.4 Hz, 1H; H-a), 2.32 (t, $^3J_{d,e}$=7.5 Hz, 2H; H-e), 2.1 (s, 6H; Ac), 1.65 (quint, $^3J_{c,d}$=7.6 Hz, 2H; H-d), 1.55 (m, 2H; H-b), 1.34 (m, 2H; H-c), 1.30 (d, 3H; H-6$^V$), 1.29 (d, 3H; H-6$^{IV}$), 1.28 (d, 3H; H-6$^I$), 1.25 (d, 3H; H-6$^{II}$), 1.18 ppm (d, 3H; H-6$^{III}$); $^{13}$C NMR (125 MHz, CDCl$_3$): δ 174.1, 169.9, 169.6, 137.7, 137.5, 137.5, 137.2, 129-128, 100.8, 100.3, 99.6, 98.8, 98.8, 77.8, 77.4, 76.8, 76.1, 75.5, 74.3, 73.9, 73.7, 72.3, 72.2, 72.0, 71.8, 70.6, 67.6, 68.4, 67.9, 67.9, 67.8, 67.3, 67.2, 64.6, 64.6, 64.2, 64.0, 63.9, 51.7, 34.1, 29.2, 25.8, 24.8, 21.1, 21.0, 18.8, 18.7, 18.6, 18.5, 18.4 ppm; HRMS (ESI): m/z calcd for C$_{69}$H$_{87}$N$_{15}$NaO$_{20}$ [M+Na]$^+$: 1468.6144; found: 1468.6140.

5-Methoxycarbonylpentyl 4-azido-3-O-benzyl-4,6-Dideoxy-α-D-mannopyranosyl (1→2) 4-azido-3-O-benzyl-4,6-dideoxy-α-D-mannopyranosyl (1→3) 4-azido-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (24)

Pentasaccharide 23 (82 mg, 57 µmol) in methanol (3 mL) was treated with a 0.1 M solution of sodium methoxide (0.1 mL). The reaction was stirred 1 hour at room temperature and then neutralized with ion exchange resin H$^+$. Filtration, evaporation and column chromatography (eluent: ethyl acetate/toluene 1:6) gave pure compound 24 (67 mg, 86%): $[\alpha]_D^{20}$=+80 (c=1.1 in CHCl$_3$); $^1$H NMR (500 MHz, CDCl$_3$): δ 7.2-7.4 (m, 20H; H—Ar), 5.04 (d, $^3J_{1,2}$=1.8 Hz, 1H; H-1$^{IV}$), 4.98 (d, $^3J_{1,2}$=1.7 Hz, 1H; H-1$^{II}$), 4.95 (d, $^3J_{1,2}$=1.8 Hz, 1H; H-1$^V$), 4.86 (d, $^3J_{1,2}$=1.7 Hz, 1H; H-1$^{III}$), 4.62 (br s, 1H; H-1$^I$), 4.06 (dd, $^3J_{2,3}$=2.9 Hz, 1H; H-2$^{IV}$), 3.99 (dd, $^3J_{2,3}$=3.1 Hz, 1H; H-2$^{II}$), 3.94 (dd, $^3J_{2,3}$=2.9 Hz, 1H; H-2$^{II}$), 3.93 (dd, $^3J_{2,3}$=3.1 Hz, 1H; H-2$^{III}$), 3.83 (app. t, $^3J_{1,2}=^3J_{2,3}$=2.9 Hz, 1H; H-2$^I$), 3.68 (s, 3H; H-g), 3.34 (dt, $^3J_{a,b}$=6.4 Hz, 1H; H-a), 3.24 (t, 1H; H-4$^I$), 2.32 (t, $^3J_{a,b}$=7.5 Hz, 2H; H-e), 1.65 (quint, $^3J_{c,d}$=7.6 Hz, 2H; H-d), 1.56 (m, 2H; H-b), 1.34 (m, 2H; H-c), 1.32 (d, 3H; H-6$^{II}$), 1.29 (d, 6H; H-6$^{IV}$, H-6$^{II}$), 1.29 (d, 3H; H-65, 1.17 ppm (d, 3H; H-6$^{III}$); $^{13}$C NMR (125 MHz, CDCl$_3$): δ 174.1, 137.5, 137.5, 137.3, 129-128, 101.1, 100.8, 100.7, 100.5, 98.8, 79.0, 77.9, 77.8, 77.8, 77.3, 73.8, 73.5, 73.4, 72.4, 73.4, 72.3, 72.3, 69.6, 67.7, 68.4, 67.9, 67.6, 67.6, 67.3, 67.3, 64.6, 64.4, 64.0, 63.9, 63.9, 51.7, 34.1, 29.2, 25.8, 24.8, 18.7, 18.7, 18.7, 18.5, 18.4 ppm; HRMS (ESI): m/z calcd for C$_{65}$H$_{83}$N$_{15}$NaO$_{18}$ [M+Na]$^+$: 1384.5933; found: 1384.5926.

5-Methoxycarbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (1)

A solution of pentasaccharide 24 (67 mg, 49 µmol) in a mixture pyridine/NEt$_3$ 1:1 (6 mL) was saturated with H$_2$S for 1 h and the media was then stirred for 24 h at room temperature. The solvent was co-evaporated with toluene and mass spectrometry of the crude product showed only one peak corresponding to compound 25 and no products arising from incomplete reduction: HRMS (ESI): m/z calcd for $C_{65}H_{94}N_5O_{18}$ [M+H]$^+$: 1232.6588; found: 1232.6577. This crude material was directly used for formylation.

Compound 25 was dissolved in methanol (5 mL) and a solution of acetic anhydride/formic acid 2:1 (0.5 mL) was added. The mixture was stirred at room temperature overnight. The solvent was evaporated and pentasaccharide 26 (43 mg, 63% over 2 steps) was purified with a chromatography column (eluent: MeOH/DCM 1:10): HRMS (ESI): m/z calcd for $C_{70}H_{93}N_5NaO_{23}$ [M+Na]$^+$: 1394.6154; found: 1394.6151.

Compound 26 (43 mg, 31 μmol) in solution in acetic acid (8 mL) with palladium on charcoal was stirred overnight at room temperature under atmosphere of hydrogen. After filtration and concentration, pentasaccharide 1 (17 mg, 54%) was purified on a reverse phase HPLC column (MeCN/H$_2$O 15:85): $^1$H NMR (600 MHz, D$_2$O): δ 8.21-8.19 (Z) and 8.02-8.00 (E) (m, 5H; NCHO), 5.20-4.90 (m, 5H; 5×H-1), 3.72-3.66 (m, 4H, H-a, H-g), 3.56-3.50 (m, 1H; H-a), 2.40 (t, $^3J_{d,e}$=7.4 Hz, 2H; H-e), 1.65-1.56 (m, 4H; H-b, H-d), 1.41-1.32 (m, 2H; H-c), 1.30-1.18 ppm (m, 15H; 5×H-6); HRMS (ESI): m/z calcd for $C_{42}H_{69}N_5NaO_{23}$ [M+Na]$^+$: 1034.4276; found: 1034.4275.

Ethyl 4-azido-3-O-benzyl-4,6-dideoxy-α-D-mannopyranosyl (1→2) 4-azido-3-O-benzyl-4,6-dideoxy-1-thio-α-D-mannopyranoside (27)

Disaccharide 14 (570 mg, 0.91 mmol) in methanol (10 mL) was treated with a 0.1 M solution of sodium methoxide (0.3 mL). The reaction was stirred 2 hours at room temperature and then neutralized with ion exchange resin H$^+$. Filtration, evaporation and column chromatography (eluent: ethyl acetate/hexane 1:4) gave pure alcohol 27 (433 mg, 81%): $[α]_D^{20}$=+175 (c=1.0 in CHCl$_3$); NMR (600 MHz, CDCl$_3$): δ 7.5-7.3 (m, 10H; H—Ar), 5.18 (d, $^3J_{1,2}$=1.4 Hz, 1H; H-1$^I$), 4.91 (d, $^3J_{1,2}$=1.5 Hz, 1H; H-1$^{II}$), 3.99 (ddd, $^3J_{2,3}$=3.2 Hz, $^3J_{2,OH}$=1.6 Hz, 1H; H-2$^{II}$), 3.96 (dd, $^3J_{2,3}$=3 Hz, 1H; H-2$^I$), 2.61 (dq, $^3J$=7.4 Hz, $^2J$=12.9 Hz, 1H; S—CH$_2$), 2.55 (dq, $^3J$=7.5 Hz, 1H; S—CH$_2$), 1.30 (d, 6H; H-6$^I$, H-6$^{II}$), 1.27 ppm (t, 3H; S—CH$_2$—CH$_3$); $^{13}$C NMR (126 MHz, CDCl$_3$): δ 137.4, 137.2, 129-128, 101.1, 83.6, 78.3, 77.8, 76.1, 72.3, 72.3, 67.7, 67.5, 67.3, 64.7, 64.0, 25.8, 18.6, 18.6, 15.0 ppm; HRMS (ESI): m/z calcd for $C_{28}H_{36}N_6NaO_6S$ [M+Na]$^+$: 607.2309; found: 607.2303.

Ethyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-1-thio-α-D-mannopyranoside (28)

Donor 19 (226 mg, 0.30 mmol) and acceptor 27 (100 mg, 0.17 mmol) were dissolved in toluene (3 mL) with molecular sieves and TMSOTf (2 μL, 11 μmol) was added at 100° C. The mixture was stirred 1 hour at 100° C. before being quenched with one drop of pyridine. After filtration, a purification on silica gel column using toluene to elute the leaving group of the donor and then a mixture ethyl acetate/toluene 5:95 gave pure tetrasaccharide 28 (159 mg, 81%): $[α]_D^{20}$=+122 (c=1.0 in CHCl$_3$); $^1$H NMR (600 MHz, CDCl$_3$): δ 7.4-7.3 (m, 20H; H—Ar), 5.41 (dd, $^3J_{1,2}$=1.8 Hz, $^3J_{2,3}$=3.4 Hz, 1H; H-2$^{IV}$), 5.10 (d, $^3J_{1,2}$=1.4 Hz, 1H; H-1$^I$), 4.95 (d, $^3J_{1,2}$=1.8 Hz, 1H; H$^{III}$), 4.85 (d, 1H; H-1$^{IV}$), 4.84 (d, $^3J_{1,2}$=1.8 Hz, 1H; H-1$^{II}$), 3.88 (dd, $^3J_{2,3}$=2.9 Hz, 1H; H-2$^{II}$), 3.85 (dd, $^3J_{2,3}$=2.9 Hz, 1H; H-2$^I$), 3.83 (dd, $^3J_{2,3}$=2.9 Hz, 1H; H-2$^{II}$), 2.59 (dq, $^3J$=7.4 Hz, $^2J$=13 Hz, 1H; S—CH$_2$), 2.53 (dq, $^3J$=7.5 Hz, 1H; S—CH$_2$), 2.11 (s, 3H; Ac), 1.27 (2d, 6H; H-6$^I$, H-6$^{II}$), 1.25 (t, 3H; S—CH$_2$—CH$_3$), 1.21 (d, 3H; H-6$^{IV}$), 1.20 ppm (d, 3H; H-6$^{III}$); $^{13}$C NMR (126 MHz, CDCl$_3$): δ 169.9, 137.6, 137.3, 137.3, 137.2, 129-128, 100.7, 100.2, 99.3, 83.5 77.9, 77.0, 76.8, 76.2, 75.6, 73.6, 73.6, 72.4, 72.3, 72.2, 71.7 (CH$_2$-Ph), 68.1, 68.0, 67.8, 67.7, 67.3, 64.7, 64.4, 64.2, 64.0, 25.7, 21.1, 18.8, 18.7, 18.6, 18.5, 15.0 ppm; HRMS (ESI): m/z calcd for $C_{56}H_{68}N_{12}NaO_{13}S$ [M+Na]$^+$: 1171.4642; found: 1171.4644.

Allyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranoside (29)

Donor 28 (197 mg, 171 μmol) and acceptor 9 (37 mg, 136 μmol) were dissolved in dry dichloromethane (5 mL) with molecular sieves, then NIS (46 mg, 200 μmop and trifluoromethanesulfonic acid (6 μL, 68 μmol) were added at 0° C. The reaction was stirred at this temperature for 15 min. and then filtered through celite. The mixture was washed with Na$_2$S$_2$O$_3$ then KHCO$_3$. Pentacaccharide 29 (125 mg, 68%) was obtained pure after flash chromatography (hexane/ethyl acetate 6:1): $[α]_D^{20}$=+88 (c=1.0 in CHCl$_3$); $^1$H NMR (600 MHz, CDCl$_3$): δ 7.5-7.2 (m, 20H; H—Ar), 5.41 (dd, $^3J_{1,2}$=1.8 Hz, $^3J_{2,3}$=3.2 Hz, 1H; H-2$^V$), 5.41 (dd, $^3J_{1,2}$=1.8 Hz, $^3J_{2,3}$=3.3 Hz, 1H; H-2$^I$), 4.93 (m, 3H; H-1$^{II}$, H-1$^{III}$, H-1$^{IV}$), 4.85 (d, 1H; H-1$^{II}$), 4.75 (d, 1H; H-1$^I$), 3.87 (dd, $^3J_{1,2}$=1.8 Hz, $^3J_{2,3}$=2.9 Hz, 1H; H-2$^{IV}$), 3.82 (dd, $^3J_{1,2}$=1.8 Hz, $^3J_{2,3}$=2.9 Hz, 1H; H-2$^{III}$), $^3$2.10, 2.08 (2s, 6H; Ac), 1.33 (d, 3H; H-6$^I$), 1.29 (d, $^3J_{5,6}$=6.2 Hz, 3H; H-6$^{III}$), 1.24 (d, $^3J_{5,6}$=6.2 Hz, 3H; H-6$^{II}$), 1.20 (d, $^3J_{5,6}$=6.2 Hz, 3H; H-6$^V$), 1.14 ppm (d, $^3J_{5,6}$=6.2 Hz, 3H; H-6$^{IV}$); $^{13}$C NMR (126 MHz, CDCl$_3$): δ 170.1, 169.9, 137.6, 137.4, 137.3, 137.3, 129-128, 133.3 118.1, 101.2, 100.5, 100.3, 99.2, 96.4, 77.4, 77.0, 76.8, 75.6, 73.6, 73.5, 73.3, 72.4, 72.2, 72.0, 71.7, 71.0, 68.6, 68.3, 68.2, 68.0, 67.8, 67.3, 67.1, 64.6, 64.4, 64.2, 64.1, 64.0, 21.1, 21.0, 18.7, 18.6, 18.6, 18.6, 18.5 ppm; HRMS (ESI): m/z calcd for $C_{65}H_{79}N_{15}NaO_{18}$ [M+Na]$^+$: 1380.562; found: 1380.5611.

2-O-Acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranose (30)

Allyl glycoside 29 (40 mg, 29 μmop was dissolved in a solution of AcOH/H$_2$O 9:1 (0.6 mL), AcONa (10 mg, 122 μmop and PdCl$_2$ (10 mg, 56 μmol) were added. The mixture was stirred overnight at room temperature and neutralized with NaHCO$_3$. The product was extracted with dichloromethane, washed with water, dried over MgSO$_4$, filtrated and concentrated. Chromatography on silica gel (hexane/ethyl acetate 2:1) gave compound 30 (24 mg, 62%): $^1$H NMR (600 MHz, CDCl$_3$): δ 7.4-7.25 (m, 20H; H—Ar), 5.40 (dd, $^3J_{1,2}$=1.8 Hz, $^3J_{2,3}$=3.2 Hz, 1H; H-2$^V$), 5.13 (br s, 1H; H-1$^I$), 5.06 (dd, $^3J_{1,2}$=1.8 Hz, $^3J_{2,3}$=3.3 Hz, 1H; H-2$^I$), 4.94 (d, $^3J_{1,2}$=1.8 Hz, 1H; H-1$^{II}$), 4.92 (d, $^3J_{1,2}$=1.7 Hz, 2H; H-1$^{III}$, H-1$^{IV}$), 4.84 (d, 1H; H-1$^V$), 3.98 (dd, $^3J_{2,3}$=2.8 Hz, 1H; H-2$^{II}$), 3.87 (dd, $^3J_{2,3}$=2.9 Hz, 1H; H-2$^{IV}$), 3.82 (dd, $^3J_{2,3}$=2.8 Hz, 1H; H-2$^{III}$), 2.10, 2.08 (2s, 6H; Ac), 1.33 (d, 3H; H-6$^I$), 1.29 (d, $^3J_{5,6}$=6.2 Hz, 3H; H-6$^{III}$), 1.24 (d, $^3J_{5,6}$=6.2 Hz, 3H; H-6$^{II}$), 1.20 (d, $^3J_{5,6}$=6.2 Hz, 3H; H-6$^{II}$), 1.14 ppm (d, $^3J_{5,6}$=6.2 Hz, 3H; H-6$^{IV}$). $^{13}$C NMR (126 MHz, CDCl$_3$): δ 170.2, 170.0, 137.6, 137.4, 137.3, 137.3, 129-128, 101.2, 100.5, 100.3, 99.2, 92.0, 77.0, 76.8, 76.6, 76.6, 75.6, 73.6, 73.6, 73.4, 72.4, 72.2, 72.0, 71.7, 71.2, 68.3, 68.2, 68.0, 67.8, 67.3, 67.1, 64.6, 64.4, 64.2, 64.1, 64.0, 21.1, 21.0, 18.7, 18.6, 18.6, 18.6, 18.5 ppm. HRMS (ESI): m/z calcd for C$_{62}$H$_{75}$N$_{18}$NaO$_{18}$ [M+Na]$^+$: 1340.5307; found: 1340.5291.

2-O-Acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranosyl N-phenyltrifluoroacetimidate (31)

To a solution of free pentasaccharide 30 (118 mg, 89 µmol) in dichloromethane (2 mL) were added N-phenyl trifluoroacetimidoyl chloride (34 µL, 270 µmol) and Cs$_2$CO$_3$ (90 mg, 280 µmol). The mixture was stirred overnight at room temperature. After filtration, a purification on silica gel column (eluent: ethyl acetate/hexane 1:9) gave donor 31 (104 mg, 79%) in α/β mixture which was used directly for the next glycosylation: HRMS (ESI): m/z calcd for C$_{70}$H$_{79}$F$_3$N$_{16}$NaO$_{18}$ [M+Na]$^+$: 1511.5603; found: 1511.5600.

5-Methoxycarbonylpentyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (32)

Donor 19 (117 mg, 160 µmol) and acceptor 22 (65 mg, 97 µmol) were dissolved in toluene (2 mL) with molecular sieves and TMSOTf (2 µL, 11 µmol) was added at 100° C. The mixture was stirred 1 hour at 100° C. before being quenched with one drop of pyridine. After filtration, a purification on silica gel column using toluene to elute the leaving group of the donor and then a mixture ethyl acetate/toluene 5:95 gave pure tetrasaccharide 32 (93 mg, 77%): [α]$_D^{20}$=+55 (c=1.0 in CHCl$_3$); $^1$H NMR (600 MHz, CDCl$_3$): δ 7.4-7.3 (m, 20H; H—Ar), 5.40 (dd, $^3J_2$=1.8 Hz, $^3J_{2,3}$=3.2 Hz, 1H; H-2$^{IV}$), 4.94 (d, $^3J_{1,2}$=1.8 Hz, 1H; H-1$^{III}$), 4.87 (d, $^3J_{1,2}$=1.9 Hz, 1H; H-1$^{II}$), 4.84 (d, 1H; H-1$^{IV}$), 4.60 (d, $^3J_{1,2}$=1.5 Hz, 1H; H-1$^I$), 3.87 (dd, $^3J_{2,3}$=3 Hz, 1H; H-2$^{III}$), 3.83 (dd, $^3J_{2,3}$=2.9 Hz, 1H; H-2$^{II}$), 3.78 (dd, $^3J_{2,3}$=2.9 Hz, 1H; H-25, 3.68 (s, 3H; H-g), 3.57 (dt, $^3J_{a,b}$=6.6 Hz, $^2J$=9.6 Hz, 1H; H-a), 3.32 (dt, $^3J_{a,b}$=6.4 Hz, 1H; H-a), 2.32 (t, $^3J_{d,e}$=7.5 Hz, 2H; H-e), 2.11 (s, 3H; Ac), 1.64 (quint, $^3J_{c,d}$=7.5 Hz, 2H; H-d), 1.55 (m, 2H; H-b), 1.34 (m, 2H; H-c), 1.26 (2d, 6H; H-6$^1$, H-6$^{II}$), 1.20 (d, 3H; H-6$^{IV}$), 1.16 ppm (d, 3H; H-6$^{III}$); $^{13}$C NMR (151 MHz, CDCl$_3$): δ 174.1, 169.9, 137.6, 137.5, 137.3, 137.3, 129-128, 100.6, 100.2, 99.2, 98.7, 77.6, 77.0, 76.8, 75.6, 74.2, 73.6, 73.6, 72.4, 72.3, 72.2, 71.7, 68.0, 67.9, 67.8, 67.7, 67.3, 67.2, 64.5, 64.4, 64.2, 64.0, 51.7, 34.1, 29.2, 25.8, 24.8, 21.1, 18.8, 18.7, 18.6, 18.5 ppm; elemental analysis calcd (%) for C$_{61}$H$_{76}$N$_{12}$O$_{16}$: C, 59.40, H, 6.21, N, 13.63; found: C, 59.62, H, 5.93, N, 13.36.

5-Methoxycarbonylpentyl 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (33)

Tetrasaccharide 32 (90 mg, 73 µmop in methanol (3 mL) was treated with a 0.1 M solution of sodium methoxide (0.1 mL). The reaction was stirred 2 hours at room temperature and then neutralized with ion exchange resin H$^+$. Filtration, evaporation and chromatography on silica gel (eluent: ethyl acetate/hexane 1:6) gave pure alcohol 33 (73 mg, 84%): [α]$_D^{20}$=+104 (c=1.0 in CHCl$_3$); $^1$H NMR (600 MHz, CDCl$_3$): δ 7.4-7.3 (m, 20H; H—Ar), 4.97 (d, $^3J_{1,2}$=1.8 Hz, 1H; H-1$^{IV}$), 4.95 (d, $^3J_{1,2}$=1.9 Hz, 1H; H-1$^{III}$), 4.87 (d, $^3J_{1,2}$=1.9 Hz, 1H; H-1$^{II}$), 4.60 (d, $^3J_{1,2}$=1.8 Hz, 1H; H-1$^I$), 5.40 (dd, $^3J_{2,3}$=3.0 Hz, 1H; H-2$^{IV}$), 3.87 (dd, $^3J_{2,3}$=3.0 Hz, 1H; H-2$^{III}$), 3.83 (dd, $^3J_{2,3}$=2.9 Hz, 1H; H-2$^{II}$), 3.78 (dd, $^3J_{2,3}$=2.9 Hz, 1H; H-2$^I$), 3.32 (dt, $^3J_{a,b}$=6.4 Hz, 1H; H-a), 2.32 (t, $^3J_{d,e}$=7.6 Hz, 2H; H-e), 2.30 (br. s, 1H; OH), 1.64 (quint, $^3J_{c,d}$=7.6 Hz, 2H; H-d), 1.55 (m, 2H; H-b), 1.34 (m, 2H; H-c), 1.26 (2d, 6H; H-6$^I$, H-6$^{II}$), 1.20 (d, 3H; H-6$^{IV}$), 1.17 ppm (d, 3H; H-6$^{III}$); $^{13}$C NMR (126 MHz, CDCl$_3$): δ 174.1, 137.5, 137.5, 137.3, 137.3, 129-128, 100.6, 100.5, 100.4, 98.7, 77.8, 77.6, 77.1, 76.7, 74.1, 73.7, 73.4, 72.4, 72.3, 72.3, 72.2, 67.9, 67.9, 67.6, 67.5, 67.3, 67.2, 64.5, 64.4, 64.3, 64.0, 51.7, 34.1, 29.2, 25.8, 24.8, 18.8, 18.7, 18.7, 18.5 ppm; HRMS (ESI): m/z calcd for C$_{59}$H$_{74}$N$_{12}$NaO$_{15}$ [M+Na]$^+$: 1213.5289; found: 1213.5278.

5-Methoxycarbonylpentyl 2-O-acetyl-4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→3) 2-O-acetyl-4-azido-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (34)

Donor 31 (104 mg, 70 µmol) and acceptor 33 (73 mg, 61 µmop were dissolved in toluene (1.5 mL) with molecular sieves and TMSOTf (1 µL, 5 µmop was added. The mixture was stirred 3 hours at room temperature before being quenched with one drop of pyridine. After filtration, a purification on silica gel column using toluene with a gradient of ethyl acetate (from 0% to 10%) gave pure nonasaccharide 34 (45 mg, 30%): [α]$_D^{20}$=+95 (c=1.0 in CHCl$_3$); $^1$H NMR (600 MHz, CDCl$_3$): δ 7.4-7.2 (m, 40H; H—Ar), 5.40 (dd, $^3J_{1,2}$=1.9 Hz, $^3J_{2,3}$=3.1 Hz, 1H; H-2$^{IX}$), 5.12 (dd, $^3J_{1,2}$=1.9 Hz, $^3J_{2,3}$=3.2 Hz, 1H; H-2$^V$), 4.97 (d, $^3J_{1,2}$=1.5 Hz, 2H; H-1), 4.94 (d, $^3J_{1,2}$=1.8 Hz, 1H; H-1), 4.93 (d, $^3J_{1,2}$=1.8 Hz, 1H; H-1), 4.86 (d, $^3J_{1,2}$=1.7 Hz, 1H; H-1), 4.85 (d, $^3J_{1,2}$=1.8 Hz, 1H; H-1), 4.84 (d, $^3J_{1,2}$=1.7 Hz, 1H; H-1$^{IX}$), 4.82 (d, $^3J_{1,2}$=1.5 Hz, 1H; H-1$^{II}$), 4.59 (d, $^3J_{1,2}$=1.1 Hz, 1H; H-1$^I$), 3.95 (dd, $^3J_{2,3}$=2.8 Hz, 1H; H-2), 3.87 (dd, $^3J_{2,3}$=3 Hz, 1H; H-2), 3.85 (dd, $^3J_{2,3}$=2.8 Hz, 1H; H-2), 3.84 (dd, $^3J_{2,3}$=3 Hz, 1H; H-2), 3.83 (dd, $^3J_{2,3}$=3 Hz, 1H; H-2), 3.80 (dd, $^3J_{2,3}$=3 Hz, 1H; H-2), 3.76 (dd, $^3J_{2,3}$=3 Hz, 1H; H-2$^I$), 3.57 (dt, $^2J$=9.7 Hz, $^3J_{a,b}$=6.7 Hz, 1H; H-a), 3.32 (dt, $^3J_{a,b}$=6.4 Hz, 1H; H-a), 2.32 (t, $^3J_{d,e}$=7.5 Hz, 2H; H-e), 2.10, 2.06 (2s, 6H; Ac), 1.64 (quint, $^3J_{c,d}$=7.6 Hz, 2H; H-d), 1.55 (m, 2H; H-b), 1.33 (m, 2H; H-c), 1.27-1.12 ppm (9d, $^3J_{5,6}$=6.2 Hz, 27H; H-6); $^{13}$C NMR (126 MHz, CDCl$_3$): δ 174.1 (C-f), 169.9, 169.6, 137.6, 137.5, 137.5, 137.4, 137.4, 137.3, 137.3, 137.3, 129-128, 100.8, 100.6, 100.5, 100.3, 100.2, 100.1, 99.2, 98.8, 98.7, 77.6, 77.0, 76.8, 76.8, 76.7, 76.6, 76.6, 76.0, 75.6, 74.3, 74.2, 73.7, 73.6, 73.6, 73.5, 73.4, 72.4, 72.4, 72.4, 72.3, 72.2, 72.2, 72.1, 71.7, 70.6, 68.4, 68.2, 68.0, 68.0, 68.0, 67.9, 67.8, 67.8, 67.3, 67.7, 67.2, 64.6, 64.5, 64.4, 64.4, 64.4, 64.2, 64.2, 64.2, 64.0, 51.7, 34.1, 29.2, 25.8, 24.8, 21.1, 21.0, 18.8, 18.7, 18.7, 18.7, 18.6, 18.6, 18.5, 18.5, 18.4 ppm; HRMS (ESI): m/z calcd for C$_{121}$H$_{147}$N$_{27}$NaO$_{32}$ [M+Na]$^+$: 2513.0598; found: 2513.0561.

5-Methoxycarbonylpentyl 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→3) 4-azido-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (35)

Nonaccharide 34 (45 mg, 18 μmol) in methanol (2 mL) was treated with a 0.1 M solution of sodium methoxide (0.1 mL). The reaction was stirred 2 hours at room temperature and then neutralized with ion exchange resin H$^+$. Filtration, evaporation and chromatography on silica gel (eluent: ethyl acetate/hexane 1:6) gave pure compound 35 (34 mg, 78%): [α]$_D^{20}$=+100 (c=1.0 in CHCl$_3$); $^1$H NMR (600 MHz, CDCl$_3$): δ 7.4-7.3 (m, 40H; H—Ar), 4.99 (d, $^3J_{1,2}$=1.6 Hz, 1H; H-1), 4.97 (d, $^3J_{1,2}$=1.6 Hz, 1H; H-1), 4.96 (d, $^3J_{1,2}$=1.6 Hz, 1H; H-1), 4.94 (br s, 2H; H-1), 4.87 (d, $^3J_{1,2}$=1.6 Hz, 1H; H-1), 4.87 (d, $^3J_{1,2}$=1.6 Hz, 1H; H-1), 4.86 (d, $^3J_{1,2}$=1.7 Hz, 1H; H-1), 4.59 (d, $^3J_{1,2}$=1.6 Hz, 1H; H-1$^I$), 3.99 (m, 2H; H-2), 3.93 (m, 2H; H-2), 3.91 (br s, 1H; H-2), 3.85 (dd, $^3J_{1,2}$=1.6 Hz, $^3J_{2,3}$=3 Hz, 1H; H-2), 3.83 (dd, $^3J_{1,2}$=1.6 Hz, $^3J_{2,3}$=3 Hz, 1H; H-2), 3.81 (dd, $^3J_{2,3}$=3 Hz, 1H; H-2), 3.77 (dd, $^3J_{2,3}$=3 Hz, 1H; H-2$^I$), 3.68 (s, 3H; H-g), 3.57 (dt, $^2J$=9.7 Hz, $^3J_{a,b}$=6.7 Hz, 1H; H-a), 3.32 (dt, $^3J_{a,b}$=6.4 Hz, 1H; H-a), 2.32 (t, $^3J_{d,e}$=7.5 Hz, 2H; H-e), 1.64 (quint, $^3J_{c,d}$=7.6 Hz, 2H; H-d), 1.55 (m, 2H; H-b), 1.33 (m, 2H; H-c), 1.27, 1.27, 1.26, 1.25, 1.20, 1.20, 1.19, 1.15, 1.15 ppm (9d, $^3J_{5,6}$=6.2 Hz, 27H; H-6); $^{13}$C NMR (126 MHz, CDCl$_3$): δ 174.1, 137.5, 137.5, 137.5, 137.3, 137.3, 137.3, 137.3, 137.3, 129-128, 100.8, 100.7, 100.6, 100.6, 100.5, 100.4, 100.3, 100.2, 98.7, 79.0, 77.8, 77.6, 77.5, 77.4, 77.0, 76.8, 76.7, 74.2, 73.6, 73.6, 73.5, 73.4, 73.4, 73.3, 72.4, 72.4, 72.4, 72.4, 72.4, 72.3, 72.2, 72.2, 69.6, 68.5, 68.2, 68.0, 68.0, 68.0, 67.9, 67.6, 67.5, 67.3 (C-5), 67.2 (C-2), 67.7 (C-a), 64.5, 64.4, 64.4, 64.4, 64.3, 64.3, 64.1, 64.0, 64.0, 51.7, 34.1, 29.2, 25.8, 24.8, 18.8, 18.7, 18.7, 18.7, 18.6, 18.6, 18.6, 18.5, 18.4 ppm; HRMS (ESI): m/z calcd for C$_{117}$H$_{143}$N$_{27}$NaO$_{30}$ [M+Na]$^+$: 2429.0386; found: 2429.0353.

5-Methoxycarbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→3) 4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (2)

A solution of nonasaccharide 35 (34 mg, 14 μmol) in a mixture pyridine/NEt$_3$ 1:1 (4 mL) was saturated with H$_2$S for 1 h and the media was then stirred for 24 h at room temperature. The solvent was co-evaporated with toluene and mass spectrometry of the crude product showed only one peak corresponding to compound 36 and no more product from incomplete reduction: HRMS (ESI): m/z calcd for C$_{117}$H$_{162}$N$_9$O$_{30}$ [M+H]$^+$: 2173.1439; found: 2173.1422. This crude material was directly used for formylation.

Compound 36 was dissolved in methanol (3 mL) and a solution of acetic anhydride/formic acid 2:1 (0.3 mL) was added. The mixture was stirred at room temperature overnight. The solvent was evaporated and nonasaccharide 37 (21 mg, 62% over 2 steps) was purified with a chromatography column (eluent: MeOH/DCM 1:10): HRMS (ESI): m/z calcd for C$_{126}$H$_{161}$N$_9$Na$_2$O$_{39}$ [M+2Na]$^{2+}$: 1235.0338; found: 1235.0333.

Compound 37 (21 mg, 8.6 μmol) in solution in acetic acid (5 mL) with palladium on charcoal was stirred overnight at room temperature under atmosphere of hydrogen. After filtration and concentration, nonasaccharide 2 (7 mg, 48%) was purified on a reverse phase HPLC column (MeCN/H$_2$O 18:82): $^1$H NMR (600 MHz, D$_2$O): δ 8.21-8.00 (m, 9H; NCHO), 5.21-4.84 (m, 9H; 9×H-1), 4.20-3.78 (m, 34H; 9×H-2, 9×H-3, 7×H-4, 9×H-5), 3.74-3.68 (m, 4H; H-a, H-g), 3.56-3.3.34 (m, 3H; 2×H-4, H-a), 2.40 (t, $^3J_{d,e}$=7.4 Hz, 2H; H-e), 1.66-1.58 (m, 4H; H-b, H-d), 1.42-1.33 (m, 2H; H-c), 1.30-1.15 ppm (m, 27H; 9×H-6); HRMS (ESI): m/z calcd for C$_{70}$H$_{113}$N$_9$O$_{39}$Na$_2$ [M+2Na]$^{2+}$: 874.846; found: 874.8467.

Proton labeling of the linker for compounds 38-41 is as follows:

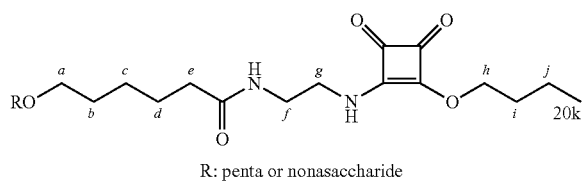

R: penta or nonasaccharide (2-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (38)

A solution of 1 (12 mg, 11.8 μmol) in freshly distilled 1,2-diaminoethane (550 μL) was stirred at 50° C. for 48 h then concentrated. The residue was dissolved in water, neutralized with acetic acid and purified by reversed phase HPLC on C18 column in gradient water-acetonitrile to give 38 as a white powder (10 mg, 81%): $^1$H NMR (500 MHz, D$_2$O): δ 8.21-8.19 and 8.02-8.00 (m, 5H; NCHO), 5.17-4.86 (m, 5H; 5×H-1), 4.19-3.76 (m, 19H; 5×H-2, 5×H-3, 4×H-4, 5×H-5), 3.71-3.66 (m, 1H; H-a), 3.55-3.51 (m, 1H; H-a), 3.50-3.32 (m, 1H; H-4), 3.27 (t, $^3J_{f,g}$=6.2 Hz, 2H; H-f), 2.80 (t, 2H; H-g), 2.26 (t, $^3J_{d,e}$=7.4 Hz, 2H; H-e), 1.64-1.54 (m, 4H; H-b, H-d), 1.40-1.31 ppm (m, 2H; H-c), 1.30-1.16 (m, 15H; 5×H-6); HRMS (ESI): m/z calcd for C$_{43}$H$_{74}$N$_7$O$_{22}$ [M+H]$^+$: 1040.4881; found: 1040.4879.

1-[(2-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside]-2-butoxycyclobutene-3,4-dione (40)

To a solution of amine 38 (5 mg, 4.8 μmol) in a mixture of water (300 μL) and ethanol (200 μL) a solution of 3,4-dibutoxy-3-cyclobutene-1,2-dione (20% in ethanol, 26 μL) was added and pH was adjusted to 8 by addition of sodium bicarbonate solution. After 0.5 h, when TLC indicated the reaction was complete, the reaction mixture was neutralized with acetic acid and purified by reversed phase HPLC (C18) using gradient water-acetonitrile. Product which came out at 20% of acetonitrile was lyophilized to afford squarate 40 as a white powder (4.2 mg, 73%): $^1$H NMR (600 MHz, D$_2$O): δ 8.23-8.18 and 8.06-7.98 (m, 5H; NCHO), 5.18-5.87 (m, 5H; 5×H-1), 4.69 (m, 2H; H-h), 3.72-3.58 (m, 3H; H-a, 2×H-f), 3.51-3.36 (m, 4H; H-4, H-a, 2×H-g). 2.24-2.17 (m, 2H; H-e), 1.82-1.74 (m, 2H; H-i), 1.61-1.49 (m, 4H; H-b, H-d), 1.49-1.38 (m, 2H; H-j), 1.33-1.18 (m, 17H; 15×H-6, H-c), 0.96-0.91 (m, 3H; H-k); HRMS (ESI): m/z calcd for C$_{51}$H$_{81}$N$_7$NaO$_{25}$ [M+Na]$^+$: 1214.5174, found: 1214.5177.

(2-Aminoethylamido)carbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→3) 4-formamido-α-D-mannopyranosyl (1-2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (39)

Methyl ester 2 (5.9 mg, 3.46 μmol) in freshly distilled ethylenediamine (400 μL) was stirred at 50° C. for 48 h. TLC indicated the reaction was almost complete. The mixture was concentrated, dissolved in water and neutralized with 10% acetic acid. It was first purified on a SepPak C18 cartridge washing it first with water and then with methanol. Methanol fractions containing the product were combined and concentrated and then purified on HPLC (C18) using water-acetonitrile gradient. The product came out at 12% of acetonitrile. It was concentrated and lyophilized to yield the title amine 39 as a white powder (4.5 mg, 75%): NMR (500 MHz, D$_2$O): δ 8.22-7.99 (m, 9H; NCHO), 5.20-4.86 (m, 9H; 9×H-1), 4.18-3.76 (m, 34H; 9×H-2, 9×H-3, 7×H-4, 9×H-5), 3.72-3.66 (m, 1H; H-a), 3.55-3.29 (m, 5H; 2×H-4, H-a, H-f), 2.81 (m, 2H; H-g), 2.26 (t, $^3J_{d,e}$=7.4 Hz, 2H; H-e), 1.65-1.58 (m, 4H; H-b, H-d), 1.40-1.30 (m, 2H; H-c), 1.30-1.16 (m, 27H; 9×H-6); HRMS (ESI): m/z calcd for C$_{71}$H$_{118}$N$_{11}$O$_{38}$ [M+H]$^+$: 1732.7634; found: 1732.7596.

1-[(2-Aminoethylamido)carbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→3) 4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside]-2-butoxycyclobutene-3,4-dione (41)

The amine 39 (4.5 mg, 2.5 μmop was dissolved in water (0.3 mL) and ethanol (0.2 mL) was added to the solution. It was stirred at room temperature and a solution of 3,4-dibutoxy-3-cyclobutene-1,2-dione in ethanol (20%, 17 μL) was added and the pH of the reaction mixture was adjusted to 8 by careful addition of NaHCO$_3$ solution. When TLC indicated the reaction was complete the mixture was neutralized with 10% acetic acid and purified by reversed phase HPLC (C18) using gradient water-acetonitrile. The product which came out at 20% of acetonitrile was concentrated and lyophilized to afford title compound 41 as a white powder (3.7 mg, 76%): $^1$H NMR (500 MHz, D$_2$O): δ 8.31-8.08 (m, 9H; NCHO), 5.30-4.94 (m, 9H; 9×H-1), 4.82-4.74 (m, 2H; H-h), 4.28-3.42 (m, 42H; 9×H-2, 9×H-3, 9×H-4, 9×H-5, H-a, H-f, H-g), 2.33-2.25 (m, 2H; H-e), 1.91-1.82 (m, 2H; H-i), 1.70-1.57 (m, 4H; H-b, H-d), 1.56-1.48 (m, 2H; H-j), 1.42-1.23 (m, 29H; 9×H-6, H-c), 1.05-0.99 (m, 3H; H-k); HRMS (ESI): m/z calcd for C$_{79}$H$_{125}$N$_{11}$Na$_2$O$_{41}$[M+2Na]$^{+2}$: 964.8909; found: 964.8904.

Methyl 4-azido-2,3-di-O-benzoyl-4,6-dideoxy-α-D-mannopyranoside (50) (Eichler et al. (1991) Glycoconjugate 8, 69-74)

Benzoyl chloride (2.0 mL, 17.2 mmol) was added dropwise to a stirred solution of Methyl 4-azido-4,6-dideoxy-α-D-mannopyranoside 3 (Bundle et al. (1998) Carbohydr. Res. 174, 239-251) (1.59 g, 7.82 mmol) in pyridine (5 mL) containing DMAP (0.191 g, 1.56 mmol) at 0° C. The resulting mixture was stirred under argon for 10 h at room temperature. Then CH$_3$OH (2 mL) was added to the reaction mixture. It was stirred for 10 min, then diluted with CH$_2$Cl$_2$ (~100 mL) and washed with aq. HCl (1M, 2×50 mL), water (100 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (3.12 g, 97%) as a white foam. Analytical data for 50: Rf=0.40 (ethyl acetate/hexane, 1/9, v/v); [α]$_D^{21}$=−130.8 (c=1.1, CHCl$_3$); $^1$H NMR (600 MHz, CDCl$_3$): δ 8.21-7.31 (m, 10H, H—Ar), 5.60 (dd, 1H, $J_{2,3}$=1.8 Hz, H-2), 5.59 (dd, 1H, $J_{3,4}$=3.6 Hz, H-3), 4.85 (d, 1H, =1.2 Hz, H-1), 3.83 (dq, 1H, $J_{4,5}$=10.2 Hz, $J_{5,6}$=6.0 Hz, H-5), 3.76 (dd, 1H, $J_{4,5}$=10.2 Hz, H-4), 3.45 (s, 3H, —OCH$_3$), 1.48 ppm (d, 3H, $J_{5,6}$=6.0 Hz, H-6); $^{13}$C NMR (126 MHz, CDCl$_3$): δ 165.4, 165.3, 133.8, 133.5, 133.3, 130.2, 129.8, 129.8, 129.5, 129.3, 128.6, 128.5, 128.4, 98.6, 71.1, 69.8, 66.9, 63.5, 55.4, 18.6 ppm; HRMS (ESI): m/z calcd for C$_{21}$H$_{21}$N$_3$O$_6$Na [M+Na]$^+$: 434.1323, found: 434.1317.

1-O-Acetyl-4-azido-2,3-di-O-benzoyl-4,6-dideoxy-α-D-mannopyranose (51)

A solution of 50 (3.10 g, 7.54 mmol) in acetic anhydride/acetic acid/sulfuric acid (50:20:0.5, 70 mL) was stirred at room temperature for 6 h, and then poured into ice-cold 1M K$_2$CO$_3$ solution (100 mL). The mixture was then diluted with CH$_2$Cl$_2$ (~200 mL) and washed with water (2×100 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (3.04 g, 92%) as a white foam. Analytical data for 51: Rf=0.30 (ethyl acetate/hexane, 1/9, v/v); $[\alpha]_D^{21}$=−119.8 (c=1.1, CHCl$_3$); $^1$H NMR (500 MHz, CDCl$_3$): δ 7.35-8.09 (m, 10H, H—Ar), 6.25 (d, J=1.5 Hz, 1H, H-1), 5.65 (dd, J$_{2,3}$=3.5 Hz, 1H, H-2), 5.61 (dd, J$_{3,4}$=10.1 Hz, 1H, H-3), 3.91 (dq, J=10.2, 6.2 Hz, 1H, H-5), 3.85 (dd, J$_{4,5}$=10.1 Hz, 1H, H-4), 2.24 (s, 3H, —OC—CH$_3$), 1.51 (d, J$_{5,6}$=6.2 Hz, 3H, H-6); $^{13}$C NMR (126 MHz, CDCl$_3$): δ 168.4, 165.4, 165.1, 133.7, 133.5, 129.9, 129.8, 129.1, 129.0, 128.6, 128.5, 90.7, 70.9, 69.4, 68.6, 63.0, 21.0, 18.7 ppm; HRMS (ESI): m/z calcd for C$_{22}$H$_{21}$N$_3$O$_7$Na [M+Na]$^+$: 462.1272, found: 462.1265.

4-Azido-2,3-di-O-benzoyl-4,6-dideoxy-α/β-D-mannopyranose (52)

Hydrazine acetate (0.056 g, 0.612 mmol) was added to a stirred solution of 51 (0.224 g, 0.510 mmol) in DMF (1 mL) under argon atmosphere and the solution was stirred at 60° C. for 30 min. Then the mixture was cooled to room temperature, diluted with ethyl acetate (50 mL), washed with water (2×50 mL) and brine (30 mL). The organic phase was separated, dried over MgSO$_4$, and concentrated in vacuo. The residue was purified by column chromatography on silica gel (ethyl acetate-hexane gradient elution) to afford the title compound (0.191 g, 95%) as a white foam. Analytical data for 52: Rf=0.30 (ethyl acetate/hexane, 1/4, v/v); NMR (500 MHz, CDCl$_3$): α:β ratio=7:1; δ 7.11-8.06 (m, 20H, H—Ar), 5.78 (dd, J$_{2,3}$=3.0 Hz, 1H, H-2$_β$), 5.66 (dd, J$_{3,4}$=10 Hz, 1H, H-3$_α$), 5.63 (dd, J$_{2,3}$=3.2 Hz, 1H, H-2$_α$), 5.36 (dd, J$_{1,2}$=1.6 Hz, 1H, H-1$_α$), 5.30 (dd, J$_{3,4}$=10.3 Hz, 1H, H-3$_β$), 5.07 (dd, J$_{1,2}$=1.5 Hz, 1H, H-1$_β$), 1.52 (d, J$_{5,6}$=6.0 Hz, 3H, H-6$_β$), 1.45 ppm (d, J$_{5,6}$=6.2 Hz, 3H, H-6$_α$); $^{13}$C NMR (126 MHz, CDCl$_3$): δ 166.1, 165.5, 165.4, 133.8, 133.5, 133.4, 130.0, 129.8 (×2), 129.4, 129.2, 129.0 (×2), 128.9, 128.7, 128.6, 128.5, 128.4, 128.2, 92.9, 92.1, 73.3, 71.4, 70.9, 70.8, 70.2, 67.1, 63.6, 62.8, 18.7, 18.6 ppm; HRMS (ESI): m/z calcd for C$_{20}$H$_{19}$N$_3$O$_6$Na [M+Na]$^+$: 420.1166, found: 420.1163.

4-Azido-2,3-di-O-benzoyl-4,6-dideoxy-α-D-mannopyranosyl Trichloroacetimidate (53)

To a stirred solution of 52 (2.0 g, 5.03 mmol) in CH2Cl2 (20 mL) containing CCl3CN (10.1 mL, 100 mmol), DBU (0.150 mL, 1.00 mmol) was added at room temperature under an argon atmosphere. After 10 min, solvents were evaporated in vacuo and the residue was purified by column chromatography on silica gel (ethyl acetate-hexane gradient elution) to afford the title compound (2.335 g, 86%) as an off-white foam. Analytical data for 53: Rf=0.60 (ethyl acetate/hexane, 1/4, v/v); $[\alpha]_D^{21}$=−101.9 (c=1.0, CHCl$_3$); $^1$H NMR (500 MHz, CDCl$_3$): δ 8.79 (s, 1H, N—H), 7.33-8.09 (m, 10H, H—Ar), 6.43 (d, J$_{1,2}$=1.5 Hz, 1H, H-1), 5.85 (dd, J$_{2,3}$=3.5 Hz, 1H, H-2), 5.68 (dd, J$_{3,4}$=10.5 Hz, 1H, H-3), 4.07 (dq, J=10.2, 6.2 Hz, 1H, H-5), 3.88 (dd, J$_{4,5}$=10.2 Hz, 1H, H-4), 1.53 ppm (d, J$_{5,6}$=6.2 Hz, 3H, H-6); $^{13}$C NMR (126 MHz, CDCl$_3$): δ 165.3, 165.1, 160.0, 133.7, 133.5, 129.9, 129.8, 129.1, 129.0, 128.7, 128.5, 94.7, 90.7, 70.9, 69.9, 68.1, 62.9, 18.7 ppm; HRMS (ESI): m/z calcd for C$_{22}$H$_{19}$Cl$_3$N$_4$O$_6$Na [M+Na]$^+$: 563.0262, found: 563.0251.

Methyl 4-azido-3-O-benzoyl-2-O-benzyl-4,6-dideoxy-α-D-mannopyranoside (55)

Benzoyl chloride (0.872 mL, 7.5 mmol) was added dropwise to a stirred solution of 54 (Peters & Bundle (1989) Can. J. Chem. 67, 497-502) (2.0 g, 6.82 mmol) in pyridine (10 mL) containing DMAP (0.166 g, 1.36 mmol) at 0° C. The resulting mixture was stirred under argon for 3 h at room temperature. Then CH$_3$OH (2 mL) was added to the reaction mixture which was stirred for 10 min, then diluted with CH$_2$Cl$_2$ (~80 mL) and washed with aq. HCl (1M, 2×50 mL), water (100 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (2.47 g, 91%) as oil. Analytical data for 55: Rf=0.50 (ethyl acetate/hexane, 1/9, v/v); $[\alpha]_D^{21}$=−18.8 (c=1.1, CHCl$_3$); $^1$H NMR (600 MHz, CDCl$_3$): δ 7.13-8.10 (m, 10H, H—Ar), 5.32 (dd, J$_{3,4}$=10.4 Hz, 1H, H-3), 4.71 (d, J$_{1,2}$=1.4 Hz, 1H, H-1), 3.37 (s, 3H, —OCH$_3$), 1.42 ppm (d, J$_{5,6}$=6.2 Hz, 3H, H-6); $^{13}$C NMR (126 MHz, CDCl$_3$): δ 165.5, 137.5, 133.3, 129.9, 129.5, 128.5, 128.3, 127.8 (×2), 98.9, 74.8, 73.3, 73.2, 67.0, 63.2, 55.0, 18.5 ppm; HRMS (ESI): m/z calcd for C$_{21}$H$_{23}$N$_3$O$_5$Na [M+Na]$^+$: 420.1530, found: 420.1521.

1-O-Acetyl-4-azido-3-O-benzoyl-2-O-benzyl-4,6-dideoxy-α-D-mannopyranose (56)

A solution of 55 (1.40 g, 3.52 mmol) in acetic anhydride/acetic acid/sulfuric acid (50:20:0.5, 35 mL) was stirred at room temperature for 3 h, and then poured into ice-cold 1M K$_2$CO$_3$ solution (100 mL). The mixture was then diluted with CH$_2$Cl$_2$ (~100 mL) and washed with water (2×80 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (1.22 g, 81%) as a white foam. Analytical data for 56: Rf=0.30 (ethyl acetate/hexane, 1/9, v/v); $[\alpha]_D^{21}$=−9.9=1.5, CHCl$_3$); $^1$H NMR (500 MHz, CDCl$_3$): δ 7.10-8.08 (m, 10H, H—Ar), 6.17 (d, J$_{1,2}$=1.3 Hz, 1H, H-1), 5.29 (dd, J$_{3,4}$=10.5 Hz, 1H, H-3), 4.00 (dd, J$_{2,3}$=3.5 Hz, 1H, H-2), 2.15 (s, 3H, —OC—CH$_3$), 1.42 ppm (d, J$_{5,6}$=6.1 Hz, 3H, H-6); $^{13}$C NMR (126 MHz, CDCl$_3$): δ 169.0, 165.6, 136.9, 133.5, 129.9, 129.2, 128.5, 128.4, 128.0, 127.9, 91.1, 73.5, 73.0, 72.7, 69.6, 62.6, 21.0, 18.5 ppm; HRMS (ESI): m/z calcd for C$_{22}$H$_{23}$N$_3$O$_6$Na [M+Na]$^+$: 448.1479, found: 448.1471.

4-Azido-3-O-benzoyl-2-O-benzyl-4,6-dideoxy-α/β-D-mannopyranose (57)

Hydrazine acetate (0.310 g, 3.35 mmol) was added to a stirred solution of 56 (1.190 g, 2.79 mmol) in DMF (10 mL) under argon atmosphere and stirred at 60° C. for 30 min. Then the mixture was cooled to room temperature, diluted with ethyl acetate (100 mL), washed with water (2×80 mL) and brine (30 mL). The organic phase was separated, dried over MgSO$_4$, and concentrated in vacuo. The residue was purified by column chromatography on silica gel (ethyl acetate-hexane gradient elution) to afford the title compound (0.912 g, 85%) as a white foam. Analytical data for 57: Rf=0.30 (ethyl acetate/hexane, 1/4, v/v); $^1$H NMR (500

MHz, CDCl$_3$): α:β ratio=5:1; δ 7.16-8.14 (m, 20H, H—Ar), 5.43 (dd, J$_{3,4}$=10.4 Hz, 1H, H-3$_α$), 5.27 (dd, =1.8 Hz, J$_{1,—OH}$=3.3 Hz, 1H, H-1$_α$), 5.13 (dd, J$_{3,4}$=10.5 Hz, 1H, H-3$_β$), 4.82 (dd, J$_{1,2}$=1.5 Hz, J$_{1,—OH}$=11.6 Hz, 1H, H-1$_β$), 4.14 (dd, J$_{2,3}$=3.0 Hz, 1H, H-2$_β$), 4.06 (dd, J$_{2,3}$=3.1 Hz, 1H, H-2$_α$), 1.46 (d, J$_{5,6}$=6.2 Hz, 3H, H-6$_β$), 1.42 ppm (d, J$_{5,6}$=6.1 Hz, 3H, H-6$_α$); $^{13}$C NMR (126 MHz, CDCl$_3$): δ 165.6 (×2), 137.4, 137.1, 133.8, 133.4, 129.9, 129.5, 128.9, 128.7, 128.5, 128.3 (×2), 128.2, 127.8, 127.8, 93.2, 92.7, 76.3, 75.8, 75.7, 75.0, 73.3, 72.9, 70.9, 67.2, 63.2, 62.6, 18.6, 18.5 ppm; HRMS (ESI): m/z calcd for C$_{20}$H$_{21}$N$_3$O$_5$Na [M+Na]$^+$: 406.1373, found: 406.1366.

4-Azido-3-O-benzoyl-2-O-benzyl-4,6-dideoxy-α-D-mannopyranosyl Trichloroacetimidate (58)

To a stirred solution of 57 (0.890 g, 2.32 mmol) in CH2Cl2 (15 mL) containing CCl3CN (4.65 mL, 46.4 mmol), DBU (70 μL, 0.464 mmol) was added at room temperature under argon atmosphere. After 10 min, solvents were evaporated in vacuo and the residue was purified by column chromatography on silica gel (ethyl acetate-hexane gradient elution) to afford the title compound (1.136 g, 93%) as an off-white foam. Analytical data for 58: Rf=0.80 (ethyl acetate/toluene, 1/9, v/v); [α]$_D^{21}$=−7.3 (c=1.5, CHCl$_3$); $^1$H NMR (600 MHz, CDCl$_3$): δ 8.66 (s, 1H, —C=NH), 7.12-8.10 (m, 10H, H—Ar), 6.36 (d, J$_{1,2}$=1.8 Hz, 1H, H-1), 5.39 (dd, J$_{3,4}$=7.2 Hz, 1H, H-3), 4.26 (dd, J$_{1,2}$=3.1 Hz, 1H, H-2), 3.91-3.99 (m, 2H, H-4, H-5), 1.48 ppm (d, J$_{5,6}$=6.0 Hz, 3H, H-6); $^{13}$C NMR (126 MHz, CDCl$_3$): δ 165.5, 160.4, 137.0, 133.5, 129.9, 129.2, 128.5, 128.4, 128.0 (×2), 127.9, 95.3, 90.8, 73.2, 73.0, 72.8, 70.1, 62.5, 18.6 ppm; HRMS (ESI): m/z calcd for C$_{22}$H$_{21}$Cl$_3$N$_4$O$_5$Na [M+Na]$^+$: 549.0470, found: 549.0465.

Methyl 4-azido-2-O-benzoyl-3-O-benzyl-4,6-dideoxy-α-D-mannopyranoside (59)

Benzoyl chloride (0.872 mL, 7.5 mmol) was added dropwise to a stirred solution of 4 (2.0 g, 6.82 mmol) in pyridine (10 mL) containing DMAP (0.166 g, 1.36 mmol) at 0° C. The resulting mixture was stirred under argon for 3 h at room temperature. Then CH$_3$OH (2 mL) was added to the reaction mixture, stirred for 10 min, then diluted with CH$_2$Cl$_2$ (~80 mL) and washed with aq. HCl (1M, 2×50 mL), water (100 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (2.32 g, 86%) as a white foam. Analytical data for 59: Rf=0.50 (ethyl acetate/hexane, 1/9, v/v); [α]$_D^{21}$=−27.9 (c=1.7, CHCl$_3$); $^1$H NMR (500 MHz, CDCl$_3$): δ 7.21-8.10 (m, 10H, H—Ar), 5.55 (dd, J$_{2,3}$=3.2 Hz, 1H, H-2), 4.77 (d, J$_{1,2}$=1.8 Hz, 1H, H-1), 3.91 (dd, J$_{3,4}$=9.7 Hz, 1H, H-3), 3.37 (s, 3H, —OCH$_3$), 1.38 ppm (d, J$_{5,6}$=6.0 Hz, 3H, H-6); $^{13}$C NMR (126 MHz, CDCl$_3$): δ 165.6, 137.3, 133.3, 129.9, 129.7, 128.4, 128.3, 128.1, 127.8, 98.8, 76.1, 71.4, 67.8, 66.8, 64.3, 55.1, 18.7 ppm; HRMS (ESI): m/z calcd for C$_{21}$H$_{23}$N$_3$O$_5$Na [M+Na]$^+$: 420.1530, found: 420.1528.

1-O-Acetyl-4-azido-2-O-benzoyl-3-O-benzyl-4,6-dideoxy-α/β-D-mannopyranose (60)

A solution of 59 (2.06 g, 5.19 mmol) in acetic anhydride/acetic acid/sulfuric acid (50:20:0.5, 35 mL) was stirred at room temperature for 3 h, and then poured into ice-cold 1M K$_2$CO$_3$ solution (100 mL). The mixture was then diluted with CH$_2$Cl$_2$ (~100 mL) and washed with water (2×80 mL), 5% aq. NaHCO$_3$ (50 mL), and brine (30 mL). The organic phase was separated, dried over MgSO$_4$, and concentrated in vacuo. The residue was purified by column chromatography on silica gel (ethyl acetate-hexane gradient elution) to afford the title compound (1.95 g, 89%) as a white foam.] α:β ratio=9:1 (isolated yield); Analytical data for 60: α/β ratio=9:1 (isolated yield); α-anomer: Rf=0.45 (ethyl acetate/hexane, 1.5/8.5, v/v); [α]$_D^{21}$=+1.8 (c=1.9, CHCl$_3$); NMR (500 MHz, CDCl$_3$): δ 7.27-8.09 (m, 10H, H—Ar), 6.16 (d, J$_{1,2}$=2.0 Hz, 1H, H-1), 2.13 (s, 3H, —OC—CH$_3$), 1.40 ppm (d, J$_{5,6}$=6.0 Hz, 3H, H-6); $^{13}$C NMR (126 MHz, CDCl$_3$): δ 168.3, 165.3, 136.9, 133.5, 129.9, 129.3, 128.5, 128.4, 128.2, 128.0, 91.1, 75.8, 71.6, 69.3, 66.7, 63.8, 20.9, 18.7 ppm; HRMS (ESI): m/z calcd for C$_{22}$H$_{23}$N$_3$O$_6$Na [M+Na]$^+$: 448.1479, found: 448.1475; β-anomer: Rf=0.40 (ethyl acetate/hexane, 1.5/8.5, v/v); [α]$_D^{21}$=−50.2 (c=1.2, CHCl$_3$); $^1$H NMR (500 MHz, CDCl$_3$): δ 7.27-8.13 (m, 10H, H—Ar), 5.82 (dd, J$_{2,3}$=3.5 Hz, 1H, H-2), 5.77 (d, J$_{1,2}$=1.5 Hz, 1H, H-1), 2.03 (s, 3H, —OC—CH$_3$,), 1.46 ppm (d, J$_{5,6}$=6.0 Hz, 3H, H-6); $^{13}$C NMR (126 MHz, CDCl$_3$): δ 168.8, 165.8, 136.6, 133.4, 130.0, 129.5, 128.5 (×2), 128.3, 128.1, 91.2, 78.1, 72.1, 71.4, 66.8, 63.6, 20.8, 18.6 ppm; HRMS (ESI): m/z calcd for C$_{22}$H$_{23}$N$_3$O$_6$Na [M+Na]$^+$: 448.1479, found: 448.1474.

4-Azido-2-O-benzoyl-3-O-benzyl-4,6-dideoxy-α/β-D-mannopyranose (61)

Hydrazine acetate (0.572 g, 6.20 mmol) was added to a stirred solution of 60 (2.20 g, 5.17 mmol) in DMF (7 mL) under argon atmosphere and stirred at 60° C. for 30 min. Then the mixture was cooled to room temperature, diluted with ethyl acetate (100 mL), washed with water (2×80 mL) and brine (30 mL). The organic phase was separated, dried over MgSO$_4$, and concentrated in vacuo. The residue was purified by column chromatography on silica gel (ethyl acetate-hexane gradient elution) to afford the title compound (1.83 g, 93%) as a white foam. Analytical data for 61: Rf=0.30 (ethyl acetate/hexane, 1/4, v/v); NMR (500 MHz, CDCl$_3$): α/β ratio=5:1; 7.25-8.15 (m, 20H, H—Ar), 5.74 (dd, J$_{2,3}$=3.5 Hz, 1H, H-2β), 5.60 (dd, J$_{2,3}$=3.1 Hz, 1H, H-2$_α$), 5.32 (d, J$_{1,2}$=1.3 Hz, 1H, H-1$_α$), 4.89 (s, 1H, H-1$_β$), 1.47 (d, J$_{5,6}$=6.2 Hz, 3H, H-6β), 1.40 ppm (d, J$_{5,6}$=6.1 Hz, 3H, H-6$_α$); $^{13}$C NMR (126 MHz, CDCl$_3$): δ 166.3, 165.7, 137.2, 136.8, 133.3, 130.0, 129.9, 129.3, 129.2, 128.5, 128.4 (×2), 128.3, 128.2, 128.0, 127.8, 93.2, 92.5, 78.5, 75.6, 71.5 (×2), 71.3, 69.2, 68.2, 67.1, 64.3, 63.7, 18.7 (×2) ppm; HRMS (ESI): m/z calcd for C$_{20}$H$_{21}$N$_3$O$_5$Na [M+Na]$^+$: 406.1373, found: 406.1374.

4-Azido-2-O-benzoyl-3-O-benzyl-4,6-dideoxy-α-D-mannopyranosyl Trichloroacetimidate (62)

To a stirred solution of 61 (1.820 g, 4.75 mmol) in CH2Cl2 (20 mL) containing CCl3CN (9.50 mL, 95.0 mmol), DBU (140 μL, 0.95 mmol) was added at room temperature under argon atmosphere. After 10 min, solvents were evaporated in vacuo and the residue was purified by column chromatography on silica gel (ethyl acetate-hexane gradient elution) to afford the title compound (2.0 g, 80%) as an off-white foam. Analytical data for 62: Rf=0.60 (ethyl acetate/hexane, 1/4, v/v); [α]$_D^{21}$=−10.8 (c=1.0, CHCl$_3$); $^1$H NMR (500 MHz, CDCl$_3$): δ 8.70 (s, 1H, —C=NH), 7.28-8.12 (m, 10H, H—Ar), 6.31 (d, J$_{1,2}$=1.8 Hz, 1H, H-1), 5.67 (dd, J$_{2,3}$=3.5 Hz, 1H, H-2), 3.98 (dd, J$_{3,4}$=10.0 Hz, 1H, H-3), 3.57-3.66 (dd, $J_{4,5}$=10.0 Hz, 1H, H-4), 1.38-1.44 ppm (d, $J_{5,6}$=6.5 Hz, 3H, H-6); $^{13}$C NMR (126 MHz, CDCl$_3$): δ 165.3, 159.8, 136.7, 133.5, 129.9, 129.3, 128.6 (×3), 128.5 (×2), 128.4, 128.1, 95.0, 90.7, 75.2, 71.6, 69.9, 66.4, 63.7, 18.7 ppm; HRMS (ESI): m/z calcd for $C_{22}H_{21}C_{13}N_4O5Na$ [M+Na]$^+$: 549.0470, found: 549.0475.

Ethyl 4-azido-2,3-di-O-benzoyl-4,6-dideoxy-α-D-mannopyranosyl (1→2) 4-azido-3-O-benzyl-4,6-dideoxy-1-thio-α-D-mannopyranoside (63)

A mixture of glycosyl donor 53 (1.010 g, 1.87 mmol), glycosyl acceptor 13 Peters & Bundle (1989) Can. J. Chem. 67, 491-496) (0.550 g, 1.70 mmol), and freshly activated molecular sieves (3 Å, 2.0 g) in CH$_2$Cl$_2$ (30 mL) was stirred under argon for 5 h at room temperature. TMSOTf (67 μL, 0.374 mmol) was added and the resulting mixture was stirred for an additional 60 min. Then Et$_3$N (1 mL) was added, the solid was filtered off and the residue was rinsed with CH$_2$Cl$_2$ (3×20 mL). The combined filtrate (~100 mL) was washed with 20% aq. NaHCO$_3$ (50 mL), water (50 mL), and brine (30 mL). The organic phase was separated, dried over MgSO$_4$, and concentrated in vacuo. The residue was purified by column chromatography on silica gel (ethyl acetate-toluene gradient elution) to afford the title compound (1.073 g, 90%) as a white foam. Analytical data for 63: Rf=0.70 (ethyl acetate/toluene, 1/9, v/v); $[α]_D^{21}$=−18.4 (c=1.1, CHCl$_3$); $^1$H NMR (600 MHz, CDCl$_3$): δ 7.12-8.03 (m, 15H, H—Ar), 5.70 (dd, $J_{2,3}$=3.2 Hz, 1H, H-2$^B$), 5.62 (dd, $J_{3,4}$=10.3 Hz, 1H, H-3$^B$), 5.24 (d, $J_{1,2}$=1.5 Hz, 1H, H-1$^A$), 4.98 (d, $J_{1,2}$=1.5 Hz, 1H, H-1$^B$), 2.54-2.67 (m, 2H, S—CH$_2$—), 1.44 (d, $J_{5,6}$=6.2 Hz, 3H, H-6$^B$), 1.37 (d, $J_{5,6}$=6.1 Hz, 3H, H-6$^A$), 1.29 ppm (t, J=7.4 Hz, 3H, S—CH$_2$—CH$_3$); $^{13}$C NMR (126 MHz, CDCl$_3$): δ 165.2, 164.9, 137.4, 133.4, 133.3, 129.8 (×2), 129.5, 129.3, 128.5 (×2), 128.4, 128.1, 127.9, 99.4, 83.3, 78.4, 76.5, 72.4, 70.8, 69.5, 67.8, 67.6, 64.2, 63.5, 25.6, 18.6, 18.4, 14.9 ppm; HRMS (ESI): m/z calcd for $C_{35}H_{38}N_6O_8SNa$ [M+Na]$^+$: 725.2364, found: 725.2350.

Ethyl 4-azido-2-O-benzoyl-3-O-benzyl-4,6-dideoxy-α-D-mannopyranosyl (1→2) 4-azido-3-O-benzyl-4,6-dideoxy-1-thio-α-D-mannopyranoside (64)

A mixture of glycosyl donor 62 (1.980 g, 3.76 mmol), glycosyl acceptor 13 (1.106 g, 3.42 mmol), and freshly activated molecular sieves (3 Å, 4.0 g) in CH$_2$Cl$_2$ (30 mL) was stirred under argon for 5 h at room temperature. TMSOTf (0.136 mL, 0.753 mmol) was added and the resulting mixture was stirred for additional 1 h. Then Et$_3$N (1 mL) was added, the solid was filtered off and the residue was rinsed with CH$_2$Cl$_2$ (3×30 mL). The combined filtrate (~120 mL) was washed with 20% aq. NaHCO$_3$ (50 mL), water (50 mL), and brine (30 mL). The organic phase was separated, dried over MgSO$_4$, and concentrated in vacuo. The residue was purified by column chromatography on silica gel (ethyl acetate-toluene gradient elution) to afford the title compound (2.010 g, 85%) as a white foam. Analytical data for 64: Rf=0.50 (ethyl acetate/hexane, 1/9, v/v); $[α]_D^{21}$=+50.0 (c=1.4, CHCl$_3$); NMR (500 MHz, CDCl$_3$): δ 7.21-8.11 (m, 15H, H—Ar), 5.63 (dd, $J_{2,3}$=2.5 Hz, 1H, H-2$^B$), 5.22 (d, $J_{1,2}$=1.0 Hz, 1H, H-1$^A$), 4.95 (d, $J_{1,2}$=1.7 Hz, 1H, H-1$^B$), 2.50-2.69 (m, 2H, S—CH$_2$—), 1.37 (d, $J_{5,6}$=6.2 Hz, 3H, H-6$^B$), 1.33 (d, $J_{5,6}$=6.2 Hz, 3H, H-6$^A$), 1.28 ppm (t, J=7.3 Hz, 3H, S—CH$_2$—CH$_3$); $^{13}$C NMR (126 MHz, CDCl$_3$): δ 165.3, 137.3, 137.1, 133.3, 129.9, 129.7, 128.6, 128.5, 128.4 (×2), 128.2, 128.1, 127.9, 99.6, 83.3, 78.1, 76.6, 75.3, 72.3, 71.4, 67.7, 67.6, 64.4, 64.1, 25.6, 18.7, 18.5, 14.9 ppm; HRMS (ESI): m/z calcd for $C_{35}H_{14}N_6O_7SNa$ [M+Na]$^+$: 711.2571, found: 711.2570.

5′-Methoxycarbonylpentyl 4-azido-2,3-di-O-benzoyl-4,6-dideoxy-α-D-mannopyranosyl (1→3) 4-azido-2-O-benzyl-4,6-dideoxy-α-D-mannopyranoside (67)

A mixture of glycosyl donor 53 (0.292 g, 0.540 mmol), glycosyl acceptor 65 (Saksena et al. (2008) Carbohydr. Res. 343, 1693-1706) (0.200 g, 0.491 mmol) and freshly activated molecular sieves (3 Å, 0.6 g) in CH$_2$Cl$_2$ (8 mL) was stirred under argon for 5 h at room temperature. TMSOTf (20 μL, 0.108 mmol) was added and the resulting mixture was stirred for an additional hour. Then Et$_3$N (1 mL) was added, the solid was filtered off and the residue was rinsed with CH$_2$Cl$_2$ (3×20 mL). The combined filtrate (80 mL) was washed with 20% aq. NaHCO$_3$ (40 mL), water (30 mL), and brine (20 mL). The organic phase was separated, dried over MgSO$_4$, and concentrated in vacuo. The residue was purified by column chromatography on silica gel (ethyl acetate-toluene gradient elution) to afford the title compound (0.374 g, 97%) as a white foam. Analytical data for 67: Rf=0.40 (ethyl acetate/toluene, 0.5/9.5, v/v); $[α]_D^{21}$=−41.2 (c=1.6, CHCl$_3$); $^1$H NMR (600 MHz, CDCl$_3$): δ 7.29-8.06 (m, 15H, H—Ar), 5.72 (dd, $J_{2,3}$=3.3 Hz, 1H, H-2$^B$), 5.66 (dd, $J_{3,4}$=10.3 Hz, 1H, H-3$^B$), 5.29 (d, $J_{1,2}$=1.8 Hz, 1H, H-1$^B$), 4.82 (d, $4_2$=1.8 Hz, 1H, H-1$^A$), 4.73 3.66 (s, 3H, —OCH$_3$), 1.37 (d, $J_{5,6}$=6.0 Hz, 3H, H-6$^B$), 1.36 (d, $J_{5,6}$=6.0 Hz, 3H, H-6$^A$); $^{13}$C NMR (126 MHz, CDCl$_3$): δ 174.0, 165.2, 165.1, 137.6, 133.5, 133.3, 129.8, 129.4, 129.3, 128.6, 128.5, 128.4, 127.9, 127.6, 99.2, 97.0, 78.6, 72.5, 70.7, 70.0, 67.7, 67.6 (×2), 64.7, 63.4, 51.5, 33.9, 29.0, 25.7, 24.6, 18.6, 18.5 ppm; HRMS (ESI): m/z calcd for $C_{40}H_{46}N_6O_{11}Na$ [M+Na]$^+$: 809.3117, found: 809.3107.

5′-Methoxycarbonylpentyl 4-azido-2,3-di-O-benzoyl-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranoside (68)

A mixture of glycosyl donor 63 (0.151 g, 0.216 mmol), glycosyl acceptor 65 (Saksena et al. (2008) Carbohydr. Res. 343, 1693-1706) (0.080 g, 0.196 mmol) and freshly activated molecular sieves (3 Å, 0.5 g) in CH$_2$Cl$_2$ (4 mL) was stirred under argon for 5 h at room temperature. MeOTf (133 μL, 1.17 mmol) was added and stirring was continued for additional 48 h. Then Et$_3$N (1 mL) was added, the solid was filtered off and the residue was rinsed with CH$_2$Cl$_2$ (3×20 mL). The combined filtrate (70 mL) was washed with 20% aq. NaHCO$_3$ (40 mL), water (30 mL), and brine (20 mL). The organic phase was separated, dried over MgSO$_4$, and concentrated in vacuo. The residue was purified by column chromatography on silica gel (ethyl acetate-toluene gradient elution) to afford the title compound (0.182 g, 89%) as a white foam. Analytical data for 68: Rf=0.40 (ethyl acetate/toluene, 0.5/9.5, v/v); $[α]_D^{21}$=−27.7 (c=2.4, CHCl$_3$); $^1$H NMR (600 MHz, CDCl$_3$): δ 7.06-8.01 (m, 20H, H—Ar), 5.71 (dd, $J_{2,3}$=3.3 Hz, 1H, H-2$^C$), 5.58 (dd, $J_{3,4}$=10.4 Hz, 1H, H-3$^C$), 5.07 (s, 2H, H-1$^B$, H-1$^C$), 4.78 (d, $J_{1,2}$=1.5 Hz, 1H, H-1$^A$), 1.46 (d, $J_{5,6}$=6.2 Hz, 3H, H-6$^C$), 1.34 (d, $J_{5,6}$=6.5 Hz, 3H, H-6$^B$), 1.32 ppm (d, $J_{5,6}$=6.2 Hz, 3H, H-6$^A$); $^{13}$C NMR (126 MHz, CDCl$_3$): δ 174.0, 165.2, 164.9, 137.6, 137.4, 133.4, 133.2, 129.8, 129.7, 129.5, 129.3, 128.5 (×2), 128.4, 128.2, 127.9, 127.8, 127.7, 127.6, 101.0, 99.2, 97.0, 78.2, 77.8, 73.4, 72.6, 72.1, 70.9, 69.3, 68.2, 67.7, 67.3, 64.9, 63.7, 63.4, 51.5, 33.9, 29.0, 25.7, 24.6, 18.6 (×2), 18.5 ppm; HRMS (ESI): m/z calcd for $C_{53}H_{61}N_9O_{14}Na$ $[M+Na]^+$: 1070.4230, found: 1070.4233.

5'-Methoxycarbonylpentyl 4-azido-3-O-benzoyl-2-O-benzyl-4,6-dideoxy-α-D-mannopyranosyl (1→2) 2) 4-azido-3-O-benzyl-4,6-dideoxy-α-D-mannopyranoside (69)

A mixture of glycosyl donor 53 (0.168 g, 0.318 mmol), glycosyl acceptor 66 Saksena et al. (2005) Tetrahedron: Asymmetry 16, 187-197) (0.118 g, 0.289 mmol) and freshly activated molecular sieves (3 Å, 0.350 g) in PhMe (3 mL) was stirred under argon for 2 h at room temperature. Then it was heated to 95° C. and TMSOTf (12 μL, 0.064 mmol) was added, and the mixture stirred for additional 1 h. Then Et₃N (1 mL) was added, the solid was filtered off and the residue was rinsed with $CH_2Cl_2$ (3×30 mL). The combined filtrate (100 mL) was washed with 20% aq. $NaHCO_3$ (50 mL), water (30 mL), and brine (30 mL). The organic phase was separated, dried over $MgSO_4$, and concentrated in vacuo. The residue was purified by column chromatography on silica gel (ethyl acetate-toluene gradient elution) to afford the title compound (0.203 g, 91%) as a white foam. Analytical data for 69: Rf=0.40 (ethyl acetate/toluene, 0.5/9.5, v/v); $[\alpha]_D^{21}$=−4.4 (c=1.2, $CHCl_3$); $^1H$ NMR (500 MHz, $CDCl_3$): δ 7.00-8.06 (m, 15H, H—Ar), 5.30 (dd, $J_{3,4}$=9.9 Hz, 1H, H-$3^B$), 5.07 (d, $J_{1,2}$=1.7 Hz, 1H, H-$1^B$), 4.70 (d, $J_{1,2}$=1.8 Hz, 1H, H-$1^A$), 3.69 (s, 3H, —OCH₃), 1.39 (d, J=5.9 Hz, 3H, H-$6^A$), 1.34 ppm (d, J=5.7 Hz, 3H, H-$6^B$); $^{13}C$ NMR (126 MHz, $CDCl_3$): δ 174.0, 165.4, 137.4, 137.3, 133.2, 129.8, 129.5, 128.5, 128.4, 128.2, 128.1, 127.8, 127.6, 99.1, 98.8, 78.6, 74.4, 73.3, 72.8, 72.6, 72.5, 67.6, 67.4, 67.3, 64.3, 63.1, 51.5, 33.9, 29.1, 25.7, 24.7, 18.5 (×2) ppm; HRMS (ESI): m/z calcd for $C_{40}H_{48}N_6O_{10}Na$ $[M+Na]^+$: 795.3324, found: 795.3314.

5'-Methoxycarbonylpentyl 4-azido-2-O-benzyl-4,6-dideoxy-α-D-mannopyranosyl (1→2) 4-azido-3-O-benzyl-4,6-dideoxy-α-D-mannopyranoside (70)

Sodium methoxide (~0.5 mL, 0.5 M solution) was added to a solution of 69 (0.910 g, 1.178 mmol) in $CH_3OH$ (20 mL) until pH ~9 and the resulting mixture was stirred under argon for 4 h at room temperature. Then the reaction mixture was neutralized with Amberlite IR 120 ($H^+$) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.755 g, 96%) as oil. Analytical data for 70: Rf=0.50 (ethyl acetate/toluene, 1/9, v/v); $[\alpha]_D^{21}$=+43.2 (c=1.2, $CHCl_3$); NMR (500 MHz, $CDCl_3$): δ 7.11-7.41 (m, 10H, H—Ar), 5.11 (d, $J_{1,2}$=1.3 Hz, 1H, H-$1^B$), 4.65 (d, =2.0 Hz, 1H, H-$1^A$), 3.68 (s, 3H, —OCH₃), 1.30 (d, $J_{5,6}$=6.5 Hz, 3H, H-$6^A$), 1.29 ppm (d, $J_{5,6}$=6.2 Hz, 3H, H-$6^B$); $^{13}C$ NMR (126 MHz, $CDCl_3$): δ 174.0, 137.3, 137.1, 128.6, 128.5, 128.2, 128.1, 128.0, 98.8, 97.9, 78.5, 76.5, 72.9, 72.6, 72.1, 69.8, 67.5, 67.2, 67.1, 66.4, 64.6, 51.5, 33.9, 29.0, 25.7, 24.7, 18.5, 18.4 ppm; HRMS (ESI): m/z calcd for $C_{33}H_{44}N_6O_9Na$ $[M+Na]^+$: 691.3062, found: 691.3054.

5'-Methoxycarbonylpentyl 4-azido-2,3-di-O-benzoyl-4,6-dideoxy-α-D-mannopyranosyl (1→3) 4-azido-2-O-benzyl-4,6-dideoxy-α-D-mannopyranosyl (1→2) 4-azido-3-O-benzyl-4,6-dideoxy-α-D-mannopyranoside (71)

A mixture of glycosyl donor 53 (0.124 g, 0.230 mmol), glycosyl acceptor 70 (0.140 g, 0.210 mmol) and freshly activated molecular sieves (3 Å, 0.5 g) in $CH_2Cl_2$ (4 mL) was stirred under argon for 5 h at room temperature. TMSOTf (8 μL, 0.046 mmol) was added and the resulting mixture was stirred for an additional hour. Then Et₃N (1 mL) was added, the solid was filtered off and the residue was rinsed with $CH_2Cl_2$ (3×20 mL). The combined filtrate (80 mL) was washed with 20% aq. $NaHCO_3$ (50 mL), water (30 mL), and brine (20 mL). The organic phase was separated, dried over $MgSO_4$, and concentrated in vacuo. The residue was purified by column chromatography on silica gel (ethyl acetate-toluene gradient elution) to afford the title compound (0.210 g, 96%) as a white foam. Analytical data for 71: Rf=0.40 (ethyl acetate/toluene, 0.5/9.5, v/v); $[\alpha]_D^{21}$=−29.0 (c=1.2, $CHCl_3$); NMR (500 MHz, $CDCl_3$): δ 7.22-8.07 (m, 20H, H—Ar), 5.70 (dd, $J_{2,3}$=3.4 Hz, 1H, H-$2^C$), 5.59 (dd, $J_{3,4}$=9.8 Hz, 1H, H-$3^C$), 5.26 (d, $J_{1,2}$=1.8 Hz, 1H, H-$1^C$), 5.10 (d, $J_{1,2}$=1.6 Hz, 1H, H-$1^B$), 4.67 (d, $J_{1,2}$=1.8 Hz, 1H, H-$1^A$), 3.68 (s, 3H, —OCH₃), 1.35 (d, $J_{5,6}$=6.0 Hz, 3H, H-$6^C$), 1.29 (d, $J_{5,6}$=6.0 Hz, 3H, H-$6^A$), 1.28 ppm (d, $J_{5,6}$=6.0 Hz, 3H, H-$6^B$); $^{13}C$ NMR (126 MHz, $CDCl_3$): δ 174.0, 165.2, 165.0, 137.4, 137.3, 133.4, 133.2, 129.8 (×2), 129.4, 129.3, 128.6, 128.5 (×2), 128.3, 128.2, 128.1, 127.8, 127.6, 99.1, 98.8, 98.4, 78.4, 77.6, 76.1, 73.4, 72.4, 71.8, 70.7, 69.8, 68.2, 67.7, 67.5, 67.1, 64.7, 64.5, 63.3, 51.5, 33.9, 29.0, 25.7, 24.7, 18.6 (×2), 18.5 ppm; HRMS (ESI): m/z calcd for $C_{53}H_{61}N_9O_{14}Na$ $[M+Na]^+$: 1070.4230, found: 1070.4249.

5'-Methoxycarbonylpentyl 4-azido-2,3-di-O-benzoyl-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranosyl (1→2) 4-azido-3-O-benzyl-4,6-dideoxy-α-D-mannopyranoside (72)

A mixture of glycosyl donor 63 (0.208 g, 0.296 mmol), glycosyl acceptor 70 (0.180 g, 0.269 mmol) and freshly activated molecular sieves (3 Å, 0.5 g) in $CH_2Cl_2$ (4 mL) was stirred under argon for 4 h at room temperature. MeOTf (213 μL, 1.88 mmol) was added and continued stirring for additional 48 h. Then Et₃N (1 mL) was added, the solid was filtered off and the residue was rinsed with $CH_2Cl_2$ (3×20 mL). The combined filtrate (70 mL) was washed with 20% aq. $NaHCO_3$ (40 mL), water (30 mL), and brine (20 mL). The organic phase was separated, dried over $MgSO_4$, and concentrated in vacuo. The residue was purified by column chromatography on silica gel (ethyl acetate-toluene gradient elution) to afford the title compound (0.321 g, 91%) as a white foam. Analytical data for 72: Rf=0.30 (ethyl acetate/toluene, 0.5/9.5, v/v); $[\alpha]_D^{21}$=−17.9 (c=1.0, $CHCl_3$); $^1H$ NMR (600 MHz, $CDCl_3$): δ 7.05-8.00 (m, 25H, H—Ar), 5.71 (dd, $J_{2,3}$=3.3 Hz, 1H, H-$2^D$), 5.58 (dd, $J_{3,4}$=10.3 Hz, 1H, H-$3^D$), 5.09 (d, $J_{1,2}$=1.5 Hz, 1H, H-$1^B$), 5.07 (d, $J_{1,2}$=1.6 Hz, 1H, H-$1^C$), 5.04 (d, $J_{1,2}$=1.6 Hz, 1H, H-$1^D$), 1.31-1.35 (m, 6H, H-$6^A$, H-$6^B$), 1.26 ppm (d, $J_{5,6}$=6.2 Hz, 3H, H-$6^C$); $^{13}C$ NMR (126 MHz, $CDCl_3$): δ 174.0, 165.2, 164.8, 137.5, 137.4, 137.3, 133.3, 133.2, 129.8, 129.7, 129.5, 129.3, 128.5 (×2), 128.4, 128.3, 128.2, 128.0, 127.8 (×2), 127.7, 127.6, 100.8, 99.2, 98.8, 98.3, 78.4, 77.9, 77.4, 76.4, 73.7, 73.2, 72.5, 72.1, 71.9, 70.9, 69.3, 68.1, 67.9, 67.7, 67.5, 67.2, 64.6, 63.6, 63.4, 51.5, 33.9, 29.1, 25.7, 24.7, 18.6 (×2), 18.5 ppm; HRMS (ESI): m/z calcd for $C_{66}H_{76}N_{12}O_{17}Na$ $[M+Na]^+$: 1331.5344, found: 1331.5341.

5'-Methoxycarbonylpentyl 4-azido-4,6-dideoxy-α-D-mannopyranosyl (1→3) 4-azido-2-O-benzyl-4,6-dideoxy-α-D-mannopyranoside (67a)

Sodium methoxide (0.2 mL, 0.5 M solution) was added to a solution of 67 (0.350 g, 0.445 mmol) in $CH_3OH$ (5 mL)

until pH ~9 and the resulting mixture was stirred under argon for 4 h at room temperature. Then the reaction mixture was neutralized with Amberlite IR 120 (H$^+$) ion exchange resin, the resin was filtered off and rinsed successively with CH$_3$OH. The combined filtrate was concentrated in vacuo and purified by column chromatography on silica gel (ethyl acetate-toluene gradient elution) to afford the title compound (0.221 g, 86%) as a white foam. Analytical data for 67a: Rf=0.50 (CH$_3$OH/CH$_2$Cl$_2$, 0.5/9.5, v/v); [α]$_D^{21}$=+73.4 (c=1.0, CHCl$_3$); NMR (500 MHz, CDCl$_3$): δ 7.28-7.41 (m, 5H, H—Ar), 5.07 (s, 1H, H-1$^B$), 4.78 (s, 1H, H-1$^A$), 1.32 (d, J$_{5,6}$=6.2 Hz, 3H, H-6$^A$), 1.27 ppm (d, J$_{5,6}$=6.2 Hz, 3H, H-6$^B$); $^{13}$C NMR (126 MHz, CDCl$_3$): δ 174.1, 137.6, 128.5, 127.9, 127.6, 101.5, 96.9, 78.3, 76.9, 72.4, 70.3, 70.2, 67.7, 67.5, 67.3, 65.7, 64.7, 51.5, 33.9, 29.0, 25.7, 24.6, 18.5, 18.3 ppm; HRMS (ESI): m/z calcd for C$_{26}$H$_{38}$N$_6$O$_9$Na [M+Na]$^+$: 601.2592, found: 601.2581.

5'-Methoxycarbonylpentyl 4,6-dideoxy-4-formamido-α-D-mannopyranosyl (1→3) 4,6-dideoxy-4-formamido-α-D-mannopyranoside (44)

To a stirred solution of 67a (0.150 g, 0.259 mmol), in a pyridine (5 mL) and water (2 mL) mixture, H$_2$S was bubbled for 0.5 h at 40° C., and then stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 67b and no products arising from incomplete reduction. HRMS (ESI): m/z calcd for C$_{26}$H$_{43}$N$_2$O$_9$ [M+H]$^+$: 527.2963; found: 527.2964. This crude material was directly used for formylation.

Compound 67b in CH$_3$OH (5 mL) at −20° C. was added a freshly prepared formic anhydride[22] (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 67c. HRMS (ESI): m/z calcd for C$_{28}$H$_{42}$N$_2$NaO$_{11}$ [M+Na]$^+$: 605.2681; found: 605.2675.

Compound 67c was dissolved in CH$_3$OH/H$_2$O (2:1, 6 mL), Pd(OH)$_2$ on carbon (20%, 0.050 g) was added. Then it was stirred under a pressure of hydrogen gas at room temperature for 16 h. After filtration through celite pad and washed with CH$_3$OH (3×10 mL), and solvents were removed in vacuo. The residue was purified by column chromatography on silica gel (methanol-dichloromethane gradient elution) to afford the title compound (0.075 g, 59%, over 3 steps) as a white foam. Analytical data for 44: Rf=0.20 (CH$_3$OH/CH$_2$Cl$_2$, 1.5/8.5, v/v); NMR (700 MHz, D$_2$O): δ 8.21 ((d, J=15.4 Hz) and 8.03 (d, J=13.3 Hz), 2H, NCHO), 4.81-4.95 (m, 2H, 2×H-1), 3.70 (s, 3H, —OCH$_3$), 1.20-1.30 ppm (m, 6H, 2×H-6); $^{13}$C NMR (126 MHz, D$_2$O): δ 178.5, 168.9, 168.8, 165.8, 165.7, 103.3, 103.2, 100.6, 100.5, 77.8 (×2), 70.2, 70.0, 69.9 (×2), 69.0, 68.9 (×2), 68.8 (×2), 68.6, 68.4, 68.2, 67.8, 57.6, 56.5, 53.1, 52.7, 52.6, 51.6, 34.6, 29.1, 25.9, 25.0, 17.8, 17.7, 17.6 ppm; HRMS (ESI): m/z calcd for C$_{21}$H$_{36}$N$_2$O$_{H}$Na [M+Na]$^+$: 515.2211, found: 515.2210.

(2'-Aminoethylamido)carbonylpentyl 4,6-dideoxy-4-formamido-α-D-mannopyranosyl (1→3) 4,6-dideoxy-4-formamido-α-D-mannopyranoside (81)

A solution of 44 (0.009 g, 0.018 mmol) in freshly distilled 1,2-diaminoethane (0.5 mL) was stirred at 65° C. for 48 h.

Then excess reagent was removed in vacuo, and the residue was co-evaporated with CH$_3$OH (3×10 mL) and dried. The residue was purified by reversed phase HPLC on C18 column in gradient water-acetonitrile and lyophilized, to give the title compound (0.0075 g, 79%) as a white foam. Analytical data for 81: Rf=0.15 (CH$_3$OH/CH$_2$Cl$_2$, 1/1, v/v); $^1$H NMR (700 MHz, D$_2$O): δ 8.19-8.22 (Z) and 8.01-8.02 (E) (m, 2H, NCHO), 4.80-4.95 (m, 2H, 2×H-1), 1.19-1.30 ppm (m, 6H, 2×H-6); $^{13}$C NMR (126 MHz, D$_2$O): δ 178.4, 168.9, 168.8, 165.8, 165.7, 103.6, 103.3 (×2), 100.6, 100.5, 77.8, 77.4, 71.1, 70.4, 70.2, 70.0, 69.8, 69.0, 68.9, 68.8 (×3), 68.6, 68.4, 68.2, 67.8, 57.6, 56.5, 54.5, 52.6, 51.8, 51.6, 41.7, 41.4, 40.9, 40.7, 36.7, 29.2, 26.0, 25.9, 17.9, 17.8, 17.7 (×2) ppm; HRMS (ESI): m/z calcd for C$_{22}$H$_{40}$N$_4$O$_{10}$Na [M+Na]$^+$: 543.2637, found: 543.2642.

1-[(2'-Aminoethylamido)carbonylpentyl 4,6-dideoxy-4-formamido-α-D-mannopyranosyl (1→3) 4,6-dideoxy-4-formamido-α-D-mannopyranoside]-2-butoxycyclobutene-3,4-dione (87)

To a stirred solution of 81 (0.0075 g, 0.014 mmol) in water (0.5 mL) and EtOH (0.4 mL), a solution of 3,4-dibutoxy-3-cyclobutene-1,2-dione (20% in ethanol, 70 μL) was added and the pH was adjusted to 8 by careful addition of aq. NaHCO$_3$ (1%) solution. After 0.5 h, TLC showed the reaction was complete; the reaction mixture was neutralized using CH$_3$COOH (10%) and concentrated in vacuo. The residue was purified by reversed phase HPLC on a C18 column with a gradient of water-acetonitrile and lyophilized, to give the title compound (0.0089 g, 92%) as a white foam. Analytical data for 87: Rf=0.20 (CH$_3$OH/CH$_2$Cl$_2$, 1.5/8.5, v/v); $^1$H NMR (500 MHz, D$_2$O): δ 8.26-8.30 (Z) and 8.09-8.12 (E) (m, 2H, NCHO), 4.83-5.03 (m, 2H, 2×H-1), 1.26-1.37 (m, 6H, 2×H-6), 0.99-1.05 ppm (m, 3H, —CH$_{31}$); $^{13}$C NMR (126 MHz, D$_2$O): δ 189.8, 189.6, 184.3 (×2), 178.5, 178.1, 178.0, 177.9, 174.8, 174.7, 168.9, 168.8, 165.8, 165.7, 103.3, 103.2, 100.5 (×2), 77.8, 75.4, 75.3, 70.2, 70.0, 69.9, 69.0, 68.9 (×2), 68.8, 68.7, 68.6, 68.4, 68.2, 67.7, 57.6, 56.5, 52.7, 52.6, 51.7, 45.2, 45.0, 40.3, 40.2, 36.7, 32.4, 31.2, 29.3 (×2), 26.2, 26.1, 25.9 (×2), 19.1, 19.0, 17.8 (×2), 17.7, 13.9 ppm; HRMS (ESI): m/z calcd for C$_{30}$H$_{48}$N$_4$O$_{13}$Na [M+Na]$^+$: 695.3110, found: 695.3113.

5'-Methoxycarbonylpentyl 4-azido-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranoside (68a)

Sodium methoxide (0.2 mL, 0.5 M solution) was added to a solution of 68 (0.352 g, 0.336 mmol) in CH$_3$OH (5 mL) until pH ~9 and the resulting mixture was stirred under argon for 4 h at room temperature. Then the reaction mixture was neutralized with Amberlite IR 120 (H$^+$) ion exchange resin, the resin was filtered off and rinsed successively with CH$_3$OH. The combined filtrate was concentrated in vacuo and purified by column chromatography on silica gel (ethyl acetate-toluene gradient elution) to afford the title compound (0.256 g, 91%) as an off-white foam. Analytical data for 68a: Rf=0.30 (ethyl acetate/toluene, 1/4, v/v); [α]$_D^{21}$=+72.4 (c=1.0, CHCl$_3$); NMR (500 MHz, CDCl$_3$): δ 7.27-7.39 (m, 10H, H—Ar), 5.02 (s, 1H, H-1$^B$), 4.93 (s, 1H, H-1$^C$), 4.77 (s, 1H, H-1$^A$), 3.67 (s, 3H, —OCH$_3$), 1.24 ppm (d, J$_{5,6}$=6.2 Hz, 3H, H-6$^C$); $^{13}$C NMR (126 MHz, CDCl$_3$): δ 174.0, 137.6, 137.4, 128.6, 128.5, 128.1, 127.9, 127.5, 101.0 (×2), 97.0, 78.3, 77.8, 73.1, 72.5, 72.1, 70.2, 69.9, 67.9, 67.6, 67.4, 67.3, 65.8, 64.8, 64.0, 51.5, 33.9, 29.0, 25.6, 24.6, 18.6, 18.5,

5'-Methoxycarbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranoside (44)

To a stirred solution of 68a (0.114 g, 0.136 mmol), in pyridine (5 mL) and water (2 mL) mixture, $H_2S$ was bubbled for 0.5 h at 40° C., and then stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 68b and no products arising from incomplete reduction. HRMS (ESI): m/z calcd for $C_{39}H_{60}N_3O_{12}$ [M+H]+: 762.4172; found: 762.4171. This crude material was directly used for formylation.

Compound 68b in $CH_3OH$ (5 mL) at −20° C. was added a freshly prepared formic anhydrid[22] (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 68c. HRMS (ESI): m/z calcd for $C_{42}H_{59}N_3O_{15}Na$ [M+Na]+: 868.3838; found: 868.3827.

Compound 68c was dissolved in $CH_3OH/H_2O$ (2:1, 5 mL), $Pd(OH)_2$ on carbon (20%, 0.040 g) was added. Then it was stirred under a pressure of hydrogen gas at room temperature for 16 h. After filtration through celite pad and washed with $CH_3OH$ (3×10 mL), and solvents were removed in vacuo. The residue was purified by column chromatography on silica gel (methanol-dichloromethane gradient elution) to afford the title compound (0.046 g, 51%, over 3 steps) as a white foam. Analytical data for 45: Rf=0.40 ($CH_3OH/CH_2Cl_2$, 3/7, v/v); NMR (700 MHz, $D_2O$): δ 8.20-8.24 (Z) and 8.02-8.06 (E) (m, 3H, NCHO), 4.82-5.08 (m, 3H, 3×H-1), 1.21-1.32 ppm (m, 9H, 3×H-6); $^{13}C$ NMR (126 MHz, $D_2O$): δ 178.5, 168.8, 168.7, 165.8 (×2), 165.6 (×2), 103.4, 103.3, 102.9, 101.8, 101.7, 100.6, 100.5, 79.0 (×2), 78.9, 78.2, 78.0, 77.7 (×3), 70.0, 69.9, 69.8, 69.4, 69.2, 69.0, 68.9 (×2), 68.8 (×2), 68.7, 68.6 (×2), 68.5 (×2), 68.3 (×2), 67.9, 67.7, 57.8, 57.7, 56.4, 53.1, 52.8, 52.7, 51.9, 34.6, 29.1, 25.9, 25.0, 18.1, 17.9 (×3), 17.8, 17.7 ppm; HRMS (ESI): m/z calcd for $C_{28}H_{47}N_3O_{15}Na$ [M+Na]+: 688.2899, found: 688.2895.

(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranoside (82)

A solution of 45 (0.012 g, 0.018 mmol) in freshly distilled 1,2-diaminoethane (0.5 mL) was stirred at 65° C. for 48 h. Then excess reagent was removed in vacuo, and the residue was co-evaporated with $CH_3OH$ (3×10 mL) and dried. The residue was purified by reversed phase HPLC on a C18 column with a gradient of water-acetonitrile and lyophilized, to give the title compound (0.0112 g, 90%) as a white foam. Analytical data for 82: Rf=0.10 ($CH_3OH/CH_2Cl_2$, 1/1, v/v); NMR (500 MHz, $D_2O$): δ 8.26-8.31 (Z) and 8.08-8.13 (E) (m, 3H, NCHO), 4.88-5.16 (m, 3H, 3×H-1), 1.20-1.37 (m, 9H, 3×H-6); $^{13}C$ NMR (126 MHz, $D_2O$): δ 178.4, 178.2, 168.8 (×2), 165.9, 165.8 (×3), 103.3, 101.7 (×2), 100.5 (×2), 79.0, 77.7, 70.0, 69.9, 69.2, 69.0, 68.9, 68.8, 68.6, 68.4, 68.0, 67.7, 57.8, 57.7, 52.8, 52.7, 51.9, 41.5 (×2), 41.5, 41.4, 40.9, 40.6 (×2), 36.6, 29.2, 26.0 (×2), 25.9, 25.8, 18.1, 18.0, 17.9 (×3), 17.7 ppm; HRMS (ESI): m/z calcd for $C_{29}H_{51}N_5O_{14}Na$ [M+Na]+: 716.3325, found: 716.3311.

1-[(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranoside]-2-butoxycyclobutene-3,4-dione (88)

To a stirred solution of 82 (0.0075 g, 0.011 mmol) in water (0.5 mL) and EtOH (0.4 mL), a solution of 3,4-dibutoxy-3-cyclobutene-1,2-dione (20% in ethanol, 50 μL) was added and the pH was adjusted to 8 by careful addition of aq. $NaHCO_3$ (1%) solution. After 0.5 h, TLC showed the reaction was complete; the reaction mixture was neutralized using $CH_3COOH$ (10%) and concentrated in vacuo. The residue was purified by reversed phase HPLC on a C18 column with a gradient of water-acetonitrile and lyophilized, to give the title compound (0.0065 g, 71%) as a white foam. Analytical data for 88: Rf=0.20 ($CH_3OH/CH_2Cl_2$, 1/4, v/v); $^1H$ NMR (500 MHz, $D_2O$): δ 8.27-8.31 (Z) and 8.08-8.13 (E) (m, 3H, NCHO), 4.86-5.15 (m, 3H, 3×H-1), 1.26-1.36 (m, 9H, 3×H-6), 0.98-1.05 ppm (m, 3H, —$CH_{31}$); $^{13}C$ NMR (126 MHz, $D_2O$): δ 189.8, 189.6, 184.3 (×2), 178.5, 178.1, 178.0, 177.9, 174.8, 174.7, 168.8, 168.7, 165.8 (×2), 165.6, 103.4, 103.3, 102.9, 101.8, 101.7, 100.6, 100.5, 79.0, 78.9, 78.8, 78.2, 78.0, 77.7 (×2), 75.4, 75.3, 70.0, 69.9, 69.3, 69.2, 69.0, 68.9, 68.9, 68.8, 68.6, 68.5 (×2), 68.4, 68.3, 67.9, 67.7, 57.8, 57.7, 56.5, 52.8, 52.8, 52.7, 51.9, 45.2, 45.0, 40.3, 40.2, 36.7, 32.4, 29.3 (×2), 26.2, 26.1, 25.9 (×2), 19.1, 19.0, 18.1, 18.0, 17.9 (×3), 17.7, 13.9 ppm; HRMS (ESI): m/z calcd for $C_{37}H_{59}N_5O_{17}Na$ [M+Na]+: 868.3798, found: 868.3800.

5'-Methoxycarbonylpentyl 4-azido-4,6-dideoxy-α-D-mannopyranosyl (1→3) 4-azido-2-O-benzyl-4,6-dideoxy-α-D-mannopyranosyl (1→2) 4-azido-3-O-benzyl-4,6-dideoxy-α-D-mannopyranoside (71a)

Sodium methoxide (0.5 mL, 0.5 M solution) was added to a solution of 71 (0.458 g, 0.437 mmol) in $CH_3OH$ (10 mL) until pH ~9 and the resulting mixture was stirred under argon for 4 h at room temperature. Then the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.341 g, 93%) as oil. Analytical data for 71a: Rf=0.30 (ethyl acetate/toluene, 1/4, v/v); $[α]_D^{21}$=+58.9 (c=1.3, $CHCl_3$); NMR (500 MHz, $CDCl_3$): δ 7.12-7.39 (m, 10H, H—Ar), 5.08 (d, $J_{1,2}$=1.8 Hz, 1H, H-1$^B$), 5.05 (d, $J_{1,2}$=1.6 Hz, 1H, H-1$^C$), 4.66 (d, $J_{1,2}$=1.6 Hz, 1H, H-1$^A$), 3.68 (s, 3H, —$OCH_3$), 1.28-1.32 (m, 6H, H-6$^A$, H-6$^B$), 1.19 ppm (d, $J_{5,6}$=6.2 Hz, 3H, H-6$^C$); $^{13}C$ NMR (126 MHz, $CDCl_3$): δ 174.1, 137.3 (×2), 128.5, 128.4, 128.2, 128.1, 127.8, 127.6, 101.5, 98.8, 98.1, 78.4, 77.5, 76.4, 73.2, 72.6, 71.7, 70.1, 70.0, 67.9, 67.5, 67.4, 67.2, 65.5, 64.7, 64.4, 51.5, 33.9, 29.0, 25.7, 24.6, 18.6, 18.5, 18.2 ppm; HRMS (ESI): m/z calcd for $C_{39}H_{53}N_9O_{12}Na$ [M+Na]+: 862.3706, found: 862.3700.

5'-Methoxycarbonylpentyl 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside (46)

To a stirred solution of 71a (0.157 g, 0.187 mmol), in pyridine (5 mL) and water (2 mL) mixture, $H_2S$ was bubbled for 0.5 h at 40° C., and then stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 71b and no products arising from incomplete reduction. HRMS (ESI): m/z calcd for $C_{39}H_{60}N_3O_{12}$ [M+H]+: 762.4172; found: 762.4182. This crude material was directly used for formylation.

Compound 71b in $CH_3OH$ (5 mL) at −20° C. was added a freshly prepared formic anhydride[22] (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 71c. HRMS (ESI): m/z calcd for $C_{42}H_{59}N_3O_{15}Na$ [M+Na]+: 868.3838; found: 868.3834.

Compound 71c was dissolved in $CH_3OH/H_2O$ (2:1, 5 mL), Pd(OH)$_2$ on carbon (20%, 0.050 g) was added. Then it was stirred under a pressure of hydrogen gas at room temperature for 16 h. After filtration through celite pad and washed with $CH_3OH$ (3×10 mL), and solvents were removed in vacuo. The residue was purified by column chromatography on silica gel (methanol-dichloromethane gradient elution) to afford the title compound (0.053 g, 43%, over 3 steps) as a white foam. Analytical data for 46: Rf=0.50 ($CH_3OH/CH_2Cl_2$, 3/7, v/v); $^1H$ NMR (700 MHz, $D_2O$): δ 8.20-8.24 (Z) and 8.02-8.06 (E) (m, 3H, NCHO), 4.92-5.04 (m, 3H, 3×H-1), 3.70 (s, 3H, —OCH$_3$), 1.22-1.31 ppm (m, 9H, 3×H-6); $^{13}C$ NMR (176 MHz, $D_2O$): δ 178.3, 168.7, 168.6, 168.5, 165.6 (×2), 165.5, 103.1, 102.9 (×2), 102.8, 102.7 (×2), 99.0 (×3), 78.6 (×2), 78.5, 77.3, 77.2, 77.1, 70.1, 70.0, 69.8, 69.5, 69.4, 68.9, 68.8 (×2), 68.7 (×2), 68.6 (×2), 68.5 (×2), 68.4 (×2), 68.3, 68.2, 67.8, 57.7, 57.4, 56.3, 52.9, 52.8, 52.4, 51.3, 34.4, 28.9, 25.7, 24.8, 17.6 (×2), 17.5, 17.4 ppm; HRMS (ESI): m/z calcd for $C_{28}H_{47}N_3O_{15}Na$ [M+Na]+: 688.2899, found: 688.2893.

(2'-Aminoethylamido)carbonylpentyl 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside (83)

A solution of 46 (0.010 g, 0.015 mmol) in freshly distilled 1,2-diaminoethane (0.5 mL) was stirred at 65° C. for 48 h. Then excess reagent was removed in vacuo, and the residue was co-evaporated with $CH_3OH$ (3×10 mL) and dried. The residue was purified by reversed phase HPLC on a C18 column with a gradient of water-acetonitrile and lyophilized, to give the title compound (0.0084 g, 81%) as a white foam. Analytical data for 83: Rf=0.10 ($CH_3OH/CH_2Cl_2$, 1/1, v/v); $^1H$ NMR (500 MHz, $D_2O$): δ 8.26-8.31 (Z) and 8.09-8.13 (E) (m, 3H, NCHO), 4.98-5.11 (m, 3H, 3×H-1), 1.26-1.38 ppm (m, 9H, 3×H-6); $^{13}C$ NMR (126 MHz, $D_2O$): δ 177.7, 177.2, 168.0, 167.9, 167.8, 164.9, 164.8, 164.6, 102.4, 102.2 (×2), 102.1, 101.9 (×2), 98.3, 98.2, 77.9, 77.8 (×3), 76.8, 76.5 (×2), 76.4, 76.2, 70.0, 69.9, 69.5, 69.3, 69.0, 68.8 (×2), 68.7, 68.2, 68.1, 68.0 (×2), 67.9, 67.8 (×2), 67.7, 67.6 (×2), 67.5, 67.1, 57.0, 56.7, 55.5, 53.5, 52.0, 51.7 (×2), 51.6, 50.7, 50.6 (×2), 40.4, 39.9, 39.5, 39.0, 35.7, 35.6, 28.2, 25.1, 24.9 (×2), 17.0, 16.9, 16.7 (×2) ppm; HRMS (ESI): m/z calcd for $C_{29}H_{51}N_5O_{14}Na$ [M+Na]+: 716.3325, found: 716.3322.

1-[(2'-Aminoethylamido)carbonylpentyl 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside]-2-butoxycyclobutene-3,4-dione (89)

To a stirred solution of 83 (0.0074 g, 0.0106 mmol) in water (0.5 mL) and EtOH (0.4 mL), a solution of 3,4-dibutoxy-3-cyclobutene-1,2-dione (20% in ethanol, 50 μL) was added and pH was adjusted to 8 by careful addition of aq. NaHCO$_3$ (1%) solution. After 0.5 h, TLC showed the reaction was complete; the reaction mixture was neutralized using $CH_3COOH$ (10%) and concentrated in vacuo. The residue was purified by reversed phase HPLC on a C18 column with a gradient of water-acetonitrile and lyophilized, to give the title compound (0.0072 g, 80%) as a white foam. Analytical data for 89: Rf=0.20 ($CH_3OH/CH_2Cl_2$, 1/4, v/v); $^1H$ NMR (500 MHz, $D_2O$): δ 8.16-8.21 (Z) and 7.99-8.03 (E) (m, 3H, NCHO), 4.87-5.01 (m, 3H, 3×H-1), 1.18-1.27 (m, 9H, 3×H-6); $^{13}C$ NMR (126 MHz, $D_2O$): δ 189.8, 189.6, 184.2, 178.5, 178.0, 177.9 (×2), 174.8, 174.7, 168.8, 168.7, 166.6, 165.8, 165.7, 103.1, 102.8, 99.1 (×2), 78.7, 77.4 (×2), 75.4, 75.3, 70.2, 69.7, 69.6, 69.1, 69.0, 68.9, 68.7 (×3), 68.5, 68.4, 53.0, 52.6, 51.5, 45.1, 44.9, 40.3, 40.1, 36.7, 32.4, 29.2, 26.1, 26.0, 25.9 (×2), 19.0 (×2), 17.8 (×3), 17.6, 13.9 ppm; HRMS (ESI): m/z calcd for $C_{37}H_{59}N_5O_{17}Na$ [M+Na]+: 868.3798, found: 868.3791.

5'-Methoxycarbonylpentyl 4-azido-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranosyl (1→2) 4-azido-3-O-benzyl-4,6-dideoxy-α-D-mannopyranoside (72a)

Sodium methoxide (0.5 mL, 0.5 M solution) was added to a solution of 72 (0.391 g, 0.299 mmol) in $CH_3OH/THF$ mixture (4:1, 15 mL) until pH ~9 and the resulting mixture was stirred under argon for 5 h at room temperature. Then the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.311 g, 95%) as oil. Analytical data for 72a: Rf=0.40 (ethyl acetate/toluene, 1/4, v/v); $[\alpha]_D^2$=+51.2 (c=1.0, CHCl$_3$); $^1H$ NMR (500 MHz, CDCl$_3$): δ 7.10-7.39 (m, 15H, H—Ar), 5.07 (d, $J_{1,2}$=1.6 Hz, 1H, H-1$^B$), 5.02 (d, $J_{1,2}$=1.6 Hz, 1H, H-1$^C$), 4.91 (d, $J_{1,2}$=1.5 Hz, 1H, H-1$^D$), 4.66 (d, $J_{1,2}$=2.0 Hz, 1H, H-1$^A$), 3.68 (s, 3H, —OCH$_3$), 1.26-1.35 (m, 9H, H-6$^A$, H-6$^B$ H-6$^C$), 1.17 ppm (d, $J_{5,6}$=5.9 Hz, 3H, H-6$^D$); $^{13}C$ NMR (126 MHz, CDCl$_3$): δ 174.0, 137.5, 137.4, 137.3, 128.5, 128.4, 128.2, 128.0 (×2), 127.8, 127.5, 101.0, 100.8, 98.8, 98.2, 78.4, 77.9, 77.5, 76.4, 73.2, 72.5, 72.1, 71.8, 70.0, 69.7, 67.9 (×2), 67.5 (×2), 67.1, 65.8 (×2), 64.7, 64.6, 63.9, 51.5, 33.9, 29.0, 25.7, 24.7, 18.6 (×2), 18.5, 18.3 ppm; HRMS (ESI): m/z calcd for $C_{52}H_{68}N_{12}O_{15}Na$ [M+Na]+: 1123.4806, found: 1123.4812.

5'-Methoxycarbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside (47)

To a stirred solution of 72a (0.146 g, 0.132 mmol), in pyridine (5 mL) and water (2 mL) mixture, H$_2$S was bubbled for 0.5 h at 40° C., and then stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 72b and no products arising from incomplete reduction. HRMS (ESI): m/z calcd for $C_{52}H_{77}N_4O_{15}$ [M+H]+: 997.5380; found: 997.5366. This crude material was directly used for formylation.

Compound 72b in $CH_3OH$ (5 mL) at −20° C. was added a freshly prepared formic anhydride Olah et al. (Angew (1979) Chem. Int. Ed. 18, 614) (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 72c. HRMS (ESI): m/z calcd for $C_{56}H_{76}N_4O_{19}Na$ [M+Na]$^+$: 1131.4996; found: 1131.4992.

Compound 72c was dissolved in $CH_3OH/H_2O$ (2:1, 5 mL), $Pd(OH)_2$ on carbon (20%, 0.050 g) was added. Then it was stirred under a pressure of hydrogen gas at room temperature for 16 h. After filtration through celite pad and washed with $CH_3OH$ (3×10 mL), and solvents were removed in vacuo. The residue was purified by column chromatography on silica gel (methanol-dichloromethane gradient elution) to afford the title compound (0.068 g, 61%, over 3 steps) as a white foam. Analytical data for 47: Rf=0.30 ($CH_3OH/CH_2Cl_2$, 3/7, v/v); $^1$H NMR (500 MHz, $D_2O$): δ 8.26-8.33 (Z) and 8.06-8.14 (E) (m, 4H, NCHO), 4.98-5.20 (m, 4H, 4×H-1), 3.85-4.28 (m, 16H, 4×H-2, 4×H-3, 4×H-4, 4×H-5), 1.28-1.39 ppm (m, 12H, 4×H-6); $^{13}$C NMR (126 MHz, $D_2O$): δ 178.5, 168.8, 168.7, 168.6, 165.8, 165.6, 103.3, 103.2, 102.9, 102.8, 102.7, 101.9, 101.6, 99.3, 99.2, 79.3, 78.9, 78.7, 78.5, 78.4, 78.1, 77.3, 69.9 (×2), 69.8, 69.7, 69.4, 69.3, 69.0, 68.9, 68.8 (×2), 68.7, 68.6, 68.5, 68.4, 68.3, 68.0, 58.0, 57.7, 56.5, 53.1, 52.9, 52.8, 52.7, 51.8, 34.6, 29.1, 25.9, 25.0, 18.1 (×2), 18.0 (×2), 17.9 (×2), 17.8 (×2), 17.7 (×2) ppm; HRMS (ESI): m/z calcd for $C_{35}H_{58}N_4O_{19}Na$ [M+Na]$^+$: 861.3587, found: 861.3580.

(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside (84)

A solution of 47 (0.0134 g, 0.016 mmol) in freshly distilled 1,2-diaminoethane (0.5 mL) was stirred at 65° C. for 48 h. Then excess reagent was removed in vacuo, and the residue was co-evaporated with $CH_3OH$ (3×10 mL) and dried. The residue was purified by reversed phase HPLC on a C18 column with a gradient of water-acetonitrile and lyophilized, to give the title compound (0.0113 g, 82%) as a white foam. Analytical data for 84: Rf=0.10 ($CH_3OH/CH_2Cl_2$, 1/1, v/v); $^1$H NMR (500 MHz, $D_2O$): δ 8.16-8.23 (Z) and 7.98-8.05 (E) (m, 4H, 4×H-1), 2.22-2.28 (m, 2H, —$CH_{2f}$—), 1.54-1.64 (m, 4H, —$CH_{2e}$—, —$CH_{2c}$—), 1.30-1.41 (m, 2H, —$CH_{2d}$—), 1.18-1.30 ppm (m, 12H, 4×H-6); $^{13}$C NMR (125 MHz, $D_2O$): δ 177.4, 167.9 (×2), 164.9, 164.6, 102.6, 102.3 (×3), 101.9 (×2), 101.0 (×2), 100.8, 98.6, 98.3, 78.1, 77.6, 77.5 (×2), 76.8, 76.4, 76.0, 70.3, 70.2, 70.1, 70.0 (×2), 69.5, 69.2, 68.9 (×3), 68.3, 68.0, 67.8, 67.6 (×2), 53.9, 53.8, 53.6, 52.0, 51.8, 50.8 (×2), 40.6 (×3), 39.7, 35.7, 28.2, 25.0, 24.9 (×2), 17.3, 17.0, 16.8 (×3) ppm; HRMS (ESI): m/z calcd for $C_{36}H_{62}N_6O_{18}Na$ [M+Na]$^+$: 889.4013, found: 889.4020.

1[(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranoside]-2-butoxycyclobutene-3,4-dione (90)

To a stirred solution of 84 (0.013 g, 0.015 mmol) in water (0.5 mL) and EtOH (0.4 mL), a solution of 3,4-dibutoxy-3-cyclobutene-1,2-dione (20% in ethanol, 70 μL) was added and pH was adjusted to 8 by careful addition of aq. $NaHCO_3$ (1%) solution. After 0.5 h, TLC showed the reaction was complete; the reaction mixture was neutralized using $CH_3COOH$ (10%) and concentrated in vacuo. The residue was purified by reversed phase HPLC on a C18 column with a gradient of water-acetonitrile and lyophilized, to give the title compound (0.0109 g, 72%) as a white foam. Analytical data for 90: Rf=0.20 ($CH_3OH/CH_2Cl_2$, 1/4, v/v); $^1$H NMR (600 MHz, $D_2O$): δ 8.18-8.24 (Z) and 7.98-8.06 (E) (m, 4H, NCHO), 4.90-5.10 (m, 4H, 4×H-1), 1.20-1.35 (m, 14H, —$CH_{2d}$—, 4×H-6) ppm; $^{13}$C NMR (126 MHz, $D_2O$): δ 189.8, 189.6, 184.3 (×2), 178.5, 178.2, 178.1, 178.0, 177.9, 174.8, 174.7, 168.8, 168.7, 168.6, 165.8, 165.6, 103.3 (×2), 103.2, 102.8 (×2), 102.7, 101.7 (×2), 101.6 (×2), 99.2, 78.9 (×2), 78.4, 78.1, 77.3, 75.4, 75.3, 69.9 (×2), 69.8 (×2), 69.7, 69.3, 69.0 (×2), 68.9, 68.8 (×4), 68.6 (×2), 68.5, 68.4 (×2), 68.0, 62.5, 52.9, 52.8 (×2), 52.7, 51.8, 45.2, 45.0, 44.2, 40.6, 40.3, 40.2, 36.7, 34.4, 32.4, 29.2, 26.2, 26.1, 26.0 (×2), 25.9 (×2), 25.8, 19.3, 19.1, 19.0, 18.1, 18.0 (×2), 17.9, 17.8 (×2), 17.7 (×2), 14.0, 13.9 ppm; HRMS (ESI): m/z calcd for $C_{44}H_{70}N_6O_{21}Na$ [M+Na]$^+$: 1041.4486, found: 1041.4484.

5'-Methoxycarbonylpentyl 4-azido-2-O-benzoyl-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (73)

A mixture of glycosyl donor 64 (0.743 g, 1.08 mmol), glycosyl acceptor 66 Cheng. et al. (2010) Angew. Chem. Int. Ed. 49, 4771-4774) (0.400 g, 0.982 mmol) and freshly activated molecular sieves (3 Å, 1.5 g) in $CH_2Cl_2$ (10 mL) was stirred under argon for 4 h at room temperature. MeOTf (0.890 mL, 7.86 mmol) was added and stirring was continued for an additional 48 h. Then $Et_3N$ (1 mL) was added, the solid was filtered off and the residue was rinsed with $CH_2Cl_2$ (3×30 mL). The combined filtrate (100 mL) was washed with 20% aq. $NaHCO_3$ (40 mL), water (30 mL), and brine (20 mL). The organic phase was separated, dried over $MgSO_4$, and concentrated in vacuo. The residue was purified by column chromatography on silica gel (ethyl acetate-toluene gradient elution) to afford the title compound (0.865 g, 85%) as oil. Analytical data for 73: Rf=0.50 (ethyl acetate/toluene, 0.5/9.5, v/v); $[α]_D^{21}$=+36.7 (c=1.3, $CHCl_3$); $^1$H NMR (500 MHz, $CDCl_3$): δ 7.15-8.11 (m, 20H, H—Ar), 5.61 (dd, $J_{2,3}$=3.0 Hz, 1H, H-2$^C$), 4.99 (d, $J_{1,2}$=1.8 Hz, 1H, H-1$^B$), 4.90 (d, $J_{1,2}$=2.0 Hz, 1H, H-1$^C$), 4.64 (s, 1H, H-1$^A$), 3.70 (s, 3H, —$OCH_3$), 1.30 (d, $J_{5,6}$=6.0 Hz, 6H, H-6$^B$, H-6$^C$), 1.25 ppm (d, $J_{5,6}$=6.0 Hz, 3H, H-6$^A$); $^{13}$C NMR (126 MHz, $CDCl_3$): δ 174.0, 165.3, 137.4, 137.3, 137.2, 133.3, 129.9, 129.8, 128.5 (×3), 128.4, 128.3, 128.1, 128.0 (×2), 127.8, 100.4, 99.2, 98.7, 77.6, 76.7, 75.4, 74.2, 74.1, 72.2, 72.1, 71.4, 67.7 (×2), 67.5, 67.1, 64.4, 64.1 (×2), 51.5, 33.9, 29.1, 25.7, 24.7, 18.7, 18.6 ppm; HRMS (ESI): m/z calcd for $C_{53}H_{63}N_9O_{13}Na$ [M+Na]$^+$: 1056.4438, found: 1056.4436.

5'-Methoxycarbonylpentyl 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (74)

Sodium methoxide (0.7 mL, 0.5 M solution) was added to a solution of 73 (0.855 g, 0.827 mmol) in $CH_3OH$ (10 mL) until pH ~9 and the resulting mixture was stirred under argon for 4 h at room temperature. Then the reaction mixture was neutralized with Amberlite IR 120 (H$^+$) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.720 g, 94%) as oil. Analytical data for 74: Rf=0.30 (ethyl acetate/toluene, 0.5/9.5, v/v); $[\alpha]_D^{21}$=+94.4 (c=1.1, CHCl$_3$); $^1$H NMR (500 MHz, CDCl$_3$): δ 7.29-7.45 (m, 15H, H—Ar), 4.95 (br. s., 2H, H-1$^B$, H-1$^C$), 4.63 (d, $J_{1,2}$=2.0 Hz, 1H, H-1$^A$), 3.70 (s, 3H, —OCH$_3$), 1.28-1.31 (m, 6H, H-6$^B$, H-6$^C$), 1.21 ppm (d, $J_{5,6}$=6.2 Hz, 3H, H-6$^A$); $^{13}$C NMR (126 MHz, CDCl$_3$): δ 174.0, 137.4, 137.3, 137.1, 128.6 (×2), 128.3 (×2), 128.2 (×3), 128.1, 100.5 (×2), 98.7, 77.6, 77.5, 76.9, 74.0, 73.3, 72.2, 72.1 (×2), 67.7, 67.5, 67.3, 67.2, 67.1, 64.4, 64.2, 63.8, 51.5, 33.9, 29.0, 25.7, 24.7, 18.6 (×2), 18.3 ppm; HRMS (ESI): m/z calcd for $C_{46}H_{59}N_9O_{12}Na$ [M+Na]$^+$: 952.4175, found: 952.4176.

5'-Methoxycarbonylpentyl 4-azido-2-O-benzoyl-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (75)

A mixture of glycosyl donor 64 (0.262 g, 0.381 mmol), glycosyl acceptor 74 (0.322 g, 0.346 mmol) and freshly activated molecular sieves (3 Å, 0.5 g) in $CH_2Cl_2$ (8 mL) was stirred under argon for 4 h at room temperature. MeOTf (320 µL, 2.77 mmol) was added and stirring was continued for an additional 48 h. Then Et$_3$N (1 mL) was added, the solid was filtered off and the residue was rinsed with $CH_2Cl_2$ (3×20 mL). The combined filtrate (70 mL) was washed with 20% aq. NaHCO$_3$ (40 mL), water (30 mL), and brine (20 mL). The organic phase was separated, dried over MgSO$_4$, and concentrated in vacuo. The residue was purified by column chromatography on silica gel (ethyl acetate-toluene gradient elution) to afford the title compound (0.461 g, 86%) as a white foam. Analytical data for 75: Rf=0.30 (ethyl acetate/toluene, 0.5/9.5, v/v); $[\alpha]_D^{21}$=+52.7 (c=1.0, CHCl$_3$); NMR (500 MHz, CDCl$_3$): δ 7.16-8.09 (m, 30H, H—Ar), 5.60 (dd, $J_{2,3}$=3.1 Hz, 1H, H-2$^E$), 4.98 (d, $J_{1,2}$=1.8 Hz, 1H, H-1$^D$), 4.92 (d, $J_{1,2}$=1.8 Hz, 1H, H-1$^E$), 4.88 (d, $J_{1,2}$=2.0 Hz, 1H, H-1$^C$), 4.86 (d, $J_{1,2}$=2.0 Hz, 1H, H-1$^B$), 1.23-1.29 (m, 9H, H-6$^B$, H-6$^C$ H-6$^D$), 1.19 (d, $J_{5,6}$=6.2 Hz, 3H, H-6$^E$), 1.15 ppm (d, $J_{5,6}$=6.2 Hz, 3H, H-6$^A$); $^{13}$C NMR (126 MHz, CDCl$_3$): δ 173.9, 165.3, 137.4, 137.3, 137.1 (×2), 133.3, 129.9, 129.8, 128.7, 128.6 (×3), 128.5 (×2), 128.4 (×2), 128.3 (×3), 128.2 (×2), 128.1 (×3), 127.9 (×2), 100.4, 100.2, 100.1, 99.2, 98.6, 77.4, 76.6, 75.3, 74.1, 74.0, 73.6, 72.2 (×2), 72.1 (×2), 71.3, 67.8 (×2), 67.7, 67.5, 67.1, 64.4, 64.3, 64.2, 64.1 (×2), 51.5, 33.9, 29.0, 25.7, 24.7, 18.6, 18.5 (×2) ppm; HRMS (ESI): m/z calcd for $C_{79}H_{93}N_{15}O_{19}Na$ [M+Na]$^+$: 1578.6664, found: 1578.6667.

5'-Methoxycarbonylpentyl 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (76)

Sodium methoxide (0.8 mL, 0.5 M solution) was added to a solution of 75 (0.450 g, 0.289 mmol) in $CH_3OH$ (10 mL) until pH ~9 and the resulting mixture was stirred under argon for 4 h at room temperature. Then the reaction mixture was neutralized with Amberlite IR 120 (H$^+$) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.395 g, 94%) as oil. Analytical data for 76: Rf=0.40 (ethyl acetate/toluene, 1/9, v/v); $[\alpha]_D^{21}$=+81.2 (c=1.0, CHCl$_3$); $^1$H NMR (600 MHz, CDCl$_3$): δ 7.28-7.41 (m, 25H, H—Ar), 4.97 (d, $J_{1,2}$=1.1 Hz, 1H, H-1$^E$), 4.96 (d, $J_{1,2}$=1.5 Hz, 1H, H-1$^D$), 4.87 (d, $J_{1,2}$=1.3 Hz, 1H, H-1$^C$), 4.85 (d, $J_{1,2}$=1.3 Hz, 1H, H-1$^B$), 1.14-1.26 ppm (m, 15H, H-6$^A$, H-6$^B$, H-6$^C$, H-6$^D$, H-6$^E$); $^{13}$C NMR (126 MHz, CDCl$_3$): δ 174.0, 137.3 (×2), 137.2, 137.1 (×2), 128.6 (×4), 128.4 (×2), 128.3 (×3), 128.2 (×2), 128.1 (×2), 100.5, 100.4, 100.2 (×2), 98.6, 77.7, 77.4, 76.6, 76.5, 74.0, 73.6, 73.5, 73.3, 72.2 (×2), 72.1 (×2), 67.8, 67.7, 67.5, 67.3, 67.1 (×2), 64.4, 64.2, 63.8, 51.5, 33.9, 29.0, 25.7, 24.7, 18.6 (×2), 18.5 (×2), 18.3 ppm; HRMS (ESI): m/z calcd for $C_{72}H_{89}N_{15}O_{18}Na$ [M+Na]$^+$: 1474.6402, found: 1474.6406.

5ζ-Methoxycarbonylpentyl 4-azido-2,3-di-O-benzoyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (77)

A mixture of glycosyl donor 53 (0.158 g, 0.292 mmol), glycosyl acceptor 76 (0.386 g, 0.266 mmol) and freshly activated molecular sieves (3 Å, 0.5 g) in $CH_2Cl_2$ (5 mL) was stirred under argon for 5 h at room temperature. TMSOTf (11 µL, 0.058 mmol) was added and the resulting mixture was stirred for an additional hour. Then Et$_3$N (1 mL) was added, the solid was filtered off and the residue was rinsed with $CH_2Cl_2$ (3×20 mL). The combined filtrate (80 mL) was washed with 20% aq. NaHCO$_3$ (50 mL), water (30 mL), and brine (20 mL). The organic phase was separated, dried over MgSO$_4$, and concentrated in vacuo. The residue was purified by column chromatography on silica gel (ethyl acetate-toluene gradient elution) to afford the title compound (0.487 g, 90%) as a white foam. Analytical data for 77: Rf=0.70 (ethyl acetate/toluene, 1/9, v/v); $[\alpha]_D^{21}$=+31.7 (c=1.4, CHCl$_3$); $^1$H NMR (600 MHz, CDCl$_3$): δ, 7.13-8.03 (m, 35H, H—Ar), 5.70 (dd, $J_{2,3}$=3.3 Hz, 1H, H-2$^F$), 5.59 (dd, $J_{3,4}$=10.2 Hz, 1H, H-3$^F$), 5.02-5.03 (m, 2H, H-1$^E$, H-1$^F$), 4.90 (d, $J_{1,2}$=1.8 Hz, 1H, H-1$^D$), 4.88 (dd, $J_{1,2}$=1.8 Hz, 1H, H-1$^C$), 4.86 (dd, $J_{1,2}$=1.8 Hz, 1H, H-1$^B$), 1.14-1.31 ppm (m, 18H, H-6$^A$, H-6$^B$, H-6$^C$, H-6$^D$, H-6$^E$, H-6$^F$); $^{13}$C NMR (126 MHz, CDCl$_3$): δ 174.0, 165.2, 164.9, 137.4, 137.3, 137.1 (×3), 133.4, 133.2, 129.8, 129.7, 129.5, 129.3, 129.0, 128.7, 128.6 (×3), 128.5 (×2), 128.4 (×3), 128.3 (×2), 128.2, 128.1 (×2), 127.9 (×3), 100.4, 100.3, 100.1, 100.0, 98.9, 98.6, 77.4, 77.1, 76.6, 76.5, 74.0, 73.8, 73.6, 73.5, 73.0, 72.3 (×2), 72.2 (×2), 72.1, 70.9, 69.4, 68.1, 67.9, 67.8 (×2), 67.6, 67.5, 67.1, 64.4, 64.3, 64.2 (×2), 63.9, 63.4, 51.5, 33.9, 29.0, 25.7, 24.7, 18.6 (×2), 18.5 (×2), 18.4 ppm; HRMS (ESI): m/z calcd for $C_{92}H_{106}N_{18}O_{23}Na$ [M+Na]$^+$: 1853.7570, found: 1853.7550.

5'-Methoxycarbonylpentyl 4-azido-3-O-benzoyl-2-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (78)

A mixture of glycosyl donor 58 (0.228 g, 0.433 mmol), glycosyl acceptor 74 (0.366 g, 0.394 mmol) and freshly activated molecular sieves (3 Å, 0.500 g) in PhMe (10 mL) was stirred under argon for 2 h at room temperature. Then it was heated to 95° C. and TMSOTf (16 μL, 0.087 mmol) was added, and the mixture was stirred for an additional 60 min. Then Et$_3$N (1 mL) was added, the solid was filtered off and the residue was rinsed with CH$_2$Cl$_2$ (3×30 mL). The combined filtrate (100 mL) was washed with 20% aq. NaHCO$_3$ (50 mL), water (30 mL), and brine (30 mL). The organic phase was separated, dried over MgSO$_4$, and concentrated in vacuo. The residue was purified by column chromatography on silica gel (ethyl acetate-toluene gradient elution) to afford the title compound (0.444 g, 87%) as a white foam. Analytical data for 78: Rf=0.50 (ethyl acetate/toluene, 0.5/9.5, v/v); $[α]_D^{21}$=+42.1 (c=1.0, CHCl$_3$); $^1$H NMR (600 MHz, CDCl$_3$): δ 7.03-8.05 (m, 25H, H—Ar), 5.29 (dd, $J_{3,4}$=10.3 Hz, 1H, H-3$^D$), 5.07 (d, $J_{1,2}$=1.6 Hz, 1H, H-1$^D$), 4.96 (d, $J_{1,2}$=1.8 Hz, 1H, H-1$^C$), 4.91 (d, $J_{1,2}$=1.8 Hz, 1H, H-1$^B$), 1.22-1.29 ppm (m, 12H, H-6$^A$, H-6$^B$, H-6$^C$, H-6$^D$); $^{13}$C NMR (126 MHz, CDCl$_3$): δ 174.0, 165.4, 137.4, 137.3 (×2), 137.1, 133.3, 129.8, 129.5, 128.7, 128.6 (×2), 128.4, 128.3 (×2), 128.2 (×2), 128.1, 127.8, 127.6, 100.6, 100.1, 98.8, 98.6, 77.9, 77.4, 76.9, 74.4, 74.2, 72.9, 72.8, 72.7, 72.6, 72.5, 72.3, 72.2, 68.1, 67.8, 67.7, 67.5, 67.1, 64.4, 64.2, 64.1, 63.1, 51.5, 33.9, 29.0, 25.7, 24.6, 18.6 (×2), 18.4, 18.3 ppm; HRMS (ESI): m/z calcd for $C_{66}H_{78}N_{12}O_{16}Na$ [M+Na]$^+$: 1317.5551, found: 1317.5549.

5'-Methoxycarbonylpentyl 4-azido-2-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (79)

Sodium methoxide (0.8 mL, 0.5 M solution) was added to a solution of 78 (0.434 g, 0.335 mmol) in CH$_3$OH (10 mL) until pH ~9 and the resulting mixture was stirred under argon for 4 h at room temperature. Then the reaction mixture was neutralized with Amberlite IR 120 (H$^+$) ion exchange resin, the resin was filtered off and rinsed successively with CH$_3$OH. The combined filtrate was concentrated in vacuo and purified by column chromatography on silica gel (ethyl acetate-toluene gradient elution) to afford the title compound (0.356 g, 89%) as a white foam. Analytical data for 79: Rf=0.50 (ethyl acetate/toluene, 1/9, v/v); $[α]_D^{21}$=+65.6 (c=1.3, CHCl$_3$); $^1$H NMR (500 MHz, CDCl$_3$): δ 7.13-7.42 (m, 20H, H—Ar), 5.10 (d, $J_{1,2}$=0.9 Hz, 1H, H-1$^D$), 4.93 (d, $J_{1,2}$=1.7 Hz, 1H, H-1$^C$), 4.90 (d, $J_{1,2}$=1.8 Hz, 1H, H-1$^B$),
1.19-1.29 ppm (m, 12H, H-6$^A$, H-6$^B$, H-6$^C$, H-6$^D$); $^{13}$C NMR (126 MHz, CDCl$_3$): δ 174.0, 137.3 (×2), 137.2, 137.1, 128.7, 128.6 (×2), 128.4, 128.3 (×2), 128.2, 128.1 (×2), 100.5, 100.2, 98.6, 97.8, 77.8, 77.5, 76.9, 76.5, 74.1, 73.1, 72.7, 72.5, 72.3, 72.2, 70.0, 67.9, 67.8, 67.5, 67.3, 67.1, 66.5, 64.5, 64.4, 64.3, 51.5, 33.9, 29.1, 25.7, 24.7, 18.7, 18.6, 18.4, 18.3 ppm; HRMS (ESI): m/z calcd for $C_{59}H_{74}N_{12}O_{15}Na$ [M+Na]$^+$: 1213.5289, found: 1213.5284.

5'-Methoxycarbonylpentyl 4-azido-2,3-di-O-benzoyl-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranosyl (1→3) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (80)

A mixture of glycosyl donor 63 (0.220 g, 0.313 mmol), glycosyl acceptor 79 (0.339 g, 0.285 mmol) and freshly activated molecular sieves (3 Å, 0.5 g) in CH$_2$Cl$_2$ (10 mL) was stirred under argon for 4 h at room temperature. MeOTf (260 μL, 2.28 mmol) was added and continued stirring for additional 48 h. Then Et$_3$N (1 mL) was added, the solid was filtered off and the residue was rinsed with CH$_2$Cl$_2$ (3×30 mL). The combined filtrate (100 mL) was washed with 20% aq. NaHCO$_3$ (40 mL), water (40 mL), and brine (20 mL). The organic phase was separated, dried over MgSO$_4$, and concentrated in vacuo. The residue was purified by column chromatography on silica gel (ethyl acetate-toluene gradient elution) to afford the title compound (0.479 g, 92%) as a white foam. Analytical data for 80: Rf=0.60 (ethyl acetate/toluene, 0.5/9.5, v/v); $[α]_D^{21}$=+15.3 (c=1.0, CHCl$_3$); $^1$H NMR (600 MHz, CDCl$_3$): δ 7.06-8.00 (m, 35H, H—Ar), 5.71 (dd, $J_{2,3}$=3.3 Hz, 1H, H-2$^F$), 5.58 (dd, $J_{3,4}$=10.3 Hz, 1H, H-3$^F$), 5.09 (d, $J_{1,2}$=1.2 Hz, 1H, H-1$^E$), 5.05-5.07 (m, 2H, H-1$^D$, H-1$^F$), 4.95 (d, $J_{1,2}$=1.5 Hz, 1H, H-1$^C$), 4.90 (d, $J_{1,2}$=1.7 Hz, 1H, H-1$^B$), 1.20-1.29 ppm (m, 15H, H-6$^A$, H-6$^B$, H-6$^C$, H-6$^D$, H-6$^E$); $^{13}$C NMR (126 MHz, CDCl$_3$): δ 174.0, 165.2, 164.9, 137.5, 137.4, 137.3, 137.2, 137.1, 133.4, 133.3, 129.8 (×2), 129.5, 129.4, 129.0, 128.7, 128.6 (×2), 128.5 (×3), 128.4 (×2), 128.3 (×2), 128.2 (×2), 128.1, 127.9, 127.8, 127.7, 127.6, 100.9, 100.5, 100.2, 99.2, 98.6, 98.2, 77.9, 77.7, 77.5, 76.9, 76.4, 74.1, 73.6, 73.1, 72.9, 72.5, 72.4, 72.2 (×2), 72.0, 71.0, 69.4, 68.2, 68.1, 67.9, 67.8, 67.7, 67.5, 67.1, 64.7, 64.5, 64.4, 64.3, 63.6, 63.5, 51.5, 33.9, 29.1, 25.7, 24.7, 18.6 (×3), 18.5 (×2), 18.4 ppm; HRMS (ESI): m/z calcd for $C_{92}H_{110}N_{19}O_{23}$ [M+NH$_4$]$^+$: 1848.8016, found: 1848.8005.

5'-Methoxycarbonylpentyl 4-azido-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (77a)

Sodium methoxide (0.8 mL, 0.5 M solution) was added to a solution of 77 (0.483 g, 0.264 mmol) in CH$_3$OH (12 mL) until pH ~9 and the resulting mixture was stirred under argon for 6 h at room temperature. Then the reaction mixture was neutralized with Amberlite IR 120 (H$^+$) ion exchange resin, the resin was filtered off and rinsed successively with CH$_3$OH. The combined filtrate was concentrated in vacuo and purified by column chromatography on silica gel (ethyl acetate-toluene gradient elution) to afford the title compound (0.375 g, 87%) as oil. Analytical data for 77a: Rf=0.30 (ethyl acetate/toluene, 1.5/8.5, v/v); $[\alpha]_D^{21}$=+101.4 (c=1.1, CHCl$_3$); $^1$H NMR (500 MHz, CDCl$_3$): δ 7.28-7.40 (m, 25H, H—Ar), 4.98 (d, $J_{1,2}$=1.5 Hz, 1H, H-1$^F$), 4.90 (d, $J_{1,2}$=1.5 Hz, 1H, H-1$^E$), 4.89 (d, $J_{1,2}$=1.5 Hz, 1H, H-1$^D$), 4.86 (d, $J_{1,2}$=2.0 Hz, 1H, H-1$^C$), 4.85 (d, $J_{1,2}$=2.0 Hz, 1H, H-1$^B$), 1.13-1.26 ppm (m, 18H, H-6$^A$, H-6$^B$, H-6$^C$, H-6$^D$, H-6$^E$, H-6$^F$); $^{13}$C NMR (126 MHz, CDCl$_3$): δ 174.0, 137.4 (×2), 137.2 (×3), 128.7 (×2), 128.6 (×2), 128.4 (×2), 128.3 (x4), 128.1 (×2), 100.7, 100.4, 100.2 (×2), 100.1, 98.6, 77.5, 76.9, 76.6 (×2), 74.1, 73.6, 73.5, 73.3, 73.2, 72.3 (×2), 72.2 (×2), 70.2, 70.0, 67.9, 67.8 (×2), 67.5, 67.4, 67.1, 65.8, 64.4, 64.3, 64.2, 51.5, 33.9, 29.1, 25.7, 24.7, 18.6 (×2), 18.5 (×3), 18.2 ppm; HRMS (ESI): m/z calcd for C$_{78}$H$_{98}$N$_{18}$O$_{21}$Na [M+Na]$^+$: 1645.7046, found: 1645.7043.

5'-Methoxycarbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (48)

To a stirred solution of 77a (0.130 g, 0.080 mmol), in pyridine (5 mL) and water (2 mL) mixture, H$_2$S was bubbled for 0.5 h at 40° C., and stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 77b and no products arising from incomplete reduction. HRMS (ESI): m/z calcd for C$_{78}$H$_{111}$N$_6$O$_{21}$ [M+H]+: 1467.7797; found: 1467.7795. This crude material was directly used for formylation.

Compound 77b in CH$_3$OH (5 mL) at −20° C. was added a freshly prepared formic anhydride (Angew (1979) Chem. Int. Ed. 18, 614) (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 77c. HRMS (ESI): m/z calcd for C$_{84}$H$_{111}$N$_6$O$_{27}$Na [M+H]$^+$: 1635.7492; found: 1635.7485.

Compound 77c was dissolved in CH$_3$OH/H$_2$O (2:1, 5 mL), Pd(OH)$_2$ on carbon (20%, 0.050 g) was added. Then it was stirred under a pressure of hydrogen gas at room temperature for 16 h. After filtration through celite pad and washed with CH$_3$OH (3×10 mL), and solvents were removed in vacuo. The residue was purified by column chromatography on silica gel (methanol-dichloromethane gradient elution) to afford the title compound (0.052 g, 55%, over 3 steps) as a white foam. Analytical data for 48: Rf=0.20 (CH$_3$OH/CH$_2$Cl$_2$, 2/3, v/v); $^1$H NMR (500 MHz, D$_2$O): δ 8.17-8.19 (Z) and 7.99-8.02 (E) (m, 6H, NCHO), 4.84-5.20 (m, 6H, 6×H-1), 1.16-1.27 ppm (m, 18H, 6×H-6); $^{13}$C NMR (126 MHz, D$_2$O): δ178.5, 168.8, 165.9, 103.0, 102.9, 101.6, 101.5 (×2), 99.2, 78.6, 78.3, 78.1 (×2), 78.0 (×2), 77.9, 69.9 (×2), 69.2 (×2), 69.0, 68.9 (×2), 68.8, 68.7, 68.6 (×2), 68.5 (×3), 57.9, 57.7, 53.1, 53.0, 52.9, 52.8 (×2), 52.7, 49.9, 34.6, 29.0, 25.8, 24.9, 17.9 (×2), 17.8, 17.7 (×2), 17.6 (×2) ppm; HRMS (ESI): m/z calcd for C$_{49}$H$_{80}$N$_6$O$_{27}$Na [M+Na]$^+$: 1207.4964, found: 1207.4941.

(2'-Aminoethylamido)carbonylpentyl 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1-42) 4,6-dideoxy-4-formamido-α-D-mannopyranoside (85)

A solution of 48 (0.034 g, 0.029 mmol) in freshly distilled 1,2-diaminoethane (0.5 mL) was stirred at 65° C. for 48 h. Then excess reagent was removed in vacuo, and the residue was co-evaporated with CH$_3$OH (3×10 mL) and dried. The residue was purified by reversed phase HPLC on a C18 column with a gradient of water-acetonitrile and lyophilized, to give the title compound (0.034 g, 97%) as a white foam. Analytical data for 85: Rf=0.20 (CH$_3$OH); $^1$H NMR (500 MHz, D$_2$O): δ 8.16-8.19 (Z) and 7.98-8.02 (E) (m, 6H, NCHO), 4.81-5.19 (m, 6H, 6×H-1), 1.14-1.26 ppm (m, 18H, 6×H-6); $^{13}$C NMR (126 MHz, D$_2$O): δ177.4, 177.1, 167.9, 167.8, 164.9, 164.6, 102.4, 102.1, 102.0 (×2), 100.8, 100.7, 100.6 (×2), 98.6, 98.3 (×2), 77.6, 77.4, 77.3, 77.2, 77.1, 77.0, 76.8, 70.4, 70.3, 70.1, 70.0, 69.4, 69.2, 69.0 (×2), 68.3 (×2), 68.0 (×2), 67.9 (×2), 67.8 (×2), 67.7 (×2), 67.6 (×2), 67.5 (×2), 67.0, 57.0, 56.9, 56.7, 53.9, 53.8, 53.6, 52.0, 51.9 (×2), 51.8 (×2), 51.7, 40.9, 40.4, 40.0, 39.7, 35.7, 28.2, 25.0 (×2), 24.9, 17.1 (×2), 17.0 (×2), 16.9 (×3), 16.8, 16.7 ppm; HRMS (ESI): m/z calcd for C$_{50}$H$_{84}$N$_8$O$_{26}$Na [M+Na]$^+$: 1235.5389, found: 1235.5384.

1-[(2'-Aminoethylamido)carbonylpentyl 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside]-2-butoxycyclobutene-3,4-dione (91)

To a stirred solution of 85 (0.0142 g, 0.012 mmol) in water (0.5 mL) and EtOH (0.4 mL), a solution of 3,4-dibutoxy-3-cyclobutene-1,2-dione (20% in ethanol, 55 μL) was added and the pH was adjusted to 8 by careful addition of aq. NaHCO$_3$ (1%) solution. After 0.5 h, TLC showed the reaction was complete; the reaction mixture was neutralized using CH$_3$COOH (10%) and concentrated in vacuo. The residue was purified by reversed phase HPLC on a C18 column with a gradient of water-acetonitrile and lyophilized, to give the title compound (0.014 g, 88%) as a white foam. Analytical data for 91: Rf=0.40 (CH$_3$OH/CH$_2$Cl$_2$, 1/1, v/v); $^1$H NMR (700 MHz, D$_2$O): δ 8.20-8.23 (Z) and 8.02-8.07 (E) (m, 6H, NCHO), 4.88-5.34 (m, 6H, 6×H-1), 1.17-1.35 (m, 20H, —CH$_{2d}$—, 6×H-6), 0.88-1.00 ppm (m, 3H, —CH$_{31}$); $^{13}$C NMR (126 MHz, D$_2$O): δ 189.8, 189.6, 184.3, 178.5, 178.1, 177.9, 174.8, 174.7, 168.8, 165.9, 102.9 (×2), 101.5 (×3), 99.2 (×2), 78.5, 78.1 (×3), 78.0 (×2), 75.4, 75.3, 69.9, 69.2, 69.0, 68.9, 68.7, 68.5, 57.9, 57.7, 53.0, 52.9 (×2), 52.6, 45.2, 45.0, 40.3, 40.2, 36.7, 32.4, 32.3, 29.2, 26.1, 26.0, 25.9 (×2), 25.9, 19.2, 19.1, 19.0, 17.9 (×2), 17.8 (×2), 17.7 (×2), 13.9 ppm; HRMS (ESI): m/z calcd for C$_{58}$H$_{92}$N$_8$O$_{29}$Na [M+Na]$^+$: 1387.5862, found: 1387.5856.

5'-Methoxycarbonylpentyl 4-azido-4,6-dideoxy-α-D-mannopyranosyl (1→2) 4-azido-3-O-benzyl-4,6-dideoxy-α-D-mannopyranosyl (1→3) 4-azido-2-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranosyl (1→2) 4-azido-3-O-benzyl-4,6-dideoxy-α-D-mannopyranoside (80a)

Sodium methoxide (0.8 mL, 0.5 M solution) was added to a solution of 80 (0.413 g, 0.225 mmol) in $CH_3OH$ (12 mL) until pH ~9 and the resulting mixture was stirred under argon for 6 h at room temperature. Then the reaction mixture was neutralized with Amberlite IR 120 ($H^+$) ion exchange resin, the resin was filtered off and rinsed successively with $CH_3OH$. The combined filtrate was concentrated in vacuo and purified by column chromatography on silica gel (ethyl acetate-toluene gradient elution) to afford the title compound (0.334 g, 91%) as a white foam. Analytical data for 80a: Rf=0.40 (ethyl acetate/toluene, 1/9, v/v); $[α]_D^{21}$=+61.0 (c=1.0, $CHCl_3$); $^1H$ NMR (500 MHz, $CDCl_3$): δ 7.14-7.38 (m, 25H, H—Ar), 5.03-5.05 (br. s., 2H, H-$1^D$, H-$1^E$), 4.94 (d, $J_{1,2}$=1.5 Hz, 1H, H-$1^C$), 4.91 (d, $J_{1,2}$=1.2 Hz, 1H, H-$1^B$), 4.90 (d, $J_{1,2}$=1.5 Hz, 1H, H-$1^F$), 1.15-1.35 ppm (m, 20H, —$CH_{2d}$—, H-$6^A$, H-$6^B$, H-$6^C$, H-$6^D$, H-$6^E$, H-$6^F$); $^{13}C$ NMR (126 MHz, $CDCl_3$): δ 174.0, 137.5, 137.4, 137.3, 137.2, 137.1, 128.7, 128.6 (×3), 128.4 (×2), 128.3 (×2), 128.2 (×2), 128.1 (×2), 128.0 (×2), 127.9, 127.5, 101.0, 100.9, 100.4, 100.2, 98.6, 98.1, 78.0, 77.6, 77.5 (×2), 76.9, 76.4, 74.0, 73.3, 73.1, 72.9, 72.5, 72.4, 72.2, 72.1, 71.9, 70.2, 69.9, 68.1, 67.9 (×2), 67.8, 67.5 (×2), 67.1, 65.8, 64.6, 64.5, 64.4, 64.3, 64.0, 51.5, 33.9, 29.1, 25.7, 24.7, 18.6 (×3), 18.5, 18.4, 18.3 ppm; HRMS (ESI): m/z calcd for $C_{78}H_{98}N_{18}O_{21}Na$ $[M+Na]^+$: 1645.7046, found: 1645.7035.

5'-Methoxycarbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (49)

To a stirred solution of 80a (0.150 g, 0.092 mmol), in pyridine (5 mL) and water (2 mL) mixture, $H_2S$ was bubbled for 0.5 h at 40° C., and stirring was continued for 16 h. Then argon was bubbled through the solution for 10 min, solvents were removed in vacuo, and the residue was co-evaporated with toluene (3×10 mL) and dried. The high resolution mass spectrometry analysis showed completion of reaction to corresponding amine compound 80b and no products arising from incomplete reduction. HRMS (ESI): m/z calcd for $C_{78}H_{111}N_6O_{21}$ $[M+H]^+$: 1467.7797; found: 1467.7781. This crude material was directly used for formylation.

Compound 80b in $CH_3OH$ (5 mL) at −20° C. was added a freshly prepared formic anhydride[22] (5 mL, ethereal solution) and stirred for 3 h, then slowly allowed to warm to room temperature. Then solvents were evaporated and the residue was passed through column chromatography on silica gel (methanol-dichloromethane gradient elution) to afford disaccharide 80c. HRMS (ESI): m/z calcd for $C_{84}H_{110}N_6O_{27}Na$ $[M+Na]^+$: 1657.7311; found: 1657.7314.

Compound 80c was dissolved in $CH_3OH/H_2O$ (2:1, 5 mL), Pd(OH)$_2$ on carbon (20%, 0.050 g) was added. Then it was stirred under a pressure of hydrogen gas at room temperature for 16 h. After filtration through celite pad and washed with $CH_3OH$ (3×10 mL), and solvents were removed in vacuo. The residue was purified by column chromatography on silica gel (methanol-dichloromethane gradient elution) to afford the title compound (0.066 g, 60%, over 3 steps) as a white foam. Analytical data for 49: Rf=0.30 ($CH_3OH/CH_2Cl_2$, 1/1, v/v); $^1H$ NMR (700 MHz, $D_2O$): δ 8.20-8.25 (Z) and 8.02-8.06 (E) (m, 6H, NCHO), 4.89-5.23 (m, 6H, 6×H-1), 1.19-1.31 ppm (m, 18H, 6×H-6); $^{13}C$ NMR (176 MHz, $D_2O$): δ 178.4, 168.6, 165.7 (×2), 165.4 (×2), 103.1, 102.4, 101.5 (×2), 101.3, 99.1 (×2), 78.8, 78.4, 78.2, 78.0, 77.9, 77.6, 77.2, 69.7 (×2), 69.6 (×2), 69.5, 69.1, 69.0, 68.8, 68.7 (×2), 68.6, 68.5, 68.4 (×2), 68.3, 68.2, 67.9, 57.8, 57.7, 57.6, 52.9, 52.8, 52.7, 52.6, 52.5, 51.7, 34.4, 28.9, 25.7, 24.8, 18.0, 17.9, 17.8 (×2), 17.7 (×2), 17.6 (×3), 17.5 ppm; HRMS (ESI): m/z calcd for $C_{49}H_{80}N_6O_{27}Na$ $[M+Na]^+$: 1207.4964, found: 1207.4963.

(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (86)

A solution of 49 (0.041 g, 0.035 mmol) in freshly distilled 1,2-diaminoethane (0.5 mL) was stirred at 65° C. for 48 h. Then excess reagent was removed in vacuo, and the residue was co-evaporated with $CH_3OH$ (3×10 mL) and dried. The residue was purified by reversed phase HPLC on a C18 column with a gradient of water-acetonitrile and lyophilized, to give the title compound (0.039 g, 93%) as a white foam. Analytical data for 86: $R_f$=0.20 ($CH_3OH$); NMR (500 MHz, $D_2O$): δ 8.25-8.32 (Z) and 8.08-8.14 (E) (m, 6H, NCHO), 4.92-5.30 (m, 6H, 6×H-1), 1.23-1.39 ppm (m, 18H, 6×H-6); $^{13}C$ NMR (126 MHz, $D_2O$): δ 178.4, 178.1, 168.8 (×2), 165.9, 165.6, 103.3 (×2), 102.6, 101.9, 101.8, 101.6, 101.5, 99.3, 99.2, 78.9, 78.6, 78.5, 78.1, 77.8, 77.4, 71.0, 69.9 (×2), 69.7 (×2), 69.6, 69.4, 69.2, 69.0, 69.0, 68.9, 68.8, 68.6 (×2), 68.5 (×2), 68.4, 68.0, 57.9 (×2), 57.8, 57.7, 56.4, 53.0, 52.8 (×2), 52.7, 51.8, 41.4, 41.1, 40.6, 36.6, 29.1, 26.0, 25.9 (×2), 18.1 (×3), 18.0, 17.9, 17.8, 17.7, 17.6 ppm; HRMS (ESI): m/z calcd for $C_{50}H_{85}N_8O_{26}$ $[M+H]^+$: 1213.5570, found: 1213.5564.

1-[(2'-Aminoethylamido)carbonylpentyl 4,6-dideoxy-4-formamido-α-D-mannopyranosyl (1→2) 4,6-dideoxy-4-formamido-α-D-mannopyranosyl (1→3) 4,6-dideoxy-4-formamido-α-D-mannopyranosyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside]-2-butoxycyclobutene-3,4-dione (92)

To a stirred solution of 86 (0.014 g, 0.011 mmol) in water (0.8 mL) and EtOH (0.6 mL), a solution of 3,4-dibutoxy-3-cyclobutene-1,2-dione (20% in ethanol, 55 μL) was added and the pH was adjusted to 8 by careful addition of aq. $NaHCO_3$ (1%) solution. After 0.5 h, TLC showed the reaction was complete; the reaction mixture was neutralized using $CH_3COOH$ (10%) and concentrated in vacuo. The residue was purified by reversed phase HPLC on a C18 column with a gradient of water-acetonitrile and lyophilized, to give the title compound (0.012 g, 76%) as a white foam. Analytical data for 92: Rf=0.40 ($CH_3OH/CH_2Cl_2$, 1/1, v/v); $^1H$ NMR (700 MHz, $D_2O$): δ 8.20-8.25 (Z) and 8.02-8.07

(E) (m, 6H, NCHO), 4.85-5.21 (m, 6H, 6×H-1), 1.18-1.35 (m, 20H, —CH$_{2d}$—, 6×H-6), 0.89-0.97 ppm (m, 3H, —CH$_{31}$);

$^{13}$C NMR (126 MHz, D$_2$O): δ 189.8, 189.7, 184.3, 178.5, 178.1, 177.9 (×2), 174.8, 174.7, 168.8, 165.9, 165.6, 103.3, 102.6, 101.6, 101.5, 99.2, 78.9, 78.5, 78.2, 77.8, 77.3, 75.4, 75.3, 70.8, 69.9, 69.7, 69.2, 69.0, 68.8, 68.7, 68.6, 68.5, 68.4, 57.9, 57.7, 53.0, 52.8, 52.7, 51.8, 45.2, 45.0, 40.3, 40.2, 36.7, 32.4, 29.2, 26.1, 26.0, 25.9 (×2), 19.1, 19.0, 18.1, 18.0, 17.9 (×2), 17.8, 17.7, 13.9 ppm; HRMS (ESI): m/z calcd for C$_{58}$H$_{92}$N$_8$O$_{29}$Na [M+Na]$^+$: 1387.5862, found: 1387.5864.

Conjugation of the Pentasaccharide Squarate 40 to BSA (42)

BSA (11.7 mg, 0.17 μmol) and squarate 40 (4.2 mg, 3.5 μmop were dissolved in 0.5 M borate buffer pH 9 (350 μL) and stirred gently at room temperature for 3 days. Then the reaction mixture was diluted with water and dialyzed against deionized water (3×2 L) at 4° C., spinned and lyophilized. The product of conjugation was obtained as a white solid (12.5 mg, 84%): MALDI-TOF-MS indicated the conjugate 42 had an average of 16.4 pentasaccharides per BSA.

Conjugation of the Nonasaccharide Squarate 41 to BSA (43)

The conjugation of BSA (5.5 mg, 0.08 μmol) and squarate 41 (3.2 mg, 1.6 μmop in borate buffer (220 μl) was performed as described for 42. After the dialysis (5×2 L) and lyophilization the conjugate 43 was obtained as a white solid (6 mg, 74%). As calculated from MALDI-TOF-MS spectrum the average number of nonasaccharides per BSA was 16.8.

Conjugation of Squarate Derivative 87 to BSA (93).

BSA (30 mg, 0.451 μmol) and disaccharide squarate 87 (4.5 mg, 6.77 μmol) were dissolved in 0.5 M borate buffer pH 9 (600 μL) and stirred gently at room temperature for 3 days. Then the reaction mixture was diluted with Mili-Q water, filtered through milipore filtration tube (10,000 MWCO, 4×10 mL), lyophilized and the BSA-conjugate 93 was obtained as a white foam (30.4 mg, 89%). The MALDI-TOF mass spectrometry analysis indicated the conjugate 93 had an average of 15.2 disaccharides per BSA.

Conjugation of Squarate Derivative 88 to BSA (94).

BSA (30 mg, 0.451 μmol) and trisaccharide squarate 88 (5.7 mg, 6.74 μmop were dissolved in 0.5 M borate buffer pH 9 (700 μL) and stirred gently at room temperature for 3 days. Then the reaction mixture was diluted with Mili-Q water, filtered through milipore filtration tube (10,000 MWCO, 4×10 mL), lyophilized and the BSA-conjugate 94 was obtained as a white foam (32.3 mg, 91%). The MALDI-TOF mass spectrometry analysis indicated the conjugate 94 had an average of 15.9 trisaccharides per BSA.

Conjugation of Squarate Derivative 89 to BSA (95).

BSA (32.5 mg, 0.489 μmol) and trisaccharide squarate 89 (6.2 mg, 7.34 μmop were dissolved in 0.5 M borate buffer pH 9 (700 μL) and stirred gently at room temperature for 3 days. Then the reaction mixture was diluted with Mili-Q water, filtered through milipore filtration tube (10,000 MWCO, 4×10 mL), lyophilized and the BSA-conjugate 95 was obtained as a white foam (33.5 mg, 87%). The MALDI-TOF mass spectrometry analysis indicated the conjugate 95 had an average of 15.7 trisaccharides per BSA.

Conjugation of Squarate Derivative 90 to BSA (96).

BSA (11 mg, 0.165 μmop and tetrasaccharide squarate 90 (2.5 mg, 2.45 μmol) were dissolved in 0.5 M borate buffer pH 9 (400 μL) and stirred gently at room temperature for 3 days. Then the reaction mixture was diluted with Mili-Q water, filtered through milipore filtration tube (10,000 MWCO, 4×10 mL), lyophilized and the BSA-conjugate 96 was obtained as a white foam (12 mg, 92%). The MALDI-TOF mass spectrometry analysis indicated the conjugate 96 had an average of 13.4 tetrasaccharides per BSA.

Conjugation of Squarate Derivative 91 to BSA (97).

BSA (5 mg, 0.0752 μmol) and hexasaccharide squarate 91 (1.5 mg, 1.099 μmol) were dissolved in 0.5 M borate buffer pH 9 (400 μL) and stirred gently at room temperature for 3 days. Then the reaction mixture was diluted with Mili-Q water, filtered through milipore filtration tube (10,000 MWCO, 4×10 mL), lyophilized and the BSA-conjugate 97 was obtained as a white foam (5.5 mg, 87%). The MALDI-TOF mass spectrometry analysis indicated the conjugate 97 had an average of 13.8 hexasaccharides per BSA.

Conjugation of Squarate Derivative 92 to BSA (98).

BSA (5 mg, 0.0752 μmop and hexasaccharide squarate 92 (1.5 mg, 1.099 μmol) were dissolved in 0.5 M borate buffer pH 9 (4004) and stirred gently at room temperature for 2 days. Then the reaction mixture was diluted with Mili-Q water, filtered through milipore filtration tube (10,000 MWCO, 4×10 mL), lyophilized and the BSA-conjugate 98 was obtained as a white foam (6 mg, 99%). The MALDI-TOF mass spectrometry analysis indicated the conjugate 98 had an average of 10.8 hexasaccharides per BSA.

Conjugation of Squarate Derivative 87 to Co-Povidone Polymer (99).

High Loading:

Co-povidone (6.9 mg, 5.95 μmol, 1 eq.) and disaccharide squarate 87 (2.0 mg, 2.97 μmol, 0.5 eq.) were dissolved in 0.5 M borate buffer pH 9 (500 μL) and stirred gently at room temperature for 2 days. Then, a solution of 5% aq. Ac$_2$O (1 mL) and saturated NaHCO$_3$ (1 mL) was added and stirred for 3 h. After that, the reaction mixture was diluted with Mili-Q water, dialyzed against deionized water (5×2 L), lyophilized to obtain the co-povidone-conjugate 99a.

Low Loading:

Co-povidone (5.0 mg, 4.31 μmol, 1 eq.) and disaccharide squarate 87 (0.5 mg, 0.74 μmol, 0.166 eq.) were dissolved in 0.5 M borate buffer pH 9 (500 μL) and stirred gently at room temperature for 2 days. Then, a solution of 5% aq. Ac$_2$O (1 mL) and saturated NaHCO$_3$ (1 mL) was added and stirred for 3 h. After that, the reaction mixture was diluted with Mili-Q water, dialyzed against deionized water (5×2 L), lyophilized to obtain the co-povidone-conjugate 99b.

Conjugation of Squarate Derivative 91 to Co-Povidone Polymer (100).

High Loading:

Co-povidone (5.0 mg, 4.31 μmol, 1 eq.) and hexasaccharide squarate 91 (2.94 mg, 2.15 μmol, 0.5 eq.) were dissolved in 0.5 M borate buffer pH 9 (500 μL) and stirred gently at room temperature for 2 days. Then, a solution of 5% aq. Ac$_2$O (1 mL) and saturated NaHCO$_3$ (1 mL) was added and stirred for 3 h. After that, the reaction mixture was diluted with Mili-Q water, dialyzed against deionized water (5×2 L), lyophilized to obtain the co-povidone-conjugate 100a.

Low Loading:

Co-povidone (5.0 mg, 4.31 μmol, 1 eq.) and hexasaccharide squarate 91 (1.0 mg, 0.73 μmol, 0.166 eq.) were dissolved in 0.5 M borate buffer pH 9 (500 μL) and stirred gently at room temperature for 2 days. Then, a solution of 5% aq. Ac$_2$O (1 mL) and saturated NaHCO$_3$ (1 mL) was added and stirred for 3 h. After that, the reaction mixture was diluted with Mili-Q water, dialyzed against deionized water (5×2 L), lyophilized to obtain the co-povidone-conjugate 100b.

Conjugation of Squarate Derivative 91 to Tetanus Toxoid (101).

Hexasaccharide squarate 91 (0.55 mg, 0.403 μmol) was added to the solution of tetanus toxoid (2 mg, 0.0133 μmop in 0.5 M borate buffer pH 9 (1 mL) and stirred gently at room temperature for 3 days. Then the reaction mixture was washed with borate buffer, filtered through milipore filtration tube (10,000 MWCO, 4×10 mL) and the resulting tetanus toxoid-conjugate 101 was stored in PBS buffer. The MALDI-TOF mass spectrometry analysis indicated the conjugate 101 had an average of 12.6 hexasaccharides per tetanus toxoid.

Conjugation of Squarate Derivative 92 to Tetanus Toxoid (102).

Hexasaccharide squarate 92 (0.55 mg, 0.403 μmol) was added to the solution of tetanus toxoid (2 mg, 0.0133 μmop in 0.5 M borate buffer pH 9 (1 mL) and stirred gently at room temperature for 2 days. Then the reaction mixture was washed with borate buffer, filtered through milipore filtration tube (10,000 MWCO, 4×10 mL) and the resulting tetanus toxoid-conjugate 102 was stored in PBS buffer. The MALDI-TOF mass spectrometry analysis indicated the conjugate 102 had an average of 6.2 hexasaccharides per tetanus toxoid.

Specific M-Antigen—Proof of Concept Studies on OPS from *Brucella* and *Y. enterocolitica* O:9

Figure 2:
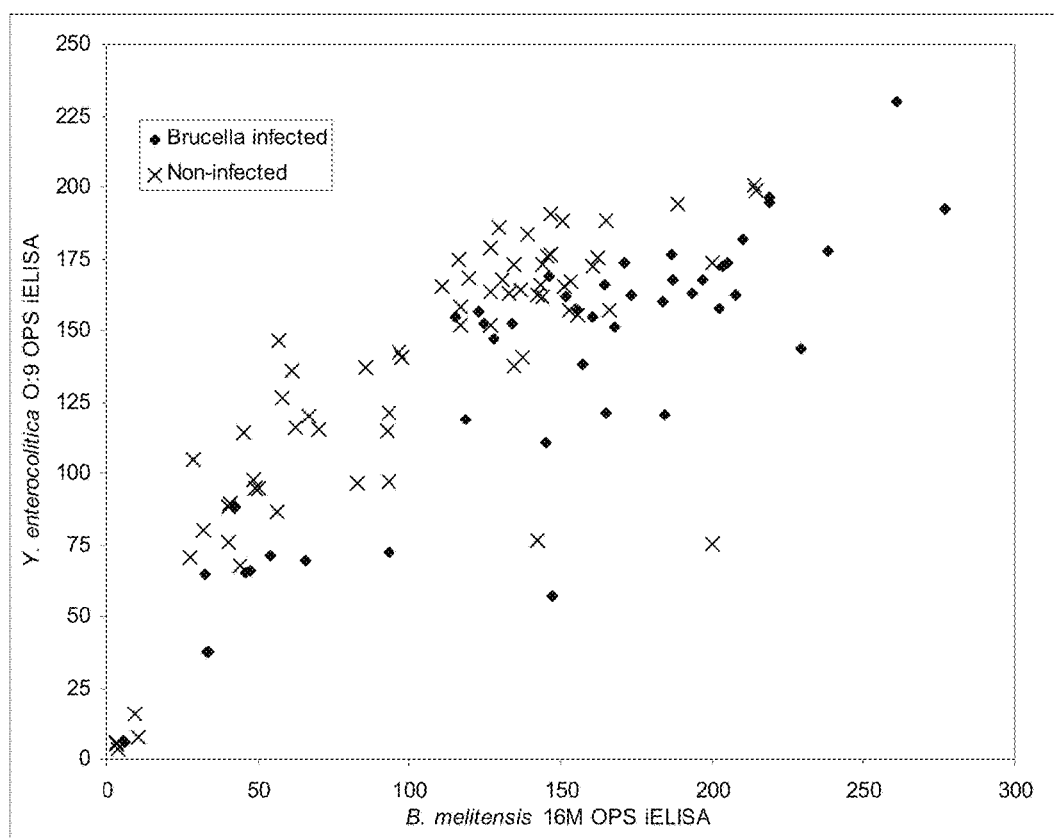
FIG. 2 shows results (expressed as a percentage of a common positive control) from the *B. melitensis* 16M OPS iELISA (x-axis) and *Y. enterocolitica* O:9 OPS iELISA (y-axis); the solid diamonds represent the results for sera from cattle confirmed as infected with *B. abortus* biovar 1 (n=45) and the crosses represent the results for sera from non-*Brucella* infected cattle that are positive in one or more conventional serodiagnostic assays (n=68)

Monoclonal antibody binding analysis using the anti-M specific antibody BM40 (Greiser et al. (1987) Ann Inst Pasteur Microbiol 138, 549-560) against *Brucella* A, M and *Y. enterocolitica* O:9 sLPS antigens, prepared by hot-phenol extraction (Westphal et al. (1952) Z. Naturforsch. 7, 148-155) confirmed the exceptionally high specificity of the BM40 response in this case. There was no measurable binding against the *Y. enterocolitica* O:9 sLPS and binding to *B. melitensis* 16M (an M dominant strain) was tenfold greater than binding to *B. abortus* S99 (an A dominant strain).

During further exploratory studies, the absorption methods described above (Alton et al. (1994) Techniques for the Brucellosis Laboratory, pages 53-54; INRA Editions, ISBN-10: 2738000428; Kittelberger et al. (1998) Vet. Microbial. 60, 45-57) were evaluated, using sera from cattle experimentally infected with *Brucella abortus* strain 544 (an A dominant strain) or *Y. enterocolitica* O:9. A residual anti-*Brucella* sLPS titre was observed in indirect ELISA in *Y. enterocolitica* O:9 absorbed samples in some, but not all, sera from the *Brucella* infected animals.

The sera from the experimentally infected cattle was also evaluated by indirect ELISAs using *B. melitensis* 16M and *Y. enterocolitica* O:9 OPS antigens purified from the smooth LPS using mild acid hydrolysis and size exclusion chromatography (Meikle et al. (1989) Infect Immun 57, 2820-2828), tested to be free of lipid-A using the limulus amebocyte lysate reaction (Ding et al. (2001) Trends Biotechnol. 19, 277-281). Samples taken from the cattle (cows) 3, 7, 16, 24 and 53 weeks post infection were taken from each of the four animals experimentally infected with *B. abortus* strain 544 and from each of the four animals experimentally infected with *Y. enterocolitica* O:9. These samples have been previously described and also tested by conventional serological assays for brucellosis as described previously (McGiven et al. (2008) Journal of Immunological Methods 20, 7-15).

The OPS from *B. melitensis* 16M was chosen in preference to OPS from a *B. abortus* A dominant strain due to the higher frequency of α-1,3 linkages and M epitopes, so that the extremes of the structural variation in the natural 4,6-dideoxy-4-formamido-α-D-mannopyranose homopolymers would be represented.

Owing to their high solubility, the purified OPS antigens do not bind effectively to ELISA polystyrene ELISA plates by passive absorption (unless conjugated to carrier molecules containing hydrophobic regions). To enable their immobilisation to a solid phase, Carbo-BIND™ 96 well ELISA plates were used (Corning, product number 2507) which have hydrazide functional groups on the well surface. These hydrazide groups react spontaneously with aldehydes which may be generated in carbohydrates by oxidation.

The OPS was oxidised at 100 μg/ml with 10 mM sodium metaperiodate and 50 mM sodium acetate buffer (SAB) pH 5.5 in the dark at 4° C. for 30 minutes. After this time the antigen was diluted to between 0.5 to 0.125 μg/ml in SAB pH 5.5 and 100 μl was added to the wells of a Carbo-BIND™ plate. The plate was incubated for 1 hour at 37° C. and then washed with 4 times 200 μl of phosphate buffered saline with 0.05% Tween-20 (PBS-T20) and tapped dry.

Serum was diluted 1/50 in buffer (Sigma #B6429) and 100 μl of this was added per well of the antigen coated plate, each sample tested in duplicate. The plate was incubated for 1 hr at room temperature on a rotary shaker at 160 rpm and then washed with PBS-T20 as described above.

An HRP conjugated Protein-G conjugate (Thermo #31499), diluted to 1 μg/ml in buffer, was then added in 100 μl volumes to each well of the plate which was then incubated and washed as described above for serum. The plate was then developed with ABTS (2,2'-Azino-bis(3-ethylbenzothiazoline-6-sulfonic acid) diammonium salt) and hydrogen peroxide substrate for 10-15 mins, stopped with 0.4 mM sodium azide and read at 405 nm wavelength. The optical density for the duplicates was averaged and the blank OD (buffer only instead of sera) was subtracted. This value was then expressed as a percentage of a common positive control serum sample from a *B. abortus* biovar 1 (A dominant) infected bovine for cattle sera.

As expected, there was much cross reaction between the *Brucella* and *Y. enterocolitica* O:9 OPS antigens with both sets of sera, i.e., those from the cattle experimentally infected with *Brucella abortus* strain 544 and those experimentally infected with *Y. enterocolitica* O:9. An additional output was calculated for each sample by dividing the result from the *B. melitensis* OPS iELISA by that from the *Y. enterocolitica* O:9 OPS iELISA to derive a simple ratiometric value (henceforth described as the 'Bm16M/YeO:9 Ratio'). Thus, higher Bm16M/YeO:9 Ratio values signify that the intensity of the reaction to the *B. melitensis* 16M OPS antigen was greater than the intensity of the reaction to the *Y. enterocolitica* O:9 antigen relative to lower Bm16M/YeO:9 Ratio values. Analysis of this data set revealed that there was a highly significant difference (P=0.008, Student's t-test for unpaired data) between the the Bm16M/YeO:9 Ratio values for the two different sample populations, whereby the mean value from the *Brucella* infected animals was higher than the mean value from the *Y. enterocolitica* O:9 infected animals. There was, therefore, a significant difference in the way that the serum from the two populations reacted to these two antigen types, with the sera from the *Brucella* infected animals reacting with a relatively higher intensity to the *B. melitensis* 16M OPS and vice versa. This result suggests that there are significant and detectable differences in the anti-OPS antibody repertoire between the two serum populations.

As a consequence of this finding with the relative OPS ELISA results, the same methods were applied to archived bovine field sera from Great Britain. A total of 45 samples from individual animals confirmed by culture to be infected with *B. abortus* biovar 1 (A dominant) were tested. Also 68 samples were tested from individual animals whose sera was collected from 1996 to 1999, more than 10 years since the declaration of officially brucellosis free status for Great Britain, that were positive in conventional serology for brucellosis such as *B. abortus* S99 sLPS iELISA, SAT and CFT (Nielsen et al. (2009) "Bovine brucellosis" In: Manual of Diagnostic Tests & Vaccines for Terrestrial Animals 2009; Office International Des Epizooties, Paris, pg 10-19) but for which there was no cultural or epidemiological evidence of brucellosis. As with the data from the experimentally infected animals there was a highly significant difference (P=0.000012, Student's t-test for unpaired data) between the Bm16/YeO:9 Ratio values for the two different serological groups. As before, sera from cattle with confirmed brucellosis had, on average, higher values (FIG. 2).

The results from both the *B. melitensis* and *Y. enterocolitica* O:9 OPS iELISAs were evaluated to find the positive/negative cut-off for each which generated the highest Youden Index (YI=diagnostic sensitivity [DSn]+diagnostic specificity [DSp]−1). These optimised YI values with the associate DSn and DSp figures are shown in Table 3.

TABLE 3

Performance statistics for OPS iELISAs as tested on bovine sera

| Assay | Optimal Youden Index (YI = DSn + DSp-1) | | | ROC - Area Under Curve | |
|---|---|---|---|---|---|
| | YI Estimate | DSn % | DSp % | AUC | 95% Confidence Interval |
| *Y. enterocolitica* O:9 OPS iELISA | 0.1297 | 64.44 | 48.53 | 0.5065 | 0.3964-0.6167 |
| *B. melitensis* 16M OPS iELISA | 0.4232 | 55.56 | 86.76 | 0.7065 | 0.6024-0.8106 |
| Bm16M/YeO:9 Ratio | 0.5343 | 66.67 | 86.76 | 0.8056 | 0.7219-0.8892 |

To further evaluate the diagnostic effectiveness of each of the OPS iELISAs Receiver Operator Characteristic (ROC) Curve analysis was used, in particular the evaluation of the Area Under the Curve (AUC) (Hanley and McNeil (1982) Radiology 143, 29-36). In this context, the AUC represents the ability of the assay to correctly classify samples from animals that are *Brucella* infected and those that are not. The data in Table 2 shows that the *B. melitensis* OPS iELISA has a higher optimised YI and AUC value than the *Y. enterocolitica* O:9 OPS iELISA.

In Table 4, P values relating to testing for significant differences between AUC data are presented. Testing for the significance of differences between AUC values was performed using the method for paired samples (Hanley and McNeil (1983) Radiology 148, 839-843).

TABLE 4

Comparison of ROC AUC statistics for the OPS iELISAs as tested on bovine sera

| Assay Difference between AUC (P = [one-tailed]) | *Y. enterocolitica* O:9 OPS iELISA | *B. melitensis* 16M OPS iELISA |
|---|---|---|
| *B. melitensis* 16M OPS iELISA | <0.0001 | |
| Bm16M/YeO:9 | <0.0001 | 0.239 |

This data shows that there is a highly significant difference (P<0.0001) between the AUC values for the *Y. enterocolitica* O:9 and *B. melitensis* 16M OPS iELISAs and therefore the assay is significantly superior. The improvement in diagnostic performance when using the Bm16M/YeO:9 Ratio values is also demonstrated in Tables 3 and 4. The optimal YI value is greater than that for both of the individual OPS iELISA assays. The DSp is equal to that of the *B. melitensis* 16M OPS iELISA and the DSn is superior. The AUC is also greater, but not significantly so, compared to the AUC for the *B. melitensis* 16m OPS iELISA (P=0.239).

This is strong evidence to demonstrate that a combinational ratiometric approach to the determination of infection status can be more advantageous than the interpretation of one test alone when there is significant cross reaction due to similar but non-identical antigens. The data for the *B. melitensis* 16M OPS iELISA alone and in combination as a ratiometric assay suggests that the M epitope is playing a major role in the significant differences in antibody binding that have been observed. The Bm16M/YeO:9 Ratio evaluation of the samples is a relatively crude attempt to delineate the contribution to overall titre made by the specific antibodies and epitopes from the contribution made by the common ones.

The same OPS iELISA methods were also applied to 41 samples from individual swine that were positive to the Rose Bengal Test (RBT) and iELISA (Olsen, (2010) "Porcine Brucellosis" In: Office International Des Epizooties, Paris) and from herds confirmed by culture to be infected with *B. suis* biovar 1, an A dominant OPS biovar (Meikle et al. (1989) Infect Immun 57, 2820-2828; Olsen, (2009) "Porcine Brucellosis" In: Office International Des Epizooties, Paris, pages 3-4). A further 52 samples were tested which were collected from individual animals in Great Britain, officially free of *B. suis*, within herds which from which one or more sample positive in conventional serology such as RBT, cELISA, iELISA (Olsen, (2009) "Porcine Brucellosis" In: Office International Des Epizooties, Paris, pages 3-4) where obtained and where there was no epidemiological evidence of brucellosis.

Figure 3A:
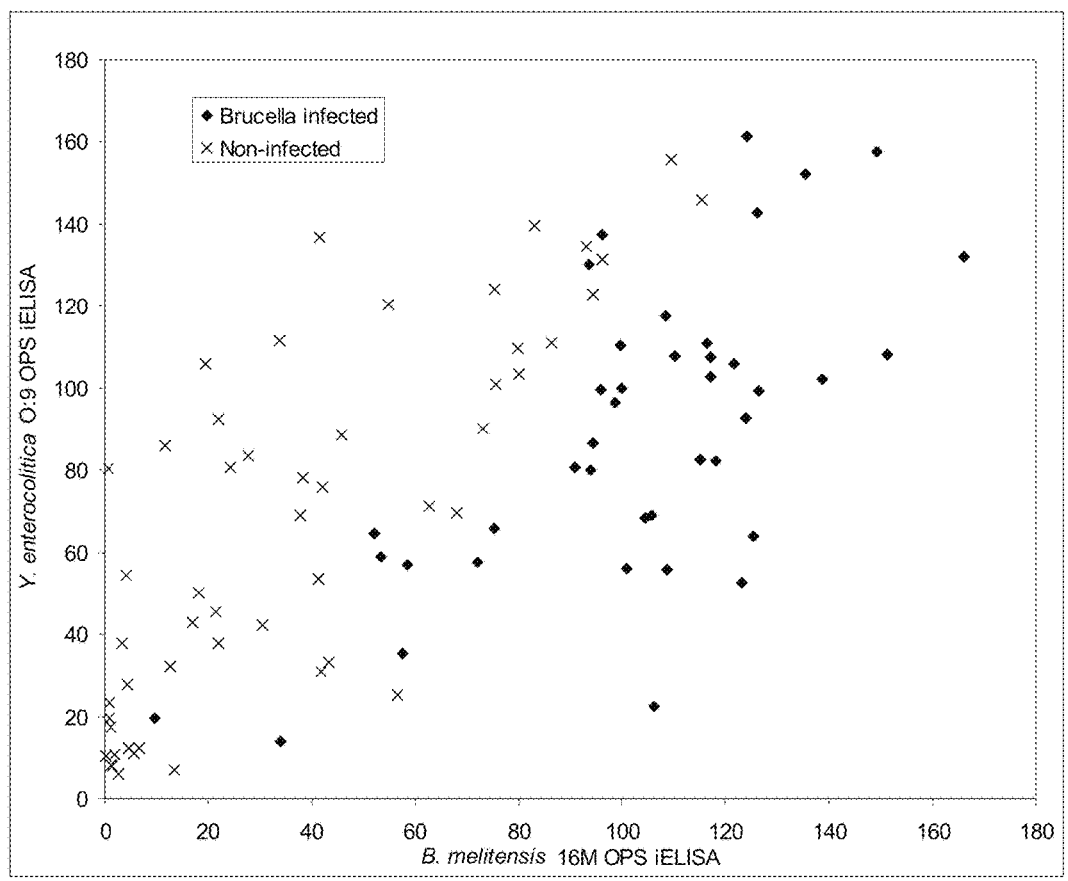
FIG. 3A shows results (expressed as a percentage of a common positive control) for *B. melitensis* 16M OPS iELISA (x the scatter plot only distinguishes between samples from different infection types, not by animal and time post infection.
Figure 3B:
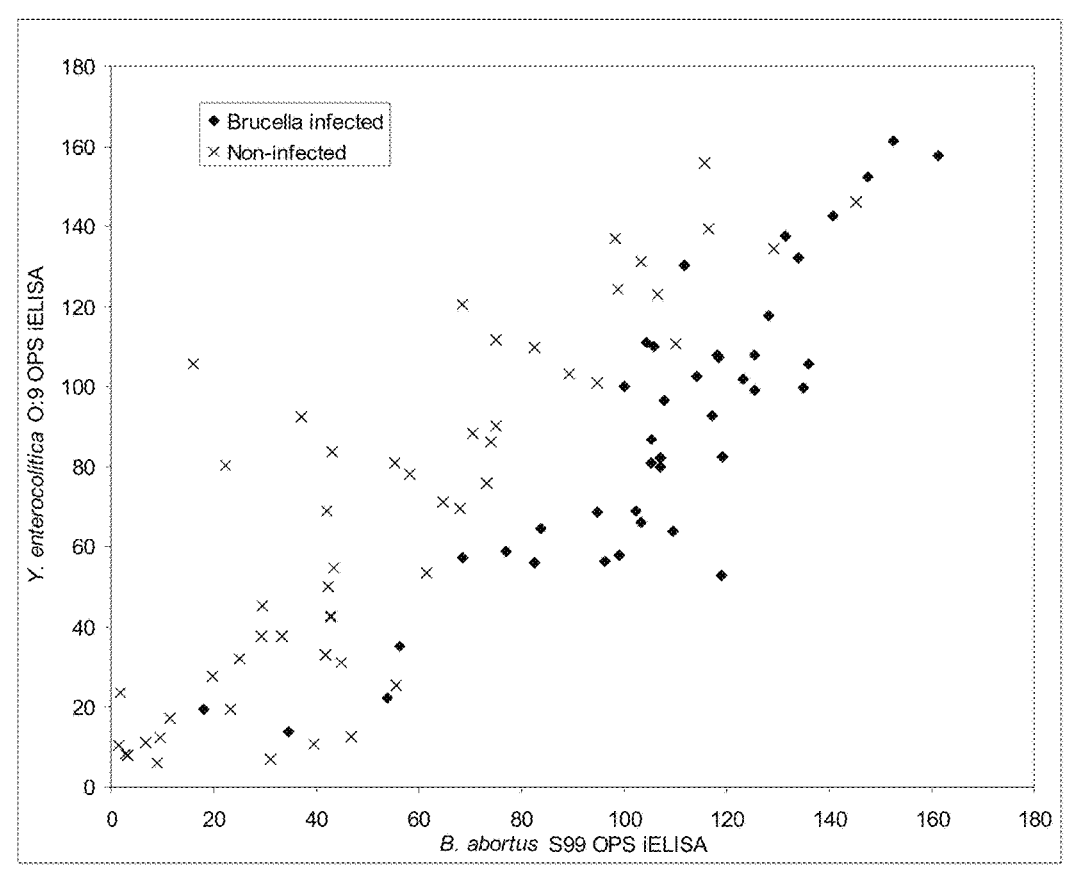

As with the data from the cattle sera samples, there was a highly significant difference (P=0.000000006, using the unpaired Student's t-test) between the Bm16/YeO:9 Ratio values for the two different serological groups. As before, sera from swine with confirmed brucellosis had a higher, on average, values than did the false positive serological samples (FIG. 3A). These samples were also tested by *B. abortus* S99 (A dominant) OPS iELISA (FIG. 3B) and a ratiometric expression of the data, analogous to the Bm16M/YeO:9 Ratio, was evaluated. There was a significant difference between the ratio of the *B. abortus* S99 to *Y. enterocolitica* O:9 OPS iELISA results for the different serum groups, but the difference was not as strong (P=0.023) as observed with the Bm16M/YeO:9 Ratio. In fact, the difference between the results from the two *Brucella* OPS antigens, *B. melitensis* 16M and *B. abortus* S99, was much more significant (P=0.000000016) than the difference between the *Y. enterocolitica* O:9 and *B. abortus* S99 results. This reflects the known structure of the these antigens with the A dominant OPS of *B. abortus* S99 having only approximately 2% α-1,3 linkages compared to the M dominant *B. melitensis* 16M OPS with 20% and *Y. enterocolitica* with 0%.

The optimised YI, as described above, for the individual OPS iELISAs and the Bm16M/YeO:9 Ratio, results for the swine sera are shown in Table 5 where: Bm16M/YeO:9 >*B. melitensis* 16M >*B. abortus* S99>*Y. enterocolitica* O:9.

TABLE 5

Performance statistics for OPS iELISAs as tested on porcine sera

| Assay | Optimal Youden Index (YI = DSn + DSp-1) | | | ROC - Area Under Curve | |
|---|---|---|---|---|---|
| | YI Estimate | DSn % | DSp % | AUC | 95% Confidence Interval |
| *Y. enterocolitica* O:9 OPS iELISA | 0.3588 | 87.80 | 48.08 | 0.6445 | 0.5328-0.7562 |
| *B. abortus* S99 OPS iELISA | 0.6472 | 87.80 | 76.92 | 0.8607 | 0.7832-0.9382 |
| *B. melitensis* 16M OPS iELISA | 0.7087 | 80.49 | 90.38 | 0.9135 | 0.8559-0.9710 |
| *B. melitensis* 16M/ *Y. enterocolitica* O:9 | 0.7678 | 90.24 | 86.54 | 0.9085 | 0.8437-0.9733 |

The data for the AUC was similar whereby: *B. melitensis* 16M>Bm16M/YeO:9 Ratio>*B. abortus* S99>*Y. enterocolitica* O:9. The AUC for the *Y. enterocolitica* O:9 OPS iELISA was significantly lower (P<0.0001) than for the other three outputs (Table 6). There was a difference of weak significance between the AUC for the *B. abortus* and *B. melitensis* OPS iELISAs (P=0.066).

TABLE 6

Comparison of ROC AUC statistics for the OPS iELISAs as tested on porcine sera

| Assay Difference between AUC (P = [one-tailed]) | *Y. enterocolitica* O:9 OPS iELISA | *B. abortus* S99 OPS iELISA | *B. melitensis* 16M OPS iELISA |
|---|---|---|---|
| *B. abortus* S99 OPS iELISA | <0.0001 | | |
| *B. melitensis* 16M OPS iELISA | <0.0001 | 0.066 | |
| Bm16M/YeO:9 | <0.0001 | 0.174 | 0.452 |

The same methods were applied to 21 serum samples from individual ELISA positive swine from herds confirmed by culture to be infected with *B. suis* biovar 2 and compared to the data from the 52 samples from non-infected swine, but seropositive herds, in Great Britain, as well as to the 41 samples from *B. suis* biovar 1 infected animals. There was no significant difference in the Bm16M/YeO:9 Ratio results between the sera from the *B. suis* biovar 2 infected animals and from sera from the non-infected animals (P=0.926). This is in keeping with the recent discovery that, uniquely for *Brucella*, the OPS from *B suis* biovar 2 contains no α-1,3 linkages (Zaccheus et al. (2013) PLoS One 8, e53941) and therefore the OPS is highly similar, if not identical, to that of *Y. enterocolitica* O:9.

The data from the swine sera demonstrates that assays using OPS with higher proportions of α-1,3 linkages provide superior diagnostic attributes. This is further evidence that the α-1,3 linkage is part of a significant and discriminating epitope for polyclonal sera derived from animals naturally infected with *Brucella*.

Developing the Discrete M Epitope Antigen (Specific M-Antigen)

The evidence described above from the OPS iELISAs provided the stimulus for additional studies to define, isolate and apply the 'M' epitope to the serodiagnosis of brucellosis in order to increase the accuracy of the results. The purified native OPS from *Y. enterocolitica* O:9, *B. melitensis* 16M ('M' dominant) and *B. abortus* S99 ('A' dominant) was partially hydrolysed using hot concentrated hydrochloric acid to obtain di- to dodeca-saccharides. These were evaluated by LC-ESI-MS/MS using a graphitized carbon column (Ruhaak et al. (2009) Anal. Bioanal. Chem. 394, 163-174) to separate them and confirm their identity as 4,6-dideoxy-4-formamido-α-D-mannopyranosyl oligomers.

The oligosaccharides from the *B. abortus* S99 OPS were subjected to affinity chromatography using an affinity chromatography column with immobilised *Brucella* anti-M monoclonal antibody BM40 and the wash and elution fractions were further evaluated by LC-ESI-MS/MS using a graphitized carbon column (Ruhaak et al. (2009) Anal. Bioanal. Chem. 394, 163-174) to separate the oligosaccharides. Tetrasaccharides of 4,6-dideoxy-4-formamido-α-D-mannopyranosyl were readily detectable in the bound and subsequently eluted, using dilute hydrochloric acid, fractions; the LC-ESI-MS chromatogram was compared to those for the tetrasaccharides found in the non-affinity selected oligosaccharides derived from the partial acid hydrolysis of the three native antigens.

Figure 4A:
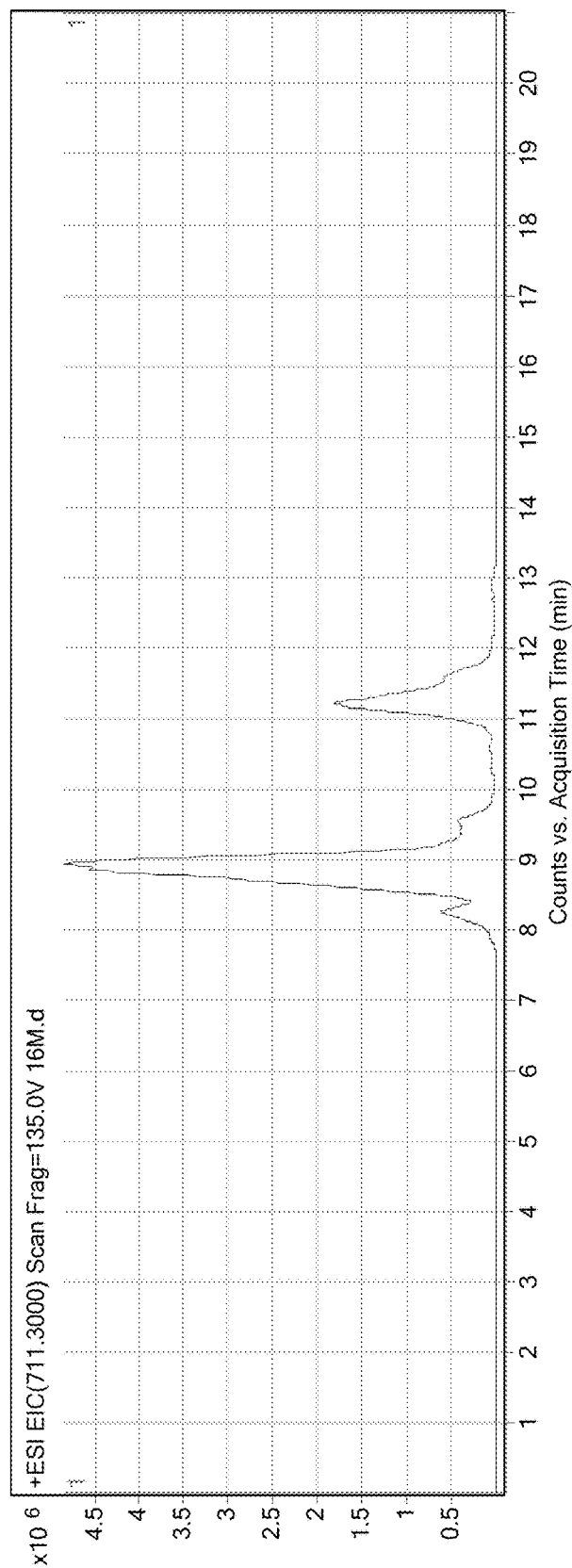
Figure 4B:
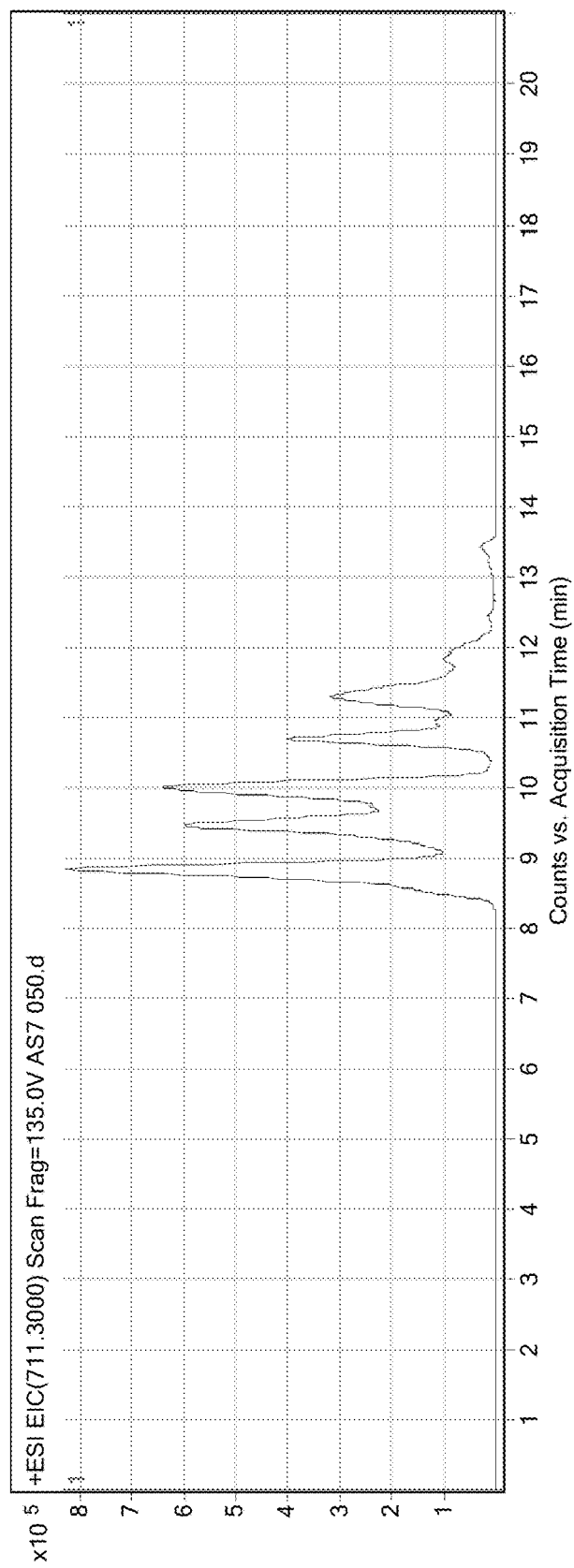
Figure 4C:
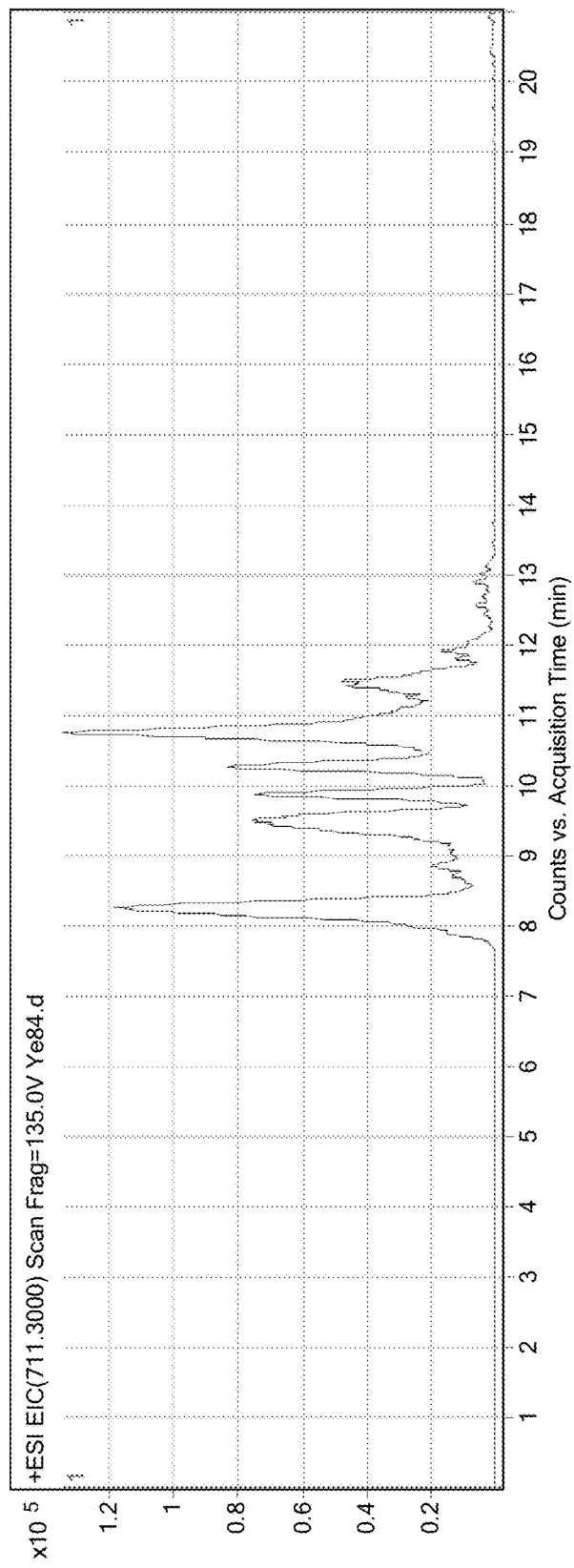
Figure 4D:
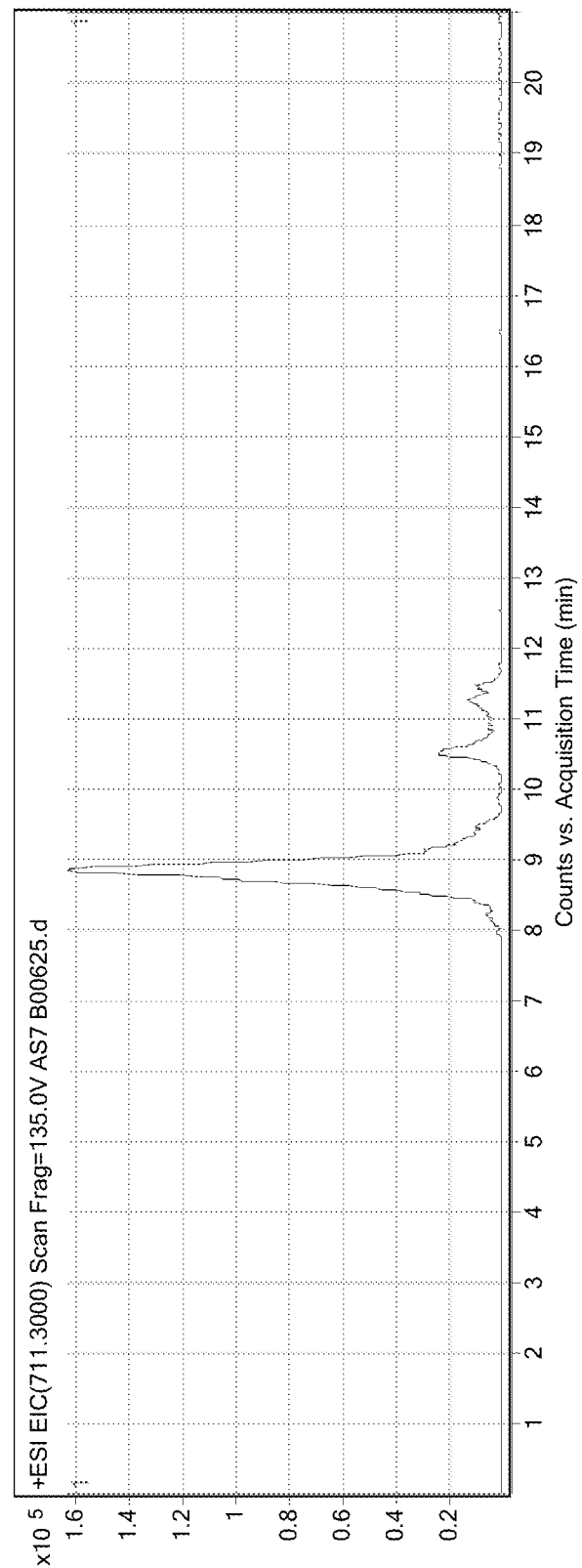
Figure 5:
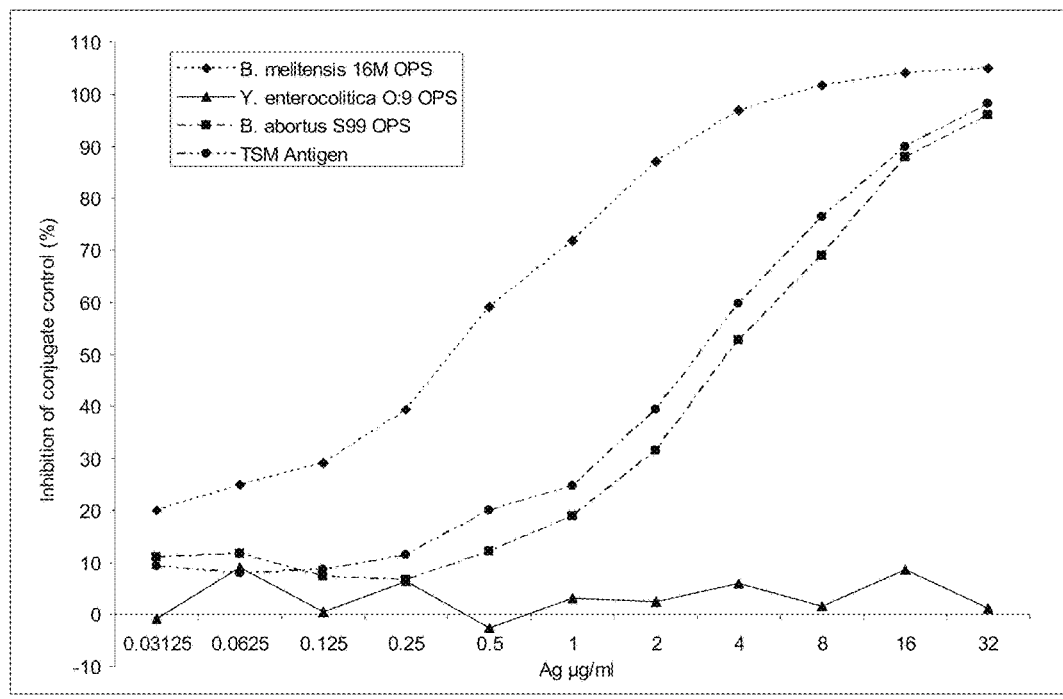
Figure 6A:
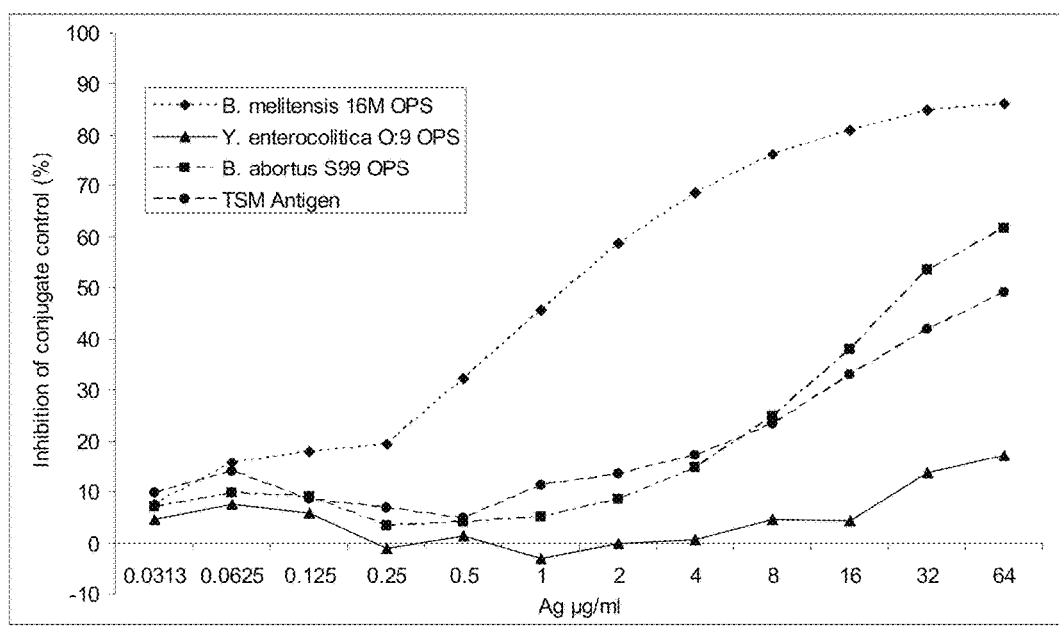
Figure 6B:
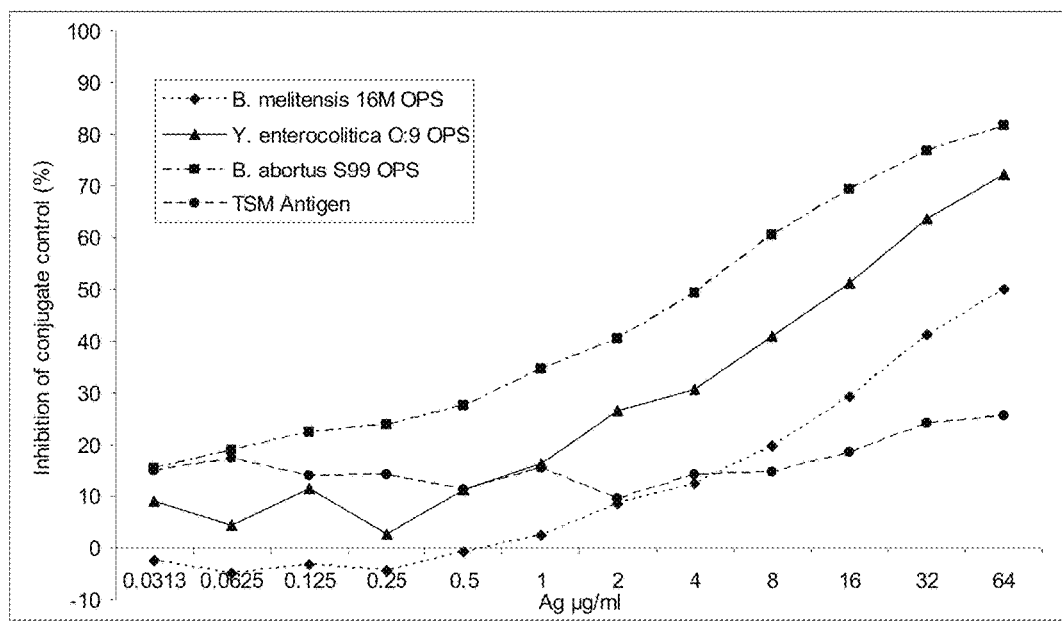

Whereas the chromatogram for the *B. melitensis* 16M derived tetrasaccharide was relatively simple (FIG. 4A), those for *B. abortus* S99 (FIG. 4B) and *Y. enterocolitica* O:9 (FIG. 4C) were more complex. As the mass was the same across the chromatogram, the differences in elution profile were most likely due to changes in conformation and interaction with other oligosaccharides during separation within the graphitised column. What is evident is that the major peak found in the *B. melitensis* 16M tetrasaccharide chromatograph, eluting at about 9 mins, is also found in the *B. abortus* S99 but not the *Y. enterocolitica* O:9 chromatograph. The chromatograph of the *B. abortus* S99 tetrasaccharide affinity selected by the anti-M monoclonal antibody (FIG. 4D) looks extremely similar to the unselected tetrasaccharide from the acid hydrolysed native *B. melitensis* 16M OPS preparation. The conclusion from this study is that a tetrasaccharide from the *Brucella* OPS is large enough to form a viable antibody epitope and that the *Brucella* specific anti-M monoclonal antibody binds to a tetrasaccharide that is detectable in *B. abortus* and not in *Y. enterocolitica* O:9. From the pre-existing structural knowledge, the only known difference is the α-1,3 linkage.

All the evidence presented above provided a good basis for the hypothesis that a tetrasaccharide antigen containing the M epitope, whilst minimising any C/Y or A epitope-like properties, would make a useful serodiagnostic antigen. Four 4,6-dideoxy-4-formamido-α-D-mannopyranose residues were synthesised (Sussex Research Laboratories Inc, Ottawa, Ontario, Canada) within a tetrasaccharide that is sequentially α-1,2, α-1,3 and α-1,2 linked, generating a tetrasaccharide having Formula VIII:

4,6-dideoxy-4-formamido-α-D-mannopyranosyl-(1-2)-4,6-dideoxy-4-formamido-α-D-mannopyranosyl-(1-3)-4,6-dideoxy-4-formamido-α-D-mannopyranosyl-(1-2)-4,6-dideoxy-4-formamido-α-D-mannopyranose (Formula VIII)

This molecule had not previously been synthesised and applied and is referred to below as the TSM antigen (the "tetrasaccharide M [like] antigen"). The key aspect of this structure is the inclusion of the α-1,3 linkage whilst incorporating the minimal number of α-1,2 linkages thought necessary for M specific antibodies to bind; this has the effect of minimising the binding of non-M specific antibodies.

Analysis of the TSM Antigen

The structure of the antigen was confirmed by MALDI-ToF and ESI-QToF mass spectrometry. The monoclonal binding properties were confirmed by competitive ELISA whereby a standard polystyrene ELISA plate was coated with *B. melitensis* 16M sLPS antigen by passive absorption in carbonate buffer. The plate was co-incubated with the anti-M monoclonal antibody BM40 and native OPS from *B. melitensis* 16M, *B. abortus* S99, *Y. enterocolitica* O:9, the TSM antigen as well as buffer controls. After washing the plate, an HRP conjugate specific for the BM40 was added and incubated. After washing, the plates were developed with an HRP substrate to determine the degree to which mAb-conjugate binding had been inhibited.

The results (FIG. 5) demonstrated that the TSM antigen was able to inhibit the binding to a greater extent than the equivalent concentration of *Y. enterocolitica* O:9 OPS and to a similar degree as the *B. abortus* S99 OPS. Taking into account the monovalency of the TSM antigen compared to the multiple binding sites available on 16M OPS, the results provide strong evidence for specific TSM-antibody binding.

A similar competitive ELISA was conducted to measure the inhibition of binding of anti-A and anti-M rabbit hyperimmunised and absorbed monospecific sera (sera as described previously) using native OPS from *B. melitensis* 16M, *B. abortus* S99, *Y. enterocolitica* O:9, the TSM antigen as well as buffer controls. The results demonstrated preferential inhibition of the anti-M sera by the TSM (FIG. 6A) compared to the inhibition of the anti-A sera (FIG. 6B), in agreement with the theoretical expectations.

Application of the TSM Antigen to Serodiagnosis

The TSM antigen was then chemically conjugated to an ELISA plate to create an indirect ELISA and enable the evaluation of non-competitive antibody interactions. Owing to the highly soluble nature of the antigen and its small size, passive absorption to an ELISA plate surface was not straightforward. Instead, it was chemically conjugated to an ELISA plate surface functionalised with hydrazide groups on the end of spacer arms (Corning Carbo-BIND™ #2507). As described above, the hydrazide groups react spontaneously with aldehydes that may be created within carbohydrates by periodate oxidation.

The TSM antigen was incubated in 2 mM sodium metaperiodate, 50 mM sodium acetate buffer at pH 5.5 for 2.5 hours in the dark at 4° C. This was sufficient to oxidise the vicinal diol hydroxyl groups on the $2^{nd}$ and $3^{rd}$ carbons of the terminal sugar (Sussich et al. (2000) Carbohydr Res 329, 87-95), the only vicinal diol group within the molecule, to generate the structure shown below:

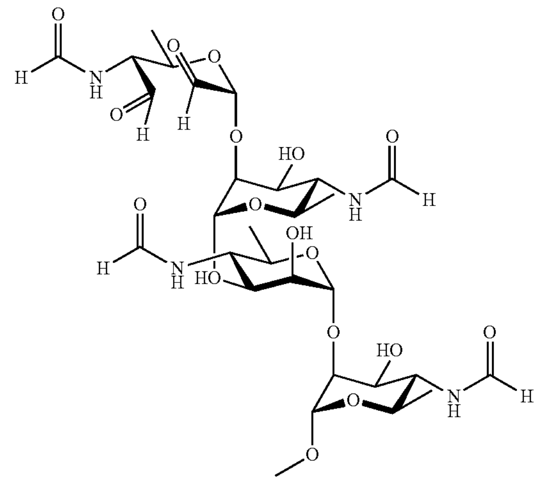

Competitive ELISA with BM40 anti-M monoclonal antibody was applied as described above to confirm that the oxidised TSM antigen (oxiTSM) shown above maintained its antibody interaction. Residual sodium metaperiodate was removed from the reaction by filtration of the TSM antigen and buffer through a short column of Sephadex G-10 (GE Healthcare) which reacted with the excess sodium metaperiodate and, with a suitable volume of elution buffer, allowed the oxiTSM antigen to flow through. Removal of the sodium metaperiodate was necessary to prevent any further oxidation of the oxiTSM and removal was confirmed by abrogation of the reaction with ABTS (2,2'-Azino-bis(3-ethylbenzothiazoline-6-sulfonic acid) diammonium salt).

The oxiTSM antigen was then diluted to 10 μg/ml in 0.1 M sodium acetate buffer pH 5.5 and 100 μl was added per well to a Carbo-BIND™ plate which was incubated at 37° C. for 3 hrs. During this incubation process the aldehyde groups on the oxidised tetrasaccharide spontaneously reacted with the hydrazide groups on the end of a linker attached to the ELISA plate surface to form stable covalent hydrazone bonds, as shown below (the hydrazone bond is shown with a dotted circle):

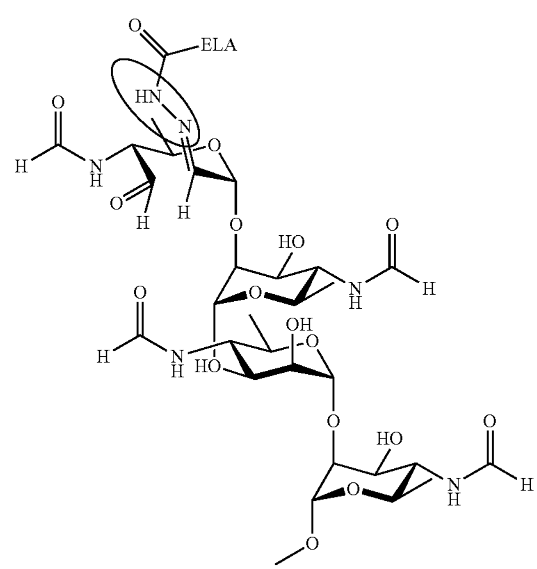

ELA = ELISA linker arm

After this time the plate was washed with 4 times 200 μl per well of phosphate buffered saline with 0.5% Tween-20 (PBS-T20) and tapped dry. These coated ELISA plates were used to test the field sera from cattle (described above) confirmed by culture to be infected with *B. abortus* (n=45) and from cattle without brucellosis but with serum cross reacting in one or more conventional serodiagnostic assay (n=68).

Serum was diluted 1/50 in buffer (Sigma #B6429) and 100 μl of this was added per well of the antigen coated plate, each sample tested in duplicate. The plate was incubated for 1 hr at room temperature on a rotary shaker at 160 rpm and then washed with PBS-T20 as described above. An HRP conjugated Protein-G conjugate (Thermo #31499), diluted to 1 μg/ml in buffer, was then added in 100 μl volumes to each well of the plate which is then incubated and washed as described above for serum. The plate was then developed with ABTS (2,2'-Azino-bis(3-ethylbenzothiazoline-6-sulfonic acid) diammonium salt) and hydrogen peroxide substrate for 10-15 mins, stopped with 0.4 mM sodium azide and read at 405 nm wavelength. The optical density for the duplicates was averaged and the blank OD (buffer only instead of sera) was subtracted. This value was then expressed as a percentage of a common positive control serum sample from a *Brucella* infected bovine.

The TSM antigen iELISA was evaluated against the same population of bovine samples as described above for the evaluation of the *B. melitensis* 16M and *Y. enterocolitica* O:9 OPS iELISAs: 45 from *B. abortus* biovar 1 (A dominant) culture positive animals and 68 from false positive serological reactors. The results for the ELISA are shown in FIG. 7.

Further Antigen Oligosaccharide Conjugates—ELISA Titrations

To begin to determine the overall length of the oligosaccharide necessary to provide specificity for binding to anti-A or anti-M antibodies, synthetic pentasaccharide and nonasaccharide BSA conjugate antigens were evaluated against the bovine sera described above. Each antigen contains one internally and centrally positioned α-1,3 link with the remaining links being α-1,2.

The pentasaccharide had Formula XI:

4,6-dideoxy-4-formamido-α-D-mannopyranosyl-(1-2)-4,6-dideoxy-4-formamido-α-D-mannopyranosyl-(1-3)-4,6-dideoxy-4-formamido-α-D-mannopyranosyl-(1-2)-4,6-dideoxy-4-formamido-α-D-mannopyranosyl-(1-2)-4,6-dideoxy-4-formamido-α-D-mannopyranose (Formula XI)

The nonasaccharide had Formula XV:

4,6-dideoxy-4-formamido-α-D-mannopyranosyl-(1-2)-4,6-dideoxy-4-formamido-α-D-mannopyranosyl-(1-2)-4,6-dideoxy-4-formamido-α-D-mannopyranosyl-(1-2)-4,6-dideoxy-4-formamido-α-D-mannopyranosyl-(1-3)-4,6-dideoxy-4-formamido-D-mannopyranosyl-(1-2)-4,6-dideoxy-4-formamido-α-D-mannopyranosyl-(1-2)-4,6-dideoxy-4-formamido-α-D-mannopyranosyl-(1-2)-4,6-dideoxy-4-formamido-α-D-mannopyranosyl-(1-2)-4,6-dideoxy-4-formamido-α-D-mannopyranose (Formula XV)

In Formulae XI and XV above, the central 4,6-dideoxy-4-formamido-D-mannopyranose is underlined. The antigens were conjugated to BSA via a reducing end -1-O—$(CH_2)_5$—COO—$CH_3$ linker as described above, to form structures 42 and 43, respectively, shown below.

42

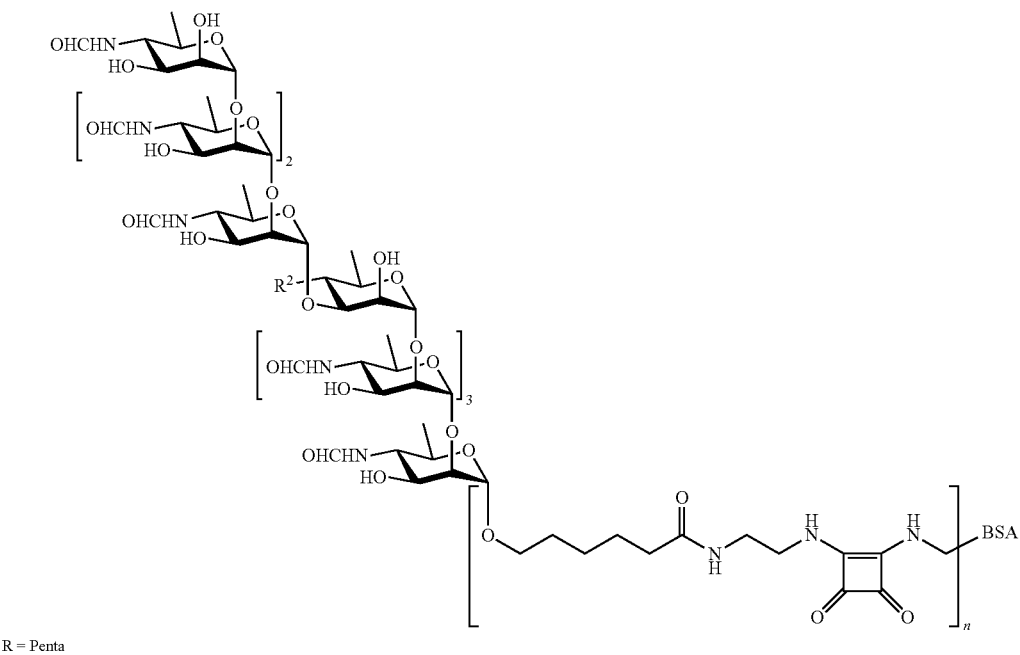

R = Penta

43

In one experiment, BSA-carbohydrate-protein conjugates 42 and 43 (5 μg/mL in PBS) were used to coat 96-well microtiter plates (MaxiSorp, Nunc) overnight at 4° C. The plate was washed 5 times with PBST (PBS containing 0.05% (v/v) Tween 20). Serial √10 dilutions of mAb YsT9.1 and Bm10 ascites fluids or supernatants form hybridoma cell culture were made in PBST containing 0.1% BSA. The solutions were distributed in duplicate on the coated microtiter plate and incubated at room temperature for 2 hours. The plate was washed with PBST (5 times) and goat anti-mouse IgG antibody conjugated to horseradish peroxidase (Kirkegaard & Perry Laboratories; 1:2000 dilution in 0.1% BSA/PBST; 100 μL/well) was added. The mixture was then incubated for 1 hour. The plate was washed 5 times with PBST before addition of a 1:1 mixture 3,3',5,5'-tetramethylbenzidine (0.4 g/L) and 0.02% $H_2O_2$ solution (Kirkegaard & Perry Laboratories; 100 μL/well). After 2 minutes, the reaction was stopped by addition of 1 M phosphoric acid (100 μL/well). Absorbance was read at 450 nm. End point titres are recorded as the dilution giving an absorbance 0.2 above background.

Figure 8:
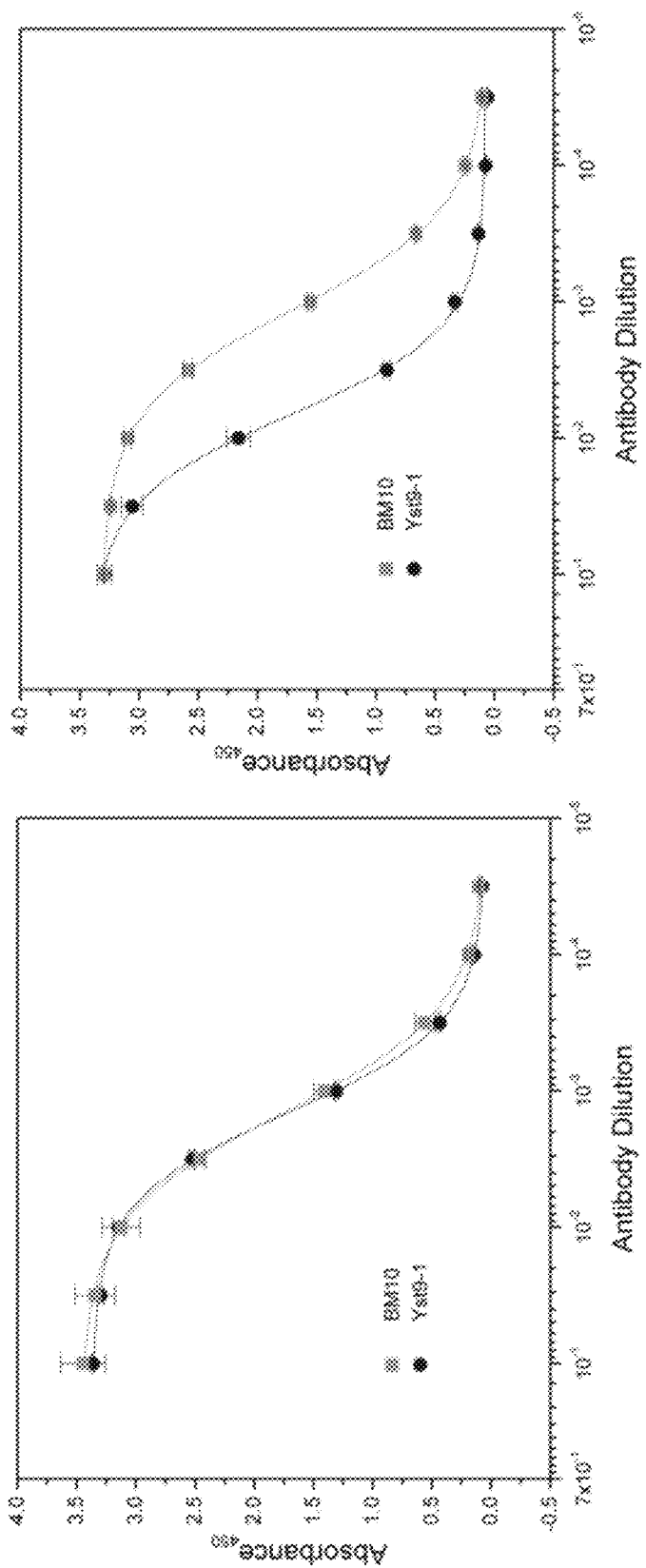
Figure 9:
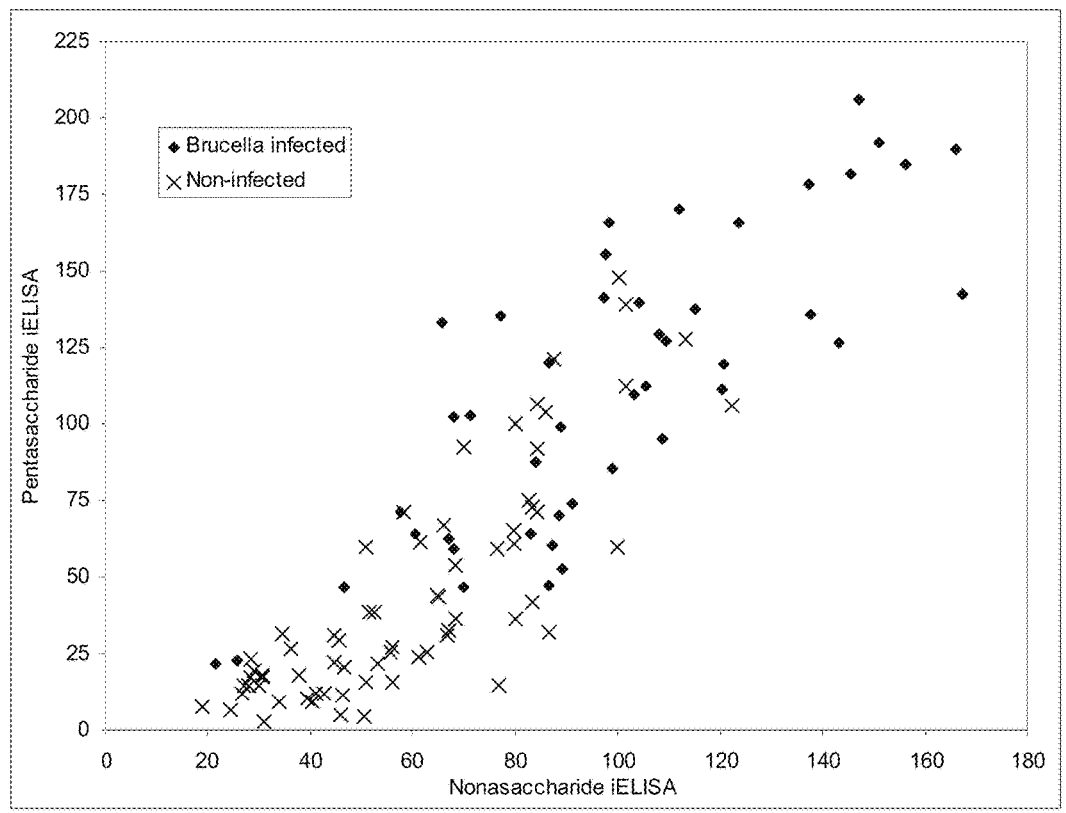
Figure 10:
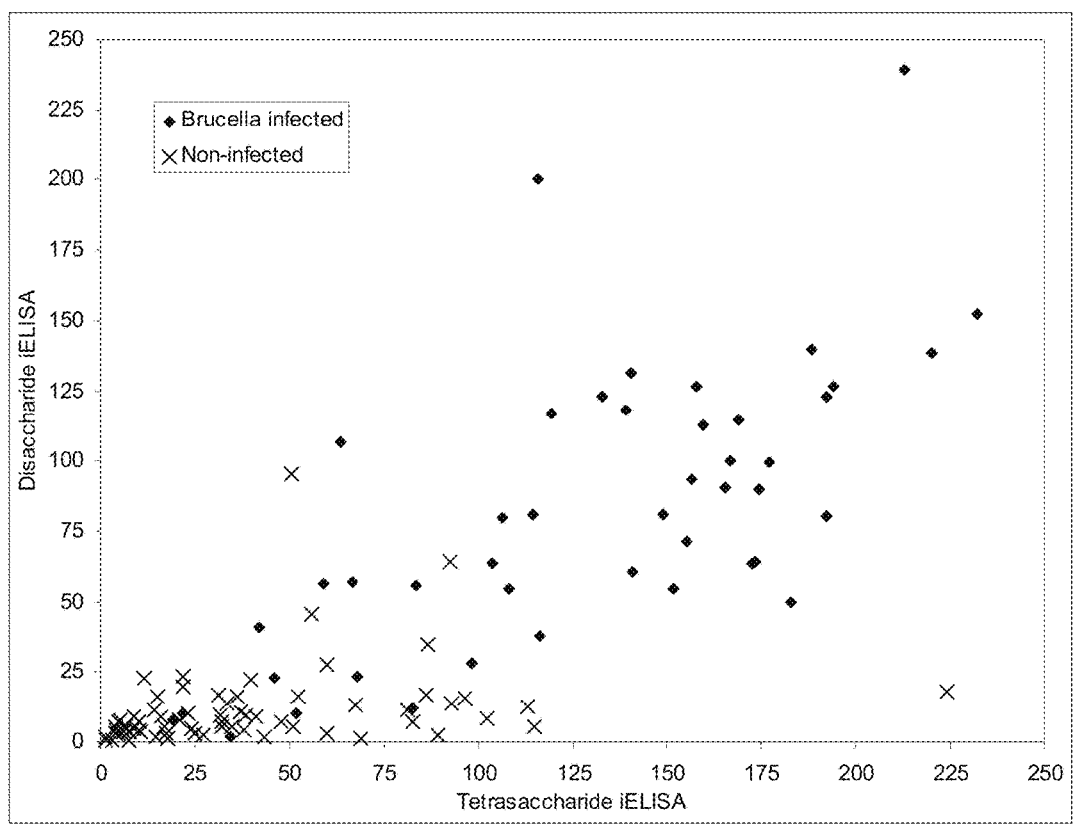
Figure 11:
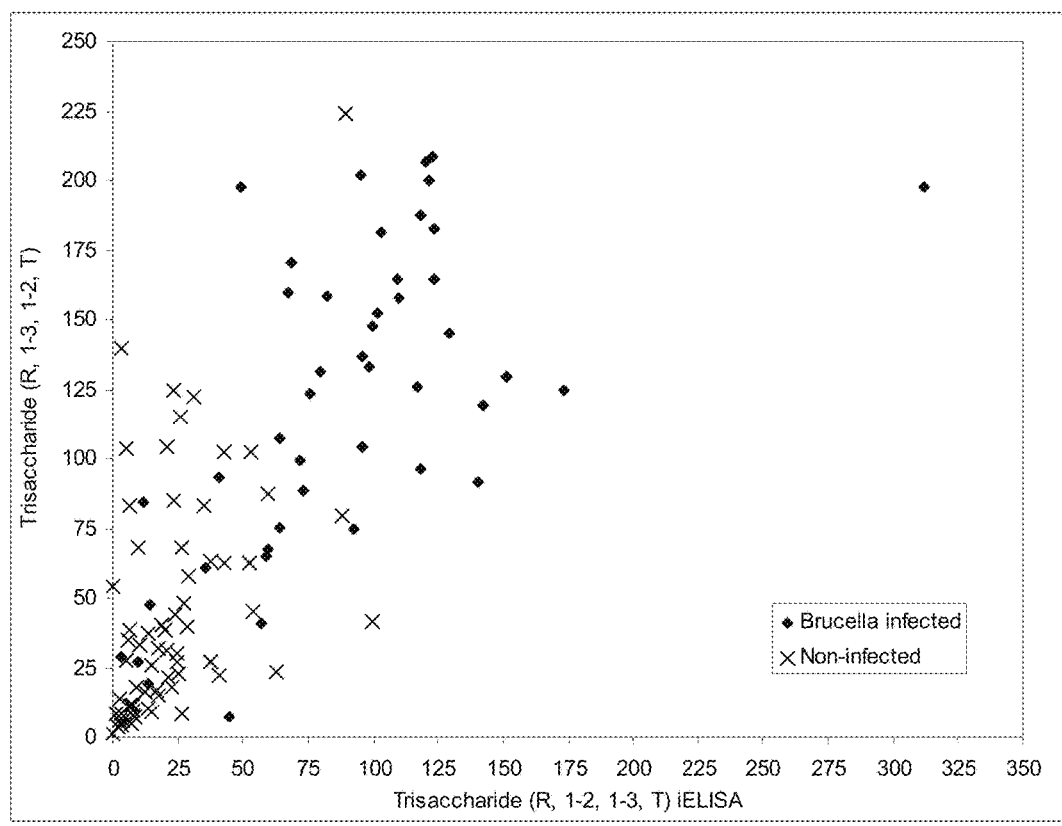
Figure 12:
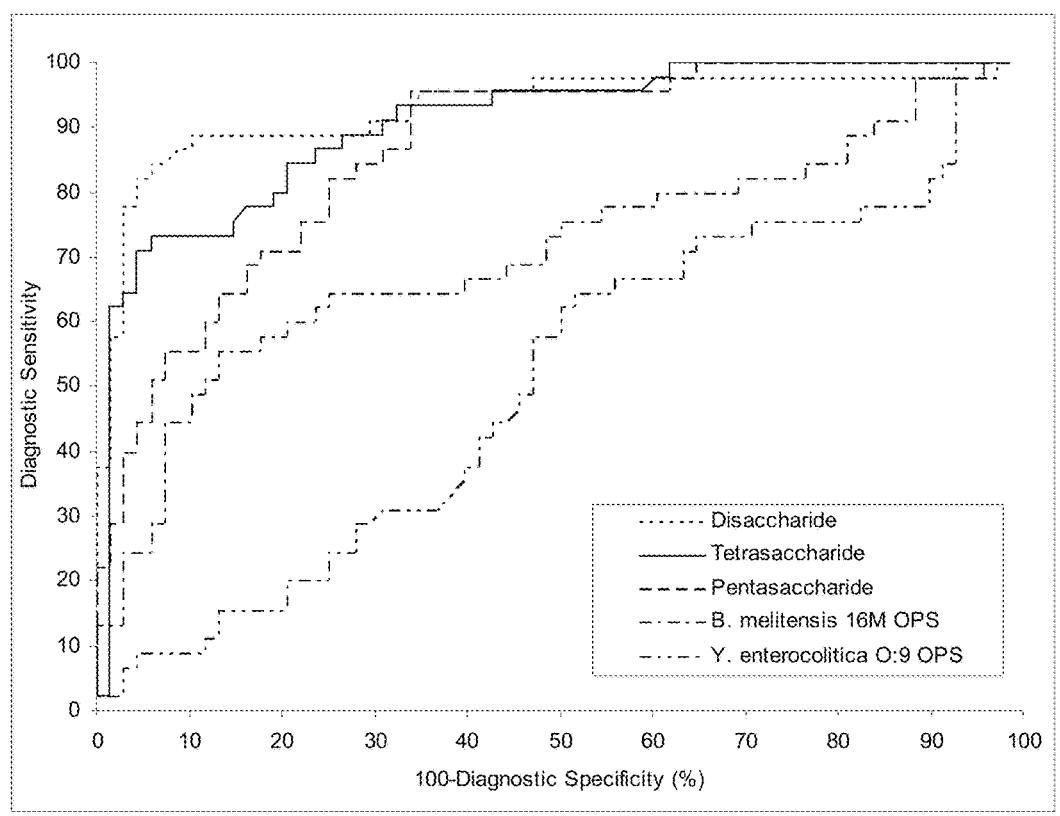

The monoclonal antibodies (YsT9-1 and BM10) previously shown to be specific for the *Brucella* A and M antigens (Bundle et al. (1989) Infect. Immun. 57, 2829-2836). were titred to their end point against the antigens 42 and 43 coated on ELISA plates (FIG. 8). The nonasaccharide antigen 43 binds anti-A and M specific antibodies with equivalent avidity, whereas the pentasaccharide 42 displays a preference for the M specific antibody, while still binding the A specific antibody but with an approximately 10 fold reduced avidity.

Previous studies showed the YsT9-1 and Bm10 antibodies possessed avidity differences of between 400-1,000 for the respective O-polysaccharide antigens (Bundle et al. (1989). Infect. Immun. 57, 2829-2836). As mentioned, the pentasaccharide antigen 42 shows a preference for M specific antibody.

Further Antigen-Oligosaccharide Conjugates—Serology Studies and Analysis

In a further experiment, the conjugates 42 and 43 were immobilised onto the surface of standard polystyrene ELISA plates passively via overnight incubation in carbonate buffer at 4° C. at 2.5 μg/ml, 100 μl/well. The plates were washed as described above and incubated with a 1/50 dilution of sera in buffer (in duplicate)(see below) for 30 mins at room temperature at 160 rpm, after which time they were washed and tapped dry as described above. For bovine sera, an HRP-conjugated mouse anti-bovine IgG1 conjugate was used. The conjugates were diluted to working strength in buffer and the plates incubated, washed and tapped dry as for the serum incubation stage. The plate was then developed with ABTS (2,2'-Azino-bis(3-ethylbenzothiazoline-6-sulfonic acid) diammonium salt) and hydrogen peroxide substrate for 10-15 mins, stopped with 0.4 mM sodium azide and read at 405 nm wavelength. The optical density for the duplicates was averaged and the blank OD (buffer only instead of sera) was subtracted. This value was then expressed as a percentage of a common positive control serum sample from a *Brucella* infected bovine.

The same method employed to evaluate bovine serum by iELISA with the pentasaccharide and nonasaccharide conjugates was used to evaluate bovine serum by a further four oligosaccharide BSA conjugates. The oligosaccharides were:

4,6-dideoxy-4-formamido-α-D-mannopyranosyl-(1-2)-4,6-dideoxy-4-formamido-α-D-mannopyranosyl-(1-3)-4,6-dideoxy-4-formamido-α-D-mannopyranosyl-(1-2)-4,6-dideoxy-4-formamido-α-D-mannopyranose (tetrasaccharide, Formula VIII)

4,6-dideoxy-4-formamido-α-D-mannopyranosyl-(1-3)-4,6-dideoxy-4-formamido-α-D-mannopyranosyl-(1-2)-4,6-dideoxy-4-formamido-α-D-mannopyranosyl (trisaccharide (terminal α-1,3 link), Formula XVI)

4,6-dideoxy-4-formamido-α-D-mannopyranosyl-(1-2)-4,6-dideoxy-4-formamido-α-D-mannopyranosyl-(1-3)-4,6- dideoxy-4-formamido-α-D-mannopyranosyl (trisaccharide (terminal α-1,2 link), Formula XVII)
4,6-dideoxy-4-formamido-α-D-mannopyranosyl-(1-3)-4,6-dideoxy-4-formamido-α-D-mannopyranose (disaccharide, Formula II)

These antigens were conjugated to BSA via a reducing end -1-O—(CH$_2$)$_5$—COO—CH$_3$ linker as described above, to form structures similar to 42 and 43 shown above. Since conjugation occurs via the reducing end, the link at the non-reducing end is referred to as the "terminal link".

The BSA-nonasaccharide, pentasaccharide, tetrasaccharide, trisaccharide and disaccharide conjugate iELISAs (and the oxiTSM iELISA described above) were evaluated against the same population of bovine field samples as described above for the evaluation of the *B. melitensis* 16M and *Y. enterocolitica* O:9 OPS iELISAs; that is, 45 from *B. abortus* biovar 1 (A dominant) culture positive animals and 68 from false positive serological reactors. The results for these iELISAs, shown by scatter plot in FIGS. 7 and 9 to 11, were evaluated to find the optimal Youden Index for each iELISA and ROC analysis was used to determine the ROC Curves and AUC. This data is presented in Table 7 below, along with the 95% confidence intervals for the AUC; Table 7 shows the data from Table 3 and the additional oligosaccharide data, for ease of comparison. Table 8 shows the probability (P) values for the testing of statistically significant differences between the AUC data from each antigen assay. The AUCs were all compared against each other and the P values was calculated using the Normal Distribution model. The evaluation was 1-tailed as the prior hypothesis under investigation was that antigens that were more 'M' like would have higher AUC values. As with Table 7, Table 8 shows the earlier information from Table 4 with the additional oligosaccharide data.

A selection of ROC curves are shown in FIG. 12. The Figure shows the ROC curves for both native antigens tested and amply demonstrates the superiority of the *B. melitensis* 16M OPS over the *Y. enterocolitica* O:9 OPS. The data from the M-like synthetic BSA-pentasaccharide, BSA-tetrasaccharide and BSA-disaccharide conjugate iELISAs is also shown and graphically depicts the improvement in diagnostic performance that is commensurate with the reduction of α-1,2 linkages in the structures and retention of the α-1,3 link.

TABLE 7

Performance statistics for OPS and Synthetic Oligosaccharide iELISAs as tested on bovine sera

| Assay | % age α-1,3 links | Optimal Youden Index (YI = DSn + DSp-1): YI Estimate | DSn % | DSp % | ROC - Area Under Curve: AUC | 95% Confidence Interval |
|---|---|---|---|---|---|---|
| *Y. enterocolitica* O:9 OPS iELISA | 0 | 0.1297 | 64.44 | 48.53 | 0.5065 | 0.3964-0.6167 |
| *B. melitensis* 16M OPS iELISA | 20 | 0.4232 | 55.56 | 86.76 | 0.7065 | 0.6024-0.8106 |
| Nonasaccharide iELISA | 12.5 | 0.5713 | 68.89 | 88.24 | 0.8317 | 0.7512-0.9122 |
| Pentasaccharide iELISA | 25 | 0.6174 | 95.56 | 66.18 | 0.8667 | 0.8019-0.9314 |
| Trisaccharide (terminal α-1,2) iELISA | 50 | 0.6091 | 73.33 | 86.76 | 0.8672 | 0.7976-0.9367 |
| oxiTSM iELISA | 33.3/50 | 0.6670 | 73.33 | 92.65 | 0.8948 | 0.8345-0.9550 |
| Trisaccharide (terminal α-1,3) iELISA | 50 | 0.7268 | 80.00 | 92.65 | 0.8987 | 0.8334-0.9640 |
| Tetrasaccharide iELISA | 33.3 | 0.6745 | 73.33 | 94.12 | 0.9046 | 0.8478-0.9613 |
| Disaccharide iELISA | 100 | 0.7860 | 84.44 | 92.65 | 0.9310 | 0.8345-0.9550 |

TABLE 8

Comparison of ROC AUC statistics for the OPS and Synthetic Oligosaccharide iELISAs as tested on bovine sera

| Difference between AUC (P = [one-tailed]) | YeO9 | Bm | Bm/Ye | NS | PS | Tri t1,2 | Oxi TSM | Tri t1,3 | Tetra |
|---|---|---|---|---|---|---|---|---|---|
| *Y. enterocolitica* O:9 OPS iELISA (YeO9) | | | | | | | | | |
| *B. melitensis* 16M OPS iELISA (Bm) | <0.0001 | | | | | | | | |
| Bm16M/YeO:9 (Bm/Ye) | <0.0001 | 0.0239 | | | | | | | |
| Nonasaccharide iELISA (NS) | <0.0001 | 0.0032 | 0.3050 | | | | | | |
| Pentasaccharide iELISA (PS) | <0.0001 | 0.0005 | 0.0918 | 0.1003 | | | | | |
| Trisaccharide (terminal α-1,2) iELISA (Tri t1,2) | <0.0001 | 0.0007 | 0.1093 | 0.2148 | 0.4920 | | | | |
| oxiTSM iELISA (oxiTSM) | <0.0001 | <0.0001 | 0.0239 | 0.0307 | 0.1867 | 0.2005 | | | |
| Trisaccharide (terminal α-1,3) iELISA (Tri t1,3) | <0.0001 | <0.0001 | 0.8080 | 0.0384 | 0.1736 | 0.1949 | 0.4522 | | |

TABLE 8-continued Comparison of ROC AUC statistics for the OPS and Synthetic Oligosaccharide iELISAs as tested on bovine sera

| Difference between AUC (P = [one-tailed]) | YeO9 | Bm | Bm/Ye | NS | PS | Tri t1,2 | Oxi TSM | Tri t1,3 | Tetra |
|---|---|---|---|---|---|---|---|---|---|
| Tetrasaccharide iELISA (Tetra) | <0.0001 | <0.0001 | 0.0228 | 0.0146 | 0.0853 | 0.0359 | 0.3632 | 0.4207 | |
| Disaccharide iELISA (Di) | <0.0001 | <0.0001 | 0.0158 | 0.0087 | 0.0322 | 0.0322 | 0.1379 | 0.0901 | 0.2005 |

The data presented in Table 7 show the antigens in ascending AUC value (lowest at the top and highest at the bottom). In this context, the AUC represents the ability of the assay to correctly classify samples from animals that are Brucella infected and those that are not. In this data analysis, all the samples from animals that were not Brucella infected were falsely positive in one or more conventional serodiagnostic assays for brucellosis. The results (based on the AUC data) show that the B. melitensis OPS is superior to the Y. enterocolitica O:9 OPS and it is proposed that this is due to the presence of α-1,3 links within the OPS of the former. The percentage of links within the antigenic structures that are α-1,3 (the remainder being α-1,2) is also shown in the table.

In general, the AUC values increase with the increase in the percentage of α-1,3 links within the antigen (and decrease in α-1,2 links). This is clearly evident in the comparison of the two native OPS antigens and is also evident in the AUC data for the nonasaccharide, pentasaccharide, tetrasaccharide and disaccharide BSA conjugates. There are, however, some nuances within the data that should be considered as described below with regard to the comparison between the nonasaccharide BSA conjugate and B. melitensis 16M OPS, the oxidised tetrasaccharide antigen and the two trisaccharide BSA conjugates.

All the synthetic BSA conjugated oligosaccharide antigens have superior diagnostic capability in this regard compared to the native OPS antigens. This includes the nonasaccharide BSA-conjugate which has proportionally fewer α-1,3 links than the B. melitensis 16M OPS. This apparent anomaly may due to do with the precise positioning of the α-1,3 links within the native structure and the multivalent nature in which antibodies may bind this structure.

It is not straightforward to evaluate the performance of the oxiTSM antigen relative to the others investigated due to the methodological differences, not least the breaking of the terminal perosamine, linking directly to a functionalised ELISA plate surface from the remnants of this structure and thus presenting the reducing sugar as the tip of the antigen. For this reason, the percentage of α-1,3 links presented in Table 7 is shown as 33.3/50 dependent upon the undetermined significance of the link to the oxidised terminal "perosamine". Despite these apparent impediments, the oxiTSM iELISA possessed a greater AUC value than the BSA-pentasaccharide and α-1,2 terminated BSA-trisaccharide conjugate iELISAs. This may be due to the loss of the terminal end 'tip' epitope, since this is not presented by the oxiTSM antigen due to the oxidation and conjugation of the terminal sugar. The natural 'tip' antigen would be similar in the OPS from A and M dominant Brucella and Y. enterocolitica O:9. This 'tip' epitope may also explain the higher AUC value for the α-1,3 terminated trisaccharide compared to the α-1,2 terminated trisaccharide. According to the structural scheme recently presented (Kubler-Kielb & Vinogradov (2013) Carbohydr. Res. 378, 144-147), the tip of most OPS molecules in M dominant OPS is a α-1,2 linked disaccharide, as would also be the case in the OPS from A dominant Brucella strains and from Y. enterocolitica O:9. The α-1,3 terminated trisaccharide does not present such a tip and thus common anti-'tip' epitope antibodies may be less likely to bind in comparison to the antibodies against the linear M epitope.

The highest AUC value is generated by the BSA-disaccharide conjugate iELISA. This was significantly higher (P=0.0322) than the AUC value for the BSA-pentasaccharide conjugate iELISA which was itself significantly higher than the AUC value derived from the native antigens (Y. enterocolitica O:9 and B. melitensis 16M OPS) The disaccharide has no α-1,2 links present, just a single α-1,3 link. On the basis of this data, this structure is highly functional and represents the minimal size M epitope. The ability of such a small structure to bind to so many polyclonal antibodies and to do so in such a selective manner is a surprising finding. The negative impact of even a single α-1,2 link was just as unexpected. The ability and the extent to which the disaccharide (and the other M-like oligosaccharides), can selectively bind to polyclonal sera raised by infection with A dominant strains of Brucella was also unexpected, but has been demonstrated here for the first time.

The data from the Max YI values largely agree with the AUC data in that the smaller BSA-oligosaccharides conjugates with fewer α-1,2 links provide superior diagnostic parameters. The main difference is the superior Max YI value for the α-1,3 terminated BSA-trisaccharide conjugate compared to the BSA-tetrasaccharide conjugate. This can be rationalised by the arguments put forward above with regards to the reduction of the 'tip' epitope as well as the elimination of a α-1,2 link.

All of the BSA-oligosaccharide conjugate iELISAs were also applied to the sera from the eight animals, described above, that were experimentally infected with either B. abortus strain 544 (n=4) or Y. enterocolitica O:9 (n=4). Only samples collected from weeks 3, 7, 16 and 24 were tested because the samples collected from the B. abortus infected animals at week 53 gave ambivalent results with conventional serodiagnostic assay.

Figure 13:
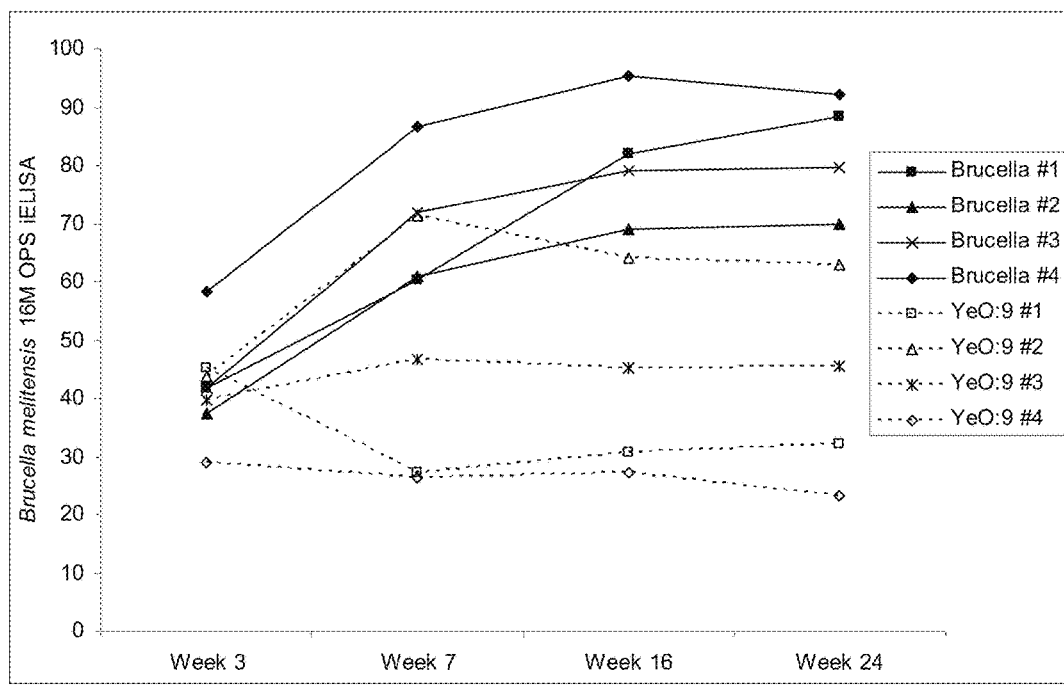
Figure 14:
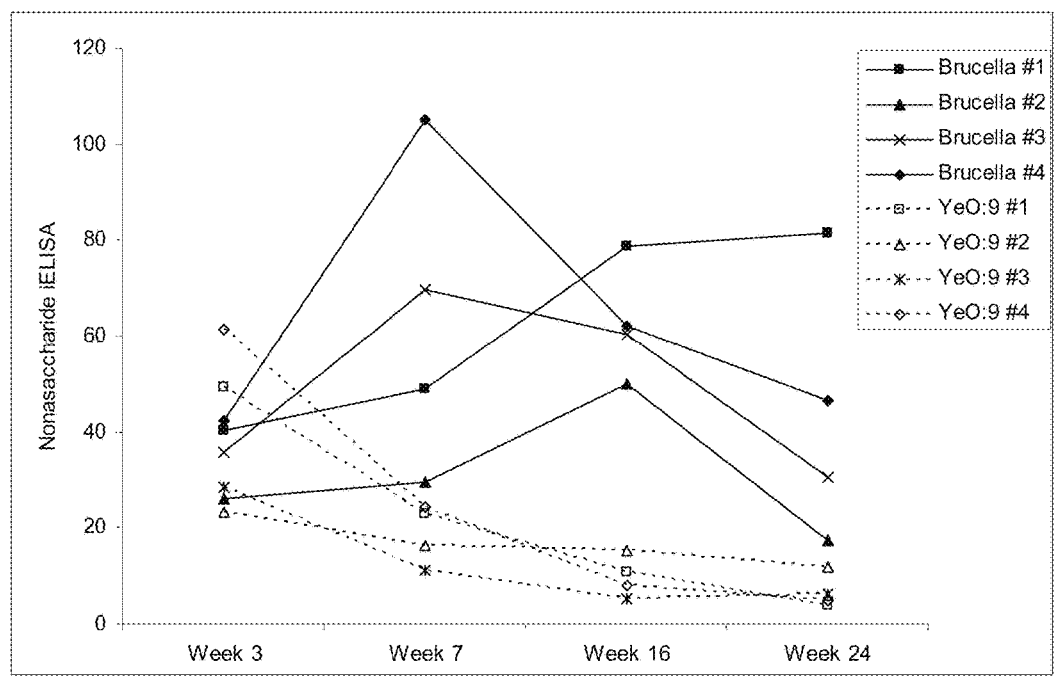
Figure 15:
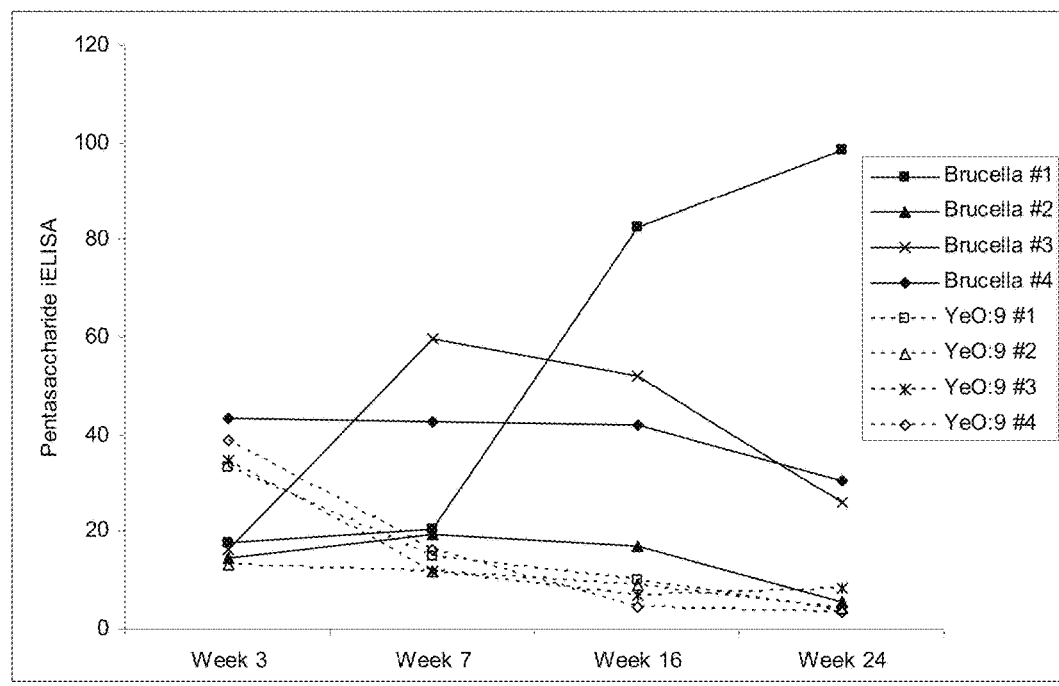
Figure 16:
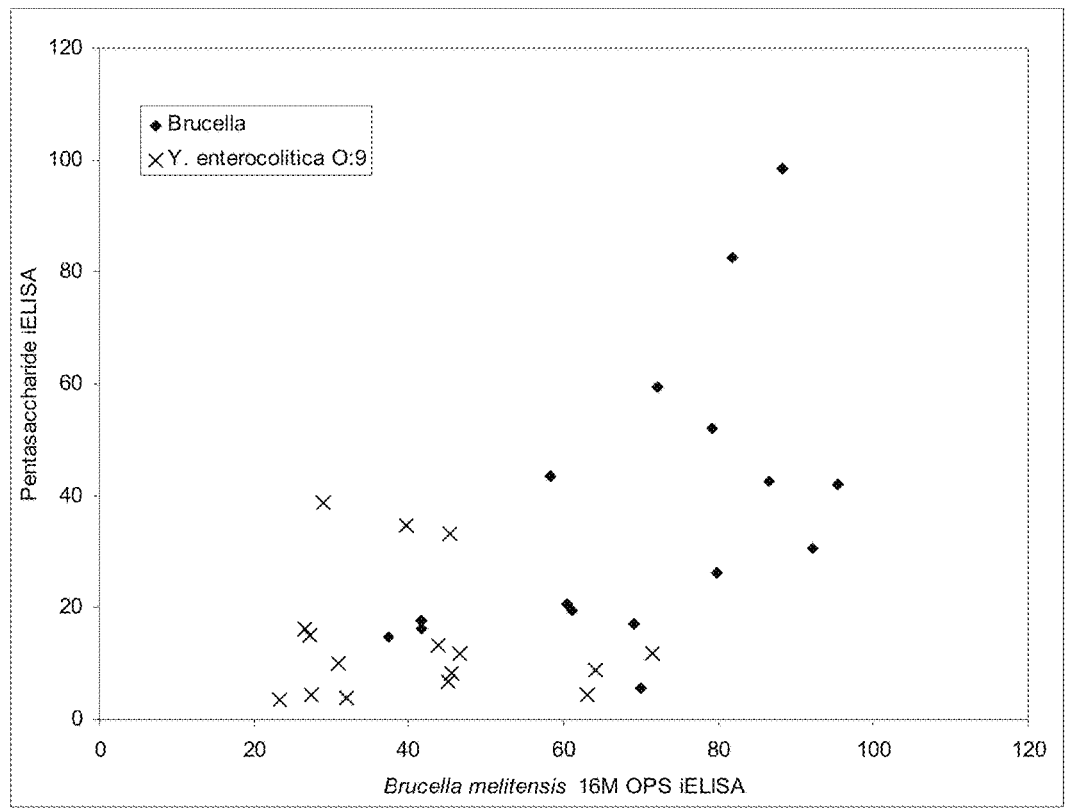
Figure 17:
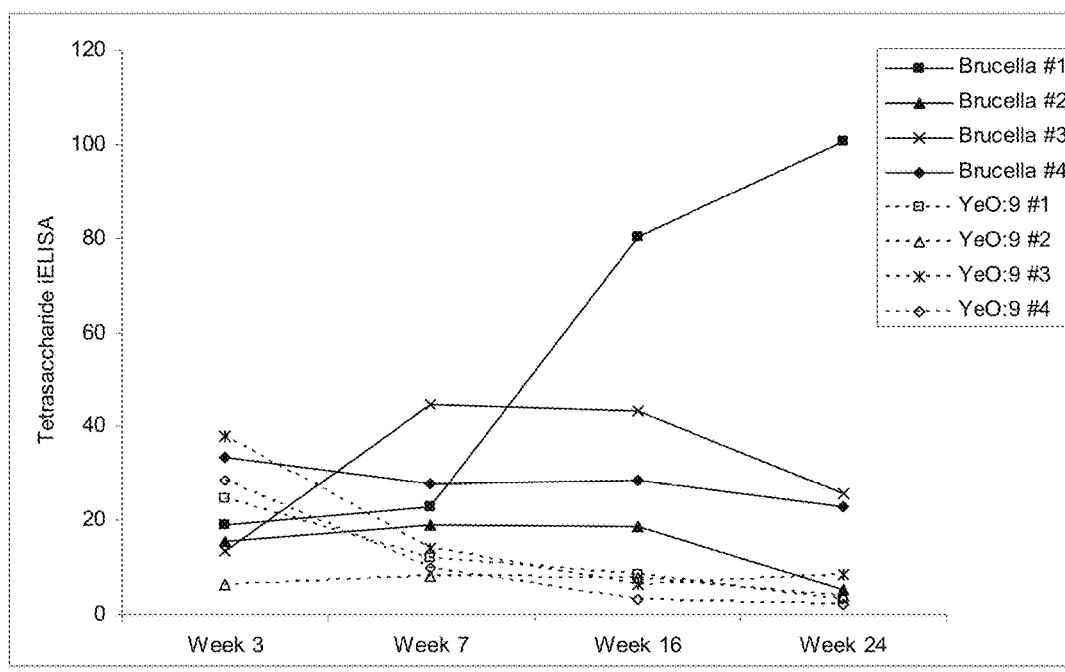
Figure 18:
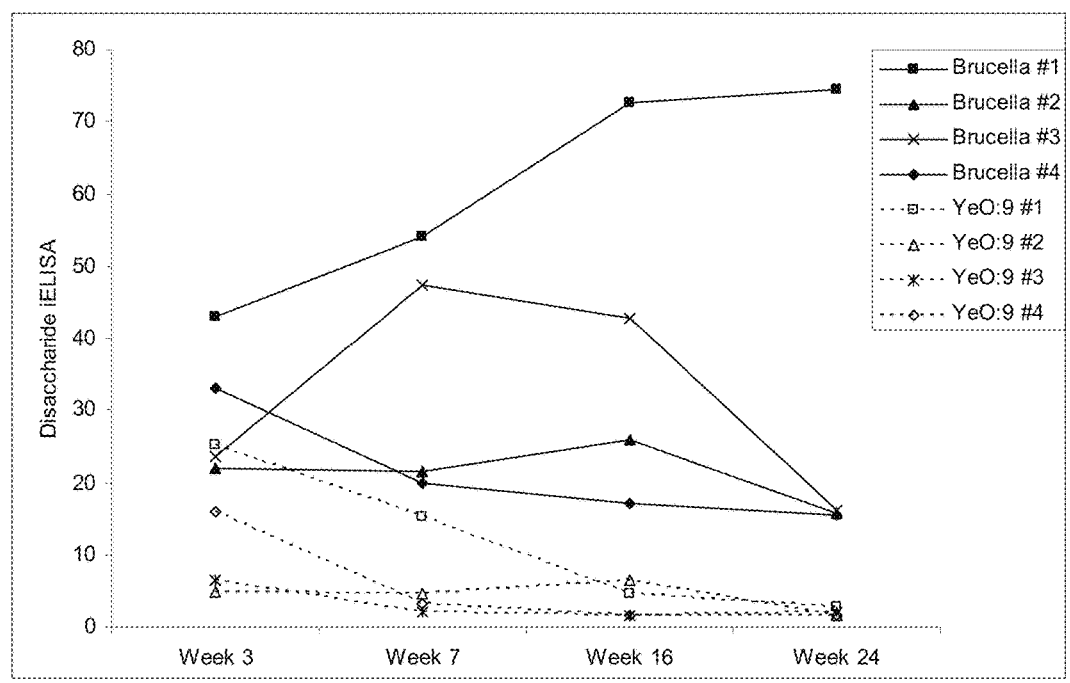
Figure 19:
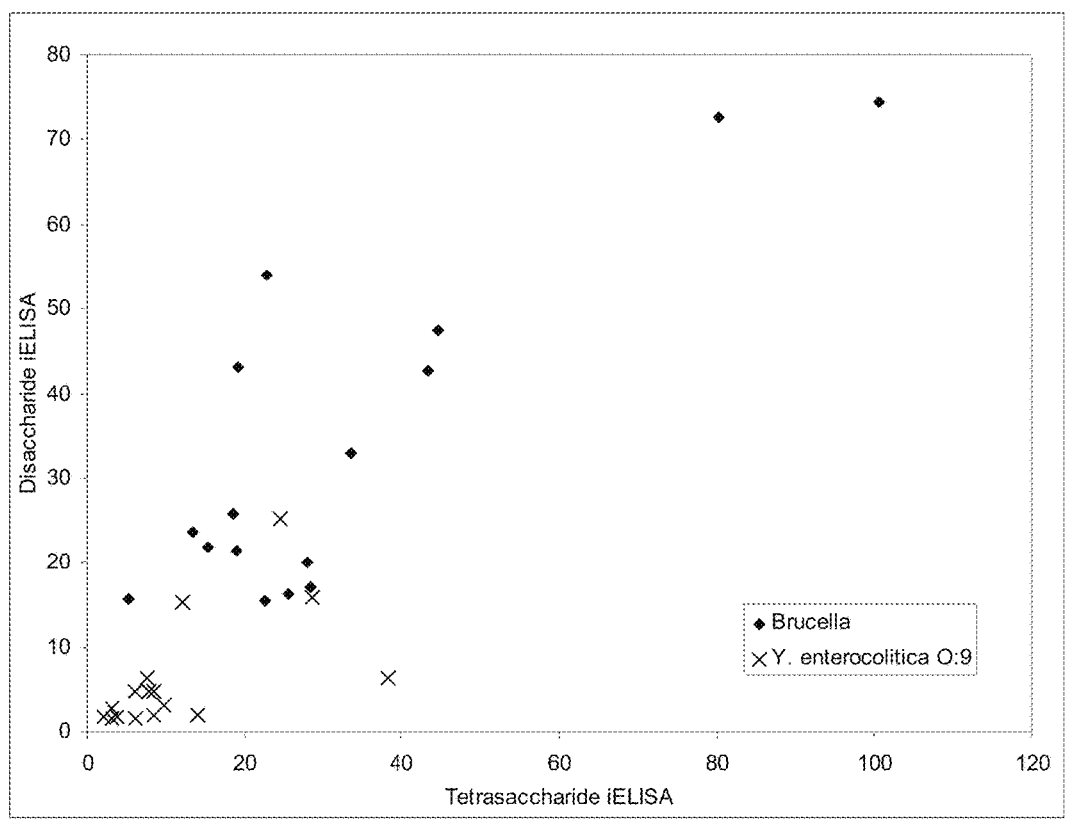

The results for the samples from the experimentally infected cattle are shown in FIGS. 13 to 19. FIG. 13 shows the results from B. melitensis 16M OPS iELISA and demonstrates that there is a considerable response from the sera derived from the Y. enterocolitica O:9 infected animals. FIGS. 14 and 15 show the data derived from the nonasaccharide and pentasaccharide BSA conjugate iELISAs respectively. The results from the B. melitensis 16M OPS iELISA and pentasaccharide BSA conjugate iELISA are shown against each other in a simple scatter plot in FIG. 16. FIGS. 17 and 18 show the data derived from the tetrasaccharide and disaccharide BSA conjugate iELISAs respectively. Although the ability to differentiate between the antibodies derived from the two infection types is not absolute, FIG. 18 shows that the disaccharide is close to achieving this aim. This differentiation is more readily visible in the scatter plot, FIG. 19, showing the results from the tetrasaccharide and disaccharide BSA conjugate iELISAs.

All the serological data from the samples from the experimentally infected animals (weeks 3, 7, 16 and 24) were evaluated by the following quantitative criteria. The percentage (of 16) samples from the cattle experimentally infected with *Y. enterocolitica* O:9 with quantitatively greater serological titres than the lowest titre sample from cattle experimentally infected with *B. abortus* strain 544 was calculated. The percentage is shown, for each serodiagnostic assay, in Table 9. The CFT, SAT, sLPS iELISA and cELISA and FPA data has been published previously (McGiven et al. (2008) J. Immun. Meth. 20, 7-15) and shows the significant degree of cross reaction that occurs with conventional and contemporary serology.

Although the data set is relatively small, the results show that the disaccharide and the trisaccharide BSA conjugate iELISAs (using the trisaccharide with a α-1,3 link at the non-conjugated terminus) were the best at differentiating between antibodies derived from the two types of infection. This demonstrates that as well as providing improved diagnostic specificity when testing field FPSRs, the disaccharide has the same beneficial effect with the samples that have been experimentally infected with a Gram-negative bacteria in possession of the OPS structure that is most similar to that of *Brucella*. In this sample set, the results from the nonasaccharide, pentasaccharide, tetrasaccharide and α-1,2 terminated trisaccharide BSA conjugate iELISAs showed no advantage over the *B. melitensis* 16M OPS iELISA. The two worst performing assays in this respect, both with a percentage of 81.25, were the iELISAs performed using the sLPS from *B. abortus* S99 (an A dominant strain) and the *Y. enterocolitica* O:9 OPS iELISA. This reflects the high degree of similarity between the OPS structures of these organisms.

TABLE 9

Percentage (of 16) samples from cattle experimentally infected with *Y. enterocolitica* O:9 with quantitatively greater serological titres than the lowest titre sample from cattle experimentally infected with *B. abortus* strain 544

|  | Percentage of samples |
|---|---|
| Classical tests and native antigens | |
| Complement Fixation Test | 31.25 |
| Serum Agglutination Tests | 56.25 |
| iELISA (sLPS, *B. abortus* S99) | 81.25 |
| cELISA (sLPS, *B. melitensis* 16M) | 43.75 |
| Fluorescence Polarisation Assay | 50.00 |
| *Y. enterocolitica* O:9 OPS iELISA | 81.25 |
| *B. melitensis* 16M OPS iELISA | 56.25 |
| Synthetic oligosaccharide antigens | |
| Nonasaccharide | 56.25 |
| Pentasaccharide | 75.00 |
| Tetrasaccharide | 75.00 |
| Trisaccharide (terminal 1,2) | 68.75 |
| Trisaccharide (terminal 1,3) | 18.75 |
| Disaccharide | 12.50 |

The nonasaccharide, pentasaccharide, tetrasaccharide and disaccharide BSA-conjugate iELISAs were also evaluated against 125 serum samples from 125 randomly sampled non-*Brucella* infected cattle. The results are presented by scatter plot, with the results from the *Brucella* infected cattle (n=45), in FIGS. 20 (nonasaccharide and pentasaccharide) and 21 (tetrasaccharide and disaccharide).

TABLE 10

Performance statistics for Synthetic Oligosaccharide iELISAs as tested on bovine sera (randomly sampled non-*Brucella* infected)

| Assay | Optimal Youden Index (YI = DSn + DSp-1) | | | ROC - Area Under Curve | |
|---|---|---|---|---|---|
| | YI Estimate | DSn % | DSp % | AUC | 95% Confidence Interval |
| Nonasaccharide iELISA | 0.9920 | 100.0 | 99.20 | 0.9998 | 0.9992-1.000 |
| Pentasaccharide iELISA | 1.0000 | 100.0 | 100.0 | 1.0000 | 1.000-1.000 |
| Tetrasaccharide iELISA | 0.9476 | 95.56 | 99.20 | 0.9964 | 0.9911-1.000 |
| Disaccharide iELISA | 0.8142 | 82.22 | 99.20 | 0.9108 | 0.8401-0.9814 |

Figure 20:
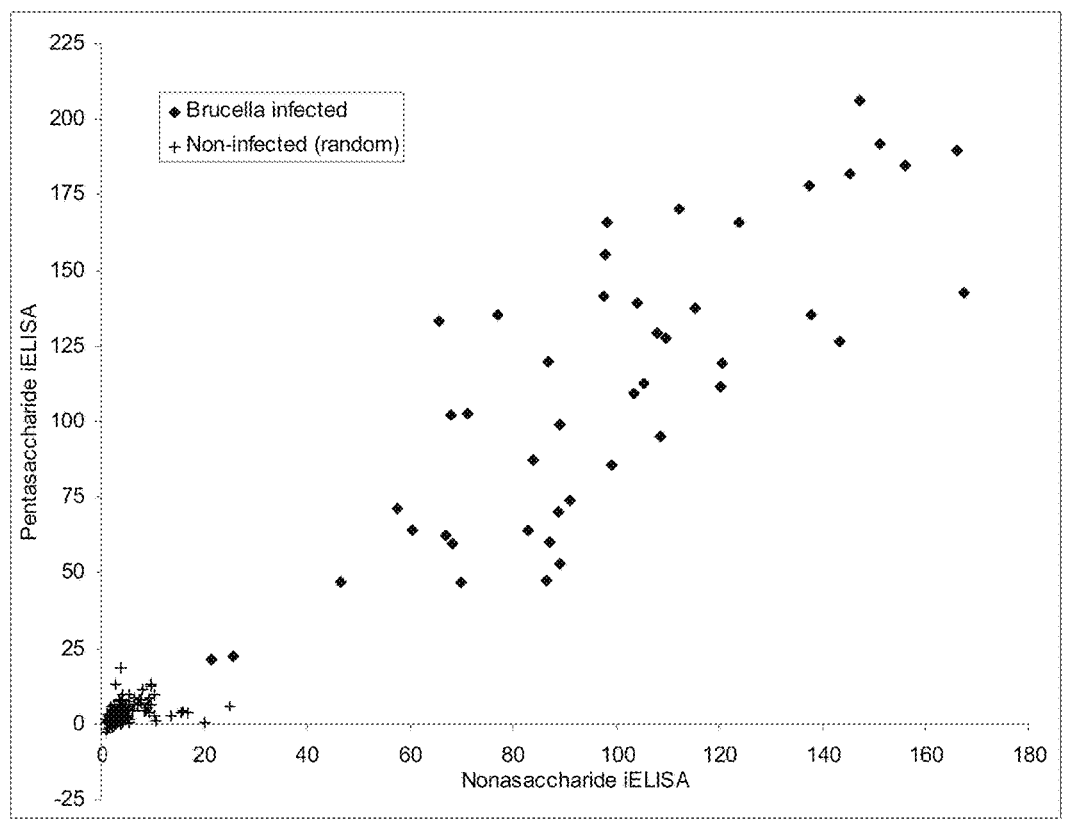
FIG. 20 shows results (expressed as a percentage of a common positive control) from the BSA-nonasaccharide conjugate iELISA (x-axis) and BSA-pentasaccharide conjugate iELISA (y-axis); the solid diamonds represent the results for sera from cattle confirmed as infected with *B. abortus* biovar 1 (n=45) and the crosses represent the results for sera from randomly sampled brucellosis free cattle (n=125)
Figure 21:
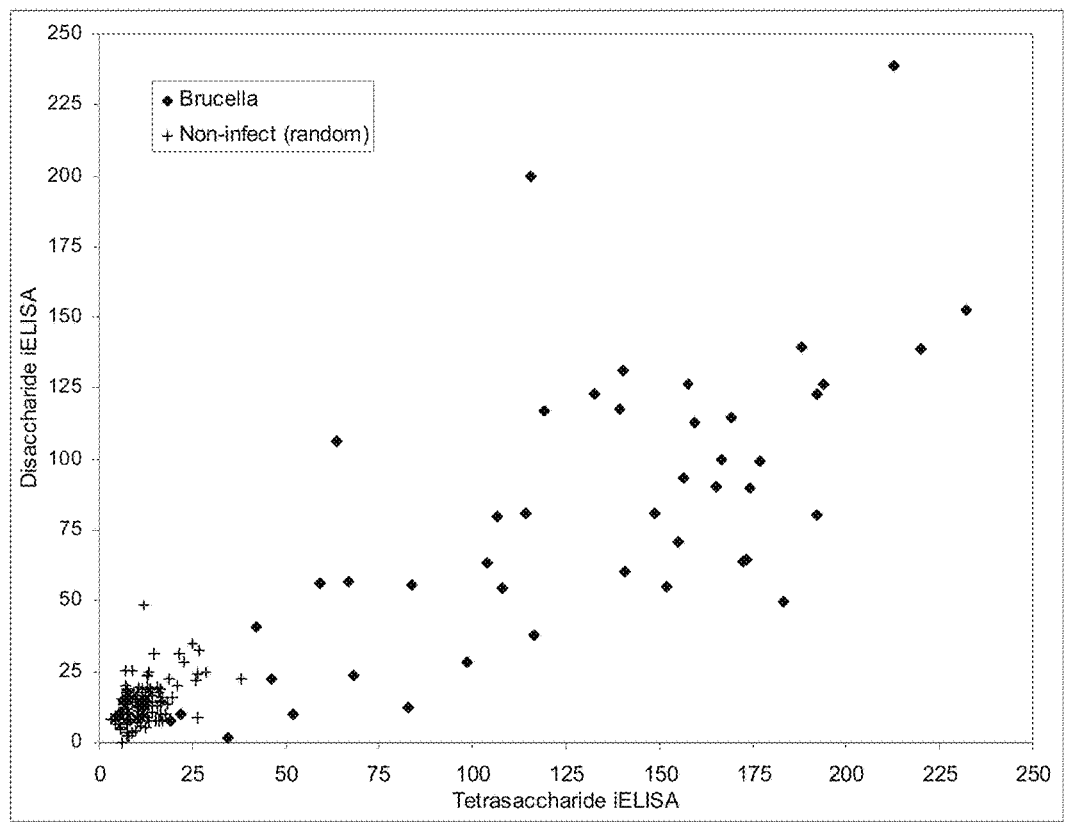
FIG. 21 shows results (expressed as a percentage of a common positive control) from the BSA-tetraasaccharide conjugate iELISA (x-axis) and BSA-disaccharide conjugate iELISA (y-axis); the solid diamonds represent the results for sera from cattle confirmed as infected with *B. abortus* biovar 1 (n=45) and the crosses represent the results for sera from randomly sampled brucellosis free cattle (n=125)

The results, shown in scatter plot FIGS. 20 and 21 and Table 10, demonstrate that the nonasaccharide, pentasaccharide and tetrasaccharide BSA-conjugate iELISAs are highly effective serodiagnostic assays. The data also suggests that the disaccharide BSA-conjugate iELISA is less effective in differentiating between these sample types than the other, larger, oligosaccharides in possession of α-1,2 links. When the disaccharide BSA-conjugate is used, the sera from the randomly sampled non-*Brucella* infected cattle have a much more similar response to that observed for the FPSR samples than is the case with the nonasaccharide, pentasaccharide and tetrasaccharide BSA-conjugate iELISAs.

The oxiTSM, BSA-pentasaccharide and BSA-nonasaccharide antigens have also been applied to the detection of specific anti-*Brucella* antibodies in small ruminant sera. The oxiTSM antigen was conjugated to the Carbo-BIND™ ELISA plates by the same method as described above and the BSA conjugated oligosaccharides were coated to ELISA plates by the same method as described above. The assay was completed using the same method as described for bovine sera above except for the use of a protein G HRP conjugate. In total, 61 samples were evaluated from individual sheep and goats from flocks confirmed as infected with *B. melitensis* biovar 3 (mixed 'A' and 'M' dominance) and positive in iELISA using *B. melitensis* sLPS antigen. Also tested were 94 sera from sheep and goats from Great Britain, that has always been free of *B. melitensis* (FIG. 22).

Figure 22:
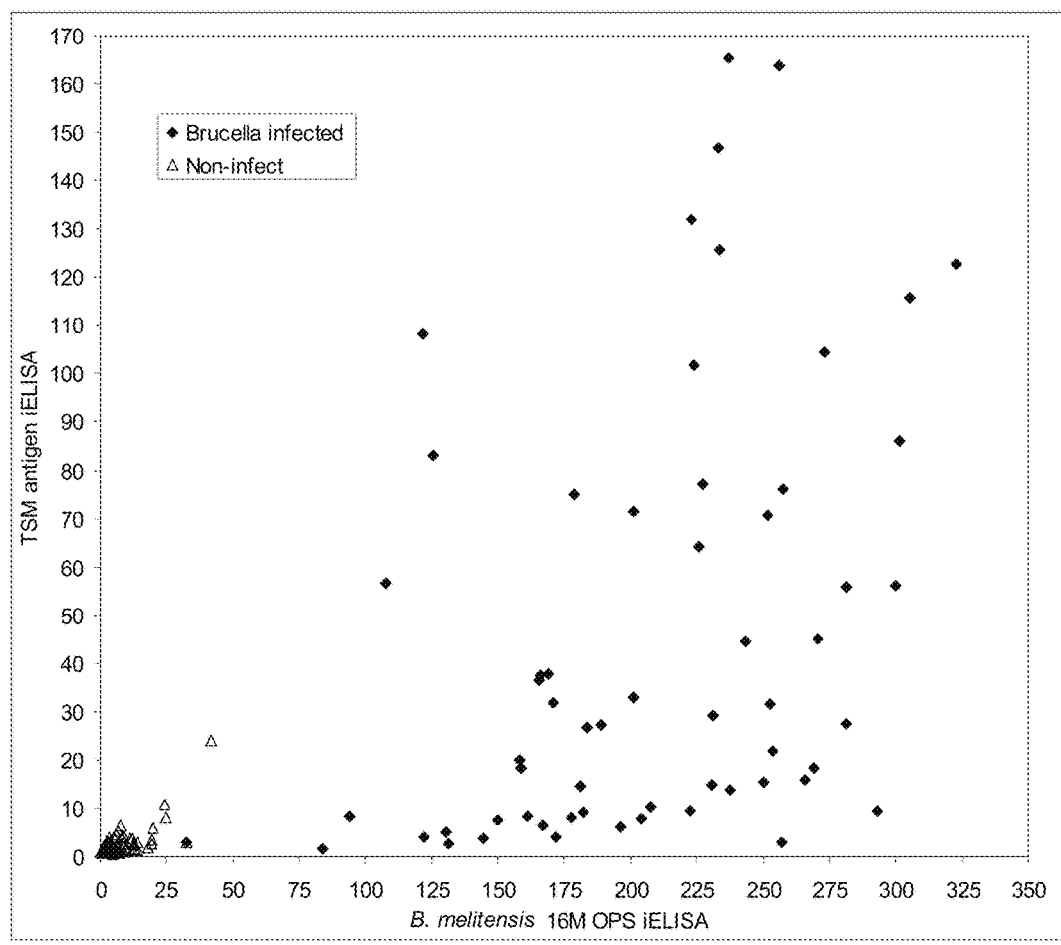
Figure 23:
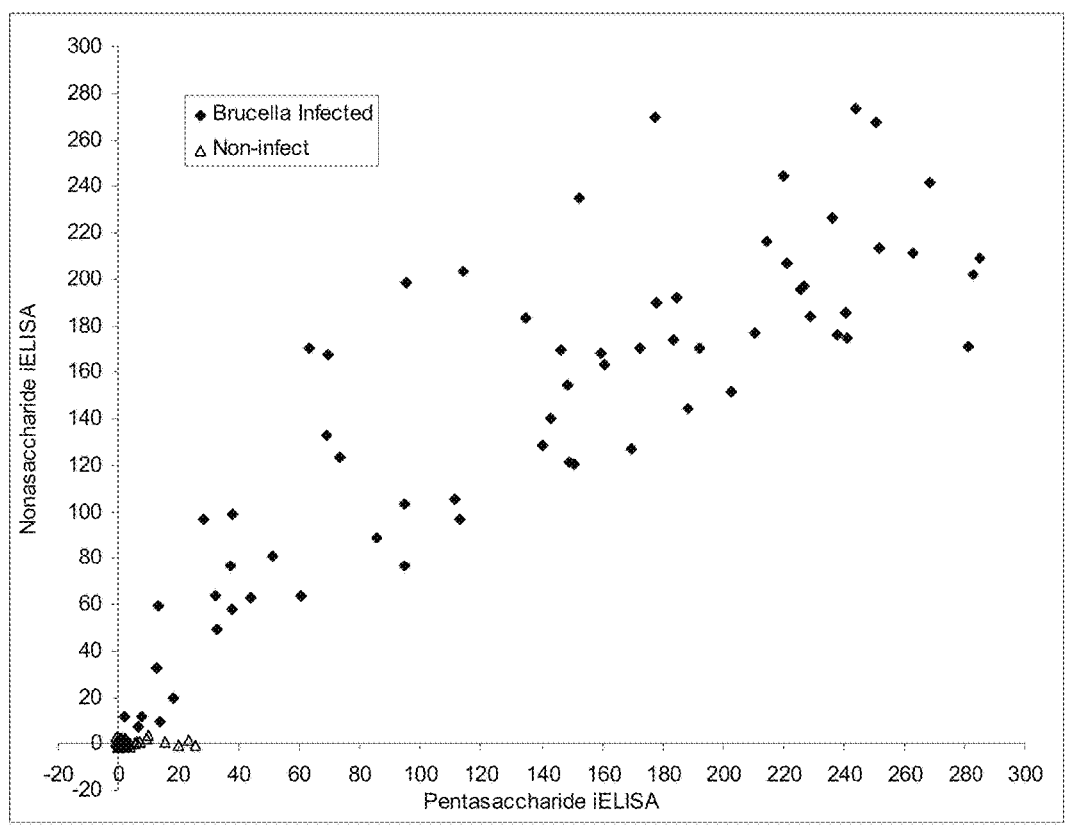
Figure 24:
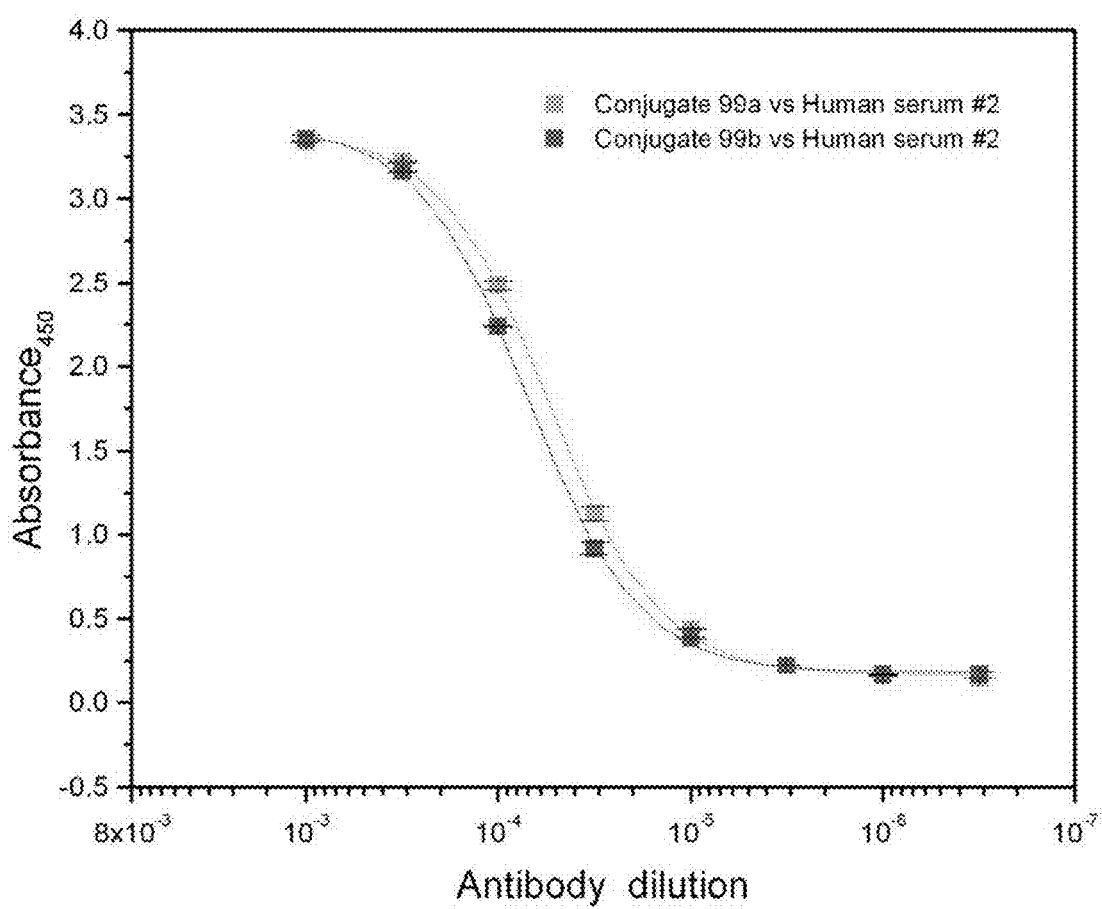
Figure 25:
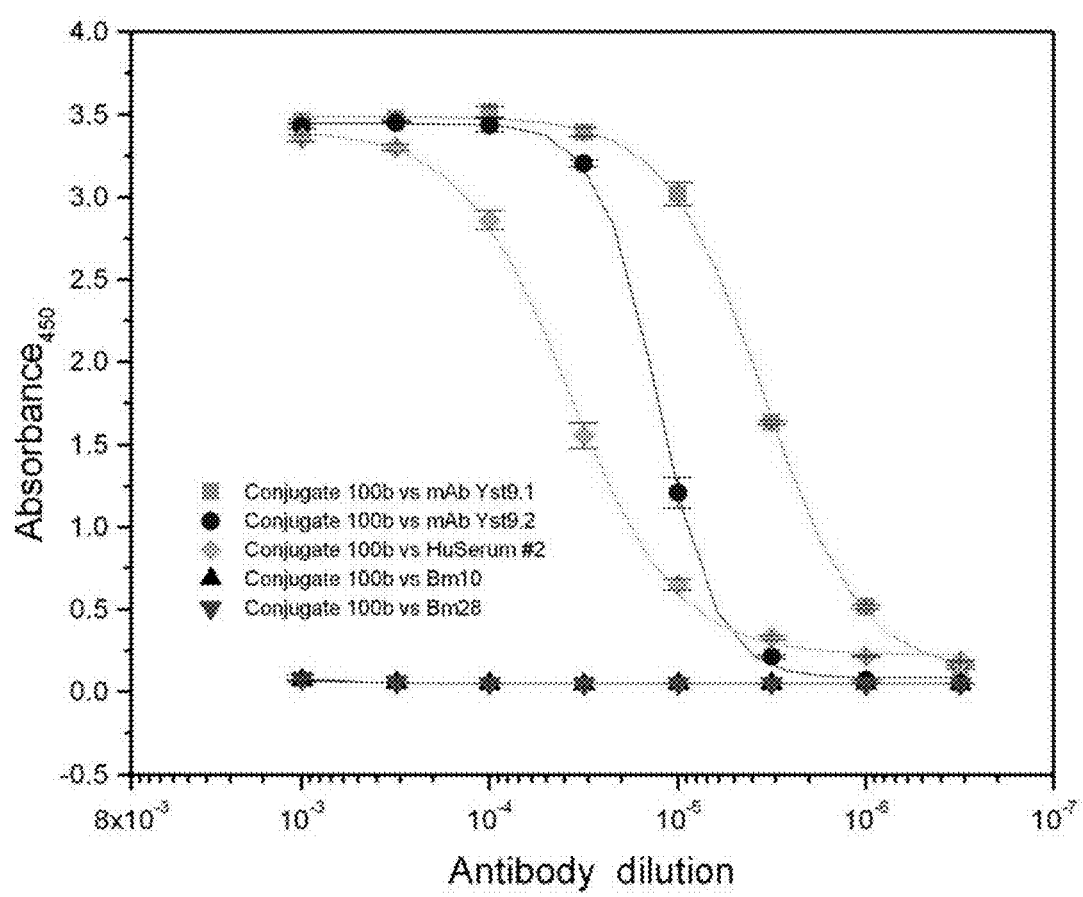
Figure 26:
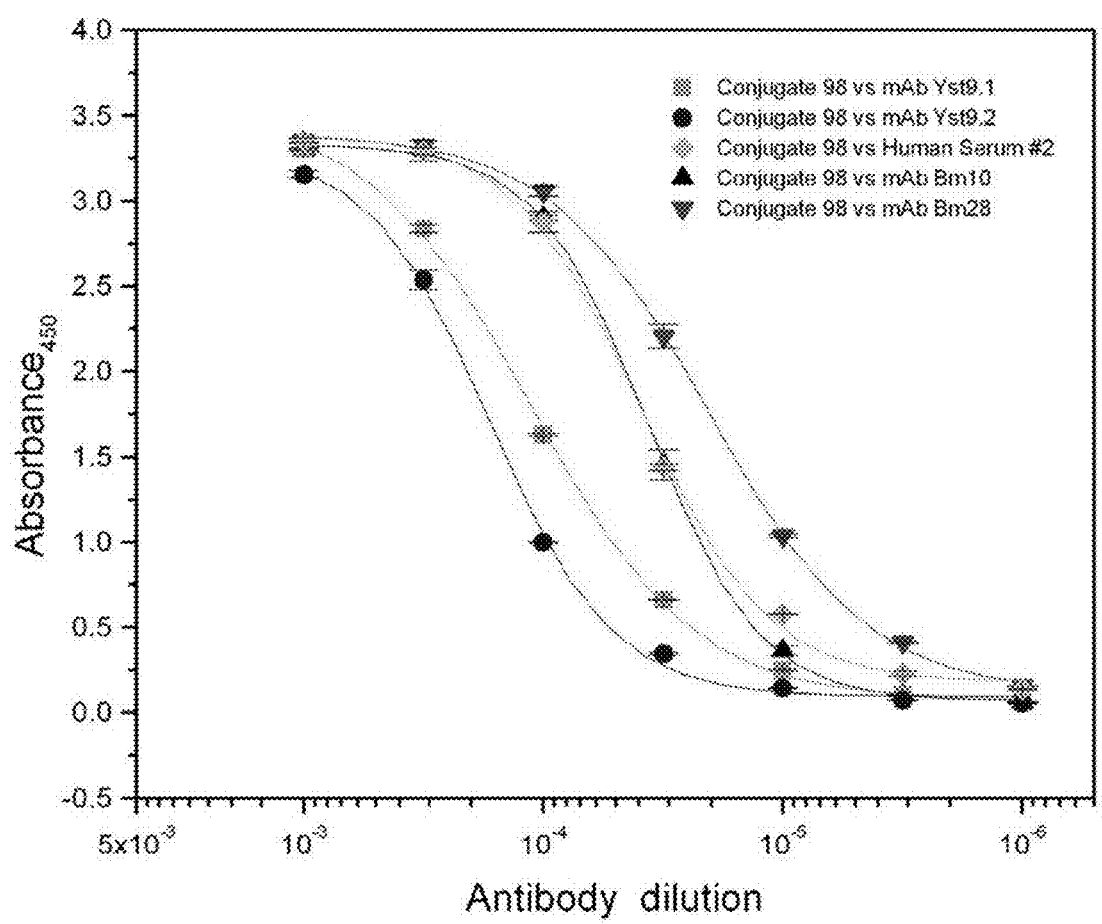
Figure 27:
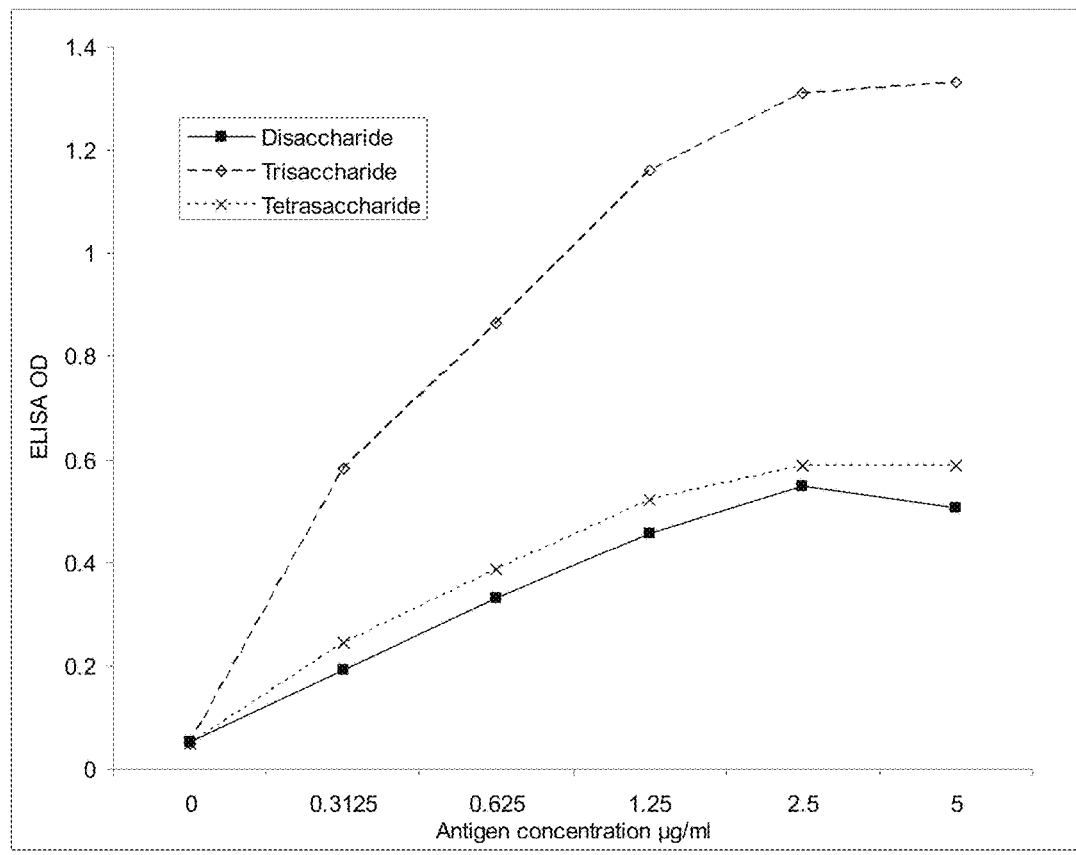

In FIG. 22, the lowest x-axis value for a sample from the *Brucella* infected population is 32.5, so there is no data from this population hidden in the overplotting of the data from the non-*Brucella* infected population. The optimised YI value for the 16M OPS iELISA was 0.984 (95% CI=0.952-1.000) and that of the 'M' tetrasaccharide iELISA was 0.816 (95% CI=0.720-0.912). The 95% confidence intervals for two YI values do not overlap, demonstrating a significant difference in diagnostic performance. However, the data does demonstrate that the TSM antigen does detect anti-*Brucella* antibodies within sera from small ruminants infected with *B. melitensis*. The data in FIG. 23 demonstrates the effectiveness of the universal nonasaccharide conjugate antigen as, based on this sample set, the DSn and DSp were both 100%.

Finally, ELISA plates were coated with co-povidone disaccharide conjugates 99a and 99b as described above for BSA conjugates. Serial √10 dilutions of human sera from a patient infected with *Brucella suis* was applied to the plate and bound antibody was detected by a goat anti human horse radish peroxidase conjugate. The results are shown in FIG.

24. This demonstrated that the disaccharide can detect infection by *Brucella* in a sample from a human patient.

Antibody Binding Studies

BSA conjugates 98 (comprising the oligosaccharide of Formula XIV) and copovidone conjugate 100b (comprising an oligosaccharide which is exclusively α-1,2 linked) were each coated on ELISA plates as described above. Serial √10 dilutions of mouse monoclonal antibodies that are A or M specific were applied to the plate and bound antibody was detected by a goat anti mouse IgG horse radish peroxidase conjugate. Antibodies YsT9.1 and YsT9.2 are anti-A antibodies. Antibodies BM10 and BM28 are M-specific. The results are shown in FIGS. 25 and 26 and demonstrate the binding specificity of the disaccharide, as well as the failure of an exclusively α-1,2 linked oligosaccharide conjugate to bind to an anti-M antibody.

To evaluate the binding of an anti-M specific mAb to the BSA-tetrasaccharide, trisaccharide and disaccharide conjugates, they were each coated to ELISA plates at 5 μg per ml (in pH 10.0 carbonate buffer), double diluted in neighbouring ELISA plate wells and the plates were incubated and washed as described previously for the bovine serum iELISAs with the BSA conjugates. A working strength dilution of HRP-conjugated BM40 mAb was added to each well and this was incubated for 30 mins at room temperature and then washed as described previously. The plates were developed with HRP ABTS substrate and the reaction stopped after 15 mins by addition of sodium azide. The ELISA plates were read at 405 nm to measure the optical density of each well.

The results (FIG. 27) show that the BM40 mAb binds to the BSA conjugates; most effectively to the trisaccharide and also, almost equally, to the tetrasaccharide and disaccharide BSA conjugates. The binding of the BM40 mAb to these three BSA-oligosaccharide structures demonstrates the presence of the M epitope within them as BM40 has been previously shown to be highly specific to M dominant OPS. As well as binding BM40 mAb, the inventors have shown that these structures also bind polyclonal sera. Therefore, it would be possible to simultaneously incubate both the HRP conjugated BM40 mAb and serum antibodies in order to create a competitive ELISA for the detection of polyclonal antibodies in serum. The ability to do this with the disaccharide is particularly noteworthy as this is already the antigen that provides the best resolution of FPSRs, incorporating a competitive element into the immunoassay is expected to yield further improvements in diagnostic capability.

Vaccination Study

A vaccine glycoconjugate comprising an oligosaccharide formed by exclusively -(1-2)- linked 4,6-dideoxy-4-acylamido-α-pyranose units, the oligosaccharide covalently linked to a carrier protein such as tetanus toxin, is evaluated for vaccine efficacy as follows. The procedures are based upon the standard model of vaccine efficacy testing as described with the OIE Manual of Diagnostic Tests and Vaccines (Nielsen et al. (2009) In: Manual of Diagnostic Tests & Vaccines for Terrestrial Animals 2009; Office International Des Epizooties, Paris, Chapter: Bovine brucellosis, pg 22-29). Control and challenge groups of mice are established for evaluation. For example, control group 1—'vaccination' with PBS only; control group 2—vaccination with unconjugated 'A' oligosaccharide and tetanus toxoid plus adjuvant; control group 3-subcutaneous vaccination with $1\times10^5$ CFU per mouse of reference vaccine *B. abortus* strain S19. The vaccine challenge groups are group 4—vaccination with type 'A' oligosaccharide tetanus toxoid glycoconjugate; and group 5—vaccination with type 'M' oligosaccharide tetanus toxoid glycoconjugate. Following vaccination mice are challenged by intraperitoneal inoculation with $2\times10^5$ CFU (per mouse) of *B. abortus* strain 544. At 15 days post challenge mice are euthanised and the number of *Brucella* cells within their spleens enumerated to provide a metric of protection. The mice are also bled and serology performed to determine the antibody response from each group to the 'A' and 'M' epitopes. This provides a means by which to evaluate the DIVA potential of the oligosaccharide tetanus toxoid glycoconjugate.

The invention claimed is:

1. A diagnostic conjugate comprising an oligosaccharide which comprises at least two units of 4,6-dideoxy-4-acylamido-α-pyranose and comprising at least one -(1-3)- link between adjacent 4,6-dideoxy-4-acylamido-α-pyranose units, in which the carbon at position 5 in the pyranose is linked to an R group, where R is independently selected from —CH2OH, —H or an alkyl group having at least one C atom, the oligosaccharide being covalently linked to a non-saccharide molecule or to a solid entity, wherein the oligosaccharide is a tetrasaccharide of 4,6-dideoxy-4-acylamido-α-pyranosyl-(1-2)-4,6-dideoxy-4-acylamido-α-pyranosyl-(1-3)-4,6-dideoxy-4-acylamido-α-pyranosyl-(1-2)-4,6-dideoxy-4-acylamido-α-pyranose.

2. The diagnostic conjugate according to claim 1 which is a specific M-antigen, capable of preferentially binding to an anti-M antibody.

3. The diagnostic conjugate according to claim 1 wherein, in the oligosaccharide, R is methyl, ethyl or butyl.

4. The diagnostic conjugate according to claim 1, wherein the non-saccharide molecule is selected from the group consisting of a protein, Bovine Serum Albumin (BSA), a non-protein carrier molecule comprising hydrophobic elements, and a fluorophore.

5. The diagnostic conjugate according to claim 1, wherein the oligosaccharide is linked to a solid entity via a protein, via Bovine Serum Albumin (BSA), or via hydrazone conjugation.

6. A kit comprising a diagnostic conjugate according to claim 1 and further comprising means for obtaining and/or containing a biological sample from an animal, and/or one or more laboratory reagents useful for conducting an antibody-antigen binding detection assay, and/or packaging materials and/or materials providing instructions for use of the kit.

* * * * *